United States Patent
Frost et al.

(10) Patent No.: US 10,596,274 B2
(45) Date of Patent: Mar. 24, 2020

(54) METHODS AND COMPOSITIONS FOR TRANSDUCING LYMPHOCYTES AND REGULATED EXPANSION THEREOF

(71) Applicant: Exuma Biotech Corp., West Palm Beach, FL (US)

(72) Inventors: Gregory Ian Frost, West Palm Beach, FL (US); James Joseph Onuffer, Alameda, CA (US); Ghiabe H. Guibinga, San Diego, CA (US)

(73) Assignee: Exuma Biotech Corp., West Palm Beach, FL (US)

( * ) Notice: Subject to any disclaimer, the term of this patent is extended or adjusted under 35 U.S.C. 154(b) by 171 days.

(21) Appl. No.: 15/462,855

(22) Filed: Mar. 19, 2017

(65) Prior Publication Data
US 2017/0296678 A1    Oct. 19, 2017

Related U.S. Application Data

(60) Provisional application No. 62/390,093, filed on Mar. 19, 2016, provisional application No. 62/360,041, filed on Jul. 8, 2016, provisional application No. 62/467,039, filed on Mar. 3, 2017.

(51) Int. Cl.
| | | |
|---|---|---|
| *C12N 15/115* | (2010.01) | |
| *A61K 48/00* | (2006.01) | |
| *C12N 15/113* | (2010.01) | |
| *C12N 15/63* | (2006.01) | |
| *C12N 15/87* | (2006.01) | |
| *C12N 15/11* | (2006.01) | |
| *C07K 14/725* | (2006.01) | |
| *C07K 14/705* | (2006.01) | |
| *C07K 14/715* | (2006.01) | |
| *C12N 5/0783* | (2010.01) | |
| *C12N 15/10* | (2006.01) | |
| *A61K 35/17* | (2015.01) | |
| *C07K 14/005* | (2006.01) | |
| *C07K 14/54* | (2006.01) | |
| *C07K 16/28* | (2006.01) | |
| *C07K 16/30* | (2006.01) | |
| *C12N 7/00* | (2006.01) | |
| *C12N 15/86* | (2006.01) | |
| *A61K 39/00* | (2006.01) | |

(52) U.S. Cl.
CPC .......... *A61K 48/0066* (2013.01); *A61K 35/17* (2013.01); *C07K 14/005* (2013.01); *C07K 14/5418* (2013.01); *C07K 14/705* (2013.01); *C07K 14/7051* (2013.01); *C07K 14/70517* (2013.01); *C07K 14/70521* (2013.01); *C07K 14/70578* (2013.01); *C07K 14/70596* (2013.01); *C07K 14/715* (2013.01); *C07K 14/7155* (2013.01); *C07K 16/2803* (2013.01); *C07K 16/2809* (2013.01); *C07K 16/2863* (2013.01); *C07K 16/30* (2013.01); *C12N 5/0636* (2013.01); *C12N 5/0646* (2013.01); *C12N 7/00* (2013.01); *C12N 15/1048* (2013.01); *C12N 15/113* (2013.01); *C12N 15/635* (2013.01); *C12N 15/86* (2013.01); *A61K 2039/505* (2013.01); *A61K 2039/5158* (2013.01); *C07K 2317/622* (2013.01); *C07K 2319/02* (2013.01); *C07K 2319/03* (2013.01); *C07K 2319/31* (2013.01); *C07K 2319/33* (2013.01); *C07K 2319/74* (2013.01); *C12N 2310/141* (2013.01); *C12N 2510/00* (2013.01); *C12N 2740/15021* (2013.01); *C12N 2740/15043* (2013.01); *C12N 2740/15052* (2013.01); *C12N 2740/16043* (2013.01); *C12N 2740/16045* (2013.01); *C12N 2760/18422* (2013.01); *C12N 2830/002* (2013.01)

(58) Field of Classification Search
None
See application file for complete search history.

(56) References Cited

U.S. PATENT DOCUMENTS

2008/0269258 A1    10/2008    Breaker et al.

FOREIGN PATENT DOCUMENTS

WO    2006055351 A2    5/2006

OTHER PUBLICATIONS

Anthony PC et al: "Folding energy landscape of the thiamine pyrophosphate riboswitch aptamer", Proceedings of the National Academy of Sciences, 109(5):1485-1489, Jan. 4, 2012.
Beisel CL et al: "Design of small molecule-responsive microRNAs based on structural requirements for Drosha processing", Nucleic acids research, 39(7):2981-2994, Dec. 11, 2010.

(Continued)

*Primary Examiner* — Maria Marvich
(74) *Attorney, Agent, or Firm* — Double Helix Law

(57) ABSTRACT

The present disclosure provides methods for genetically modifying lymphocytes and methods for performing adoptive cellular therapy that include transducing T cells and/or NK cells without prior ex vivo stimulation. The methods typically include engineered signaling polypeptides that can include a lymphoproliferative element, and/or a chimeric antigen receptor (CAR), for example a microenvironment restricted CAR. Additional elements of such engineered signaling polypeptides are provided herein, as well as vectors, such as retroviral vectors, packaging cell lines and methods of making the same. Furthermore, recombinant retroviruses and methods of making the same are provided. Numerous controls are provided, including riboswitches that are controlled, for example in vivo, by nucleoside analogues.

24 Claims, 24 Drawing Sheets
Specification includes a Sequence Listing.

(56) References Cited

OTHER PUBLICATIONS

Chen YY et al: "Genetic control of mammalian T-cell proliferation with synthetic RNA regulatory systems"; Proceedings of the National Academy of Sciences, 107(19):8531-8536, Apr. 26, 2010.

Dambach MD et al: "Expanding roles for metabolite-sensing regulatory RNAs", Current opinion in microbiology, 12(2):161-169, Feb. 26, 2009.

Edwards A et al: "A structural basis for the recognition of 2'-deoxyguanosine by the purine riboswitch", Journal of molecular biology, 385(3):938-948, Nov. 5, 2008.

Garst AD et al: "Riboswitches: structures and mechanisms", Cold Spring Harbor perspectives in biology, 3(6):a003533, Oct. 18, 2010.

Harris KA et al: "Biochemical analysis of pistol self-cleaving ribozymes", RNA, 21(11):1852-1858, Sep. 18, 2015.

Jensen MC: "Enhancing the IQ of CAR-modified T Cells", International Society & Gene Therapy abstract, Jun. 1, 2012.

Kim DS et al: "Ligand-induced sequestering of branchpoint sequence allows conditional control of splicing", BMC molecular biology, 9(1):23, Feb. 12, 2008.

Kim JN et al: "Guanine riboswitch variants from Mesoplasma florum selectively recognize 2'-deoxyguanosine", Proceedings of the National Academy of Sciences, 104(41):16092-16097, Oct. 2, 2007.

Levay A et al: "Identifying high-affinity aptamer ligands with defined cross-reactivity using high-throughput guided systematic evolution of ligands by exponential enrichment", Nucleic Acids Research, 43(12):e82, May 24, 2015.

Lienert F et al: "Synthetic biology in mammalian cells: next generation research tools and therapeutics", Nature reviews Molecular cell biology, 15(2):95, Jan. 17, 2014.

Mandal M et al: "Riboswitches control fundamental biochemical pathways in Bacillus subtilis and other bacteria", Cell, 113(5):577-586, May 29, 2003.

Ogawa A: "Rational design of artificial riboswitches based on ligand-dependent modulation of internal ribosome entry in wheat germ extract and their applications as label-free biosensors", RNA, 17(3):478-488, Jan. 11, 2011.

Park JW et al: "Immobilization-free screening of aptamers assisted by graphene oxide", Chem. Commun., 48 (15):2071-2073, Dec. 5, 2011.

Pikovskaya O et al: "Structural principles of nucleoside selectivity in a 2'-deoxyguanosine riboswitch", Nature chemical biology, 7(10):748, Aug. 14, 2011.

Schütze T et al: "Probing the SELEX Process with Next-Generation Sequencing", PLoS ONE, 6(12):e29604, Dec. 29, 2011.

Townshend B et al: "High-throughput cellular RNA device engineering", Nature methods, 12(10):989-994, Aug. 10, 2015.

Vu MM et al: "Convergent evolution of adenosine aptamers spanning bacterial, human, and random sequences revealed by structure-based bioinformatics and genomic SELEX", Chemistry & biology, 19(10):1247-1254, Oct. 25, 2012.

Wang J et al: "Particle Display: A Quantitative Screening Method for Generating High-Affinity Aptamers", Angewandte Chemie International Edition, 53(19):4796-4801, Mar. 18, 2014.

Zeng S et al: "Exploration on the mechanism of DNA adsorption on graphene and graphene oxide via molecular simulations", Journal of Physics D: Applied Physics, 48(27):275402, Oct. 10, 2015.

Zichel R et al: "Aptamers as a sensitive tool to detect subtle modifications in therapeutic proteins", PloS One, 7(2):e31948, Feb. 27, 2012.

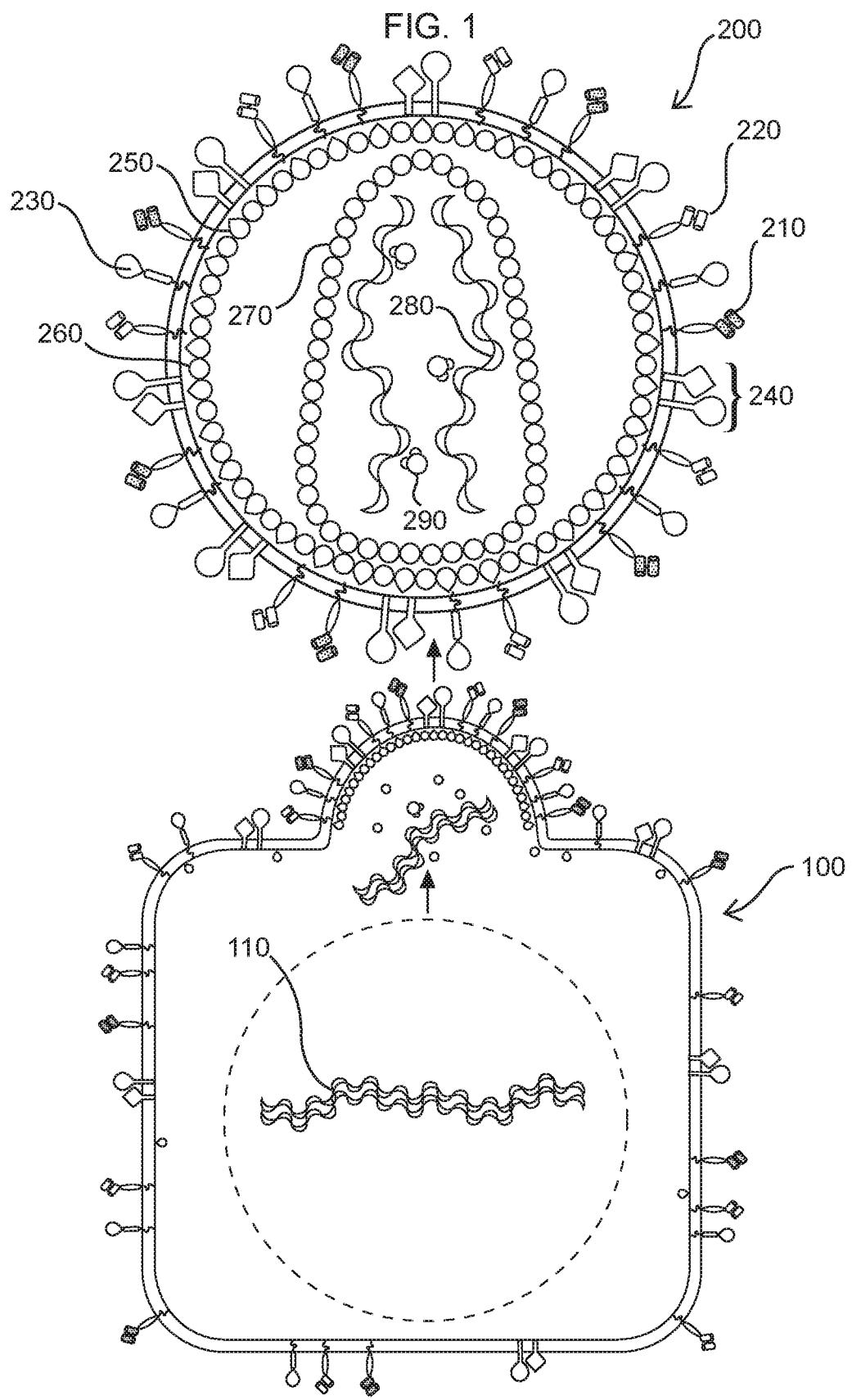

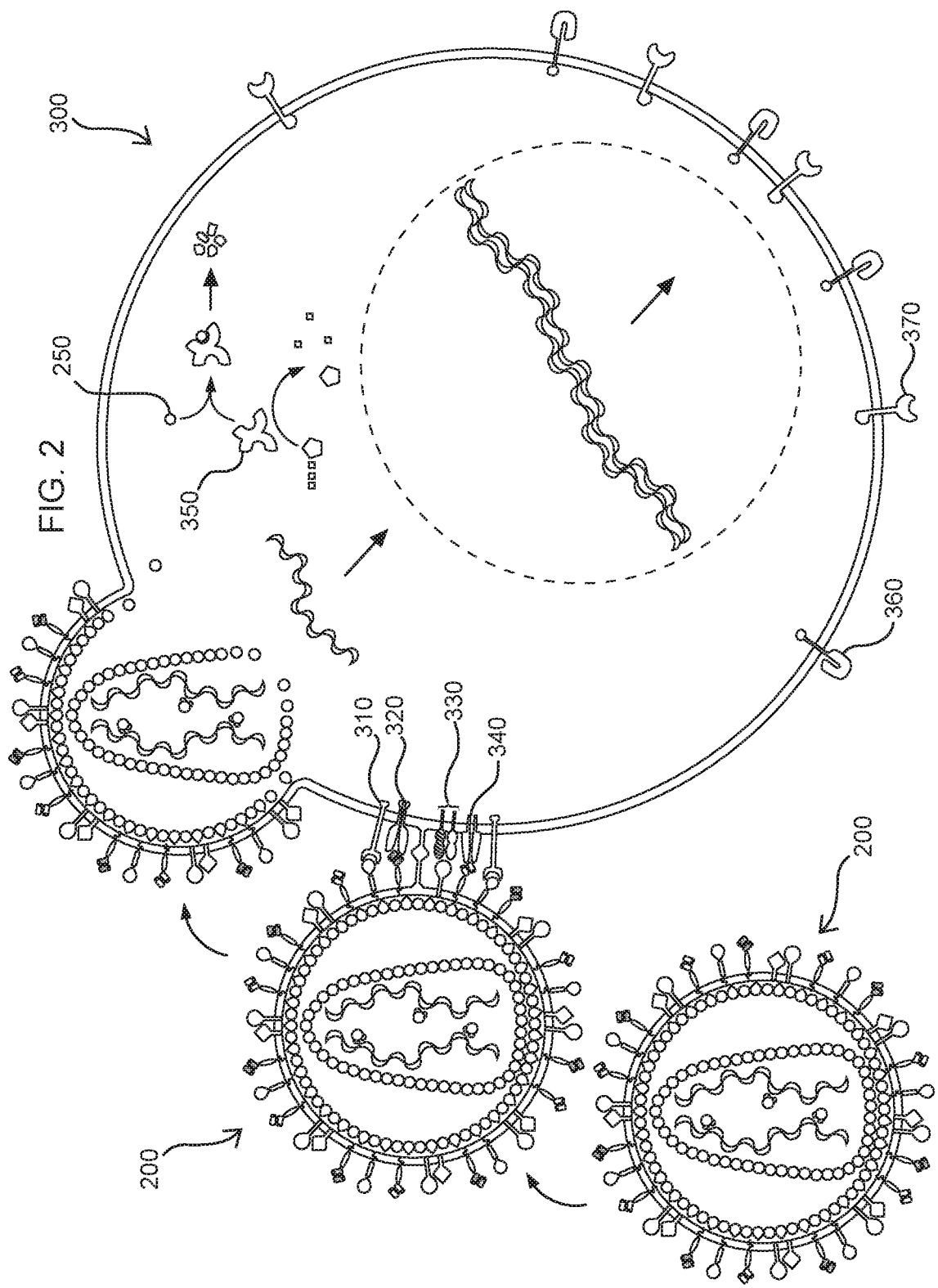

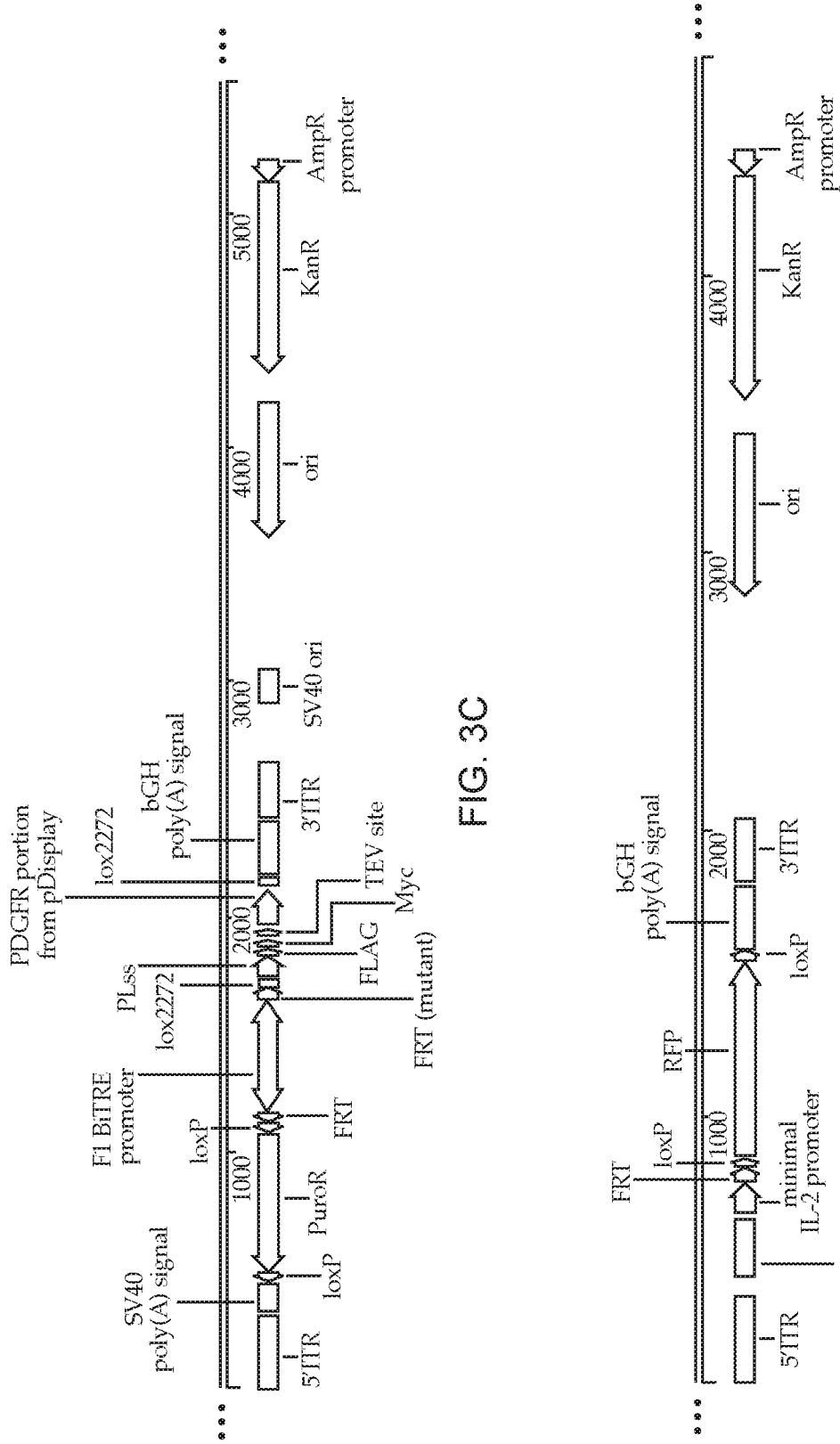

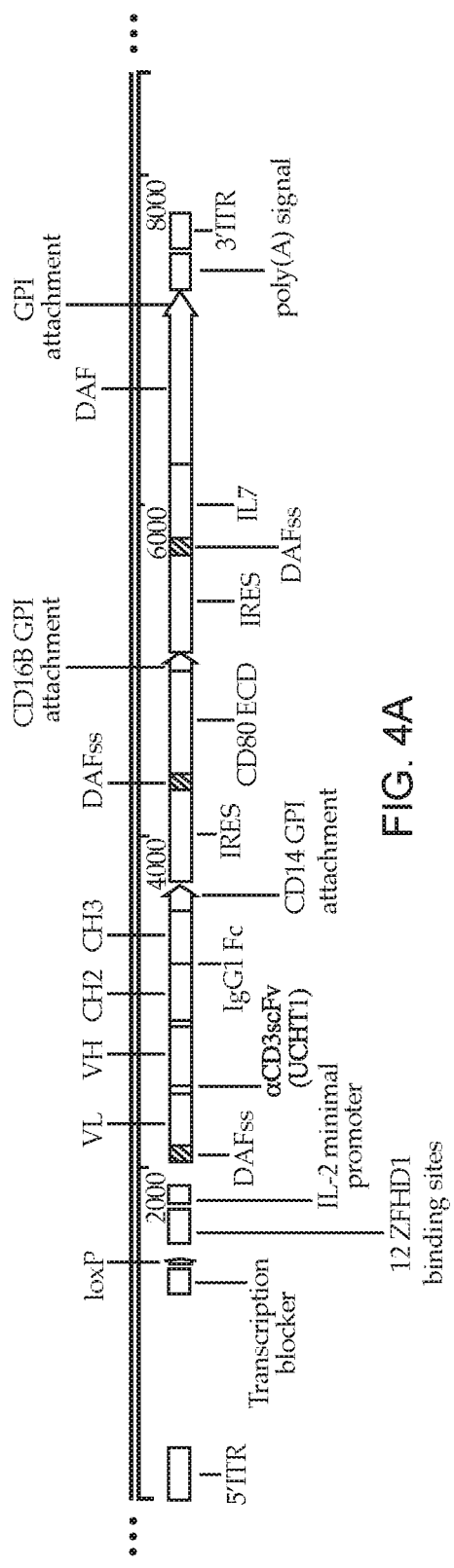
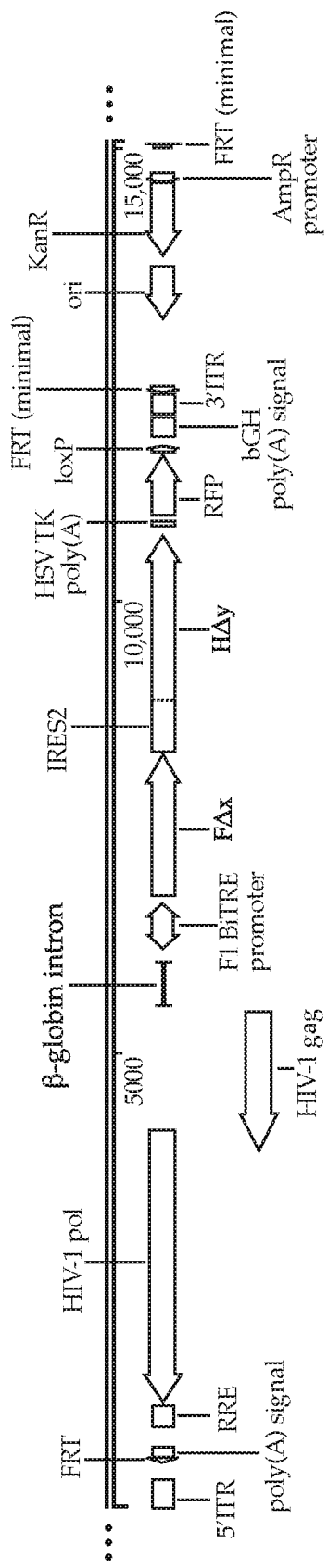
FIG. 4A
FIG. 4B

Acyclovir

Penciclovir

2'-Deoxyguanosine aaaaaaaataaaatcaatagcaaatattaagattttaagaaataaaaaattaatattaatttacaactgaatataaaagaaactta
tacagggtagcataatgggctactgaccccgccttcaaacctatttggagactataagtgaaaaaccactctttaattatta
aagtttcttttatgtccaaaagacaagaagaaacttttttatttagttgaatttataataagagaaaaagaaaggatattatATGGC
AAAAATAAAAAACCAATATTACAACGAGTCTGTTTCGCCAATTGAATATGCGCAACAAGGATTTA
AAGGAAAAATGCGTTCAGTAAACTGAAACGTAGTAAATGATGAAAAAGATTTAGAGGTATGAAAT
AGAATTACACAAAACTTCTGATTGCCTGAAAAAATTCCAGTTTCAAATGATTTAACTTCATGAAGA
ACTTTGACACCAGAATGACAAGAATTAATTACAAGAACTTTTACAGGATTAACATTGTTAGATACA
ATTCAAGCTACTGTTGGTGATGTGGCTCAAGTTCCTAACTCATTAACTGACCATGAACAAGTAATT
TACACAAACTTTGCATTTATGGTTGCAGTTCACGCTAGATCATATGGTTCAATCTTTTCAACTTTAT
GTTCAAGTGAACAAATTGAAGAGGCTCATGAATGAGTTATCAATACAGAAACATTACAAGAAAGA
GCTAAAGCATTAATTCCTTATTATGTGAATGATGACCCTTTAAAGTCAAAAGTTGCAGCTGCTTTA
ATGCCAGGCTTCTTATTATATGGAGGCTTCTATTTACCATTTTACCTATCAGCTAGAGGTAAATTACC
AAACACTTCAGATATTATTAGATTAATATTAAGAGATAAAGTTATACATAACTACTATAGTGGTTATA
AATATCAAAAGAAAGTTGCTAAACTTTCTCCAGAAAAACAAGCTGAAATGAAAGAATTTGTTTTT
AAATTATTATATGAATTAATAGATTTAGAAAAAGCTTATTTGAAAGAATTGTATGAGGATTTTGGATT
AGCTGATGATGCTATTAGATTTAGTGTTTACAACGCAGGTAAATTTTTACAAAATTTAGGTTATGAT
TCACCGTTTACAGAAGAAGAAACAAGAATTGAGCCAGAAATATTCACACAATTATCAGCTAGAGC
TGATGAAAACCATGATTTCTTTTCAGGGAATGGCTCATCATATATTATGGGAGTTTCAGAAGAAAC
TGAAGATGACGATTGGGAGTTTtaa (SEQ ID NO:236)

Oligo library for screen
CGCGGGACACTTATAGTCNNNAAATAGGTTTNNGGCNNNNNNNNCNNNAGCCCATTATGCTNNNNTGTATAAGTGCCGCCC (SEQ ID NO:239)

T7 promoter amplification primer
TAATACGACTCACTATAGGGCGGCACTTATACA (SEQ ID NO:240)

Reverse amplification primer
CGCGGGACACTTATAGTC (SEQ ID NO:241)

tcaaaagcctggcggcgcggtcgtcagactcttttatatcgaatcccttgaaatacgaatgatatctaaaaaaac
aaaattaaagttcgggaattttatttcagcctatgcaagagattagaatcttgatataatttattacaatataatagg
aa<u>cactcatataatcgcgtggatatggcacgcaagtttctaccgggcaccgtaaatgtccgactatgggtg</u>
agcaatggaaccgcacgtgtacggttttttgtgatatcagcattgcttgctctttatttgagcgggcaatgctttttta
ttctcataacggaggtagacaggATGGAAGCACTGAAACGGAAAATAGAGGAAGAAGGCGTC
GTATTATCTGATCAGGTATTGAAAGTGGATTCTTTTTTGAATCACCAAATTGATCCGCTG
CTTATGCAGAGAATTGGTGATGAATTTGCGTCTAGGTTTGCAAAAGACGGTATTACCAA
AATTGTGACAATCGAATCATCAGGTATCGCTCCCGCTGTAATGACGGGCTTGAAGCTG
GGTGTGCCAGTTGTCTTCGCGAGAAAGCATAAATCGTTAACACTCACCGACAACTTGC
TGACAGCGTCTGTTTATTCCTTTACGAAGCAAACAGAAAGCCAAATCGCAGTGTCTGG
GACCCACCTGTCGGATCAGGATCATGTGCTGATTATCGATGATTTTTTGGCAAATGGAC
AGGCAGCGCACGGGCTTGTGTCGATTGTGAAGCAAGCGGGAGCTTCTATTGCGGGAA
TCGGCATTGTTATTGAAAAGTCATTTCAGCCGGGAAGAGATGAACTTGTAAAACTGGG
CTACCGAGTGGAATCTTTGGCAAGAATTCAGTCTTTAGAAGAAGGAAAAGTGTCCTTC
GTACAGGAGGTTCATTCAtga (SEQ ID NO:242)

Oligo library for screen
CGCGGGACCACCCATAGTCNNNCATTTACGGTGNNNGGTNNNNNNNNCNNNCGTGCCATATCCACG
NNNNTATATGAGTGGCCGCCC (SEQ ID NO:245)

T7 promoter amplification primer
TAATACGACTCACTATAGGGCGGCCACTCATATA (SEQ ID NO:246)

Reverse amplification primer
CGCGGGACCACCCATAGTC (SEQ ID NO:247)

| F1A-795 | F1A-996 | F1A-935 | F1A-946 | F1A-961 | F1A-769 | F1A-582 |
|---|---|---|---|---|---|---|
| ΔG = -23.30 kcal/mol | ΔG = -25.50 kcal/mol | ΔG = -25.40 kcal/mol | ΔG = -25.10 kcal/mol | ΔG = -27.40 kcal/mol | ΔG = -23.70 kcal/mol | ΔG = -23.10 kcal/mol |
| Sequence (5'->3'): GGG CGG CAC UUA UAC AGC GAA GCA UAA UGG CUA CUG ACG CCC UCA AAC CCU AUU UGC AGA CUA UAA GUG UCG CGC G | Sequence (5'->3'): GCG CGG CAC UUA UAC AGG GUA GCA UAA UGG CUU AGG ACG CCU UCA AAC CCU UCA AGA CUA UAA GUC UCG CGC G | Sequence (5'->3'): GGG CGG CAC UUA UAC AGG GUA GCA UAA UGG GCU ACU UGA CGC CUU CAC CUA UAU GUA GAC UAA AAG UGU CGC GCG | Sequence (5'->3'): GGG CGG CAC UUA UAC AGC GUA GCA UAA UGG GCU GCA GAC GCC GUC RAA CCU AUU UGC AGA CUA UAA GUG UCG CGC G | Sequence (5'->3'): GGG CGG CAC UUA UAC ACC GUA GCA UAA UGG GCU ACU GCC GCC GUC GAC CUU UUG GAG ACU AUA AGU GUC GCG | Sequence (5'->3'): GGG CGG CAC UUA UAC AGC UCA GCA UAA UGG GCU AGU GCC CUA AGU AAC CUA UUU AGA GAC UAU AAG UGU CGC GCG | Sequence (5'->3'): GGG CGG CAC UUA UAC AGC UUA GCG UAA UGG GCU ACU CGG ACG CUA UCC AAA CCU AUU UAC AGA GUG UCG CGC G |
| (SEQ ID NO:87) | (SEQ ID NO:88) | (SEQ ID NO:89) | (SEQ ID NO:90) | (SEQ ID NO:91) | (SEQ ID NO:92) | (SEQ ID NO:93) |

FIG. 17

| F1P-584 | F1P-710 | F1P-923 | F1P-991 | F1P-837 | F1P-718 | F1P-932 |
|---|---|---|---|---|---|---|
| ΔG = -24.10 kcal/mol | ΔG = -28.90 kcal/mol | ΔG = -23.00 kcal/mol | ΔG = -25.00 kcal/mol | ΔG = -23.70 kcal/mol | ΔG = -25.00 kcal/mol | ΔG = -27.70 kcal/mol |
| Sequence (5'->3'): GGG CGG CAC UUA UAC AGG UUA GCA UAA UGG GCU ACU GAC GCC UGU AAA CCU AUU UGA GGA CUA UAA GUG GCG CGC G | Sequence (5'->3'): GGG CGG CAC UUA UAC AUG GAA GCA UAA UGG GCU GCC GAC GGC CCU UAA CCU UUG GAG ACU AUA AGU GUC GCG CG | Sequence (5'->3'): GGG CGG CAC UUA UAC AGA UUA GCA UAA UGG GCU ACU GAC CCC GCC GGC AAA CCU AUU UGA AGA CUA UAA GUG UCG CGC G | Sequence (5'->3'): GGG CGG CAC UUA UAC AGU UUA GCA UAA UGG GCU ACU GUC GCA UCA AAC CUA UUU GGA GAC UAU AAG UGU CGC GCG | Sequence (5'->3'): GGG CGG CAC UUA UAC AGU GAA GCA UAA UGG GCU ACU GAC ACC CUU AAA CCU AUU UGC AGA CUA UAA GUG GCG CGC G | Sequence (5'->3'): GGG CGG CAC UUA UAC AGA UUA GCA UAA UGG GCU ACA GAC GCC GUC AAA CCU AUU UAC CGA CUA UAA GUG GCG UCG CGC G | Sequence (5'->3'): GGG CGG CAC UUA UAC AGG UUU CAU AAU GGG CUA GUC ACG CCU AAA CCU AUU UGU A GAC UAU AAG UGU CGC GCG |
| (SEQ ID NO:94) | (SEQ ID NO:95) | (SEQ ID NO:96) | (SEQ ID NO:97) | (SEQ ID NO:98) | (SEQ ID NO:99) | (SEQ ID NO:100) |

FIG. 18

▲ MV(Ed)-FΔ30/HΔ18
(SEQ ID NO:105) (SEQ ID NO:106)

■ MV(Ed)-FΔ30/HΔ24
(SEQ ID NO:105) (SEQ ID NO:235)

○ VSV-G

FIG. 20

Multiplicity of Infection (MOI)

Transduction Efficiency CD3+ GFP+ (%)

METHODS AND COMPOSITIONS FOR TRANSDUCING LYMPHOCYTES AND REGULATED EXPANSION THEREOF

CROSS-REFERENCE TO RELATED APPLICATIONS

This application claims benefit of U.S. Provisional Application No. 62/390,093, filed Mar. 19, 2016; U.S. Provisional Application No. 62/360,041, filed Jul. 8, 2016; and U.S. Provisional Application No. 62/467,039, filed Mar. 3, 2017. These applications are hereby incorporated by reference in their entirety.

SEQUENCE LISTING

This application hereby incorporates by reference the material of the electronic Sequencing Listing filed concurrently herewith. The materials in the electronic Sequence Listing is submitted as a text (.txt) file entitled "F1_001_Sequence_listing.txt" created on Mar. 16, 2017, which has a file size of 230 KB, and is herein incorporated by reference in its entirety.

FIELD OF INVENTION

This disclosure relates to the field of immunology, or more specifically, to the genetic modification of T lymphocytes or other immune cells, and methods of making retroviruses and controlling the expression of genes.

BACKGROUND OF THE DISCLOSURE

Lymphocytes isolated from a subject (e.g. patient) can be activated in vitro and genetically modified to express synthetic proteins that enable redirected engagement with other cells and environments based upon the genetic programs incorporated. An example of such a synthetic protein is a chimeric antigen receptor (CAR). One CAR that is currently used is a fusion of an extracellular recognition domain (e.g., an antigen-binding domain), a transmembrane domain, and one or more intracellular signaling domains encoded by a replication incompetent retrovirus.

While retroviruses have shown efficacy in infecting non-dividing cells, resting CD4 and CD8 lymphocytes are refractory to genetic transduction by these vectors. To overcome this difficulty, these cells are typically activated in vitro using stimulation reagents before genetic modification with the CAR gene vector can occur. Following stimulation and transduction, the genetically modified cells are expanded in vitro and subsequently reintroduced into a lymphodepleted patient. Upon antigen engagement in vivo, the intracellular signaling portion of the CAR can initiate an activation-related response in an immune cell and release of cytolytic molecules to induce tumor cell death.

Such current methods require extensive manipulation and manufacturing of proliferating T cells outside the body prior to their reinfusion into the patient, as well as lymphodepleting chemotherapy to free cytokines and deplete competing receptors to facilitate T cell engraftment. Such CAR therapies further cannot be controlled for propagation rate in vivo once introduced into the body, nor safely directed towards targets that are also expressed outside the tumor. As a result, CAR therapies today are typically infused from cells expanded ex vivo from 12 to 28 days using doses from $1 \times 10^5$ to $1 \times 10^8$ cells/kg and are directed towards targets, for example tumor targets, for which off tumor on target toxicity is generally acceptable. These relatively long ex vivo expansion times create issues of cell viability and sterility, as well as sample identity in addition to challenges of scalability. Thus, there are significant needs for a safer, more effective scalable T cell or NK cell therapy.

SUMMARY

In one aspect, provided herein is a method for genetically modifying and expanding lymphocytes of a subject, comprising:
  A. contacting resting T cells and/or NK cells of the subject ex vivo without requiring prior ex vivo stimulation, with recombinant retroviruses comprising:
    i. a pseudotyping element on its surface that is capable of binding to a T cell and/or NK cell and facilitating membrane fusion of the recombinant retrovirus thereto; and
    ii. a polynucleotide comprising one or more transcriptional units operatively linked to a promoter active in T cells and/or NK cells, wherein the one or more transcriptional units encode a first engineered signaling polypeptide regulated by an in vivo control element, wherein said first engineered signaling polypeptide comprises a lymphoproliferative element, wherein said contacting facilitates transduction of at least some of the resting T cells and/or NK cells by the recombinant retroviruses, thereby producing genetically modified T cells and/or NK cells;
  B. introducing the genetically modified T cells and/or NK cells into the subject; and
  C. exposing the genetically modified T cells and/or NK cells in vivo to a compound that binds the in vivo control element to affect expression of the first engineered signaling polypeptide and promote and/or potentiate expansion, engraftment, and/or persistence of the lymphocytes in vivo, thereby genetically modifying and expanding lymphocytes of the subject. In illustrative embodiments, the transduction is carried out without ex vivo stimulation.

In the above aspect and any of the method aspects for genetically modifying and expanding lymphocytes or for performing cellular therapy herein, if not recited in the broadest aspect, in certain embodiments the polynucleotide further comprises a transcriptional unit that encodes a second engineered signaling polypeptide comprising a first chimeric antigen receptor comprising an antigen-specific targeting region (ASTR), a transmembrane domain, and an intracellular activating domain.

In another aspect, provided herein is a method for performing adoptive cell therapy on a subject, comprising:
  A. collecting blood from the subject;
  B. contacting resting T cells and/or NK cells from the blood of the subject ex vivo with recombinant retroviruses, wherein the recombinant retroviruses comprise
    i. a pseudotyping element on their surface that is capable of binding to a T cell and/or NK cell and facilitating membrane fusion of the recombinant retroviruses thereto; and
    ii. a polynucleotide comprising one or more transcriptional units operatively linked to a promoter active in T cells and/or NK cells, wherein the one or more transcriptional units encode a first engineered signaling polypeptide comprising a lymphoproliferative element whose expression is regulated by an in vivo control element, and a second engineered signaling polypeptide comprising a chimeric antigen receptor comprising an antigen-specific targeting region (ASTR), a transmembrane domain, and an intracellular activating domain, wherein said contacting results in at least some of the resting T cells and/or NK cells becoming genetically modified; and C. reintroducing the genetically modified T cells and/or NK cells into the subject, wherein expansion, engraftment, and/or persistence of the genetically modified T cells and/or NK cells occurs in vivo within the subject, and wherein the method between the collecting blood and the reintroducing the genetically modified T cells and/or NK cells is performed in no more than 24 hours, thereby performing adoptive cell therapy on the subject.

Provided in another aspect herein is a method for performing adoptive cell therapy on a subject, comprising:

A. collecting blood from a subject;

B. isolating peripheral blood mononuclear cells (PBMCs) comprising resting T cells and/or resting NK cells;

C. contacting the resting T cells and/or resting NK cells of the subject ex vivo, with recombinant retroviruses, wherein the recombinant retroviruses comprise a pseudotyping element on their surface that is capable of binding a resting T cell and/or NK cell and facilitating membrane fusion of the recombinant retrovirus thereto, wherein said contacting facilitates transduction of the resting T cells and/or NK cells by the recombinant retroviruses, thereby producing genetically modified T cells and/or NK cells; and D. reintroducing the genetically modified cells into the subject within 24 hours of collecting blood from the subject, thereby performing adoptive cell therapy in the subject.

Provided in another aspect herein, is a method of transducing resting lymphocytes of a subject, comprising contacting resting T cells and/or resting NK cells of a subject ex vivo, with recombinant retroviruses, wherein the recombinant retroviruses comprise a pseudotyping element on their surface that is capable of binding a resting T cell and/or resting NK cell and facilitating membrane fusion of the recombinant retrovirus thereto, wherein said contacting facilitates transduction of the resting T cells and/or NK cells by the recombinant retroviruses, thereby producing genetically modified T cells and/or NK cells. In illustrative embodiments of this aspect, at least 10, 20, or 25% of the resting T cells and/or NK cells, or between 10% and 70%, or 20% and 50% of T cells and/or NK cells are transduced as a result of the process are transduced as a result of the process.

Provided in another aspect herein is a method for transducing resting T cells and/or resting NK cells from isolated blood, comprising:

A. collecting blood from a subject;

B. isolating peripheral blood mononuclear cells (PBMCs) comprising resting T cells and/or resting NK cells;

C. contacting the resting T cells and/or resting NK cells of the subject ex vivo, with recombinant retroviruses, wherein the recombinant retroviruses comprise a pseudotyping element on their surface that is capable of binding a resting T cell and/or resting NK cell and facilitating membrane fusion of the recombinant retrovirus thereto, wherein said contacting facilitates transduction of at least 5% of the resting T cells and/or resting NK cells by the recombinant retroviruses, thereby producing genetically modified T cells and/or NK cells, thereby transducing resting T cells and/or NK cells.

In one aspect, provided herein is a recombinant retrovirus, comprising:

A. one or more pseudotyping elements capable of binding to a T cell and/or an NK cell and facilitating membrane fusion of the recombinant retrovirus thereto;

B. a polynucleotide comprising one or more transcriptional units operatively linked to a promoter active in T cells and/or NK cells, wherein the one or more transcriptional units encode a first engineered signaling polypeptide comprising a chimeric antigen receptor comprising an antigen-specific targeting region, a transmembrane domain, and an intracellular activating domain, and a second engineered signaling polypeptide comprising a lymphoproliferative element; wherein expression of the first engineered signaling polypeptide and/or the second engineered signaling polypeptide are regulated by an in vivo control element; and C. an activation element on its surface, wherein the activation element is capable of binding to a T cell and/or NK cell and is not encoded by a polynucleotide in the recombinant retrovirus.

In another aspect, provided herein is a recombinant retrovirus, comprising:

A. a pseudotyping element on its surface that is capable of binding to a T cell and/or NK cell and facilitating membrane fusion of the recombinant retrovirus thereto, wherein said pseudotyping element comprises cytoplasmic domain deletion variants of a measles virus F polypeptide and/or a measles virus H polypeptide;

B. a polynucleotide comprising one or more transcriptional units operatively linked to a promoter active in T cells and/or NK cells, wherein the one or more transcriptional units encode a first engineered signaling polypeptide comprising a chimeric antigen receptor comprising an antigen-specific targeting region, a transmembrane domain, and an intracellular activating domain, and a second engineered signaling polypeptide comprising a constitutively active IL-7 receptor mutant; wherein expression of the IL-7 receptor mutant is regulated by a riboswitch that binds a nucleoside analog antiviral drug; and C. a polypeptide capable of binding to CD3 and a polypeptide capable of binding to CD28, wherein said polypeptides are expressed on the surface of a recombinant retrovirus; are capable of binding to a T cell and/or NK cell; and are not encoded by a polynucleotide in the recombinant retrovirus. In illustrative embodiments of this aspect, binding of the nucleoside analog antiviral drug to the riboswitch increases expression of the IL-7 receptor mutant.

In any of the method or composition aspects provided herein, if not already recited in the broadest aspect, the recombinant retrovirus or retroviruses comprises or further comprise an activation element on their surface that is capable of activating a resting T cell and/or a resting NK cell.

In any of the methods or compositions herein that recite a T cell and/or a NK cell, or a resting T cell or a resting NK cell, in certain illustrative embodiments, the cell is a T cell.

Typically, the recombinant retrovirus in any of the methods and compositions provided herein, is replication defective. That is, the virus cannot replicate. In illustrative embodiments, the retrovirus is a lentivirus, such as a replication defective HIV lentivirus.

In illustrative embodiments of any of the methods aspects for genetically modifying and expanding lymphocytes or for performing adoptive cellular therapy herein, or similar methods, between 10% and 75%, or 10% and 70%, or 10% and 60%, or 10% and 50%, or 10% and 25%, or 20% and 75%, or 20% and 50%, or at least 10%, 20%, or 25% of resting T cells are transduced and between 0% and 75% of NK cells are transduced. In other embodiments, between 5% and 80%, or 10% and 80%, or 10% and 70%, or 10% and 60%, or 10% and 50%, or 10% and 25%, or 10% and 20%, or 20% and 50% of resting NK cells are transduced.

In illustrative embodiments of any of the methods aspects for genetically modifying and expanding lymphocytes or for performing adoptive cellular therapy herein, or similar methods or any compositions provided herein, if not explicitly recited in the broadest aspect, expression of said second engineered signaling polypeptide is regulated by the in vivo control element.

In illustrative embodiments of any of the methods aspects for genetically modifying and expanding lymphocytes or for performing cellular therapy herein, or similar methods, if not explicitly recited in the broadest aspect the method, the contacting can be carried out for between 15, 30 or 45 minutes or 1, 2, 3, 4, 5, 6, 7, or 8 hours on the low end of the range, and between 6, 8, 10, 12, 18, 24, 36, 48, and 72 hours on the high end of the range. For example, in illustrative embodiments, the contacting is carried out for between 2 and 24 hours, or between 4 and 12 hours, or between 4 and 8 hours.

In illustrative embodiments of any of the methods aspects for genetically modifying and expanding lymphocytes or for performing adoptive cellular therapy herein, or similar methods, if not explicitly recited in the broadest aspect the method can further comprise exposing the genetically modified T cells and/or NK cells in vivo to a compound that binds the in vivo control element to affect expression of the first engineered signaling polypeptide and optionally the second engineered signaling polypeptide, and to promote expansion, engraftment, and/or persistence of the lymphocytes in vivo.

In illustrative embodiments of any of the methods aspects for genetically modifying and expanding lymphocytes or for performing adoptive cellular therapy herein, or similar methods, if not explicitly recited in the broadest aspect, the genetically modified T cells and/or NK cells undergo 8, 7, 6, 5, 4, 3 or fewer cell divisions ex vivo prior to being introduced or reintroduced into the subject.

In illustrative embodiments of any of the methods aspects for genetically modifying and expanding lymphocytes or for performing cellular therapy herein, or similar methods, if not explicitly recited in the broadest aspect, expansion, engraftment, and/or persistence of genetically modified T cells and/or NK cells in vivo is dependent on either the presence or absence of the compound that binds the in vivo control element, and in illustrative embodiments, is dependent on the presence of the compound that binds the in vivo control element.

In illustrative embodiments of any of the methods aspects for genetically modifying and expanding lymphocytes or for performing adoptive cellular therapy herein, or similar methods, if not explicitly recited in the broadest aspect, the subject is not exposed to a lymphodepleting agent within 7, 14, or 21 days of performing the contacting, during the contacting, and/or within 7, 14, or 21 days after the modified T cells and/or NK cells are introduced into the subject. In other embodiments, the subject is not exposed to a lymphodepleting agent during the contacting.

In illustrative embodiments of any of the methods aspects for genetically modifying and expanding lymphocytes or for performing cellular therapy herein, or similar methods, if not explicitly recited in the broadest aspect, the resting T cells and/or resting NK cells are in contact with the recombinant retroviruses for between 15 minutes and 12 hours.

In illustrative embodiments of any of the methods aspects for genetically modifying and expanding lymphocytes or for performing adoptive cellular therapy herein, or similar methods, if not explicitly recited in the broadest aspect, the method further includes the step of separating the recombinant retroviruses from the T cells and/or NK cells after the contacting but before the introducing. In illustrative embodiments of any of the methods aspects for genetically modifying and expanding lymphocytes or for performing cellular therapy herein, or similar methods, if not explicitly recited in the broadest aspect, said exposing step comprises administering a dose of the compound to the subject prior to or during the contacting, and/or after the genetically modified T cells and/or NK cells have been introduced into the subject.

In illustrative embodiments of any of the methods aspects for genetically modifying and expanding lymphocytes or for performing adoptive cellular therapy herein, or similar methods, if not explicitly recited in the broadest aspect, the method comprises collecting blood comprising the T cells and/or the NK cells from the subject prior to contacting the T cells and/or NK cells ex vivo with the recombinant retroviruses, and wherein the introducing is reintroducing. For example, between 20 and 250 ml of blood are withdrawn from the subject.

In illustrative embodiments of any of the methods aspects for genetically modifying and expanding lymphocytes or for performing cellular therapy herein, or similar methods, if not explicitly recited in the broadest aspect, no more than 8, 12, 24, or 48 hours pass between the time blood is collected from the subject and the time the modified T cells and/or NK cells are reintroduced into the subject.

In illustrative embodiments of any of the methods aspects for genetically modifying and expanding lymphocytes or for performing cellular therapy herein, or similar methods, if not explicitly recited in the broadest aspect, between 4 or 8 hours on the low end and 12. 24, 36, or 48 hours on the high end of the range pass between the time blood is collected from the subject and the time the modified T cells and/or NK cells are reintroduced into the subject.

In illustrative embodiments of any of the methods aspects for genetically modifying and expanding lymphocytes or for performing adoptive cellular therapy herein, or similar methods, if not explicitly recited in the broadest aspect, all steps after the blood is collected and before the blood is reintroduced, are performed in a closed system in which a person monitors the closed system throughout the processing. In another embodiment, after the blood is collected and before the blood is reintroduced, are performed in a closed system that remains in the same room with the subject.

In illustrative embodiments of any of the methods and compositions provided herein that include one or more engineered signaling polypeptides, if not recited in the broadest aspect, one of the engineered signaling polypeptide comprises or further comprises an antigen-specific targeting region (ASTR) and a transmembrane domain connecting the ASTR to the lymphoproliferative element. The ASTR of this engineered signaling polypeptide is capable of binding to a first tumor antigen and where present, the ASTR of the second engineered signaling polypeptide is capable of binding to a second tumor antigen. In illustrative embodiments, the first engineered signaling polypeptide and/or the second engineered signaling polypeptide further comprise a co-stimulatory domain. Furthermore, the first engineered signaling polypeptide and/or the second engineered signaling polypeptide further comprise a stalk. Furthermore, the first engineered signaling polypeptide further comprises an intracellular activating domain. The intracellular activating domain on the first engineered signaling polypeptide and/or the second engineered signaling polypeptide can be derived from CD3 zeta.

In illustrative embodiments of any of the methods and compositions provided herein that include a lymphoproliferative element, the lymphoproliferative element can comprise a T cell survival motif. The T cell survival motif can comprise all or a functional fragment of IL-7 receptor. IL-15 receptor, or CD28. In other embodiments, the lymphoproliferative element can include a cytokine or cytokine receptor polypeptide. or a fragment thereof comprising a signaling domain. For example, the lymphoproliferative element can comprise an interleukin polypeptide covalently attached to its cognate interleukin receptor polypeptide via a linker. Alternatively, the lymphoproliferative element can be an intracellular signaling domain of an IL-7 receptor, an intracellular signaling domain of an IL-12 receptor, an intracellular signaling domain of IL-23, an intracellular signaling domain of IL-27. an intracellular signaling domain of an IL-15 receptor, an intracellular signaling domain of an IL-21 receptor, or an intracellular signaling domain of a transforming growth factor β (TGFβ) decoy receptor. In other illustrative embodiments. the lymphoproliferative element is constitutively active. Furthermore, the lymphoproliferative element can include a mutated IL-7 receptor or a fragment thereof, which can further include a constitutively active mutated IL-7 receptor or a constitutively active fragment thereof.

In illustrative embodiments of any of the methods and compositions provided herein that include a recombinant retrovirus or retroviruses, if not explicitly recited in the broadest aspect, the recombinant retroviruses can comprise on their surface an activation element comprising:

A. a membrane-bound polypeptide capable of binding to CD3; and/or
B. a membrane-bound polypeptide capable of binding to CD28.

Furthermore, the membrane-bound polypeptide capable of binding to CD3 is a polypeptide capable of binding to CD3 that can be fused to a heterologous GPI anchor attachment sequence and the membrane-bound polypeptide capable of binding to CD28 can be a polypeptide capable of binding to CD28 that 8 is fused to a heterologous GPI anchor attachment sequence. In some embodiments, he membrane-bound polypeptide capable of binding to CD28 is CD80, CD86, or a functional fragment thereof that is capable of inducing CD28-mediated activation of Akt, such as the extracellular domain of CD80.

In illustrative embodiments of any of the methods and compositions provided herein that include a recombinant retrovirus, the membrane-bound polypeptide capable of binding CD3 can be an anti-CD3 scFv bound to a CD14 GPI anchor attachment sequence, and the membrane-bound polypeptide capable of binding to CD28 can be CD80, or the extracellular domain thereof, bound to a CD16B GPI anchor attachment sequence. In illustrative embodiments of any of the methods and compositions provided herein that include a recombinant retrovirus, the recombinant retroviruses can comprise on their surface, an anti-CD3 scFv bound to a CD14 GPI anchor attachment sequence, CD80, or the extracellular domain thereof, bound to a CD16B GPI anchor attachment sequence, and a fusion polypeptide of IL-7, or an active fragment thereof, and DAF comprising a GPI anchor attachment sequence. In illustrative embodiments of any of the methods and compositions provided herein that include a recombinant retrovirus, the IL-7, or an active fragment thereof, and DAF fusion, the anti-CD3 scFV, and the CD80, or extracellular domain thereof each comprises a DAF signal sequence.

In illustrative embodiments of any of the methods and compositions provided herein that include a recombinant retrovirus or retroviruses, if not explicitly recited in the broadest aspect, the recombinant retroviruses can comprise on their surface a membrane-bound cytokine. The membrane-bound cytokine can be IL-7, IL-15, or an active fragment thereof. In other embodiments, the membrane-bound cytokine is a fusion polypeptide of IL-7, or an active fragment thereof, and DAF. For example, the fusion polypeptide can comprise the DAF signal sequence (nucleotides 1-31 of SEQ ID NO:107), IL-7 without its signal sequence (nucleotides 32-187 of SEQ ID NO:107), and a fragment of DAF that includes its GPI anchor attachment sequence (nucleotides 188-527 of SEQ ID NO:107).

Illustrative embodiments of any of the method and composition aspects provided herein the pseudotyping element can comprise one or more heterologous envelope proteins. In other examples, the pseudotyping element can include one or more viral polypeptides recognized by T cells. The one or more pseudotyping elements can comprise a Measles Virus F polypeptide, a Measles Virus H polypeptide, and/or a fragment thereof. The one or more pseudotyping elements can be cytoplasmic domain deletion variants of a measles virus F polypeptide and/or a measles virus H polypeptide.

In illustrative embodiments of any of the methods and compositions provided herein that include the in vivo control element the in vivo control element is the lymphoproliferative element, wherein the lymphoproliferative is inactive or less active at promoting proliferation of the T cells and/or NK cells in the absence of the compound, and wherein the compound is a molecular chaperone that binds the lymphoproliferative element and induces the activity of the lymphoproliferative element.

In illustrative embodiments of any of the methods and compositions provided herein that include the in vivo control element, the in vivo control element can be a polynucleotide comprising a riboswitch. The riboswitch can be capable of binding a nucleoside analog and the compound that binds the in vivo control element is the nucleoside analog. The nucleoside analog can be an antiviral agent. The antiviral agent can be acyclovir or penciclovir.

In illustrative embodiments of any of the methods and compositions provided herein that include an engineered signaling polypeptide, that includes an ASTR, the ASTR of either or both of the engineered signaling polypeptides can bind to a tumor associated antigen. In some illustrative embodiments, the antigen-specific targeting region of the second engineered polypeptide is a microenvironment restricted antigen-specific targeting region.

In illustrative embodiments of any of the methods and compositions provided herein that include a recombinant retrovirus or retroviruses, if not explicitly recited in the broadest aspect, the recombinant retroviruses can encode a recognition domain for a monoclonal antibody approved biologic. In some embodiments, the recognition domain is expressed on the same transcript as the chimeric antigen receptor and wherein the recognition domain is separated from the chimeric antigen receptor by a ribosome skipping and/or cleavage signal. The ribosome skipping and/or cleavage signal can be 2A-1. The recognition domain can include a polypeptide that is recognized by an antibody that recognizes EGFR, or an epitope thereof. The recognition domain can be an EGFR mutant that is recognized by an EGFR antibody and expressed on the surface of transduced T cells and/or NK cells as another control mechanism provided herein. In related embodiments, the recognition domain can include a polypeptide that is recognized by an antibody that recognizes EGFR, or an epitope thereof.

In any of the methods or compositions provided herein that include a lymphoproliferative element, the lymphoproliferative element can be a miRNA or shRNA that stimulates the STAT5 pathway or inhibits the SOCS pathway. For example, said miRNA or shRNA is a miRNA that binds to a nucleic acid encoding a protein selected from the group consisting of: ABCG1, SOCS, TGFbR2, SMAD2, cCBL, and PD1. In illustrative embodiments for any of the recombinant retroviruses, or transduced cells provided herein, or methods including the same, such recombinant retroviruses or transduced cells can encode an miRNA or shRNA, for example within an intron, in some embodiments, 1, 2, 3, or 4 embodiments that bind nucleic acids encoding one or more of the following target endogenous T cell expressed genes: PD-1; CTLA4; TCR alpha; TCR beta; CD3 zeta; SOCS; SMAD2; miR-155; IFN gamma; cCBL; TRAIL2; PP2A; or ABCG1. For example, in one embodiment, a combination of the following miRNAs can be included in a genome of a recombinant retrovirus or transduced cell: TCR alpha, CD3 zeta, IFN gamma, and PD-1; and in another embodiment SOCS 1, IFN gamma, TCR alpha, and CD3 zeta.

In illustrative embodiments of any of the methods and compositions provided herein, the recombinant retroviruses, mammalian cells, and/or packaging cells, can comprise a Vpx polypeptide. The Vpx polypeptide can be, for example, a fusion polypeptide, and in some examples, especially in packaging cells, a membrane bound Vpx polypeptide.

In any of the methods or compositions provided herein, the one or more pseudotyping elements can include a vesicular stomatitis virus (VSV-G) envelope protein, a feline endogenous virus (RD114) envelope protein, an oncoretroviral amphotropic envelope protein, or an oncoretroviral ecotropic envelope protein, or functional fragments thereof.

Provided herein in another aspect is a genetically modified T cell and/or NK cell comprising:
  a. a first engineered signaling polypeptide comprising a lymphoproliferative element; and
  b. a second engineered signaling polypeptide comprising a chimeric antigen receptor comprising an antigen-specific targeting region (ASTR), a transmembrane domain, and an intracellular activating domain.

In any of the methods provided herein that include a mammalian packaging cell, including a recombinant retrovirus packaging system aspect, or a method for making a recombinant retrovirus, for example, the packagable RNA genome is encoded by a polynucleotide operably linked to a promoter, wherein said promoter is either constitutively active or inducible by either the first transactivator or the second transactivator. The packagable RNA genome can be encoded by a polynucleotide operably linked to a promoter, wherein said promoter is inducible by the second transactivator. A promoter used herein to drive expression of the first and/or second engineered signaling polypeptide, is typically active in target cells, for example lymphocytes, PBLs, T-cells and/or NK cells, but in illustrative embodiments, is not active in the packaging cell line. The second transactivator can regulate the expression of an activation element capable of binding to and activating the target cell. I any of the methods provided herein that include a mammalian packaging cell, including a recombinant retrovirus packaging system aspect, or a method for making a recombinant retrovirus, for example, the packagable RNA genome in some embodiments, expression of the packagable RNA genome can be regulated can be regulated by the second transactivator.

Furthermore, the packagable RNA genome can comprise, from 5' to 3':
  1.) a 5' long terminal repeat, or active fragment thereof;
  2.) a nucleic acid sequence encoding a retroviral cis-acting RNA packaging element;
  3.) a nucleic acid sequence encoding a first target polypeptide;
  4.) a promoter that is active in the target cell; and
  5.) a 3' long terminal repeat, or active fragment thereof.

In some embodiments, the nucleic acid sequence encoding the first target polypeptide is in reverse orientation to an RNA encoding retroviral components for packaging and assembly.

In any of the methods provided herein that include a mammalian packaging cell, including a recombinant retrovirus packaging system aspect, or a method for making a recombinant retrovirus, for example, the first target polypeptide comprises a first engineered signaling polypeptide and wherein said first engineered signaling polypeptide comprises a lymphoproliferative element. The packagable RNA genome can further comprises a nucleic acid sequence encoding a second target polypeptide. The second target polypeptide can comprise a second engineered signaling polypeptide including a chimeric antigen receptor comprising:
  1.) a first antigen-specific targeting region;
  2.) a first transmembrane domain; and
  3.) a first intracellular activating domain.

In any of the methods provided herein that include a mammalian packaging cell, including a recombinant retrovirus packaging system aspect, or a method for making a recombinant retrovirus, for example, the mammalian cell, for example the packaging cell can include a nucleic acid sequence encoding Vpx, for example on the second or an optional third transcriptional unit, or on an additional transcriptional unit that is operably linked to the first inducible promoter. The mammalian cell, which can be a packaging cell, can be a 293 cell.

In any of the methods provided herein that include a mammalian packaging cell, including a recombinant retrovirus packaging system aspect, or a method for making a recombinant retrovirus, a first ligand can be rapamycin and a second ligand can be tetracycline or doxorubicin or the first ligand can be tetracycline or doxorubicin and the second ligand can be rapamycin.

In some aspects, provided herein is a cell that has been transduced with any of the recombinant retroviruses provided herein. The cell can be, for example, a lymphocyte, such as a T cell or NK cell. The cell in illustrative embodiments, is a human cell.

In one aspect provided herein, is a method of expanding modified T cells and/or NK cells in a subject, said method comprising:
  a.) contacting isolated resting T cells and/or resting NK cells obtained from said subject recombinant retrovirus of any of the embodiments disclosed herein;
  b.) introducing the genetically modified T cells and/or NK cells into the subject; and c.) providing an effective amount of acyclovir, an acyclovir prodrug, penciclovir, or a penciclovir prodrug to said subject, wherein said modified T cells and/or NK cells proliferate in said subject upon administration of acyclovir, an acyclovir prodrug, penciclovir, or a penciclovir prodrug, thereby expanding the modified T cells and/or NK cells in the subject.

In another aspect, provided herein is a method of stopping the expansion, engraftment, and; or persistence of modified T cells and/or NK cells in a subject, said method comprising:
a.) contacting isolated quiescent T cell and/or NK cells obtained from said subject with e recombinant retrovirus of any of the embodiments disclosed herein;
b.) introducing the modified T cell and/or NK cells into the subject;
c.) administering an effective amount of acyclovir, an acyclovir prodrug, penciclovir, or a penciclovir prodrug to said subject to expand the modified T cell and/or NK cells in the subject, wherein said modified T cell and/or NK cells proliferate in said subject upon administration of acyclovir, an acyclovir prodrug, penciclovir, or a penciclovir prodrug, thereby expanding the modified PBLs in the subject; and
d.) stopping administration of acyclovir, an acyclovir prodrug, penciclovir, or a penciclovir prodrug, wherein said modified. T cell and/or NK cells stop proliferating in said. subject upon stopping administration of acyclovir, an acyclovir prodrug, penciclovir, or a penciclovir prodrug, thereby controlling the expansion, expansion, and/or persistence of the modified T cell and/or NK cells in the subject.

In another aspect, provided herein is a method. of treating cancer in a subject, said method. comprising:
a. contacting isolated quiescent T cells and/or NK cells obtained from said subject with the recombinant vector according to any of the embodiments disclosed herein;
b. introducing the genetically modified T cells and/or NK cells into the subject; and
c. administering an effective amount of acyclovir, an acyclovir prodrug, penciclovir, or a penciclovir prodrug to said subject to expand the modified cell and/or NK cells in the subject, wherein said modified T cell and/or NK cells proliferate in said subject upon administration of acyclovir, an acyclovir prodrug, penciclovir, or a penciclovir prodrug, and wherein the chimeric antigen receptor in said modified T cell and/or NK cells binds cancer cells in said subject, thereby treating cancer in the subject.

In another aspect, provided herein is a transduced T cell and/or NK cell, comprising a recombinant polynucleotide comprising one or more transcriptional units operatively linked to a promoter active in T cells and/or NK cells, wherein the one or more transcriptional units encode a first engineered signaling polypeptide regulated by an in vivo control element, wherein said first engineered signaling polypeptide comprises a constitutively active IL-7 receptor mutant, and wherein the in vivo control element is capable of binding, and/or designed and/or configured to bind, to a compound in vivo.

In another aspect, provided herein is a retroviral packaging system, comprising:
a mammalian cell comprising:
A. a first transactivator expressed from a constitutive promoter and capable of binding a first ligand and a first inducible promoter for affecting expression of a nucleic acid sequence operably linked thereto in the presence versus absence of the first ligand;
B. a second transactivator capable of binding a second ligand and a second inducible promoter, and affecting expression of a nucleic acid sequence operably linked thereto in the presence versus absence of the second ligand; and
C. a packagable RNA genome for a retroviral particle, wherein the first transactivator regulates expression of the second transactivator and a retroviral REV protein, wherein the second transactivator regulates expression of a gag polypeptide, a pol polypeptide, and one or more pseudotyping elements capable of binding to a target cell and facilitating membrane fusion thereto, and wherein the retroviral proteins are derived from a retrovirus. Embodiments of this aspect, can include any of the embodiments provided herein for the recited elements in other aspects.

In another aspect, provided herein is a method for making a recombinant retrovirus, comprising:
A. culturing a population of packaging cells to accumulate a first transactivator, wherein the packaging cells comprise the first transactivator expressed from a first constitutive promoter, wherein the first transactivator is capable of binding a first ligand and a first inducible promoter for affecting expression of a nucleic acid sequence operably linked thereto in the presence versus absence of the first ligand, and wherein expression of a second transactivator and a retroviral REV protein is regulated by the first transactivator;
B. incubating the population of packaging cells comprising accumulated first transactivator in the presence of the first ligand to accumulate the second transactivator and the retroviral REV protein, wherein the second transactivator is capable of binding a second ligand and a second inducible promoter for affecting expression of a nucleic acid sequence operably linked thereto in the presence versus absence of the second ligand; and
C. incubating the population of packaging cells comprising accumulated second transactivator and retroviral REV protein in the presence of the second ligand thereby inducing expression of a gag polypeptide, a pol polypeptide, and one or more pseudotyping elements, thereby making the recombinant retrovirus,
wherein a packagable RNA genome is encoded by a polynucleotide operably linked to a third promoter, wherein said third promoter is either constitutively active or inducible by either the first transactivator or the second transactivator, and wherein the one or more pseudotyping elements are capable of binding to a target cell and/or facilitating membrane fusion of the recombinant retrovirus thereto.

In some embodiments of the retroviral packaging system and method for making a recombinant retrovirus aspects provided herein, the mammalian cell further comprises an activation element capable of binding to and activating a target cell, and the first transactivator regulates the expression of the activation element. The activation element is on the surface of the retrovirus and wherein the activation element can include: a membrane-bound polypeptide capable of binding to CD3; and/or a membrane-bound polypeptide capable of binding to CD28. The membrane-bound polypeptide capable of binding to CD3 is a polypeptide capable of binding to CD3 that is fused to a heterologous GPI anchor attachment sequence and the membrane-bound polypeptide capable of binding to CD28 is a polypeptide capable of binding to CD28 that is fused to a heterologous GPI anchor attachment sequence. The membrane-bound polypeptide capable of binding to CD28 in some embodiments comprises CD80, CD86, or a functional fragment thereof that is capable of inducing CD28-mediated activation of Akt, such as the extracellular domain of CD80. In other embodiments, membrane-bound polypeptide capable of binding CD3 is an anti-CD3 scFv bound to a CD14 GPI anchor attachment sequence, and wherein the membrane-bound polypeptide capable of binding to CD28 is CD80, or an extracellular fragment thereof, bound to a CD16B GPI anchor attachment sequence.

In some embodiments of the retroviral packaging system and method for making a recombinant retrovirus aspects provided herein, the mammalian cell further comprises a membrane-bound cytokine, and the first transactivator regulates the expression of the membrane-bound cytokine. The membrane-bound cytokine can be, for example, IL-7, IL-15, or an active fragment thereof. The membrane-bound cytokine in embodiments can be a fusion polypeptide of IL-7, or an active fragment thereof, and DAF. For example, the fusion polypeptide can comprise the DAF signal sequence and IL-7 without its signal sequence, followed by residues 36-525 of DAF.

In some embodiments of the retroviral packaging system and method for making a recombinant retrovirus aspects provided herein, the mammalian cell comprises associated with its membrane, an activation element comprising an anti-CD3 scFv bound to a CD14 GPI anchor attachment sequence and a CD80 bound, or an extracellular fragment thereof to a CD16B GPI anchor attachment sequence; and membrane-bound cytokine comprising a fusion polypeptide of IL-7, or an active fragment thereof, and DAF comprising a GPI anchor attachment sequence, and wherein the first transactivator regulates the expression of each of the activation element and membrane-bound cytokine. In some embodiments, the IL-7, or an active fragment thereof, and DAF fusion, the anti-CD3 scFV, and the CD80, or extracellular fragment thereof, each comprises a DAF signal sequence.

In some embodiments of the retroviral packaging system and method for making a recombinant retrovirus aspects provided herein, the mammalian cell further comprises a Vpx polypeptide. In these or other embodiments, the one or more pseudotyping elements comprise one or more viral polypeptides recognized by T cells. The one or more pseudotyping elements can comprise a Measles Virus F polypeptide, a Measles Virus H polypeptide, and/or a fragment thereof. In certain illustrative embodiments, the one or more pseudotyping elements are cytoplasmic domain deletion variants of a measles virus F polypeptide and/or a measles virus H polypeptide.

In some embodiments of the retroviral packaging system and method for making a recombinant retrovirus aspects provided herein, the packagable RNA genome is encoded by a polynucleotide operably linked to a third promoter, wherein said third promoter is either constitutively active or inducible by either the first transactivator or the second transactivator. In illustrative embodiments, the packagable RNA genome is encoded by a polynucleotide operably linked to a third promoter, wherein said third promoter is inducible by the second transactivator.

In some embodiments of the retroviral packaging system and method for making a recombinant retrovirus aspects provided herein, the packagable RNA genome further comprises, from 5' to 3':
  a) a 5' long terminal repeat, or active fragment thereof;
  b) a nucleic acid sequence encoding a retroviral cis-acting RNA packaging element;
  c) a nucleic acid sequence encoding a first target polypeptide and an optional second target polypeptide;
  d) a fourth promoter operably linked to the first target polypeptide and the optional second polypeptide, wherein said fourth promoter is active in the target cell but not active in the packaging cell line; and
  e) a 3' long terminal repeat, or active fragment thereof.

In some embodiments of the retroviral packaging system and method for making a recombinant retrovirus aspects provided herein including the construct immediately above, the third promoter promotes transcription or expression in the opposite direction from transcription or expression promoted from the fourth promoter.

In some embodiments of the retroviral packaging system and method for making a recombinant retrovirus aspects provided herein, the packagable RNA genome encodes the recombinant retrovirus of any embodiment disclosed in this disclosure, wherein the first target polypeptide and the second target polypeptide are the first engineered signaling polypeptide and the second engineered signaling polypeptide, respectively. In some embodiments, for example, the packagable RNA genome further comprises an in vivo control element operably linked to the nucleic acid encoding the first engineered signaling polypeptide or the second engineered signaling polypeptide. The in vivo control element in illustrative embodiments is a riboswitch. The riboswitch in illustrative embodiments is capable of binding a compound and the compound that binds the in vivo control element is a nucleoside analog, and the nucleoside analog can be an antiviral drug, for example acyclovir or penciclivir.

In some embodiments of the retroviral packaging system and method for making a recombinant retrovirus aspects provided herein, the packagable RNA genome further comprises an intron comprising a polynucleotide encoding an miRNA or shRNA. The intron can be adjacent to and downstream of the fourth promoter.

In some embodiments of the retroviral packaging system and method for making a recombinant retrovirus aspects provided herein, the target cell can be a T cell and/or an NK cell.

In some embodiments of the retroviral packaging system and method for making a recombinant retrovirus aspects provided herein, the one or more pseudotyping elements comprise a vesicular stomatitis virus (VSV-G) envelope protein, a feline endogenous virus (RD114) envelope protein, an oncoretroviral amphotropic envelope protein, or an oncoretroviral ecotropic envelope protein, or functional fragments thereof.

In some embodiments of the retroviral packaging system and method for making a recombinant retrovirus aspects provided herein, the packagable RNA genome is 11,000 KB or less or 10,000 KB or less in size. In some embodiments of the retroviral packaging system and method for making a recombinant retrovirus aspects provided herein, the first target polypeptide comprises a first engineered signaling polypeptide and wherein said first engineered signaling polypeptide comprises a lymphoproliferative element, and the second target polypeptide comprises a second engineered signaling polypeptide including a CAR.

In one aspect, provided herein is an isolated polynucleotide for regulating expression of a target polynucleotide, comprising:
  a polynucleotide encoding a target polynucleotide operably linked to a promoter and a riboswitch, wherein the riboswitch comprises:
    a.) an aptamer domain capable of binding a nucleoside analogue antiviral drug and having reduced binding to guanine or 2'-deoxyguanosine relative to the nucleoside analogue antiviral drug; and b.) a function switching domain capable of regulating expression of the target polynucleotide, wherein binding of the nucleoside analogue by the aptamer domain induces or suppresses the expression regulating activity of the function switching domain, thereby regulating expression of the target polynucleotide.

In illustrative embodiments of any of the methods and compositions provided herein that include the in vivo control element can be a polynucleotide comprising a riboswitch. The riboswitch can be capable of binding a nucleoside analog and the compound that binds the in vivo control element is the nucleoside analog. The nucleoside analog can be an antiviral agent. The antiviral agent can be acyclovir or penciclovir. The riboswitch can preferentially bind acyclovir over penciclovir or preferentially bind penciclovir over acyclovir. The riboswitch can have reduced binding to the nucleoside analogue antiviral drug at temperatures above 37° C., 37.5° C., 38° C., 38.5° C., or 39° C., for example, above 39° C. The riboswitch can be between 35, 40, 45, and 50 nucleotides in length on the low end of the range and 60, 65, 70, 75, 80, 85, 90, 95, and 100 nucleotides in length on the high end of the range, for example, between 45 and 80 nucleotides in length. In illustrative embodiments of any of the methods and compositions provided herein that include the riboswitch, the target polynucleotide that is regulated by the riboswitch can include a region encoding a miRNA, an shRNA, and/or a polypeptide. The target polynucleotide can encode a lymphoproliferative element. The target polynucleotide can be operably linked to a promoter. The target polynucleotide can include a region encoding a polypeptide and the polypeptide can include a chimeric antigen receptor comprising an antigen-specific targeting region, a transmembrane domain, and an intracellular activating domain. In illustrative embodiments of any of the methods and compositions provided herein that include the riboswitch, the function switching domain can regulate an internal ribosome entry site, pre-mRNA splice donor accessibility in the viral gene construct, translation, termination of transcription, transcript degradation, miRNA expression, or shRNA expression, thereby regulating expression of the target polynucleotide. The riboswitch can include a ribozyme. In illustrative embodiments of any of the methods and compositions provided herein that include the riboswitch, the isolated polynucleotide can be a molecular cloning vector or an expression vector. In illustrative embodiments of any of the methods and compositions provided herein that include the riboswitch, the isolated polynucleotide can be integrated into a retroviral genome or into a mammalian chromosome, or fragment thereof.

Another aspect provided herein, is a method for genetically modifying and expanding lymphocytes of a subject, comprising:

A. collecting blood from the subject;
B. contacting T cells and/or NK cells from the blood of the subject ex vivo with recombinant retroviruses comprising:
   i. a pseudotyping element on its surface that is capable of binding to a T cell and/or NK cell and facilitating membrane fusion of the recombinant retrovirus thereto, wherein said pseudotyping element comprises cytoplasmic domain deletion variants of a measles virus F polypeptide and/or a measles virus H polypeptide;
   ii. a polypeptide capable of binding to CD3 and a polypeptide capable of binding to CD28, wherein said polypeptides are expressed on the surface of a recombinant retrovirus and are capable of binding to a T cell and/or a NK cell and further wherein said polypeptides are not encoded by a polynucleotide in the recombinant retrovirus; and
   iii. a polynucleotide comprising one or more transcriptional units operatively linked to a promoter active in T cells and/or NK cells, wherein the one or more transcriptional units encode a first engineered signaling polypeptide comprising a constitutively active IL-7 receptor mutant and a second engineered signaling polypeptide comprising a chimeric antigen receptor comprising an antigen-specific targeting region (ASTR), a transmembrane domain, and an intracellular activating domain, wherein expression of the IL-7 receptor mutant is regulated by a riboswitch that binds a nucleoside analog antiviral drug, wherein binding of the nucleoside analog antiviral drug to the riboswitch increases expression of the IL-7 receptor mutant, and wherein said contacting results in at least some of the resting T cells and/or NK cells becoming genetically modified;
C. reintroducing the genetically modified T cells and/or NK cells into the subject; and
D. exposing the genetically modified T cells and/or NK cells in vivo to the nucleoside analog antiviral drug to promote expansion of the T cells and/or NK cells, wherein the method between the collecting blood and the reintroducing the genetically modified T cells and/or NK cells is performed in no more than 24 hours and/or without requiring prior ex vivo stimulation, thereby genetically modifying and expanding lymphocytes of the subject.

In illustrative embodiments of this method aspect, the retrovirus is a lentivirus. In another illustrative embodiment, the recombinant retrovirus genetically modifies a T cell. In another illustrative embodiment, the polypeptide capable of binding to CD3 and the polypeptide capable of binding to CD28 are each fused to a heterologous GPI anchor attachment sequence. In some instances, the polypeptide capable of binding to CD3 can be anti-CD3 scFvFc or anti-CD3 scFv, and the polypeptide capable of binding to CD28 can be CD80. The anti-CD3 scFvFc or anti-CD3 scFv and CD80 can each be further fused to a DAF signal sequence. In another illustrative embodiment, the recombinant retroviruses further comprise on their surface a fusion polypeptide comprising a cytokine covalently attached to DAF. In some instances, the cytokine can be IL-7 or IL-15, and the fusion polypeptide can comprise the DAF signal sequence, IL-7 without its signal sequence, and a fragment of DAF comprising a GPI anchor attachment sequence.

In another illustrative embodiment of this method aspect immediately above, the riboswitch further controls expression of the chimeric antigen receptor in a manner regulated by binding of the riboswitch to the nucleoside analog antiviral drug, which in some instances is acyclovir and/or penciclovir. In another embodiment, the constitutively active IL-7 can be replaced with a miRNA or shRNA. In some instances, the miRNA or shRNA can be encoded by nucleic acids within an intron.

Another aspect provided herein is a recombinant retrovirus, comprising:

A. a pseudotyping element on its surface that is capable of binding to a T cell and/or NK cell and facilitating membrane fusion of the recombinant retrovirus thereto, wherein said pseudotyping element comprises cytoplasmic domain deletion variants of a measles virus F polypeptide and/or a measles virus H polypeptide;

B. a polynucleotide comprising one or more transcriptional units operatively linked to a promoter active in T cells and/or NK cells, wherein the one or more transcriptional units encode a first engineered signaling polypeptide comprising a chimeric antigen receptor comprising an antigen-specific targeting region, a transmembrane domain, and an intracellular activating domain, and a second engineered signaling polypeptide comprising a constitutively active IL-7 receptor mutant; wherein expression of the IL-7 receptor mutant is regulated by a riboswitch that binds a nucleoside analog antiviral drug, wherein binding of the nucleoside analog antiviral drug to the riboswitch increases expression of the IL-7 receptor mutant; and C. a polypeptide capable of binding to CD3 and a polypeptide capable of binding to CD28, wherein said polypeptides are expressed on the surface of a recombinant retrovirus; are capable of binding to a T cell and/or NK cell; and are not encoded by a polynucleotide in the recombinant retrovirus.

In illustrative embodiments of the recombinant retrovirus aspect immediately above, the retrovirus is a lentivirus. In other illustrative embodiments of the method, the polypeptide capable of binding to CD3 and the polypeptide capable of binding to CD28 are each fused to a heterologous GPI anchor attachment sequence. In some instances, the polypeptide capable of binding to CD3 can be anti-CD3 scFvFc or anti-CD3 scFv, and the polypeptide capable of binding to CD28 can be CD80. The anti-CD3 scFvFc or anti-CD3 scFv and CD80 can each be further fused to a DAF signal sequence. In another illustrative embodiment, the recombinant retroviruses further comprise on their surface a fusion polypeptide comprising a cytokine covalently attached to DAF. In some instances, the cytokine can be IL-7 or IL-15, and the fusion polypeptide can comprise the DAF signal sequence, IL-7 without its signal sequence, and a fragment of DAF comprising a GPI anchor attachment sequence.

In another illustrative embodiment of the recombinant retrovirus aspect immediately above, the riboswitch further controls expression of the chimeric antigen receptor in a manner regulated by binding of the riboswitch to the nucleoside analog antiviral drug, which in some instances is acyclovir and/or penciclovir. In another embodiment, the constitutively active IL-7 can be replaced with a miRNA or shRNA. The miRNA or shRNA can be encoded by nucleic acids within an intron.

Another aspect provided herein is a method for making a recombinant retrovirus, comprising:

A. culturing a population of packaging cells to accumulate a first transactivator, wherein the packaging cells comprise the first transactivator expressed from a constitutive promoter, wherein the first transactivator is capable of binding a first ligand and a first inducible promoter for affecting expression of a nucleic acid sequence operably linked thereto in the presence versus absence of the first ligand, and wherein expression of a second transactivator and a retroviral REV protein is regulated by the first transactivator;

B. incubating the population of packaging cells comprising accumulated first transactivator in the presence of the first ligand to accumulate the second transactivator and the retroviral REV protein and an activation element typically on their surface, comprising a polypeptide capable of binding to CD3 and a polypeptide capable of binding to CD28, wherein the second transactivator is capable of binding a second ligand and a second inducible promoter for affecting expression of a nucleic acid sequence operably linked thereto in the presence versus absence of the second ligand; and C. incubating the population of packaging cells comprising accumulated second transactivator and retroviral REV protein in the presence of the second ligand thereby inducing expression of a gag polypeptide, a pol polypeptide and a pseudotyping element capable of binding to a T cell and/or an NK cell and facilitating membrane fusion of the recombinant retrovirus thereto, wherein said pseudotyping element comprises cytoplasmic domain deletion variants of a measles virus F polypeptide and/or a measles virus H polypeptide, wherein a packagable RNA genome is encoded by a polynucleotide operably linked to a third promoter and wherein said promoter is inducible by the second transactivator, wherein the packagable RNA genome comprises, from 5' to 3':

i. a 5' long terminal repeat, or active fragment thereof;
  ii. a nucleic acid sequence encoding a retroviral cis-acting RNA packaging element;
  iii. a nucleic acid sequence encoding a first engineered signaling polypeptide comprising a chimeric antigen receptor and a second engineered signaling polypeptide comprising a constitutively active IL-7 receptor mutant separated by a cleavage signal;
  iv. a fourth promoter that is active in the T cell and/or the NK cell; and
  v. a 3' long terminal repeat, or active fragment thereof, and wherein the packagable RNA genome further comprises a riboswitch that binds a nucleoside analog antiviral drug, wherein binding of the riboswitch to the nucleoside analog antiviral drug to the riboswitch increases expression of the IL-7 receptor mutant, thereby making the recombinant retrovirus.

In an illustrative embodiment of the method, the riboswitch further controls expression of the chimeric antigen receptor in a manner regulated by binding of the riboswitch to the nucleoside analog antiviral drug. In another illustrative embodiment, the nucleoside analog antiviral drug is acyclovir and/or penciclovir. In another illustrative embodiment, the packagable RNA genome further comprises a recognition domain, wherein the recognition domain comprises a polypeptide that is recognized by an antibody that recognizes EGFR or an epitope thereof. In another illustrative embodiment, the first ligand is rapamycin and the second ligand is tetracycline or doxorubicin or the first ligand is tetracycline or doxorubicin and the second ligand is rapamycin. In another illustrative embodiment, the packaging cell further comprises a nucleic acid sequence encoding Vpx on the second or an optional third transcriptional unit, or on an additional transcriptional unit that is operably linked to the first inducible promoter. In another illustrative embodiment, the polypeptide capable of binding to CD3 and the polypeptide capable of binding to CD28 are each fused to a heterologous GPI anchor attachment sequence. In some instances, the polypeptide capable of binding to CD3 can be anti-CD3 scFvFc or anti-CD3 scFv, or anti-CD3 scFv, and the polypeptide capable of binding to CD28 can be CD80. The anti-CD3 scFvFc or anti-CD3 scFv and CD80 can each be further fused to a DAF signal sequence. In another illustrative embodiment, expression of a fusion polypeptide comprising a cytokine covalently attached to DAF is also induced. In some instances, the cytokine can be IL-7 or IL-15, and the fusion polypeptide can comprise the DAF signal sequence, IL-7 without its signal sequence, and a fragment of DAF comprising a GPI anchor attachment sequence. In another illustrative embodiment, the riboswitch further controls expression of the chimeric antigen receptor in a manner regulated by binding of the riboswitch to the nucleoside analog antiviral drug, which in some instances is acyclovir and/or penciclovir. In another embodiment, the constitutively active IL-7 can be replaced with a miRNA or shRNA. The miRNA or shRNA can be encoded by nucleic acids within an intron. In an illustrative embodiment, the retrovirus that is made is a lentivirus.

Provided in another aspect herein is a genetically modified lymphocyte comprising:
A. a first engineered signaling polypeptide comprising a constitutively active IL-7 receptor mutant; and
B. a second engineered signaling polypeptide comprising a chimeric antigen receptor comprising an antigen-specific targeting region (ASTR), a transmembrane domain, and an intracellular activating domain.

In illustrative embodiments of the genetically modified lymphocyte aspect above, the genetically modified lymphocyte is a T cell and/or an NK cell. In certain embodiments, the lymphocyte is a T cell. In another illustrative embodiment, expression of said first engineered signaling polypeptide and/or said second engineered signaling polypeptide is regulated by a riboswitch that binds a nucleoside analog antiviral drug, wherein binding of the nucleoside analog antiviral drug to the riboswitch increases expression of the IL-7 receptor mutant. In another embodiment, the constitutively active IL-7 receptor may be replaced with a miRNA or an shRNA. The miRNA or shRNA can further be encoded by nucleic acids within an intron.

Provided in another aspect herein is a genetically modified T cell and/or NK cell comprising:
a. a first engineered signaling polypeptide comprising a lymphoproliferative element; and
b. a second engineered signaling polypeptide comprising a chimeric antigen receptor comprising an antigen-specific targeting region (ASTR), a transmembrane domain, and an intracellular activating domain.

In illustrative embodiments of the genetically modified T cell and/or NK cell aspect, the lymphoproliferative element is constitutively active, and in some instances, is a constitutively active mutated IL-7 receptor or a fragment thereof. In another illustrative embodiment, expression of the first engineered signaling polypeptide and/or the second engineered signaling polypeptide is regulated by an in vivo control element. In some instances, the in vivo control element is a polynucleotide comprising a riboswitch. In some instances, the riboswitch is capable of binding a nucleoside analog and when the nucleoside analog is present, the first engineered signaling polypeptide and/or the second engineered polypeptide are expressed. In other illustrative embodiments, the genetically modified T cell and/or NK cell has on its surface an activation element, a pseudotyping element, and/or a membrane-bound cytokine. In some instances, the activation element comprises a membrane-bound polypeptide capable of binding to CD3; and/or a membrane-bound polypeptide capable of binding to CD28. In a certain embodiment, the activation element comprises anti-CD3 scFv fused to a heterologous GPI anchor attachment sequence and/or CD80 fused to a heterologous GPI anchor attachment sequence. In an illustrative embodiment, the pseudotyping element comprises a Measles Virus F polypeptide, a Measles Virus H polypeptide, and/or cytoplasmic domain deletion variants of a measles virus F polypeptide and/or a measles virus H polypeptide. In other embodiments, the membrane-bound cytokine is a fusion polypeptide comprising IL-7, or a fragment thereof, fused to DAF, or a fragment thereof comprising a GPI anchor attachment sequence.

In one aspect, provided herein is a method for genetically modifying and expanding lymphocytes of a subject, comprising:
A. contacting resting T cells and/or NK cells of the subject ex vivo, typically without requiring prior ex vivo stimulation, with recombinant retroviruses comprising:
  i. a pseudotyping element on its surface that is capable of binding to a T cell and/or NK cell and facilitating membrane fusion of the recombinant retrovirus thereto; and
  ii. a polynucleotide comprising one or more transcriptional units operatively linked to a promoter active in T cells and/or NK cells, wherein the one or more transcriptional units encode a first engineered signaling polypeptide regulated by an in vivo control element, wherein said first engineered signaling polypeptide comprises a lymphoproliferative element and optionally encode a second engineered signaling polypeptide optionally regulated by an in vivo control element, wherein the second engineered signaling polypeptide comprises an intracellular activating domain and optionally other components of a CAR,
  wherein said contacting facilitates transduction of at least some of the resting T cells and/or NK cells by the recombinant retroviruses, thereby producing genetically modified T cells and/or NK cells;
B. introducing the genetically modified T cells and/or NK cells into the subject; and
exposing the genetically modified T cells and/or NK cells in vivo to a compound that acts as the in vivo control element to affect expression of the first engineered signaling polypeptide and promote expansion, engraftment, and/or persistence of the lymphocytes in vivo, thereby genetically modifying and expanding lymphocytes of the subject.

In illustrative embodiments, the transduction is carried out without ex vivo stimulation. In illustrative embodiments, the compound is a molecular chaperone, such as a small molecular chaperone. In illustrative embodiments, binding of the molecular chaperone to the lymphoproliferative element increases the proliferative activity of the lymphoproliferative element. The molecular chaperone can be administered to the subject before the blood is collected, during the contacting, and/or after the T cells and/or NK cells are introduced into the subject. It will be understood with this aspect where the compound is the in vivo control element, that such compound typically is capable of binding to a lymphoproliferative element and/or a component of a CAR, and does bind to such lymphoproliferative element or car component during performance of the method. Other embodiments and teaches related to methods provided herein that include transfecting a T cell and/or an NK cell with a recombinant retrovirus, apply to this aspect, including a molecular chaperone embodiment, as well.

In another aspect, provided herein is a method for selecting a microenvironment restricted antigen-specific targeting region, comprising panning a polypeptide display library by:
a. subjecting polypeptides of the polypeptide display library to a binding assay under a normal physiological condition and a binding assay under an aberrant condition; and
b. selecting a polypeptide which exhibits an increase in binding activity at the aberrant condition compared to the physiological condition, thereby selecting the microenvironment restricted antigen specific targeting region.

In another aspect, provided herein is a method for isolating a microenvironment restricted antigen-specific targeting region, comprising:
panning a polypeptide library by:
  a) contacting the polypeptide library under aberrant conditions with a target antigen bound to a solid support, wherein clones expressing polypeptides that bind the target antigen remain bound to the solid support through the target antigen;
  b) incubating the solid supports with bound polypeptides under physiological conditions; and
  c) collecting clones that elute from the solid support under the physiological conditions, thereby isolating the microenvironment restricted antigen-specific targeting region.

In another aspect, provided herein is a chimeric antigen receptor for binding a target antigen, comprising:
  a) at least one microenvironment restricted antigen specific targeting region selected by panning a polypeptide library and having an increase in activity in a binding assay at an aberrant condition compared to a normal physiological condition;
  b) a transmembrane domain; and
  c). an intracellular activating domain.

In another aspect, provided herein is a chimeric antigen receptor for binding a target antigen, comprising:
  a) a microenvironment restricted antigen-specific targeting region that exhibits an increase in binding to the target antigen in an aberrant condition compared to a normal physiological environment, wherein the antigen-specific targeting region binds to the target;
  b) a transmembrane domain; and
  c) an intracellular activating domain.

In illustrative embodiments of any of the methods and compositions provided herein that include a microenvironment restricted antigen specific targeting region (ASTR), the ASTR can have at least a 5%, 10%, 15%, 20%, 25%, 30%, 40%, 50%, 60%, 70%, 80%, 90%, or 100% increase in binding affinity to the target antigen in the assay at the aberrant condition compared to the normal condition. The aberrant conditions can be hypoxia, an acidic pH, a higher concentration of lactic acid, a higher concentration of hyaluronan, a higher concentration of albumin, a higher concentration of adenosine, a higher concentration of R-2-hydroxyglutarate, a higher concentration of PAD enzymes, a higher pressure, a higher oxidation, and a lower nutrient availability. The microenvironment restricted ASTR can exhibit an increase in antigen binding at a pH of 6.7 as compared to a pH of 7.4. The microenvironment restricted ASTR can exhibit an increase in antigen binding in a tumor environment and/or in an in vitro tumor surrogate assay condition, relative to a corresponding physiologcal condition. The target can be 4-1BB,ST4, adenocarcinoma antigen, alpha-fetoprotein, AXL, BAFF, B-lymphoma cell, C242 antigen, CA-125, carbonic anhydrase 9 (CA-IX), C-MET, CCR4, CD 152, CD 19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin nSP1, integrin nvP3, MORAb-009, MS4A1, MUC1, mucin CanAg, Nglycolylneuraminic acid, NPC-1C, PDGF-R a, PDL192, phosphatidylserine, prostatic carcinoma cells, RANKL, RON, ROR1, ROR2 SCH 900105, SDC1, SLAMF7, TAG-72, tenascin C, TGF beta 2, TGF-P, TRAIL-R1, TRAIL-R2, tumor antigen CTAA16. 88, VEGF-A, VEGFR-1, VEGFR2, and vimentin. The ASTR can be an antibody, an antigen, a ligand, a receptor binding domain of a ligand, a receptor, a ligand binding domain of a receptor, or an affibody. The ASTR can be a full-length antibody, a single-chain antibody, an Fab fragment, an Fab' fragment, an (Fab')$_2$ fragment, an Fv fragment, and a divalent single-chain antibody or a diabody. The ASTR can include a heavy chain and a light chain from an antibody. The antibody can be a single-chain variable fragment. In some embodiments, the heavy and light chains can be separated by a linker, wherein the linker is between 6 and 100 amino acids in length. In some embodiments, the heavy chain can be positioned N-terminal to the light chain on the chimeric antigen receptor and in some embodiments the light chain can be positioned N-terminal to the heavy chain on the chimeric antigen receptor.

In illustrative embodiments of any of the methods that include a polypeptide display library, the polypeptide display library can be a phage display library or a yeast display library. The polypeptide display library can be an antibody display library. The antibody display library can be a human or humanized antibody display library. The antibody display library can be a naïve library. The methods can include infecting bacterial cells with the collected phage to generate a refined phage display library, and repeating the contacting, incubating, and collecting for 1 to 1000 cycles, using the refined phage display library generated from a previous cycle.

In illustrative embodiments of any of the methods provided herein that include isolating or selecting a microenvironment restricted ASTR, the method can include determining the nucleotide sequence of a polynucleotide encoding the microenvironment restricted antigen-specific targeting region, thereby determining the polypeptide sequence of the microenvironment restricted ASTR. The methods can include making a microenvironment restricted biologic chimeric antigen receptor by generating a polynucleotide that encodes a polypeptide comprising the microenvironment restricted ASTR, a transmembrane domain, and an intracellular activating domain. The library can be a single chain antibody library.

The methods for isolating a microenvironment restricted ASTR can include the panning is repeated for between 1 and 1000 times. The methods for isolating a microenvironment restricted ASTR can be performed without mutating polynucleotides encoding the isolated microenvironment restricted antigen-specific targeting region between rounds of panning. The methods for isolating a microenvironment restricted ASTR can be performed by culturing, high fidelity amplifying, and/or diluting polynucleotides encoding antigen-specific targeting regions, or host organisms including the same, between rounds of panning. The methods can include, prior to repeating, mutagenizing the selected and/or isolated microenvironment restricted antigen-specific targeting region. The methods can include determining the sequence of the selected and/or isolated microenvironment restricted antigen-specific targeting region, and/or a polynucleotide encoding the same after one or more round of panning via long read DNA sequencing. The methods can include determining the sequence before and after expansion of the isolated microenvironment restricted ASTR. The methods for isolating a microenvironment restricted ASTR can be performed without repeating the panning. The methods for isolating a microenvironment restricted ASTR can be performed without mutating a polynucleotide encoding the isolated microenvironment restricted ASTR after the microenvironment restricted ASTR is isolated.

In illustrative embodiments of any of the compositions provided herein that include a chimeric antigen receptor with a microenvironment restricted ASTR, the microenvironment restricted ASTR can be identified by panning an antibody library. In some embodiments, the microenvironment restricted ASTR is identified by panning a phage display or a yeast display library. In some embodiments, the chimeric antigen receptor comprises a bispecific ASTR.

Provided herein in another aspect is a transduced T cell and/or NK cell, comprising a recombinant polynucleotide comprising one or more transcriptional units operatively linked to a promoter active in T cells and/or NK cells, wherein the one or more transcriptional units encode a first engineered signaling polypeptide regulated by an in vivo control element, wherein said first engineered signaling polypeptide comprises a constitutively active IL-7 receptor mutant, and wherein the in vivo control element is capable of binding to a compound in vivo or is configured to bind a compound in vivo.

Provided herein in another aspect is a recombinant retrovirus, comprising a recombinant polynucleotide comprising one or more transcriptional units operatively linked to a promoter active in T cells and/or NK cells, wherein the one or more transcriptional units encode a first engineered signaling polypeptide regulated by an in vivo control element, wherein said first engineered signaling polypeptide comprises a constitutively active IL-7 receptor mutant, and wherein the in vivo control element is capable of binding to a compound in vivo or is configured to bind a compound in vivo.

Provided herein in another aspect is a method of transducing a T cell and/or NK cell, comprising contacting a T cell and/or NK cell, with a recombinant retrovirus comprising a recombinant polynucleotide comprising one or more transcriptional units operatively linked to a promoter active in T cells and/or NK cells, wherein the one or more transcriptional units encode a first engineered signaling polypeptide regulated by an in vivo control element, wherein said first engineered signaling polypeptide comprises a constitutively active IL-7 receptor mutant, and wherein the in vivo control element is capable of binding to a compound in vivo, under transduction conditions, thereby transducing the T cell and/or NK cell.

In illustrative embodiments of the transduced T cell and/or NK cell aspects, the recombinant retrovirus aspects, and the method aspects, provided in the preceding paragraphs, the recombinant polynucleotide further comprises a transcriptional unit that encodes a second engineered signaling polypeptide comprising a first chimeric antigen receptor comprising an antigen-specific targeting region (ASTR), a transmembrane domain, and an intracellular activating domain. In other illustrative embodiments, the lymphoproliferative element comprises a mutated IL-7 receptor or a fragment thereof. In other illustrative embodiments, the in vivo control element is a polynucleotide comprising a riboswitch. In some instances, the riboswitch is capable of binding a nucleoside analog and the compound that binds the in vivo control element is the nucleoside analog. In some instances, the nucleoside analog is an antiviral agent such as for example acyclovir or penciclovir. In certain embodiments, the antiviral agent is acyclovir. In other illustrative embodiments, the constitutively active IL-7 receptor mutant is fused to EGFR or an epitope thereof. In other illustrative embodiments, the constitutively active IL-7 receptor mutant comprises an eTag. In other illustrative embodiments, the constitutively active IL-7 receptor mutant comprises a PPCL insertion. In other illustrative embodiments, the constitutively active IL-7 receptor mutant comprises a PPCL insertion at a position equivalent to position 243 in a wild-type human IL-8 receptor. In other illustrative embodiments, the transduced T cell or NK cell is a transduced T cell.

BRIEF DESCRIPTION OF THE DRAWINGS

FIG. 1 shows a schematic of illustrative compositions including a packaging cell (100) and a recombinant retrovirus (200) produced by the packaging cell (100). In FIG. 1, various vectors (referred to as recombinant polynucleotides (110)) capable of encoding aspects of the invention are packaged into a recombinant retrovirus (200) that includes in its genome a first engineered signaling polypeptide that includes a lymphoproliferative element and in some embodiments, a second engineered signaling polypeptide that is a chimeric antigen receptor, or a CAR. The recombinant retrovirus expresses on its membrane, a pseudotyping element (in a non-limiting embodiment, a Measles Virus hemagglutinin (H) polypeptide and a Measles Virus fusion (F) polypeptide, or cytoplasmic domain deletion variants thereof (240) that allows the retrovirus to bind to and fuse with a target cell; an activation element (in non-limiting embodiments an activation element that has a polypeptide capable of binding to CD28 and a polypeptide capable of binding to CD3) (210 and 220, respectively) that is capable of binding to and activating a resting T cell; and a membrane-bound cytokine (in a non-limiting embodiment, and IL-7 DAF fusion polypeptide) (230). Parts labeled as (250), (260), (270), (280), and (290) are the Src-FLAG-Vpx, HIV gag matrix, HIV gag capsid, RNA, and HIV pol, respectively.

FIG. 2 shows a schematic of illustrative compositions including a recombinant retrovirus produced by a packaging cell (200) and a resting T cell (300) transfected by the recombinant retrovirus (200). The elements on the surface of the retrovirus bind to receptors and/or ligands on the surface of a resting T cell. The pseudotyping element can include a binding polypeptide and a fusogenic polypeptide (in non-limiting embodiments, a Measles Virus hemagglutinin (H) polypeptide and a Measles Virus fusion (F) polypeptide, or cytoplasmic domain deletion variants thereof) that facilitate the binding and fusion of the retrovirus to the T cell. In non-limiting embodiments, the retrovirus includes on its surface an activation element (in non-limiting embodiments an activation element that has a polypeptide capable of binding to CD28 and a polypeptide capable of binding to CD3) that is capable of activating the resting T cell by engaging the T-cell receptor complex and optionally a co-receptor (320). Furthermore, membrane-bound cytokines (in non-limiting embodiments, an IL-7 DAF fusion polypeptide) present on the surface of the retrovirus bind to IL-7Rα (310) on the surface of the resting T cell. The retrovirus fuses with the T cell, and polynucleotides that encode the first engineered signaling polypeptide that includes the lymphoproliferative element (in illustrative embodiments, a constitutively active IL-7Rα)_(370), are reverse transcribed in the cytosol prior to migrating to the nucleus to be incorporated into the DNA of the activated T cell. In some embodiments, Src-FLAG-Vpx (250) packaged with the virus enters the cytosol of the resting T cells and promotes the degradation of SAMHD1 (350), resulting in an increased pool of cytoplasmic dNTPs available for reverse transcription. In some embodiments, the polynucleotides can also encode a second engineered signaling polypeptide that includes a CAR (360). In some embodiments, the lymphoproliferative element is expressed when a compound binds to an in vivo control element that regulates its expression (in non-limiting example, the in vivo control element is a riboswitch that binds a nucleoside analog). In some embodiments, expression of the CAR is also regulated by the in vivo control element. Part (330) is SLAM and CD46. Part (340) is CD3.

FIGS. 3A-3E show schematics of vector systems. FIG. 3A shows a construct containing a polynucleotide sequence encoding an FRB domain fused to the NFκB p65 activator domain (p65 AD) and ZFHD1 DNA binding domain fused to three FKBP repeats that is constitutively expressed. The construct in FIG. 3A also includes HIV1 REV and Vpx as a SrcFlagVpx fusion under the rapamycin-inducible ZFHD1/p65 AD promoter. FIG. 3B shows a construct containing a polynucleotide encoding an rtTA sequence under the control of the ZFHD1/p65 AD promoter. FIG. 3C shows a construct containing a polynucleotide encoding a puromycin resistance gene flanked by loxP sites and the extracellular MYC tag flanked by lox2272 sites. Both selectable markers are under the control of a BiTRE promoter, which is flanked by FRT sites. FIG. 3D shows a construct that contains a polynucleotide encoding RFP flanked by loxP sites that is under the control of a TRE promoter and a single FRT site between the TRE promoter and the 5' loxP site of RFP. FIG. 3E shows a construct containing a polynucleotide encoding GFP flanked by loxP sites that is under the control of the TRE promoter and a single FRT site between the TRE promoter and the 5' loxP site of GFP. The constructs in FIGS. 3C-3E function as landing pads for other polynucleotide sequences to insert into the genome of the packaging cell line.

FIGS. 4A-4C show schematics of constructs. FIG. 4A shows a construct containing a tricistronic polynucleotide encoding anti-CD3 (clone UCHT1) scFvFc with a CD14 GPI anchor attachment site, CD80 extra cellular domain (ECD) capable of binding CD28, with a CD16B GPI anchor attachment site, and IL-7 fused to decay-accelerating factor (DAF) with transposon sequences flanking the polynucleotide region for integration into the HEK293S genome. FIG. 4B shows a construct containing a polynucleotide with a BiTRE promoter and a polynucleotide region encoding the gag and pol polypeptides in one direction and a polynucleotide region encoding the measles virus FΔx and HΔy proteins in the other direction. FIG. 4C shows a construct containing a polynucleotide sequence encoding a CAR and the lymphoproliferative element IL7Rα-insPPCL under the control of a CD3Z promoter which is not active in HEK293S cells, wherein the CAR and IL7Rα-insPPCL are separated by a polynucleotide sequence encoding a T2A ribosomal skip sequence and the IL7Rα-insPPCL has an acyclovir riboswitch controlled ribozyme. The CAR-containing construct further includes cPPT/CTS, an RRE sequence, and a polynucleotide sequence encoding HIV-1 Psi (ψ). The entire polynucleotide sequence on the CAR-containing construct to be integrated into the genome is flanked by FRT sites.

FIG. 6 represents the *Mesoplasma forum* type I-A deoxyguanosine riboswitch regulatory region and associated gene product. The sequence is the reverse complement of *M. forum* L1 genomic DNA (AE017263.1) nt624396 to nt625670 which is same as *M. forum* W37 genomic DNA (CP006778.1) nt636277 to nt 637550. The deoxyguanosine binding aptamer sequence used for initial screen indicated in bold and underline. The downstream gene product (Ribonucleotide reductase of class Ib (aerobic), beta subunit) is indicated in capital letters.

In FIG. 8A, nucleotides within boxes with solid lines are sequence regions targeted for randomization and nucleotides within boxes with dashed lines are sequence regions targeted for insertion/deletion and randomization. FIG. 8B shows possible sequences generated through mutation ("random nucleotides ("N")) and deletion/insertion.

FIG. 9 represents the *M. forum* type I-A deoxyguanosine riboswitch aptamer oligo library synthesized as a reverse complement with additional base pairs added to allow for PCR amplification and T7 promoter addition for in vitro transcription for library screening. The corresponding T7 promoter amplification primer and reverse amplification primer are also shown.

FIG. 10 represents the *Bacillus subtilis* guanosine xpt riboswitch regulatory region and associated gene product. The sequence is the reverse complement of *B. subtilis* subsp. *subtilis* 6051-HGW genomic DNA (CP003329.1) nt2319439 to nt2320353. The guanosine binding aptamer sequence used for initial screen indicated in bold and underline. The downstream gene product (Xanthine phosphoribosyltransferase xpt) is indicated in capital letters.

In FIG. 12A, nucleotides within boxes with solid lines are sequence regions targeted for randomization and nucleotides within boxes with dashed lines are sequence regions targeted for insertion/deletion and randomization. FIG. 12B shows possible sequences generated through mutation (random nucleotides ("N")) and deletion/insertion.

FIG. 13 represents the *B. subtilis* guanosine xpt riboswitch aptamer oligo library synthesized as a reverse complement with additional base pairs added to allow for PCR amplification and T7 promoter addition for in vitro transcription for library screening. The corresponding T7 promoter amplification primer and reverse amplification primer are also shown.

FIG. 17 shows seven aptamer candidates against acyclovir. The free energy for each aptamer was computed at 37° C. and 1 M Na+ by Quikfold 3.0 (Zuker 2003). Sequences were identified using proprietary algorithms. The underlined regions in each sequence are the PCR primer annealing regions.

FIG. 18 shows seven aptamer candidates against penciclovir. The free energy for each aptamer was computed at 37° C. and 1 M Na+ by Quikfold 3.0 (Zuker 2003). Sequences were identified using proprietary algorithms. The underlined regions in each sequence are the PCR primer annealing regions.

FIG. 20 shows a plot of transduction efficiency against MOI for negatively selected and unstimulated T cells transduced using lentiviruses pseudotyped with either VSV-G or truncated versions of MV(Ed) F and H polypeptides. Symbols are staggered for improved clarity.

DEFINITIONS

Figures 3A, 3B:
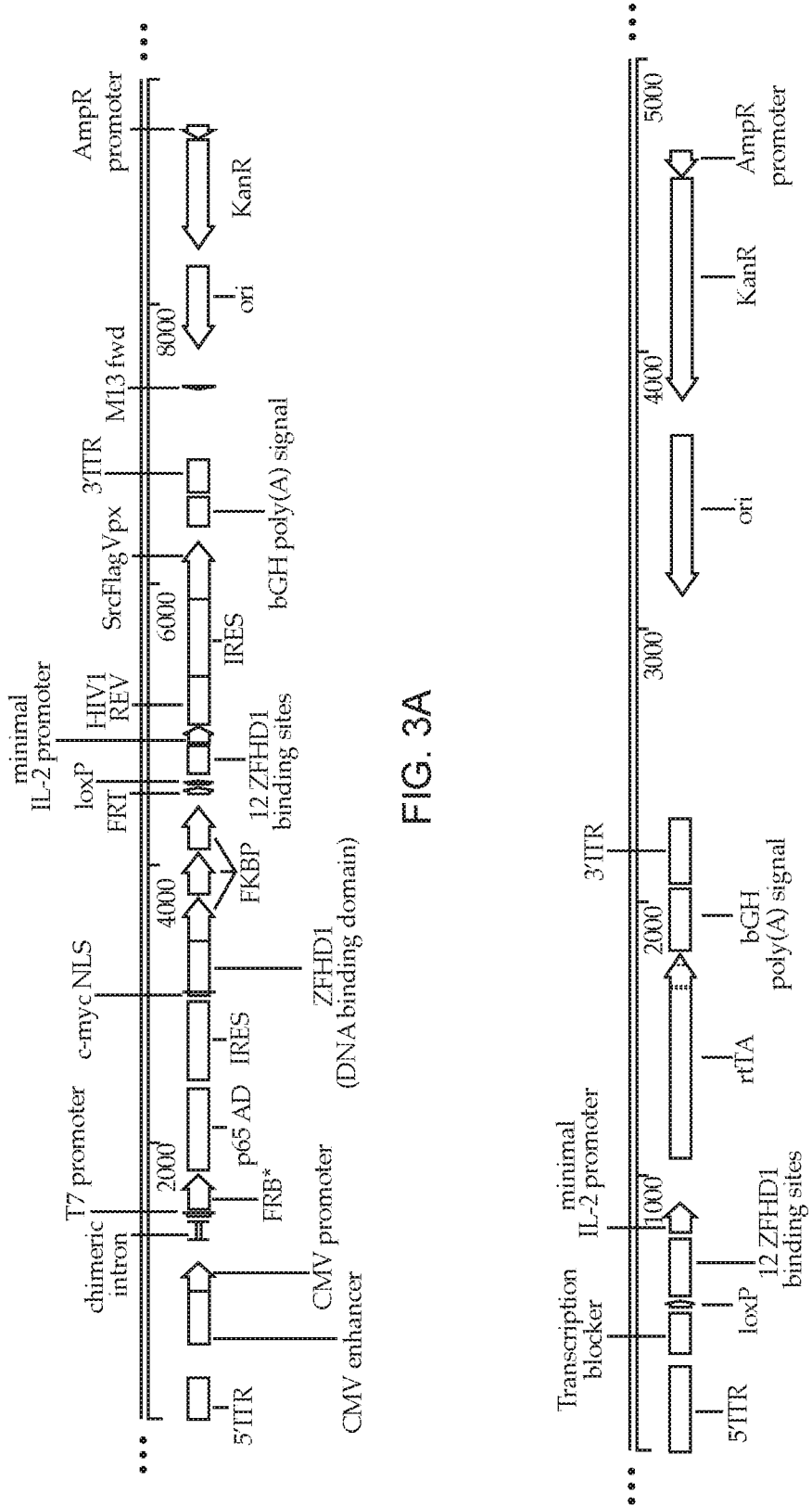
Figure 3E:
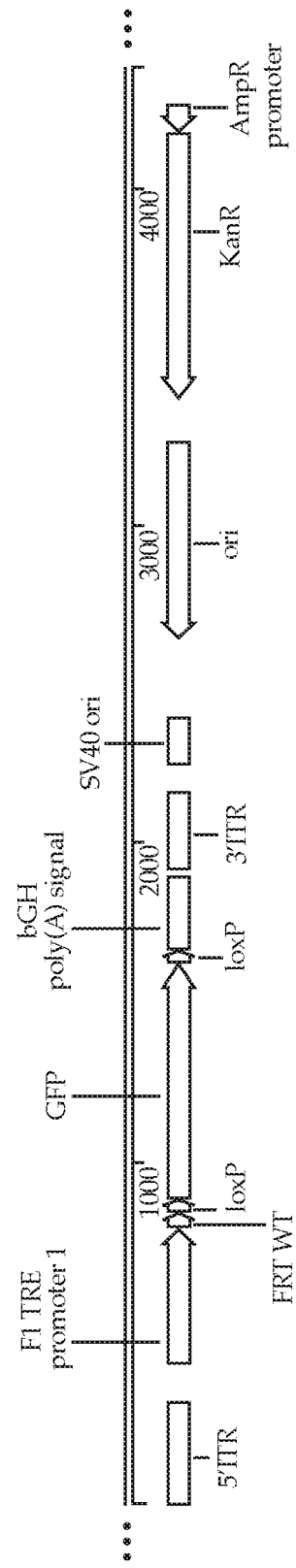

As used herein, the term "chimeric antigen receptor" or "CAR" or "CARs" refers to engineered receptors, which graft an antigen specificity onto cells, for example T cells, NK cells, macrophages, and stem cells. The CARs of the invention include at least one antigen-specific targeting region (ASTR) and an intracellular activating domain (IAD) and can include a stalk, a transmembrane domain (TM), and one or more co-stimulatory domains (CSDs). In another embodiment, the CAR is a bispecific CAR, which is specific to two different antigens or epitopes. After the ASTR binds specifically to a target antigen, the IAD activates intracellular signaling. For example, the IAD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

As used herein, the term "microenvironment" means any portion or region of a tissue or body that has constant or temporal, physical, or chemical differences from other regions of the tissue or regions of the body. For example, a "tumor microenvironment" as used herein refers to the environment in which a tumor exists, which is the non-cellular area within the tumor and the area directly outside the tumorous tissue but does not pertain to the intracellular compartment of the cancer cell itself. The tumor microenvironment can refer to any and all conditions of the tumor milieu including conditions that create a structural and or functional environment for the malignant process to survive and/or expand and/or spread. For example, the tumor microenvironment can include alterations in conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions a skilled artisan will understand.

As used interchangeably herein, the terms "polynucleotide" and "nucleic acid" refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

As used herein, the term "antibody" includes polyclonal and monoclonal antibodies, including intact antibodies and fragments of antibodies which retain specific binding to antigen. The antibody fragments can be, but are not limited to, fragment antigen binding (Fab) fragments, Fab' fragments, F(ab')₂ fragments, Fv fragments, Fab'-SH fragments, (Fab')₂ Fv fragments, Fd fragments, recombinant IgG (rIgG) fragments, single-chain antibody fragments, including single-chain variable fragments (scFv), divalent scFv's, trivalent scFv's, and single domain antibody fragments (e.g., sdAb, sdFv, nanobody). The term includes genetically engineered and/or otherwise modified forms of immunoglobulins, such as intrabodies, peptibodies, chimeric antibodies, single-chain antibodies, fully human antibodies, humanized antibodies, fusion proteins including an antigen-specific targeting region of an antibody and a non-antibody protein, heteroconjugate antibodies, multispecific, e.g., bispecific, antibodies, diabodies, triabodies, and tetrabodies, tandem di-scFv's, and tandem tri-scFv's. Unless otherwise stated, the term "antibody" should be understood to include functional antibody fragments thereof. The term also includes intact or full-length antibodies, including antibodies of any class or sub-class, including IgG and sub-classes thereof, IgM, IgE, IgA, and IgD.

As used herein, the term "antibody fragment" includes a portion of an intact antibody, for example, the antigen binding or variable region of an intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

As used interchangeably herein, the terms "single-chain Fv," "scFv," or "sFv" antibody fragments include the $V_H$ and $V_L$ domains of antibody, wherein these domains are present in a single polypeptide chain. In some embodiments, the Fv polypeptide further includes a polypeptide linker or spacer between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

As used herein, "naturally occurring" VH and VL domains refer to VH and VL domains that have been isolated from a host without further molecular evolution to change their affinities when generated in an scFv format under specific conditions such as those disclosed in U.S. Pat. No. 8,709,755 B2 and application WO/2016/033331A1.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

As used herein, the term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, reference to a "cell surface expression system" or "cell surface display system" refers to the display or expression of a protein or portion thereof on the surface of a cell. Typically, a cell is generated that expresses proteins of interest fused to a cell-surface protein. For example, a protein is expressed as a fusion protein with a transmembrane domain.

As used herein, the term "element" includes polypeptides, including fusions of polypeptides, regions of polypeptides, and functional mutants or fragments thereof and polynucleotides, including microRNAs and shRNAs, and functional mutants or fragments thereof.

As used herein, the term "region" is any segment of a polypeptide or polynucleotide.

As used herein, a "domain" is a region of a polypeptide or polynucleotide with a functional and/or structural property.

As used herein, the terms "stalk" or "stalk domain" refer to a flexible polypeptide connector region providing structural flexibility and spacing to flanking polypeptide regions and can consist of natural or synthetic polypeptides. A stalk can be derived from a hinge or hinge region of an immunoglobulin (e.g., IgG1) that is generally defined as stretching from Glu216 to Pro230 of human IgG1 (Burton (1985) Molec. Immunol., 22:161-206). Hinge regions of other IgG isotypes may be aligned with the IgG1 sequence by placing the first and last cysteine residues forming inter-heavy chain disulfide (S—S) bonds in the same positions. The stalk may be of natural occurrence or non-natural occurrence, including but not limited to an altered hinge region, as disclosed in U.S. Pat. No. 5,677,425. The stalk can include a complete hinge region derived from an antibody of any class or subclass. The stalk can also include regions derived from CD8, CD28, or other receptors that provide a similar function in providing flexibility and spacing to flanking regions.

The term "isolated" as used herein means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, a "polypeptide" is a single chain of amino acid residues linked by peptide bonds. A polypeptide does not fold into a fixed structure nor does it have any post-translational modification. A "protein" is a polypeptide that folds into a fixed structure. "Polypeptides" and "proteins" are used interchangeably herein.

As used herein, a polypeptide may be "purified" to remove contaminant components of a polypeptide's natural environment, e.g. materials that would interfere with diagnostic or therapeutic uses for the polypeptide such as, for example, enzymes, hormones, and other proteinaceous or nonproteinaceous solutes. A polypeptide can be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

As used herein, "T cell" includes all types of immune cells expressing CD3 including T-helper cells (CD4$^+$ cells), cytotoxic T cells (CD8$^+$ cells), T-regulatory cells (Treg) and gamma-delta T cells.

As used herein, a "cytotoxic cell" includes CD8$^+$ T cells, natural-killer (NK) cells, NK-T cells, γδ T cells, a subpopulation of CD4$^+$ cells, and neutrophils, which are cells capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoeitic stem cells (HSC); bone marrow derived cells, etc.).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As used interchangeably herein, the terms "individual", "subject", "host", and "patient" refer to a mammal, including, but not limited to, humans, murines (e.g., rats, mice), lagomorphs (e.g., rabbits), non-human primates, humans, canines, felines, ungulates (e.g., equines, bovines, ovines, porcines, caprines), etc.

As used herein, the terms "therapeutically effective amount" or "efficacious amount" refers to the amount of an agent, or combined amounts of two agents, that, when administered to a mammal or other subject for treating a disease, is sufficient to affect such treatment for the disease. The "therapeutically effective amount" will vary depending on the agent(s), the disease and its severity and the age, weight, etc., of the subject to be treated.

As used herein, the term "evolution" or "evolving" refers to using one or more methods of mutagenesis to generate a different polynucleotide encoding a different polypeptide, which is itself an improved biological molecule and/or contributes to the generation of another improved biological molecule. "Physiological" or "normal" or "normal physiological" conditions are conditions such as, but not limited to, pressure, temperature, pH, ionic strength, osmotic pressure, osmolality, oxidative stress, concentration of one or more solutes, concentration of electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors, as well as other conditions, that would be considered within a normal range at the site of administration, or at the tissue or organ at the site of action, to a subject.

As used herein, a "genetically modified cell" includes cells that contain exogenous nucleic acids whether or not the exogenous nucleic acids are integrated into the genome of the cell.

A "polypeptide" as used herein can include part of or an entire protein molecule as well as any posttranslational or other modifications.

A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. The "binding polypeptide" as used herein, can also be referred to as a "T cell and/or NK cell binding polypeptide" or a "target engagement element," and the "fusogenic polypeptide" can also be referred to as a "fusogenic element".

A "resting" lymphocyte, such as for example, a resting T cell, is a lymphocyte in the G0 stage of the cell cycle that does not express activation markers such as Ki-67. Resting lymphocytes can include naïve T cells that have never encountered specific antigen and memory T cells that have been altered by a previous encounter with an antigen. A "resting" lymphocyte can also be referred to as a "quiescent" lymphocyte.

As used herein, "lymphodepletion" involves methods that reduce the number of lymphocytes in a subject, for example by administration of a lymphodepletion agent. Lymphodepletion can also be attained by partial body or whole body fractioned radiation therapy. A lymphodepletion agent can be a chemical compound or composition capable of decreasing the number of functional lymphocytes in a mammal when administered to the mammal One example of such an agent is one or more chemotherapeutic agents. Such agents and dosages are known, and can be selected by a treating physician depending on the subject to be treated. Examples of lymphodepletion agents include, but are not limited to, fludarabine, cyclophosphamide, cladribine, denileukin diftitox, or combinations thereof.

It is to be understood that the present disclosure and the aspects and embodiments provided herein, are not limited to particular examples disclosed, as such may, of course, vary. It is also to be understood that the terminology used herein is for the purpose of disclosing particular examples and embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. When multiple low and multiple high values for ranges are given, a skilled artisan will recognize that a selected range will include a low value that is less than the high value. All headings in this specification are for the convenience of the reader and are not limiting.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chimeric antigen receptor" includes a plurality of such chimeric antigen receptors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

DETAILED DESCRIPTION

The present disclosure overcomes these prior art challenges by providing methods and compositions for genetically modifying lymphocytes and methods for performing adoptive cellular therapy that include transducing T cells and/or NK cells, that requires far less time ex vivo, for example, 24, 12, or 8 hours or less, and in some embodiments without prior ex vivo stimulation. These methods are well-suited for closed system ex vivo processing of blood from a subject, and can be performed with the subject present in the same room as and/or in some embodiments, within their line of sight of their blood or isolated blood cells thereof at all times during performance of the method. More specifically, the aspects and embodiments of the disclosure herein overcome problems associated with current adoptive cellular therapies by providing methods for transducing resting T cells and/or resting NK cells, that typically utilize a pseudotyping element that facilitates binding and fusion of a recombinant retrovirus to a resting T cell and/or a resting NK cell, to facilitate genetic modification of the resting T cells and/or NK cells by the recombinant retroviruses. Furthermore, methods provided herein overcome problems of the art by utilizing in illustrative embodiments, a chimeric antigen receptor and a lymphoproliferative element whose expression is under the control of an in vivo control element, such that exposure of the subject to a compound that binds the in vivo control element, or termination of such exposure, promotes expansion of the genetically modified T cells and/or NK cells in vivo.

As a result of these and other improvements disclosed in detail herein, in one aspect, provided herein is a method for modifying resting T cells and/or resting NK cells of a subject, such as a patient having a disease or disorder, wherein blood from the subject is collected; resting T cells and/or NK cells are genetically modified. by contacting them with a recombinant retrovirus and the genetically modified cells are reintroduced into the subject typically within a shorter period of time than prior methods, for example within 24 hours and in some non-limiting embodiments, within 12 hours and/or without further expanding the population of genetically modified T cells and/or NK cells ex vivo, for example such that the genetically modified resting I cells and/or NK cells do not undergo more than 4 cell divisions ex vivo. Thus, methods provided herein can be performed in much less time than current CAR therapies, thereby providing processes by which a subject can remain in a clinic for the entire time of the ex vivo steps. This facilitates performance of the ex vivo steps in a closed system, which reduces the chances for contamination and mixing of patient samples and can be performed more readily by clinical labs.

Accordingly, FIGS. 1 and 2 provide schematic diagrams of illustrative compositions used in methods provided herein. FIG. 1 provides a diagram of a packaging cell (100) and a recombinant retrovirus produced by such a packaging cell (200). The packaging cell (100) includes recombinant polynucleotides (110) incorporated into its genome that include recombinant transcriptional elements that express retroviral proteins and various different membrane-bound polypeptides under the control of inducible promoters that are regulated by transactivators, which bind and are activated by ligands. These transactivators, inducible promoters, and ligands are used to induce the sequential expression and accumulation of cell membrane-bound polypeptides that will be incorporated into the membrane of the recombinant retrovirus as well as retroviral components necessary for packaging and assembly of the retrovirus.

As a result of the sequential induced expression of the various polynucleotides as discussed in detail herein below, the illustrative packaging cell (100) illustrated in FIG. 1 is produced, and can be used in illustrative methods to produce recombinant retroviruses used in methods of transfecting resting T cells and/or NK cells ((300) in FIG. 2) provided herein. The packaging cell (100), in non-limiting illustrative embodiments, includes in its genome nucleic acids encoding a packagable retroviral RNA genome that includes at least some of the elements of a retroviral genome necessary for packaging and assembly of the retrovirus (as non-limiting illustrative examples, a retroviral psi element, a retroviral gag polypeptide and a retroviral pot polypeptide).

Some membrane bound polypeptides incorporated or associated with the cell membrane of the packaging cell will become incorporated or associated into the retrovirus, but are not encoded by the retroviral genome. For example, the packaging cell and recombinant retrovirus formed therefrom, can include a retroviral Vpx polypeptide (250), which in non-limiting illustrative examples can be expressed as a membrane associated fusion protein, for example a Src-Flag-Vpx polypeptide; a pseudotyping element that can include a binding polypeptide and a fusogenic polypeptide (240), which in a non-limiting embodiment includes a Measles Virus hemagglutinin (H) polypeptide and a Measles Virus fusion (F) polypeptide, or cytoplasmic domain deletion variants thereof; optionally, one or more activation elements (210, 220), which in a non-limiting embodiment includes a membrane-bound polypeptide capable of binding to CD3 and a membrane-bound polypeptide capable of binding to CD28; and/or optionally a membrane-bound cytokine (230), a non-limiting embodiment of which is a fusion polypeptide that includes IL-7 fused to DAF, or a fragment thereof. Various other specific types of these membrane bound polypeptides are provided herein.

As a result of the sequential expression of the transcriptional elements by the packaging cell, a recombinant retrovirus is produced. The RNA retroviral genome inside of and typically integrated into the genome of the packaging cell that becomes the genome of the recombinant retrovirus, includes retroviral components (as non-limiting illustrative examples, retroviral Gag and Pol polynucleotides) that are necessary for retroviral production, infection and integration into the genome of a host cell, which is typically a resting T cell and/or NK cell. Furthermore, the retroviral genome furthermore includes polynucleotides encoding one or typically two engineered signaling polypeptides provided herein. One of the engineered signaling polypeptides typically encodes a lymphoproliferative element (in non-limiting examples a constitutive interleukin 7 receptor mutant) and the other engineered signaling polypeptide typically encodes a chimeric antigen receptor.

The recombinant retrovirus (200) is then used to transduce a resting T cell and/or resting NK cell (300) in methods provided herein. As shown in FIG. 2, after the resting T cell and/or NK cell (300) is contacted with the recombinant retrovirus (200), membrane polypeptides discussed. above on the surface of the retrovirus bind to receptors and/or ligands on the surface of the resting T cell and/or NK cell (300). For example, the pseudotyping element, which as indicated above can include a binding polypeptide that binds to molecules on the surface of resting T cells and/or resting NK cells and a fusogenic polypeptide, facilitates the binding and fusion of the retrovirus (200) to the T cell and/or NK cell membrane. The activation element(s) (210, 220) activate the resting T cell and/or NK cell (300) by engaging the T-cell receptor complex, a process which occurs over the time course of the contacting or an incubation thereafter. Furthermore, the membrane-bound cytokines (230) can be present on the surface of the retrovirus and bind cytokine receptors (310) on the surface of the resting T cell and/or NK cell (300), thus further promoting binding and activation. Thus, not to be limited by theory, in illustrative embodiments provided herein, as a result of one or more of these recombinant retrovirus (200) components, ex vivo stimulation or activation by an element that is not already in or on the retrovirus (200) is not required. This in turn, helps to cut down the ex vivo time that is required for completion of the methods in these illustrative methods provided herein.

Upon binding to the T cell and/or NK cell (200), the retrovirus then fuses with the T cell and/or NK cell (300), and polypeptides and nucleic acids in the retrovirus enter the T cell and/or NK cell (300). As indicated above, one of these polypeptides in the retrovirus is the Vpx polypeptide (250). The Vpx polypeptide (250) binds to and induces the degradation of the SAMHD1 restriction factor (350), which degrades free dNTPs in the cytoplasm. Thus, the concentration of free dNTPs in the cytoplasm increases as Vpx degrades SAMHD1, and reverse transcription activity is increased, thus facilitating reverse transcription of the retroviral genome and integration into the T cell and/or NK cell genome.

After integration of the retroviral genome into the T cell and/or NK cell (200), the T cell and/or NK cell genome includes nucleic acids encoding the signaling polypeptide encoding the lymphoproliferative element (370) and optionally the signaling polypeptide encoding the CAR (360). Expression of the lymphoproliferative element and optionally the CAR are under the control of an in vivo control element, Exposure to a compound that binds the in vivo control element, which occurs in vivo by administering it to a subject whose T cell and/or NK cell (300) was transduced, promotes proliferation of the T cell and/or NK cell (300) in vivo by expressing the lymphoproliferative element and optionally as a result of expression of the CAR and binding of the CAR to its target cell. Thus, T cells and/or NK cells that are transduced with recombinant retroviruses herein, have one or mare signals that drive proliferation and/or inhibit cell death, which in turn in illustrative embodiments, avoids the requirements of prior methods to lymphodeplete a host before returning transduced T cells and/or NK cells back into the subject. This in turn, in illustrative embodiments, further reduces the requirement for days of processing before transduced T cells and/or NK cells are reintroduced into a subject. Thus, in illustrative embodiments, no more than 36 hours, 24 hours, 12 hours, or in some instances even 8 hours, of time is required from collection of blood from the subject to reintroduction of the blood to the subject, which fundamentally changes the CAR-T process from prior methods. Furthermore, the in vivo control element provides one of the safety mechanisms provided herein as well. For example, ceasing administration of the compound can down-regulate or even terminate expression of the lymphoproliferative element and optionally the CAR, thus ending a proliferation and/or survival signal to the transduced T cell and/or NK cell and its progeny.

Methods for Performing Adoptive Cell Therapy

In certain aspects, provided herein are methods for performing adoptive cell therapy on a subject, As an illustrative example, the method can include the following:

A. collecting blood from a subject;

B. isolating peripheral blood mononuclear cells (PBMCs) comprising resting T cells and/or resting NK cells;

C. contacting the resting T cells and/or resting NK cells of the subject ex vivo, with recombinant retroviruses, wherein the recombinant retroviruses comprise a pseudotyping element on their surface that is capable of binding a resting T cell and/or NK cell and facilitating membrane fusion of the recombinant retrovirus thereto, wherein said contacting facilitates transduction of the resting T cells and/or NK cells by the recombinant retroviruses, thereby producing genetically modified T cells and/or NK cells; and D. reintroducing the genetically modified cells into the subject within 36, 24, 12, or even 8 hours of collecting blood from the subject, thereby performing adoptive cell therapy in the subject.

In some aspects provided herein, methods with similar steps are referred to as methods for genetically modifying and expanding lymphocytes of a subject. A skilled artisan will understand that the discussion herein as it applies to methods and compositions for performing adoptive cell therapy apply to methods for genetically modifying and expanding lymphocytes of a subject as well.

Typically, the adoptive cell therapy methods of the present disclosure are carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject. In some embodiments of the methods and compositions disclosed herein, a subject having a disease or disorder enters a medical facility where the subject's blood is drawn using known methods, such as venipuncture. In certain embodiments, the volume of blood drawn from a subject is between 10, 15, 20, 25, 30, 35, 40, 50, 75, or 100 ml on the low end of the range and 200, 250, 300, 350, 400, 500, 750, 1000, 2000, or 2500 ml on the high end of the range. In some embodiments, between 10 and 400 ml are drawn from the subject. In some embodiments, between 20 and 250 ml of blood are drawn from the subject. In some embodiments, the blood is fresh when it is processed. In any of the embodiments disclosed herein, fresh blood can be blood that was withdrawn from a subject less than 15, 30, 45, 60, 90, 120, 150, or 180 minutes prior. In some embodiments, the blood is processed in the methods provided herein without storage.

Contact between the T cells and/or NK cells and the recombinant retroviruses typically facilitates transduction of the T cells and/or NK cells by the recombinant retrovirus. Throughout this disclosure, a transduced T cell and/or NK cell includes progeny of ex vivo transduced cells that retain at least some of the nucleic acids or polynucleotides that are incorporated into the cell during the ex vivo transduction. In methods herein that recite "reintroducing" a transduced cell, it will be understood that such cell is typically not in a transduced state when it is collected from the blood of a subject. A subject in any of the aspects disclosed herein can be for example, an animal, a mammal, and in illustrative embodiments a human.

Not to be limited by theory, in non-limiting illustrative methods, the delivery of a polynucleotide encoding a lymphoproliferative element, such as an IL7 constitutively active mutant, to a resting T cell and/or NK cell ex vivo, which can integrate into the genome of the T cell or NK cell, provides that cell with a driver for in vivo expansion without the need for lymphodepleting the host. Thus, in illustrative embodiments, the subject is not exposed to a lymphodepleting agent within 1, 2, 3, 4, 5, 6, 7, 10, 14, 21, or 28 days, or within 1 month, 2 months, 3 months or 6 months of performing the contacting, during the contacting, and/or within 1, 2, 3, 4, 5, 6, 7, 10, 14, 21, or 28 days, or within 1 month, 2 months, 3 months or 6 months after the modified T cells and/or NK cells are reintroduced back into the subject. Furthermore, in non-limiting illustrative embodiments, methods provided herein can be performed without exposing the subject to a lymphodepleting agent during a step wherein a recombinant retrovirus is in contact with resting T cells and/or resting NK cells of the subject and/or during the entire ex vivo method.

Hence, methods of expanding genetically modified T cells and/or NK cells in a subject in a vivo is a feature of some embodiments of the present disclosure. In illustrative embodiments, such methods are ex vivo propagation-free or substantially propagation-free.

This entire method/process from blood draw from a subject to reintroduction of blood back into the subject after ex vivo transduction of T cells and/or NK cells, in non-limiting illustrative embodiments herein, can occur over a time period less than 48 hours, less than 36 hours, less than 24 hours, less than 12 hours, less than 11 hours, less than 10 hours, less than 9 hours, less than 8 hours, less than 7 hours, less than 6 hours, less than 5 hours, less than 4 hours, less than 3 hours, or less than 2 hours. In other embodiments, the entire method/process from blood draw/collection from a subject to reintroduction of blood back into the subject after ex vivo transduction of T cells and/or NK cells, in non-limiting illustrative embodiments herein, occurs over a time period between 1 hour and 12 hours, or between 2 hours and 8 hours, or between 4 hours and 12 hours, or between 4 hours and 24 hours, or between 8 hours and 24 hours, or between 8 hours and 36 hours, or between 8 hours and 48 hours, or between 12 hours and 24 hours, or between 12 hours and 36 hours, or between 12 hours and 48 hours, or over a time period between 15, 30, 60, 90, 120, 180, and 240 minutes on the low end of the range, and 120, 180, and 240, 300, 360, 420, and 480 minutes on the high end of the range. In other embodiments, the entire method/process from blood draw/collection from a subject to reintroduction of blood back into the subject after ex vivo transduction of T cells and/or NK cells, occurs over a time period between 1, 2, 3, 4, 6, 8, 10, and 12 hours on the low end of the range, and 8, 9, 10, 11, 12, 18, 24, 36, or 48 hours on the high end of the range. In some embodiments, the genetically modified T cells and/or NK cells are separated from the recombinant retroviruses after the time period in which contact occurs.

Because methods provided herein for adoptive cell therapy and related methods for modifying resting T cells and/or resting NK cells ex vivo before expanding them in vivo, can be performed in significantly less time than prior methods, fundamental improvements in patient care and safety as well as product manufacturability are made possible. Therefore, such processes are expected to be favorable in the view of regulatory agencies responsible for approving such processes when carried out in vivo for therapeutic purposes. For example, the subject in non-limiting examples, can remain in the same building (e.g. infusion clinic) or room as the instrument processing their blood or sample for the entire time that the sample is being processed before modified T cells and/or NK cells are reintroduced into the patient. In non-limiting illustrative embodiments, a subject remains within line of site and/or within 100, 50, 25, or 12 feet or arm's distance of their blood or cells that are being processed, for the entire method/process from blood draw/collection from the subject to reintroduction of blood to the subject after ex vivo transduction of T cells and/or NK cells. In other non-limiting illustrative embodiments, a subject remains awake and/or at least one person can continue to monitor the blood or cells of the subject that are being processed, throughout and/or continuously for the entire method/process from blood draw/collection from the subject to reintroduction of blood to the subject after ex vivo transduction of T cells and/or NK cells. Because of improvements provided herein, the entire method/process for adoptive cell therapy and/or for transducing resting T cells and/or NK cells from blood draw/collection from the subject to reintroduction of blood to the subject after ex vivo transduction of T cells and/or NK cells can be performed with continuous monitoring by a human. In other non-limiting illustrative embodiments, at no point the entire method/process from blood draw/collection from the subject to reintroduction of blood to the subject after ex vivo transduction of T cells and/or NK cells, are blood cells incubated in a room that does not have a person present. In other non-limiting illustrative embodiments, the entire method/process from blood draw/collection from the subject to reintroduction of blood to the subject after ex vivo transduction of T cells and/or NK cells, is performed next to the subject and/or in the same room as the subject and/or next to the bed or chair of the subject. Thus, sample identity mix-ups can be avoided, as well as long and expensive incubations over periods of days or weeks. This is further provided by the fact that methods provided herein are readily adaptable to closed and automated blood processing systems, where a blood sample and its components that will be reintroduced into the subject, only make contact with disposable, single-use components.

Methods for performing adoptive cell therapy provided herein, typically include methods of transducing resting T cells and/or NK cells, which themselves form distinct aspects of the present disclosure. A skilled artisan will recognize that details provided herein for transducing T cells and/or NK cells can apply to any aspect that includes such step(s). Accordingly, provided herein in certain aspects, is a method of transducing a T cell and/or an NK cell, typically a resting T cell and/or resting NK cell, that includes contacting the resting T cell and/or resting NK cell with a recombinant retrovirus, wherein the recombinant retrovirus typically comprises a pseudotyping element on its surface that is capable of binding the resting T cell and/or NK cell and facilitating membrane fusion of the recombinant retrovirus thereto, wherein said contacting (and incubation under contacting conditions) facilitates transduction of the resting T cell and/or NK cell by the recombinant retroviruses, thereby producing the genetically modified T cell and/or NK cell. Further embodiments of such a method can include any of the embodiments of retroviruses, lymphoproliferative elements, CARs, pseudotyping elements, riboswitches, activation elements, membrane-bound cytokines, miRNAs, and/or other elements disclosed herein. Such a method for transducing a T cell and/or NK cell can be performed in vitro or ex vivo.

In methods for adoptive cell therapy and any method provided herein that include transducing resting T cells and/or resting NK cells ex vivo, typically, neutrophils/granulocytes are separated away from the blood cells before the cells are contacted with recombinant retrovirus. In some embodiments, peripheral blood mononuclear cells (PBMCs) including peripheral blood lymphocytes (PBLs) such as T cell and/or NK cells, are isolated away from other components of a blood sample using for example, apheresis, and/or density gradient centrifugation. In some embodiments, neutrophils are removed before PBMCs and/or T cells and/or NK cells are processed, contacted with a recombinant retrovirus, transduced, or transfected. With reference to the subject to be treated, the cells may be allogeneic and/or autologous.

As non-limiting examples, in some embodiments, for performing the PBMCs are isolated using a Sepax or Sepax 2 cell processing system (BioSafe). In some embodiments, the PBMCs are isolated using a CliniMACS Prodigy cell processor (Miltenyi Biotec). In some embodiments, an automated apheresis separator is used which takes blood from the subject, passes the blood through an apparatus that sorts out a particular cell type (such as, for example, PBMCs), and returns the remainder back into the subject. Density gradient centrifugation can be performed after apheresis. In some embodiments, the PBMCs are isolated using a leukoreduction filter device. In some embodiments, magnetic bead activated cell sorting is then used for purifying a specific cell population from PBMCs, such as, for example, PBLs or a subset thereof, according to a cellular phenotype (i.e. positive selection). Other methods for purification can also be used, such as, for example, substrate adhesion, which utilizes a substrate that mimics the environment that a T cell encounters during recruitment, allowing them to adhere and migrate, or negative selection, in which unwanted cells are targeted for removal with antibody complexes that target the unwanted cells. In some embodiments, red blood cell rosetting can be used to purify cells.

In some illustrative embodiments of any of the relevant aspects herein, the PBLs include T cells and/or NK cells. The T cells and/or NK cells that are contacted by recombinant retroviruses of the present disclosure during certain embodiments herein, for example in methods of modifying lymphocytes and methods of performing adoptive cellular therapy, are mainly resting T cells. In some embodiments, the T cells and/or NK cells consist of between 95 and 100% resting cells (Ki-67). In some embodiments, the T cell and/or NK cells that are contacted by recombination retroviruses include between 90, 91, 92, 93, 94, and 95% resting cells on the low end of the range and 96, 97, 98, 99, or 100% resting cells on the high end of the range. In some embodiments, the T cells and/or NK cells include naïve cells.

In some embodiments of the methods and compositions disclosed herein, T cells and/or NK cells are contacted ex vivo with recombinant retroviruses to genetically modify T cells and/or NK cells to illicit a targeted immune response in the subject when reintroduced into the subject. During the period of contact, the recombinant retroviruses identify and bind to T cells and/or NK cells at which point the retroviral and host cell membranes start to fuse. Then, through the process of transduction, genetic material from the recombinant retroviruses enters the T cells and/or NK cells and is incorporated into the host cell DNA. Methods of lentiviral transduction are known. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505.

Many of the methods provided herein include transduction of T cells and/or NK cells. Methods are known in the art for transducing T cells and/or NK cells ex vivo with retroviruses, such as lentiviruses. Methods provided herein, in illustrative embodiments, do not require ex vivo stimulation or activation. Thus, this common step in prior methods can be avoided in the present method, although ex vivo stimulatory molecule(s) such as anti-CD3 and/or anti-CD28 beads, can be present during the transduction. However, with illustrative methods provided herein, ex vivo stimulation is not required. In certain exemplary methods, between 3 and 10 multiplicity of infection (MOI), and in some embodiments, between 5 and 10 MOI units of retrovirus, for example lentivirus, can be used.

The transduction reaction can be carried out in a closed system, such as a Sepax system, as discussed herein, wherein the transduction reaction can be carried out in disposable bags loaded on the system. Blood cells, such as PBMCs, from the collected blood sample from the subject, can be contacted with recombinant retroviruses disclosed herein, in a bag as soon as these blood cells are separated, isolated, and/or purified away from granulocytes, including neutrophils, which are typically not present during the contacting step (i.e. the transduction reaction).

The retrovirus can be introduced into the bag that contains the isolated PBMCs, thereby contacting the PBMCs. The time from blood collection from the subject to the time when blood cells, such as PBMCs are added to the transduction reaction bag, can be between 30 minutes and 4 hours, between 30 minutes and 2 hours, or around 1 hour, in some examples. Additives such as media, human serum albumin, human AB+ serum, and/or serum derived from the subject can be added to the transduction reaction mixture. Media is typically present, such as those known in the art for ex vivo processes (as non-limiting examples, X-VIVO 15 (Lonza) or CTS media (Thermo Fisher Scientific). Supportive cytokines can be added to the transduction reaction mixture, such as IL2, IL7, or IL15, or those found in HSA.

The transduction reaction mixture can be incubated at between 23 and 39° C., and in some illustrative embodiments at 37° C. In certain embodiments, the transduction reaction can be carried out at 37-39° C. for faster fusion/transduction. dGTP can be added to the transduction reaction. The transduction reaction mixture can be incubated for 1 to 12 hours, and in some embodiments, 6 to 12 hrs. After transduction, before the transduced T cells and/or NK cells are infused back into the subject, the cells are washed out of the transduction reaction mixture. For example, the system, such as a Sepax instrument, can be used to wash cells, for example with 10-50 ml of wash solution, before the transduced cells are infused back into the subject. In some embodiments, neutrophils are removed before PBMCs and/or T cells and/or NK cells are processed, contacted with a recombinant retrovirus, transduced, or transfected.

In an illustrative embodiment for performing adoptive cell therapy, blood is collected from a subject into a blood bag and the blood bag is attached to a cell processing system such as a Sepax cell processing system. PBMCs isolated using the cell processing system are collected into a bag, contacted with the recombinant retrovirus in conditions sufficient to transduce T cells and/or NK cells, and incubated. After incubation, the bag containing the mixture of PBMCs and recombinant retrovirus is attached to a cell processing system and the PBMCs are washed. The washed PBMCs are collected into a bag and reinfused into the subject. In some embodiments, the entire method, from collecting blood to reinfusing transduced T and/or NK cells, is performed within 1, 2, 3, 4, 5, 6, 7, 8, 9, 10, 11, 12, 15, 18, or 24 hours. In illustrative embodiments, the entire method is performed within 12 hours.

In some embodiments, the target cells for the recombinant retroviruses are PBLs. In some embodiments, the target cells are T cells and/or NK cells. In some embodiments, the T cells are helper T cells and/or killer T cells.

In some embodiments, the recombinant retroviruses provided herein have pseudotyping elements on their surface that are capable of binding to T cells and/or NK cells and facilitating membrane fusion of the recombinant retroviruses thereto. In other embodiments, the recombinant retroviruses have activation elements on their surface that are capable of binding to resting T cells and/or NK cells. In still other embodiments, the recombinant retroviruses have membrane-bound cytokines on their surface. In some embodiments, the recombinant retroviruses include a polynucleotide having one or more transcriptional units encoding one or more engineered signaling polypeptides, one or more of which includes a lymphoproliferative element. In other embodiments, when two signaling polypeptides are utilized, one includes a lymphoproliferative element and the other is typically a chimeric antigen receptor (CAR) that includes an antigen-specific targeting region (ASTR), a transmembrane domain, and an intracellular activating domain. As indicated herein, an activation element(s) that is typically associated with the surface of a recombinant retrovirus provided herein, is capable of, and as a resulting of contacting resting T cells and/or NK cells for a sufficient period of time and under appropriate conditions, activates resting T cells and/or NK cells. It will be understood that such activation occurs over time during a contacting step of methods herein. Furthermore, it will be understood that in some embodiments where a pseudotyping element is found on the surface of a recombinant retrovirus, that binds a T cell and/or an NK cell, in methods herein, activation can be induced by binding of the pseudotyping element. An activation element is optional in those embodiments.

Further details regarding a pseudotyping element, an activation element, a membrane-bound cytokine, an engineered signaling polypeptide, a lymphoproliferative element, and a CAR are provided in other sections herein.

In some embodiments of the methods and compositions disclosed herein, between 5% and 90% of the total lymphocytes collected from the blood are transduced. In some embodiments, the percent of lymphocytes that are transduced is between 5, 10, 15, 20, 25, 30, 35, 40, 45, 50, 55, and 60% on the low end of the range, and 50, 55, 60, 65, 70, 75, 80, 85, and 90% on the high end of the range. In some embodiments, the percent of lymphocytes that are transduced is at least 5%, at least 10%, at least 15%, at least 20%, at least 25%, at least 30%, at least 35%, at least 40%, at least 45%, at least 50%, at least 55%, or at least 60%.

In some embodiments of the methods and compositions disclosed herein, the genetically modified T cells and/or NK cells are introduced back, reintroduced, or reinfused into the subject without additional ex vivo manipulation, such as stimulation and/or activation of T cells and/or NKs. In the prior art methods, ex vivo manipulation is used for stimulation/activation of T cells and/or NK cells and for expansion of genetically modified T cells and/or NK cells prior to introducing the genetically modified T cells and/or NK cells into the subject. In prior art methods, this generally takes days or weeks and requires a subject to return to a clinic for a blood infusion days or weeks after an initial blood draw. In some embodiments of the methods and compositions disclosed herein, T cells and/or NK cells are not stimulated ex vivo by exposure to anti-CD3/anti-CD28 solid supports such as, for example, beads coated with anti-CD3/anti-CD28, prior to contacting the T cells and/or NK cells with the recombinant retroviruses. As such provided herein is an ex vivo propagation-free method. In other embodiments, genetically modified T cells and/or NK cells are not expanded ex vivo, or only expanded for a small number of cell divisions (e.g. 1, 2, 3, 4, 5, 6, 7, 8, 9, or 10 rounds of cell division), but are rather expanded, or predominantly expanded, in vivo, i.e. within the subject. In some embodiments, no additional media is added to allow for further expansion of the cells. In some embodiments, no cell manufacturing of the PBLs occurs while the PBLs are contacted with the recombinant retrovirus. In illustrative embodiments, no cell manufacturing of the PBLs occurs while the PBLs are ex vivo. In previous methods of adoptive cell therapy, subjects were lymphodepleted prior to reinfusion with genetically modified T cells and or NK cells. In some embodiments, patients or subjects are not lymphodepleted prior to blood being withdrawn. In some embodiments, patients or subjects are not lymphodepleted prior to reinfusion with genetically modified T cells and or NK cells.

In any of the embodiments disclosed herein, the number of T cells and/or NK cells to be reinfused into a subject can be between $1\times10^3$, $2.5\times10^3$, $5\times10^3$, $1\times10^4$, $2.5\times10^4$, $5\times10^4$, $1\times10^5$, $2.5\times10^5$, $5\times10^5$, $1\times10^6$, $2.5\times10^6$, $5\times10^6$, and $1\times10^7$ cells/kg on the low end of the range and $5\times10^4$, $1\times10^5$, $2.5\times10^5$, $5\times10^5$, $1\times10^6$, $2.5\times10^6$, $5\times10^6$, $1\times10^7$, $2.5\times10^7$, $5\times10^7$, and $1\times10^8$ cells/kg on the high end of the range. In illustrative embodiments, the number of T cells and/or NK cells to be reinfused into a subject can be between $1\times10^4$, $2.5\times10^4$, $5\times10^4$, and $1\times10^5$ cells/kg on the low end of the range and $2.5\times10^4$, $5\times10^4$, $1\times10^5$, $2.5\times10^5$, $5\times10^5$, and $1\times10^6$ cells/kg on the high end of the range. In some embodiments, the number of PBLs to be reinfused into a subject can be fewer than $5\times10^5$, $1\times10^6$, $2.5\times10^6$, $5\times10^6$, $1\times10^7$, $2.5\times10^7$, $5\times10^7$, and $1\times10^8$ cells and the low end of the range and $2.5\times10^6$, $5\times10^6$, $1\times10^7$, $2.5\times10^7$, $5\times10^7$, $1\times10^8$, $2.5\times10^8$, $5\times10^8$, and $1\times10^9$ cells on the high end of the range. In some embodiments, the number of T cells and/or NK cells available for reinfusion into a 70 kg subject or patient is between $7\times10^5$ and $2.5\times10^8$ cells. In other embodiments, the number of T cells and/or NK cells available for transduction is approximately $7 \times 10^6$ plus or minus 10%.

In the methods disclosed herein, the entire adoptive cell therapy procedure, from withdrawing blood to the reinfusion of genetically modified T cells and/or NK cells, can advantageously be performed in a shorter time than previous methods. In some embodiments, the entire adoptive cell therapy procedure can be performed in less than 1, 2, 3, 4, 5, 6, 7, 8, 9, 10, 11, 12, 15, 18, or 24 hours. In illustrative embodiments, the entire adoptive cell therapy procedure can be performed in less than 1, 2, 3, 4, 5, 6, 7, 8, 9, 10, 11, or 12 hours. In some embodiments, the entire adoptive cell therapy procedure can be performed in between 1, 2, 3, 4, 5, 6, 7, 8, 9, 10, 11, 12, or 15 hours on the low end of the range and 1, 2, 3, 4, 5, 6, 7, 8, 9, 10, 11, 12, 15, 18, or 24 hours on the high end of the range.

In some embodiments provided herein, the steps of withdrawing a blood sample from a subject, contacting T cells and/or NK cells with recombinant retroviruses, and/or introducing genetically modified T cells and/or NK cells into the subject, occur in a closed system. A closed system is a culture process that is generally closed or fully closed to contamination. An advantage of the present invention, is that provided herein are methods for performing CAR therapy in a closed system. One of the greatest risks to safety and regulatory control in the cell processing procedure is the risk of contamination through frequent exposure to the environment as is found in traditional open cell culture systems. To mitigate this risk, particularly in the absence of antibiotics, some commercial processes have been developed that focus on the use of disposable (single-use) equipment. However even with their use under aseptic conditions, there is always a risk of contamination from the opening of flasks to sample or add additional growth media. To overcome this problem, provided herein is a closed-system process, a process that is designed and can be operated such that the product is not exposed to the outside environment. This is important because the outside environment is typically not sterile. Material transfer occurs via sterile connections or tube welding. Air for gas exchange occurs via a gas permeable membrane or like other additions, via 0.2 μm filter to prevent environmental exposure.

In some embodiments, the closed system includes an ex vivo circulating system connected to the in vivo circulatory system of the subject such that blood is drawn and then circulated to the ex vivo circulatory system before being introduced back into the subject. In some embodiments, the ex vivo circulatory system includes a system or apparatus for isolating PBLs and/or a system or apparatus for isolating T cells and/or NK cells, in combination with the system or apparatus for exposing the cells to the recombinant retrovirus. In some embodiments, the closed system does not allow the T cells and/or NK cells to be exposed to air.

Such closed system methods can be performed with commercially available devices. For example, the method can be carried out in devices adapted for closed system T cell production. Such devices include a G-Rex™, a WAVE Bioreactor™, an OriGen PermaLife™ bags, and a VueLife® bags.

In some embodiments of the methods and compositions disclosed herein, genetically modified T cells and/or NK cells within a subject are exposed to a compound that binds to an in vivo control element present therein, in which the in vivo control element is a part of the genetic material introduced by the recombinant retroviruses. In some embodiments, the in vivo control element can be a riboswitch and the compound can bind the aptamer domain of the riboswitch. In some embodiments, the in vivo control element can be a molecular chaperone. In any of the embodiments disclosed herein, the compound can be a nucleoside analogue. In some embodiments, the nucleoside analogue can be a nucleoside analogue antiviral drug, wherein an antiviral drug is a compound approved by the Food and Drug Administration for antiviral treatment or a compound in an antiviral clinical trial in the United States. In illustrative embodiments, the compound can be acyclovir or penciclovir. In some embodiments, the compound can be famciclovir, the oral prodrug of penciclovir, or valaciclovir, the oral prodrug of acyclovir. Binding of the compound to the in vivo control element affects expression of the introduced genetic material and hence, propagation of genetically modified T cells and/or NK cells.

In some embodiments, the nucleoside analogue antiviral drug or prodrug, for example acyclovir, valaciclovir, penciclovir or famciclovir, is administered to the subject prior to, concurrent with, and/or following PBLs being isolated from the blood of the subject and before T cells and/or NK cells are contacted with a recombinant retrovirus. In some embodiments, the nucleoside analogue antiviral drug or prodrug is administered to the subject for between 5, 10, 15, 30, and 60 minutes on the low end of the range and 1.5, 2, 3, 4, 5, 6, 8, 12, or 24 hours on the high end of the range prior to PBLs being isolated from the blood or prior to T cells and/or NK cells being contacted with a recombinant retrovirus. In other embodiments, the nucleoside analogue antiviral drug or prodrug is administered to the subject for between 1.5, 2, 3, 4, 5, 6, 8, 12, or 24 hours on the low end of the range and ½, 1, 2, 3, 4, 5, 6, 7, 10, 14, 21, or 28 days on the high end of the range after PBLs are isolated from the blood and T cells and/or NK cells are contacted with a recombinant retrovirus in methods provided herein. In some embodiments, the nucleoside analogue antiviral drug or prodrug is administered to the subject for at least 1.5, 2, 3, 4, 5, 6, 8, 12, or 24 hours, or at least 2, 3, 4, 5, 6, 7, 10, 14, 21, or 28 days after PBLs are isolated from the blood and T cells and/or NK cells are contacted with a recombinant retrovirus in methods provided herein. In some embodiments, the nucleoside analogue antiviral drug or prodrug is administered to the subject for at least 1, 2, 3, 4, 5, 7, 10, 14, 21, 28, 30, 60, 90, or 120 days or 5, 6, 9, 12, 24, 36, 48, 60, 72, 84, 96, 120 months or indefinitely after the PBLs have been reinfused into the subject. In any of the embodiments disclosed herein, the nucleoside analogue antiviral drug or prodrug can be administered before and/or during the reinfusion of the PBLs and/or after the PBLs have been reinfused.

In some embodiments, the compound that binds to the in vivo control element is administered once, twice, three times, or four times daily to the subject. In some embodiments, daily doses of the compound are provided for 1 week, 2 weeks, 4 weeks, 3 months, 6 months, 1 year, until a subject is disease free, such as cancer free, or indefinitely. The drug, in illustrative embodiments is a nucleoside analogue antiviral drug that binds to a nucleoside analog, such as a riboswitch, as disclosed in further detail herein.

Methods are known in the art for delivering drugs, whether small molecules or biologics, and can be used in methods provided herein. Any such methods can be used to deliver drugs or candidate compounds or antibodies for use in methods of the present invention. For example, common routes of administration include non-invasive peroral (through the mouth), topical (skin), transmucosal (nasal, buccal/sublingual, vaginal, ocular and rectal) and inhalation routes. Many protein and peptide drugs, such as monoclonal antibodies, have to be delivered by injection or a nanoneedle array. For example, many immunizations are based on the delivery of protein drugs and are often done by injection.

Engineered Signaling Polypeptide(s)

In some embodiments, the recombinant retroviruses used to contact T cells and/or NK cells have a polynucleotide having one or more transcriptional units that encode one or more engineered signaling polypeptides, one or more of which includes a lymphoproliferative element. In some embodiments, a signaling polypeptide includes any combination of the following: an extracellular antigen-binding domain (or antigen-specific targeting region or ASTR), a stalk, a transmembrane domain, an intracellular activating domain, a lymphoproliferative element, a modulatory domain (such as a co-stimulatory domain), and a T cell survival motif. In illustrative embodiments, at least one, two, or all of the engineered signaling polypeptides is a CAR. In some embodiments, when two signaling polypeptides are utilized, one encodes a lymphoproliferative element and the other encodes a chimeric antigen receptor (CAR) that includes an antigen-specific targeting region (ASTR), a transmembrane domain, and an intracellular activating domain. In other embodiments, a CAR can include a lymphoproliferative element fused to an antigen-specific targeting region. In other embodiments, when the lymphoproliferative element is a constitutively active interleukin receptor, such as a known variant of IL-7Rα, no antigen-specific targeting region is needed because binding is not dependent on the presence of the ligand. One of ordinary skill in the art would be able to reconfigure the system to put the lymphoproliferative element and the CAR on distinct polynucleotides with similar or dissimilar control elements for the methods and compositions disclosed herein. A skilled artisan will recognize that such engineered polypeptides can also be referred to as recombinant polypeptides.

Antigen-Specific Targeting Region

In some embodiments, an engineered signaling polypeptide includes a member of a specific binding pair, which is typically an ASTR, sometimes called an antigen binding domain herein. Specific binding pairs include, but are not limited to, antigen-antibody binding pairs; ligand-receptor binding pairs; and the like. Thus, a member of a specific binding pair suitable for use in an engineered signaling polypeptide of the present disclosure includes an ASTR that is an antibody, an antigen, a ligand, a receptor binding domain of a ligand, a receptor, a ligand binding domain of a receptor, and an affibody.

An ASTR suitable for use in an engineered signaling polypeptide of the present disclosure can be any antigen-binding polypeptide. In certain embodiments, the ASTR is an antibody such as a full-length antibody, a single-chain antibody, an Fab fragment, an Fab' fragment, an (Fab')2 fragment, an Fv fragment, and a divalent single-chain antibody or a diabody.

In some embodiments, the ASTR is a single chain Fv (scFv). In some embodiments, the heavy chain is positioned N-terminal of the light chain in the engineered signaling polypeptide. In other embodiments, the light chain is positioned N-terminal of the heavy chain in the engineered signaling polypeptide. In any of the disclosed embodiments, the heavy and light chains can be separated by a linker as discussed in more detail herein. In any of the disclosed embodiments, the heavy or light chain can be at the N-terminus of the engineered signaling polypeptide and is typically C-terminal of another domain, such as a signal sequence or peptide.

Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use with the engineered signaling polypeptides and methods using the engineered signaling polypeptides of the present disclosure. In some instances, T cell receptor (TCR) based recognition domains such as single chain TCR (scTv, single chain two-domain TCR containing VαVβ) are also suitable for use.

In some embodiments, the ASTR can be multispecific, e.g. bispecific antibodies. Multispecific antibodies have binding specificities for at least two different sites. In certain embodiments, one of the binding specificities is for one target antigen and the other is for another target antigen. In certain embodiments, bispecific antibodies may bind to two different epitopes of to target antigen. Bispecific antibodies may also be used to localize cytotoxic agents to cells which express a target antigen. Bispecific antibodies can be prepared as full length antibodies or antibody fragments.

An ASTR suitable for use in an engineered signaling polypeptide of the present disclosure can have a variety of antigen-binding specificities. In some cases, the antigen-binding domain is specific for an epitope present in an antigen that is expressed by (synthesized by) a target cell. In one example, the target cell is a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Non-limiting examples of antigens to which an ASTR of an engineered signaling polypeptide can bind include, e.g., CD19, CD20, CD38, CD30, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, Axl, Ror2, and the like.

In some cases, a member of a specific binding pair suitable for use in an engineered signaling polypeptide is an ASTR that is a ligand for a receptor. Ligands include, but are not limited to, cytokines (e.g., IL-13, etc.); growth factors (e.g., heregulin; vascular endothelial growth factor (VEGF); and the like); an integrin-binding peptide (e.g., a peptide comprising the sequence Arg-Gly-Asp); and the like.

Where the member of a specific binding pair in an engineered signaling polypeptide is a ligand, the engineered signaling polypeptide can be activated in the presence of a second member of the specific binding pair, where the second member of the specific binding pair is a receptor for the ligand. For example, where the ligand is VEGF, the second member of the specific binding pair can be a VEGF receptor, including a soluble VEGF receptor.

As noted above, in some cases, the member of a specific binding pair that is included in an engineered signaling polypeptide is an ASTR that is a receptor, e.g., a receptor for a ligand, a co-receptor, etc. The receptor can be a ligand-binding fragment of a receptor. Suitable receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an IL-2 receptor; etc.); CD27; a natural cytotoxicity receptor (NCR) (e.g., NKP30 (NCR3/CD337) polypeptide (receptor for HLA-B-associated transcript 3 (BAT3) and B7-H6); etc.); etc.

Stalk

In some embodiments, the engineered signaling polypeptide includes a stalk which is located in the portion of the engineered signaling polypeptide lying outside the cell and interposed between the ASTR and the transmembrane domain. In some cases, the stalk has at least 85, 90, 95, 96, 97, 98, 99, or 100% identity to a wild-type CD8 stalk region (TTTPAPRPPTPAPTIASQPLSLRPEACRPAAGG AVHTRGLDFA (SEQ ID NO:79), has at least 85, 90, 95, 96, 97, 98, 99, or 100% identity to a wild-type CD28 stalk region (FCKIEVMYPPPYLDNEKSNGTIIHVKGKHL-CPSPLFPGPSKP (SEQ ID NO:80)), or has at least 85, 90, 95, 96, 97, 98, 99, or 100% identity to a wild-type immunoglobulin heavy chain stalk region. In an engineered signaling polypeptide, the stalk employed allows the antigen-specific targeting region, and typically the entire engineered signaling polypeptide, to retain increased binding to a target antigen.

The stalk region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

In some cases, the stalk of an engineered signaling polypeptide includes at least one cysteine. For example, in some cases, the stalk can include the sequence Cys-Pro-Pro-Cys (SEQ ID NO:62). If present, a cysteine in the stalk of a first engineered signaling polypeptide can be available to form a disulfide bond with a stalk in a second engineered signaling polypeptide.

Stalks can include immunoglobulin hinge region amino acid sequences that are known in the art; see, e.g., Tan et al. (1990) *Proc. Natl. Acad. Sci. USA* 87:162; and Huck et al. (1986) *Nucl. Acids Res.* 14:1779. As non-limiting examples, an immunoglobulin hinge region can include a domain with at least 50, 60, 70, 75, 80, 85, 90, 95, 96, 97, 98, 99 or 100% sequence identity to a stretch of at least 10, 15, 20, or all of the amino acids of any of the following amino acid sequences: DKTHT (SEQ ID NO:63); CPPC (SEQ ID NO:62); CPEPKSCDTPPPCPR (SEQ ID NO:64) (see, e.g., Glaser et al. (2005) J. Biol. Chem. 280:41494); ELKTPL-GDTTHT (SEQ ID NO:65); KSCDKTHTCP (SEQ ID NO:66); KCCVDCP (SEQ ID NO:67); KYGPPCP (SEQ ID NO:68); EPKSCDKTHTCPPCP (SEQ ID NO:69) (human IgG1 hinge); ERKCCVECPPCP (SEQ ID NO:70) (human IgG2 hinge); ELKTPLGDTTHTCPRCP (SEQ ID NO:71) (human IgG3 hinge); SPNMVPHAHHAQ (SEQ ID NO:72) (human IgG4 hinge); and the like. The stalk can include a hinge region with an amino acid sequence of a human IgG1, IgG2, IgG3, or IgG4, hinge region. The stalk can include one or more amino acid substitutions and/or insertions and/or deletions compared to a wild-type (naturally-occurring) hinge region. For example, His229 of human IgG 1 hinge can be substituted with Tyr, so that the stalk includes the sequence EPKSCDKTYTCPPCP (see, e.g., Yan et al. (2012) *J. Biol. Chem.* 287:5891). The stalk can include an amino acid sequence derived from human CD8; e.g., the stalk can include the amino acid sequence: TTTPAPRPPTPAPTIA-SQPLSLRPEACRPAAGGAVHTRGLDFACD (SEQ ID NO:73), or a variant thereof.

Transmembrane Domain

An engineered signaling polypeptide of the present disclosure can include transmembrane domains for insertion into a eukaryotic cell membrane. The transmembrane domain can be interposed between the ASTR and the co-stimulatory domain. The transmembrane domain can be interposed between the stalk and the co-stimulatory domain, such that the chimeric antigen receptor includes, in order from the amino terminus (N-terminus) to the carboxyl terminus (C-terminus): an ASTR; a stalk; a transmembrane domain; and an activating domain.

Any transmembrane (TM) domain that provides for insertion of a polypeptide into the cell membrane of a eukaryotic (e.g., mammalian) cell is suitable for use in aspects and embodiments disclosed herein. Non-limiting examples of TM domains suitable for any of the aspects or embodiments provided herein, include a domain with at least 50, 60, 70, 75, 80, 85, 90, 95, 96, 97, 98, 99 or 100% sequence identity to a stretch of at least 10, 15, 20, or all of the amino acids of any of the following TM domains: a) CD* alpha (IYI-WAPLAGTCGVLLLSLVITLYC (SEQ ID NO:46)); b) CD8 beta (LGLLVAGVLVLLVSLGVAIHLCC (SEQ ID NO:47)); c) CD4 (ALIVLGGVAGLLLFIGLGIFFCVRC (SEQ ID NO:48)); d) CD3Z (LCYLLDGILFIYGVILTAL-FLRV (SEQ ID NO:49); e) CD28 (FWVLVVVGGVLA-CYSLLVTVAFIIFWV (SEQ ID NO:50)); f) CD134 (OX40): (VAAILGLGLVLGLLGPLAILLALYLL (SEQ ID NO:51)); g) CD7 (ALPAALAVISFLLGLGLGVACVLA (SEQ ID NO:52)), h) CD8 TTTPAPRPPTPAPTIASQPLSL-RPEACRPAAGGAVHTRGLDFACDIYIWAPLAGTCGV-LLLSLVITL YC (SEQ ID NO:75), and i) CD28 IEVMYP-PPYLDNEKSNGTIIHVKGKHLCPSPLFPGPSKPFWV-LVVVGGVLACYSLLVTVAFIIFWV (SEQ ID NO:76).

As non-limiting examples, a transmembrane domain of an aspect of the invention can have at least 80, 90, or 95% sequence identity to the SEQ ID NO:46 transmembrane domain, the CD8 beta transmembrane domain, the CD4 transmembrane domain, the CD3 zeta transmembrane domain, the CD28 transmembrane domain, the CD134 transmembrane domain, or the CD7 transmembrane domain.

Intracellular Activating Domain

Intracellular activating domains suitable for use in an engineered signaling polypeptide of the present disclosure when activated, typically induce the production of one or more cytokines; increased cell death; and/or increased proliferation of $CD8^+$ T cells, $CD4^+$ T cells, natural killer T cells, γδ T cells, and/or neutrophils. Activating domains can also be referred to as activation domains herein.

In some embodiments, the intracellular activating domain includes at least one (e.g., one, two, three, four, five, six, etc.) ITAM motifs as described below. In some embodiments, the intracellular activating domain includes DAP10/CD28 type signaling chains. In some embodiments, the intracellular activating domain is not covalently attached to the membrane bound engineered signaling polypeptide, but is instead diffused in the cytoplasm. As non-limiting examples, an intracellular activating domain of an aspect of the invention can have at least 80%, 90%, or 95% sequence identity to the CD3Z, CD3D, CD3E, CD3G, CD79A, DAP12, FCERIG, DAP10/CD28, or ZAP70 domains as described below.

Intracellular activating domains suitable for use in an engineered signaling polypeptide of the present disclosure include immunoreceptor tyrosine-based activation motif (ITAM)-containing intracellular signaling polypeptides. An ITAM motif is $YX_1X_2L/I$, where $X_1$ and $X_2$ are independently any amino acid. In some cases, the intracellular activating domain of an engineered signaling polypeptide includes 1, 2, 3, 4, or 5 ITAM motifs. In some cases, an ITAM motif is repeated twice in an intracellular activating domain, where the first and second instances of the ITAM motif are separated from one another by 6 to 8 amino acids, e.g., $(YX_1X_2L/I)(X_3)_n(YX_1X_2L/I)$, where n is an integer from 6 to 8, and each of the 6-8 $X_3$ can be any amino acid. In some cases, the intracellular activating domain of an engineered signaling polypeptide includes 3 ITAM motifs.

A suitable intracellular activating domain can be an ITAM motif-containing portion that is derived from a polypeptide that contains an ITAM motif. For example, a suitable intracellular activating domain can be an ITAM motif-containing domain from any ITAM motif-containing protein. Thus, a suitable intracellular activating domain need not contain the entire sequence of the entire protein from which it is derived. Examples of suitable ITAM motif-containing polypeptides include, but are not limited to: CD3Z (CD3 zeta); CD3D (CD3 delta); CD3E (CD3 epsilon); CD3G (CD3 gamma); CD79A (antigen receptor complex-associated protein alpha chain); DAP12; and FCERIG (Fc epsilon receptor I gamma chain).

In some cases, the intracellular activating domain is derived from T cell surface glycoprotein CD3 zeta chain (also known as CD3Z, T cell receptor T3 zeta chain, CD247, CD3-ZETA, CD3H, CD3Q, T3Z, TCRZ, etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms): MKWKALFTAAILQAQLPITEAQSFGLLDPKLCYLLDGILFIYGVILTALFLRVKFSRSADAPAYQQ GQNQL YNELNLGRREEYDVLDKRRGRDPEMGGKPRRKN-PQEGLYNELQKDKMAEAYSEIGM KGERRRGKGH-DGLYQGLSTATKDTYDALHMQALPPR (SEQ ID NO:11) or MKWKALFTAAILQAQLPITEAQSFGLLDP-KLCYLLDGILFIYGVILTALFLRVKFSRSADAPAYQQ GQNQLYNELNLGRREEYDVLDKRRGRDPEMGG-KPQRRKNPQEGLYNELQKDKMAEAYSEIG MKGER-RRGKGHDGLYQGLSTATKDTYDALHMQALPPR (SEQ ID NO:12), where the ITAM motifs are in bold and are underlined.

Likewise, a suitable intracellular activating domain polypeptide can include an ITAM motif-containing a portion of the full length CD3 zeta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: RVKFSRSADAPAYQQGQNQL YNELNLGRREEYDVLDKRRGRDPEMGGKPR- RKN-PQEGLYNELQKDKMAEAYSEIGMKGERRRGKGH-DGLYQGLSTATKDTYDALHMQALPPR (SEQ ID NO:13); RVKFSRSADAPAYQQGQNQLYNELNLG-RREEYDVLDKRRGRDPEMGGKPQRRKNPQEGLYNE LQKDKMAEAYSEIGMKGERRRGKGHDGLYQGLS-TATKDTYDALHMQALPPR (SEQ ID NO:81); NQL YNELNLGRREEYDVLDKR SEQ ID NO:14); EGL YNELQKDKMAEAYSEIGMK (SEQ ID NO:15); or DGL YQGLSTATKDTYDALHMQ (SEQ ID NO:16), where the ITAM motifs are in bold and are underlined.

In some cases, the intracellular activating domain is derived from T cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T cell receptor T3 delta chain; T cell surface glycoprotein CD3 delta chain; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MEHSTFLSGLVLATLLSQVSP-FKIPIEELEDRVFVNCNTSITWVEGTVGTLLSDITRLD-LGKRILDP RGIYRCNGTDIYKDKESTVQVHYRMC-QSCVELDPATVAGIIVTDVIATLLLALGVFCFAGHETGR LSGAADTQALLRNDQVYQPLRDRDDAQYSHLGG-NWARNK (SEQ ID NO:17) or MEHSTFLSGLV-LATLLSQVSPFKIPIEELEDRVFVNCNTSITWVEGT-VGTLLSDITRLDLGKRILDP RGIYRCNGTDIYKD-KESTVQVHYRTADTQALLRNDQVYQPLRDRDDAQ YSHLGGNWARNK (SEQ ID NO:18), where the ITAM motifs are in bold and are underlined.

Likewise, a suitable intracellular activating domain polypeptide can comprise an ITAM motif-containing portion of the full length CD3 delta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQVYQPLRDRDDAQYSHLGGN (SEQ ID NO:19), where the ITAM motifs are in bold and are underlined.

In some cases, the intracellular activating domain is derived from T cell surface glycoprotein CD3 epsilon chain (also known as CD3e, T cell surface antigen T3/Leu-4 epsilon chain, T cell surface glycoprotein CD3 epsilon chain, AI504783, CD3, CD3epsilon, T3e, etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa of the following amino acid sequence: MQSGTHWRVLGLCLLSVGVWGQDGNEE-MGGITQTPYKVSISGTTVILTCPQYPGSEILWQHNDK NIGGDEDDKNIGSDEDHLSLKEFSELEQSGYYVCY-PRGSKPEDANFYLYLRARVCENCMEMDMS VATIVIVDICITGGLLLLVYYWSKNRKAKAKPVTR-GAGAGGRQRGQNKERPPPVPNPD<u>YEPI</u>RK GQRDL <u>YSGL</u>NQRRI (SEQ ID NO:20), where the ITAM motifs are in bold and are underlined.

Likewise, a suitable intracellular activating domain polypeptide can comprise an ITAM motif-containing portion of the full length CD3 epsilon amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: NPD<u>YEPI</u>RKGQRDL<u>YSGL</u>NQR (SEQ ID NO:21), where the ITAM motifs are in bold and are underlined.

In some cases, the intracellular activating domain is derived from T cell surface glycoprotein CD3 gamma chain (also known as CD3G, T cell receptor T3 gamma chain, CD3-GAMMA, T3G, gamma polypeptide (TiT3 complex), etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence: MEQGKGLAVLILAIILLQGTLAQSIKGN-HLVKVYDYQEDGSVLLTCDAEAKNITWFKDGK-MIGF LTEDKKKWNLGSNAKDPRGMYQCKGSQNK-SKPLQVYYRMCQNCIELNAATISGFLFAEIVSIFV LAVGVYFIAGQDGVRQSRASDKQTLLPNDQLYQ-PLKDREDDQYSHLQGNQLRRN (SEQ ID NO:22), where the ITAM motifs are in bold and are underlined.

Likewise, a suitable intracellular activating domain polypeptide can comprise an ITAM motif-containing portion of the full length CD3 gamma amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQL<u>YQPL</u>KDREDDQ<u>YSHL</u>QGN (SEQ ID NO:23), where the ITAM motifs are in bold and are underlined.

In some cases, the intracellular activating domain is derived from CD79A (also known as B-cell antigen receptor complex-associated protein alpha chain; CD79a antigen (immunoglobulin-associated alpha); MB-1 membrane glycoprotein; Ig-alpha; membrane-bound immunoglobulin-associated protein; surface IgM-associated protein; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences: MPGGPGVLQALPATIFLLFLL-SAVYLGPGCQALWMHKVPASLMVSLGEDAH-FQCPHNSSNNAN VTWWRVLHGNYTWPPEFLG-PGEDPNGTLIIQNVNKSHGGIYVCRVQEGNESYQQS-CGTYLRVR QPPPRPFLDMGEGTKNRIITAEGIILLF-CAVVPGTLLLFRKRWQNEKLGLDAGDEYEDENL <u>YEGL</u> NLDDCSM<u>YEDI</u>SRGLQGTYQDVGSLNIGD-VQLEKP (SEQ ID NO:24) or MPGGPGVLQALPATIFLL-FLLSAVYLGPGCQALWMHKVPASLMVSLGEDAH-FQCPHNSSNNAN VTWWRVLHGNYTWPPEFLG-PGEDPNEPPPRPFLDMGEGTKNRIITAEGIILLFCAVV-PGTLLLFRK RWQNEKLGLDAGDEYEDENLYEGLN-LDDCSMYEDISRGLQGTYQDVGSLNIGDVQLEKP (SEQ ID NO:25), where the ITAM motifs are in bold and are underlined.

Likewise, a suitable intracellular activating domain polypeptide can comprise an ITAM motif-containing portion of the full length CD79A amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ENL<u>YEGL</u>NLDDCSM<u>YEDI</u>SRG (SEQ ID NO:26), where the ITAM motifs are in bold and are underlined.

In some cases, the intracellular activating domain is derived from DAP12 (also known as TYROBP; TYRO protein tyrosine kinase binding protein; KARAP; PLOSL; DNAX-activation protein 12; KAR-associated protein; TYRO protein tyrosine kinase- binding protein; killer activating receptor associated protein; killer-activating receptor- associated protein; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (4 isoforms): MGGLEPCSRLLLLPLLLAVSGL-RPVQAQAQSDCSCSTVSPGVLAGIVMGDLVLTVLIA-LAVYFLG RLVPRGRGAAEAATRKQRITETESP <u>YQEL</u>QGQRSDV<u>YSDL</u>NTQRPYYK (SEQ ID NO:27), MGGLEPCSRLLLLPLLLAVSGLRPVQAQAQSDCSC-STVSPGVLAGIVMGDLVLTVLIALAVYFLG RLVPRGRGAAEATRKQRITETESP<u>YQEL</u>QGQRSDV <u>YSDL</u>NTQ (SEQ ID NO:28), MGGLEPCSRLLLLPLL-LAVSDCSCSTVSPGVLAGIVMGDLVLTVLIALAVYFL-GRLVPRGRGAAE AATRKQRITETESP<u>YQEL</u>QGQR-SDV<u>YSDL</u>NTQRPYYK (SEQ ID NO:29), or MGGLEPC-SRLLLLPLLLAVSDCSCSTVSPGVLAGIVMGDLVLTV-LIALAVYFLGRLVPRGRGAAE ATRKQRITETESP <u>YQEL</u>QGQRSDV<u>YSDL</u>NTQRPYYK (SEQ ID NO:30), where the ITAM motifs are in bold and are underlined.

Likewise, a suitable intracellular activating domain polypeptide can comprise an ITAM motif-containing portion of the full length DAP12 amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence:

ESPYQELQGQRSDVYSDLNTQ (SEQ ID NO:31), where the ITAM motifs are in bold and are underlined.

In some cases, the intracellular activating domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 50 amino acids to about 60 amino acids (aa), from about 60 aa to about 70 aa, from about 70 aa to about 80 aa, or from about 80 aa to about 88 aa, of the following amino acid sequence: MIPAVVLLLLLLVEQAAALGEPQL-CYILDAILFLYGIVLTLLYCRLKIQVRKAAITSYEKS-DGVYTGLSTRNQETYETLKHEKPPQ (SEQ ID NO:32), where the ITAM motifs are in bold and are underlined.

Likewise, a suitable intracellular activating domain polypeptide can comprise an ITAM motif-containing portion of the full length FCER1G amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DGVYTGLSTRNQETYETLKHE (SEQ ID NO:33), where the ITAM motifs are in bold and are underlined.

Intracellular activating domains suitable for use in an engineered signaling polypeptide of the present disclosure include a DAP10/CD28 type signaling chain. An example of a DAP10 signaling chain is the amino acid sequence is: RPRRSPAQDGKVYINMPGRG (SEQ ID NO:34). In some embodiments, a suitable intracellular activating domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: RPRRSPAQDGKVYINMPGRG (SEQ ID NO:34).

An example of a CD28 signaling chain is the amino acid sequence is FWVLVVVGGVLACYSLLVTVAFIIFWVR-SKRSRLLHSDYMNMTPRRPGPTRKHYQPYAPPRDF AAYRS (SEQ ID NO:35). In some embodiments, a suitable intracellular domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence:

```
                                        (SEQ ID NO: 35)
FWVLVVVGGVLACYSLLVTVAFIIFWVRSKRSRLLHSDYMNMTPRRP
GPTRKHYQPYAPPRDFAAYRS.
```

Intracellular activating domains suitable for use in an engineered signaling polypeptide of the present disclosure include a ZAP70 polypeptide, For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 300 amino acids to about 400 amino acids, from about 400 amino acids to about 500 amino acids, or from about 500 amino acids to 619 amino acids, of the following amino acid sequence:

```
                                        (SEQ ID NO: 36)
MPDPAAHLPFFYGSISRAEAEEHLKLAGMADGLFLLRQCLRSLGGYV

LSLVHDVRFHHFPIERQLNGTYAIAGGKAHCGPAELCEFYSRDPDGL

PCNLRKPCNRPSGLEPQPGVFDCLRDAMVRDYVRQTWKLEGEALEQA

IISQAPQVEKLIATTAHERMPWYHSSLTREEAERKLYSGAQTDGKFL

LRPRKEQGTYALSLIYGKTVYHYLISQDKAGKYCIPEGTKFDTLWQL

VEYLKLKADGLIYCLKEACPNSSASNASGAAAPTLPAHPSTLTHPQR

RIDTLNSDGYTPEPARITSPDKPRPMPMDTSVYESPYSDPEELKDKK

LFLKRDNLLIADIELGCGNFGSVRQGVYRMRKKQIDVAIKVLKQGTE

KADTEEMMREAQIMHQLDNPYIVRLIGVCQAEALMLVMEMAGGGPLH

KFLVGKREEIPVSNVAELLHQVSMGMKYLEEKNFVHRDLAARNVLLV

NRHYAKISDFGLSKALGADDSYYTARSAGKWPLKWYAPECINFRKFS

SRSDVWSYGVTMWEALSYGQKPYKKMKGPEVMAFIEQGKRMECPPEC

PPELYALMSDCWIYKWEDRPDFLTVEQRMRACYYSLASKVEGPPGST

QKAEAACA.
```

Lymphoproliferative Elements

Peripheral T lymphocyte numbers are maintained at remarkably stable levels throughout adulthood, despite the continuing addition of cells, due to emigration from the thymus and proliferation in response to antigen encounter, and loss of cells owing to the removal of antigen-specific effectors after antigen clearance (Marrak, P. et al. 2000. *Nat Immunol* 1:107-111; Freitas, A. A. et al. 2000. *Annu Rev Immunol* 18:83-111). The size of the peripheral T cell compartment is regulated by multiple factors that influence both proliferation and survival. However, in a lymphopenic environment, T lymphocytes divide independently of cognate antigen, due to "acute homeostatic proliferation" mechanisms that maintain the size of the peripheral T cell compartment. Conditions for lymphopenia have been established in subjects or patients during adoptive cell therapy by proliferating T cells in vitro and introducing them into lymphodepleted subjects, resulting in enhanced engraftment and antitumor function of transferred T cells. However, lymphodepletion of a subject is not desirable because it can cause serious side effects, including immune dysfunction and death.

Studies have shown that lymphodepletion removes endogenous lymphocytes functioning as cellular sinks for homeostatic cytokines, thereby freeing cytokines to induce survival and proliferation of adoptively transferred cells. Some cytokines, such as for example, IL-7 and IL-15, are known to mediate antigen-independent proliferation of T cells and are thus capable of eliciting homeostatic proliferation in non-lymphopenic environments. However, these cytokines and their receptors have intrinsic control mechanisms that prevent lymphoproliferative disorders at homeostasis.

Many of the aspects provided herein include a lymphoproliferative element, or a nucleic acid encoding the say, typically as part of an engineered signaling polypeptide. In illustrative embodiments herein, a lymphoproliferative element is introduced into a resting T cell and/or resting NK cell, typically by transducing the resting T cell and/or resting NK cell with a retrovirus whose genome encodes the lymphoproliferative element as part of an engineered signaling polypeptide. The lymphoproliferative element can be a cytokine or in further illustrative embodiments, a cytokine receptor, or a fragment that includes a signaling domain thereof, that activates a STAT3 pathway, a STAT4 pathway, or in even further illustrative embodiments, a Jak/STAT5 pathway. As such, a lymphoproliferative element, can be, in a non-limiting example, a cytokine receptor, or active fragment that includes a signaling domain thereof, such as an interleukin receptor, or an active fragment that includes a signaling domain thereof, that activates STAT5. Thus, a lymphoproliferative element is a polypeptide that induces proliferation of a T cell and/or NK cell. Illustrative lymphoproliferative elements induce proliferation by activating STAT5. Thus, fragments of such lymphoproliferative elements retain the ability to induce proliferation of T cells and/or NK cells, in illustrative embodiments, by activating STAT5.

In some of the methods and compositions presented herein, a lymphoproliferative element is used to promote proliferation or expansion of genetically modified T cells in vivo without having to lymphodeplete subjects. As such, non-limiting illustrative embodiments of methods provided herein that include inserting a lymphoproliferative element into a resting T cell and/or NK cell of a subject, typically by transducing such T cell and/or NK cell can be performed without lymphodepleting the subject before, during and/or after performing the method, or without lymphodepleting the subject before, during and/or after collecting blood from a subject before performing such method, or without lymphodepleting the subject before, during, and/or after genetically modifying T cells or NK cells ex vivo from the subject, and/or before, during, or after reintroducing the genetically modified T cells and/or NK cells into the subject. Factors that promote proliferation of T cells in vivo include cytokines and their receptors, in which a receptor typically includes a ligand binding domain and a signaling domain. In some embodiments, the lymphoproliferative element used in the methods and compositions disclosed herein is a cytokine and/or a cytokine receptor. The cytokine can be an interleukin, and the cytokine receptor can be an interleukin receptor. The lymphoproliferative element can be a functional fragment of a cytokine and/or a functional fragment of a cytokine receptor, such as a signaling domain thereof, wherein the fragment is capable of promoting proliferation of T cells, for example by activating STAT5.

In some embodiments, the cytokine lymphoproliferative element in the methods and compositions herein include one or more of the following: Interleukin-7 (IL-7) or its receptor (IL-7R), or a signaling domain thereof; Interleukin-12 (IL-12) or its receptor (IL-12R), or a signaling domain thereof; Interleukin-23 (IL-23) or its receptor composed of IL-12R β1 and IL-23R, or a signaling domain thereof; Interleukin-27 (IL-27) or its receptor (IL-27R), or a signaling domain thereof; Interleukin-15 (IL-15) or its receptor (IL-15R), or a signaling domain thereof; Interleukin-21 (IL-21) or its receptor (IL-21R), or a signaling domain thereof; or transforming growth factor β (TGFβ) or its receptor (TGFβR) or a signaling domain thereof; or the TGFβ decoy receptor (TGF-β-dominant-negative receptor II (DNRII)). In some embodiments, the lymphoproliferative element is the IL-12R or the TGFβ decoy receptor (TGF-β-dominant-negative receptor II (DNRII)).

IL-7 binds to the IL-7 receptor, a heterodimer consisting of IL-7R alpha and common gamma chain receptor. Binding results in a cascade of signals important for T cell development within the thymus and survival within the periphery. Binding of IL-7 to the IL-7 receptor is known to activate the Jak/STAT5 pathway.

IL-12 is involved in the differentiation of naïve T cells into Th1 cells (Hsieh C S et al. 1993. *Science*. 260(5107): 547-9) and is known as a T cell-stimulating factor. IL-12 binds to the IL-12 receptor, which is a heterodimeric receptor formed by IL-12R-β1 and IL-12R-β2. IL12 can act by activating STAT4, but has been shown to activate STAT5 in T cells as well (Ahn, H., et al. 1998. *J. Immun*. 161:5893-5900). The IL-12 family is composed of the cytokines IL-12, IL-23, and IL-27. The receptor for IL-23 is composed of IL-12R β1 and IL-23R. IL-27 is a heterodimeric cytokine that is composed of two distinct genes, Epstein-Barr virus-induced gene 3(EBI3) and IL-27p28. IL-27 interacts with IL-27 receptor.

IL-15 is a T and NK cell stimulatory factor that is similar in structure and function to IL-2. Both cytokines induce proliferation of T cells; and their shared functions are thought to result from both receptors using the IL-2/IL-15R13 and common γ chains. Signaling pathway of IL-15 begins with binding to IL-15Rα receptor, with subsequent presentation to surrounding cells bearing IL-15Rβγc complex on their cell surface. Upon binding IL-15β subunit activates Janus kinase 1 (Jak1) and γc subunit Janus kinase 3 (Jak3), which leads to phosphorylation and activation of STAT3 and STAT5.

IL-21 is expressed in activated human $CD4^+$ T cells and in NK T cells, and IL-21 expression is up-regulated in Th2 and Th17 subsets of T helper cells. The IL-21 receptor (IL-21R) is expressed on the surface of T, B and NK cells and is similar in structure to the receptors for other type I cytokines like IL-2R or IL-15. IL-21R requires dimerization with the common gamma chain (γc) in order to bind IL-21. When bound to IL-21, the IL-21 receptor acts through the Jak/STAT pathway, activating STAT1, STAT3, and STAT5.

TGFβ decoy receptors (TGF-β-dominant-negative receptor II (DNRII)) block TGFβ signaling by competing with the natural receptors for TGFβ binding. TGFβ-DNRII is a kinase-dead truncated form of RII that contains the extracellular TGFβ binding domain and the transmembrane domain of RII. TGFβ-DNRII binds the ligand but does not phosphorylate and activate RI, which thereby diminishes or eliminates Smad phosphorylation.

Gain-of-function mutations in IL-7Rα have been identified in subjects with B and T cell acute lymphoblastic leukemias (B-ALL and T-ALL) (Zenatti P P, et al. 2011. *Nat Genet* 43:932-939; Snochat, C. et al. 2011. *J Exp Med* 208:901-908; McElroy, C. A. et al. 2012. *PNAS* 109(7): 2503-2508). The mutations included insertions and deletions in the N-terminal region of the IL-7Rα TMD, with nearly all of the sequences containing an extra Cys residue, and an S165-to-C165 mutation. The cysteine resulted in constitutive activation of the receptor. Some of the mutations in the T-all group activated JAK1. These gain-of-function IL-7R mutants can be used in any of the aspects provided herein as one of the lymphoproliferative element(s).

Accordingly, in some embodiments, the lymphoproliferative element is a mutated IL-7 receptor. In other embodiments, the mutated IL-7 receptor is constitutively active, activating the JAK-STAT5 pathway in the absence of the cytokine ligand. In still other embodiments, the mutated IL-7 receptor comprises a 1 to 10 amino acid insertion at a position between 237 and 254 that includes a cysteine residue that includes the ability to constitutively activate the STAT5 pathway. In some embodiments, the mutated IL-7 receptor is IL-7Rα-insPPCL (represented by SEQ ID NO:82).

In some embodiments, the lymphoproliferative element is a chimeric cytokine receptor such as but not limited to a cytokine tethered to its receptor that typically constitutively activates the same STAT pathway as a corresponding activated wild-type cytokine receptor such as STAT3, STAT4, and in illustrative embodiments, STAT5. In some embodiments, the chimeric cytokine receptor is an interleukin, or a fragment thereof, tethered to or covalently attached to its cognate receptor, or a fragment thereof, via a linker. In some embodiments, the chimeric cytokine receptor is IL-7 tethered to IL-7Rα. In other embodiments, the chimeric cytokine receptor is IL-7 tethered to a domain of IL-7Rα, such as for example, the extracellular domain of IL-7Rα and/or the transmembrane domain of IL-7Rα. In some embodiments, the lymphoproliferative element is a cytokine receptor that is not tethered to a cytokine, and in fact in illustrative embodiments, provided herein a lymphoproliferative element is a constitutively active cytokine receptor that is not tethered to a cytokine. These chimeric IL-7 receptors typically constitutively activate STAT5 when expressed.

In some embodiments, the lymphoproliferative element is not a cytokine or a cytokine receptor but is a miRNA that stimulates the STAT5 pathway typically by potentiating activation of STAT5 by degrading a negative regulator in the SOCS pathway. In some embodiments, the miRNA is to proteins that affect proliferation such as but not limited to ABCG1, SOCS1, TGFbR2, SMAD2, cCBL, and PD1. In illustrative embodiments, as exemplified herein, such miRNAs can be located in introns in a packaging cells and/or a recombinant retrovirus genome, typically with expression driven by a promoter that is active in a T cell and/or NK cell. Not to be limited by theory, inclusion of introns in transcription units are believed to result in higher expression and/or stability of transcripts. As such, the ability to place miRNAs within introns of a retroviral genome adds to the teachings of the present disclosure that overcome challenges in the prior art of trying to get maximum activities into the size restrictions of a retroviral, such as a lentivirus genome. In some embodiments, 1, 2, 3, 4, 5, 6, 7, 8, 9, or 10 miRNAs, in illustrative embodiments between 2 and 5, for example 4 miRNAs, one or more of which each bind nucleic acids encoding one or more of ABCG1, SOCS1, TGFbR2, SMAD2, cCBL, and PD1, can be included in the recombinant retroviral genome and delivered to a target cell, for example T cells and/or NK cells, using methods provided herein. In fact, as provided herein 1, 2, 3, or 4 miRNAs can be delivered in a single intron such as the EF1a intron.

ABCG1 is an ATP-binding cassette transporter that negatively regulates thymocyte and peripheral lymphocyte proliferation (Armstrong et al. 2010. *J Immunol* 184(1):173-183).

SOCS1 is a member of the SOCS (Suppressor of cytokine signaling) family of negative regulators of cytokine signal transduction that inhibit the Jak/Stat pathway such as STAT5. SOCS1 is also known as JAB (Janus Kinase binding protein), SSI-1 (Stat-induced Stat inhibitor-1), and TIP3 (Tec-interacting protein).

TGFbR2 is a member of the serine/threonine protein kinase family that binds TGF-β, forming a complex that phosphorylates proteins that then enter the nucleus and regulate transcription of genes related to proliferation.

SMAD2 mediates the signal of the transforming growth factor (TGF)-β and regulates multiple cellular processes, such as cell proliferation, apoptosis, and differentiation.

cCBL is an E3 ubiquitin ligase that inhibits TCR signaling by dephosphorylation and inactivation of ZAP-70 and through internalization of the TCR.

PD1 (CD279) is a cell surface receptor expressed on T cells and ProB cells. PD-1 binds two ligands, PD-L1 and PD-L2. Signaling through PD-1 functions to prevent activation of cells.

In some of the methods and compositions disclosed herein, expression of the lymphoproliferative element is induced by and can even dependent on binding of a compound to an in vivo control element (as discussed elsewhere herein), which in non-limiting embodiments is a ribowsitch. In some embodiments, the lymphoproliferative element is expressed from a promoter active in a T cell and/or an NK cell. For methods and compositions provided herein, a skilled artisan will recognize that promoters are known that are active in T cells and/or NK cells and can be used to express a first engineered signaling polypeptide or a second engineered signaling polypeptide, or any component thereof. In illustrative embodiments, such a promoter is not active in a packaging cell line, such as the packaging lines disclosed herein. In some embodiments, the promoter is the EF1a promoter or the murine stem cell virus (MSCV) promoter (Jones et al., *Human Gene Therapy* (2009) 20: 630-40). In illustrative embodiments, the promoter is the T cell specific CD3 zeta promoter.

In some embodiments, the lymphoproliferative element is microenvironment restricted. For example, the lymphoproliferative element can be a mutated receptor that binds its respective cytokine differentially in aberrant versus physiological conditions. For example, an IL-7R that can bind IL7 more strongly in a tumor environment than in a normal physiological environment can be used.

In some embodiments, the lymphoproliferative element is fused to a recognition or elimination domain Such recognition or elimination domains are disclosed in more detail herein. Such fusion provides the advantage, especially when a truncated or other mutated lymphoproliferative element is used, of requiring less polynucleotides in the retroviral genome. This is important in illustrative embodiments provided herein, because it helps to permit more nucleic acids encoding functional elements to be included in the retroviral genome. In other embodiments, the lymphoproliferative element is fused to a co-stimulatory domain and/or an intracellular activating domain. A lymphoproliferative element as disclosed herein, is not a chimeric antigen receptor (CAR) or an intracellular activating domain or co-stimulating domain thereof. However, in some embodiments, a lymphoproliferative element can be fused to an antigen-specific targeting region (ASTR) and activated by binding of the ASTR to its antigen. In still other embodiments, an engineered signaling polypeptide can include an ASTR, an intracellular activation domain (such as a CD3 zeta signaling domain), a co-stimulatory domain, and a lymphoproliferative domain. Further details regarding co-stimulatory domains, intracellular activating domains, ASTRs and other CAR domains, are disclosed elsewhere herein.

In illustrative embodiments herein, a T cell and/or NK cell survival element is introduced into a resting T cell and/or resting NK cell, typically by transducing the resting T cell and/or resting NK cell with a retrovirus whose genome encodes the T cell and/or NK cell survival element as part of an engineered signaling polypeptide. In some embodiments, a lymphoproliferative element is also a T cell and/or NK cell survival element. As discussed above, some of the lymphoproliferative elements not only promote proliferation, but they promote cell survival as well. In some embodiments, the T cell and/or NK survival motif is not a lymphoproliferative element. For example, the T cell and/or NK cell survival motif can be a CD28 T cell survival motif or a CD137 cell survival motif. Such T cell survival motifs can be found on engineered signaling polypeptides that include an ASTR, such as an scFV. In an illustrative embodiment, the T cell survival motif is a CD28 T cell survival motif or a CD137 motif connected to an scFv through a CD8a transmembrane domain or a CD28 transmembrane domain. In certain embodiments, said intracellular signaling domain comprises a polypeptide sequence comprising an immunoreceptor tyrosine-based activation motif (ITAM). In a certain embodiment, said polypeptide sequence is a CD3 signaling domain.

Modulatory Domains

Modulatory domains can change the effect of the intracellular activating domain in the engineered signaling polypeptide, including enhancing or dampening the downstream effects of the activating domain or changing the nature of the response. Modulatory domains suitable for use in an engineered signaling polypeptide of the present disclosure include co-stimulatory domains. A modulatory domain suitable for inclusion in the engineered signaling polypeptide can have a length of from about 30 amino acids to about 70 amino acids (aa), e.g., a modulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

Co-stimulatory domains typically enhance and/or change the nature of the response to an activation domain. Co-stimulatory domains suitable for use in an engineered signaling polypeptide of the present disclosure are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), CD27, CD28, CD28 deleted for Lck binding (ICA), ICOS, OX40, BTLA, CD27, CD30, GITR, and HVEM. For example, a co-stimulatory domain of an aspect of the invention can have at least 80%, 90%, or 95% sequence identity to the co-stimulatory domain of 4-1BB (CD137), CD27, CD28, CD28 deleted for Lck binding (ICA), ICOS, OX40, BTLA, CD27, CD30, GITR, or HVEM. For example, a co-stimulatory domain of an aspect of the invention can have at least 80%, 90%, or 95% sequence identity to the co-stimulatory domain of Non-limiting examples of suitable co-stimulatory polypeptides include, but are not limited to, 4-1BB (CD137), CD27, CD28, CD28 deleted for Lck binding (ICA), ICOS, OX40, BTLA, CD27, CD30, GITR, and HVEM. For example, a co-stimulatory domain of an aspect of the invention can have at least 80%, 90%, or 95% sequence identity to the co-stimulatory domain of 4-1BB (CD137), CD27, CD28, CD28 deleted for Lck binding (ICA), ICOS, OX40, BTLA, CD27, CD30, GITR, or HVEM.

A co-stimulatory domain suitable for inclusion in an engineered signaling polypeptide can have a length of from about 30 amino acids to about 70 amino acids (aa), e.g., a co-stimulatory domain can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, the co-stimulatory domain can have a length of from about 70 aa to about 100 aa, from about 100 aa to about 200 aa, or greater than 200 aa.

In some cases, the co-stimulatory domain is derived from an intracellular portion of the transmembrane protein CD137 (also known as TNFRSF9; CD137; 4-1BB; CDw137; ILA; etc.). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: KRGRKKL-LYIFKQPFMRPVQTTQEEDGCSCRFPEEEEGGCEL (SEQ ID NO:1). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 (also known as Tp44). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RSKRSRLLHSDYMNMTPRRPGPTRKHYQPYAPPRD-FAAYRS (SEQ ID NO:2). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 deleted for Lck binding (ICA). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RSKRSRLLHSDYMNMTPRRPGP-TRKHYQAYAAARDFAAYRS (SEQ ID NO:3). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein ICOS (also known as AILIM, CD278, and CVID1). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: TKKKYSSSVHDPNGEYMFM-RAVNTAKKSRLTDVTL (SEQ ID NO:4). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein OX40 (also known as TNFRSF4, RP5-902P8.3, ACT35, CD134, OX-40, TXGP1L). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RRDQRLPPDAHKPPGGGSFRTPIQEEQADAHSTLAKI (SEQ ID NO:5). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD27 (also known as S 152, T 14, TNFRSF7, and Tp55). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: HQRRKYRSNKGESPVE-PAEPCRYSCPREEEGSTIPIQEDYRKPEPACSP (SEQ ID NO:6). In some of these embodiments, the co-stimulatory domain has a length of from about 30 aa to about 35 aa, from about 35 aa to about 40 aa, from about 40 aa to about 45 aa, from about 45 aa to about 50 aa, from about In some cases, the co-stimulatory domain is derived from an intracellular portion of the transmembrane protein BTLA (also known as BTLA1 and CD272). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 7)
CCLRRHQGKQNELSDTAGREINLVDAHLKSEQTEASTRQNSQVLLSE

TGIYDNDPDLCFRMQEGSEVYSNPCLEENKPGIVYASLNHSVIGPNS

RLARNVKEAPTEYASICVRS.

In some cases, the co-stimulatory domain is derived from an intracellular portion of the transmembrane protein CD30 (also known as TNFRSF8, D1S166E, and Ki-1). For example, a suitable co-stimulatory domain can include a domain with at least 50%, 60%, 70%, 75%, 80%, 85%, 90%, 95%, 96%, 97%, 98%, 99% or 100% sequence identity to a stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, or from about 160 aa to about 185 aa of the following amino acid sequence:

(SEQ ID NO: 8)
RRACRKRIRQKLHLCYPVQTSQPKLELVDSRPRRSSTQLRSGASVTE

PVAEERGLMSQPLMETCHSVGAAYLESLPLQDASPAGGPSSPRDLPE

PRVSTEHTNNKIEKIYIMKADTVIVGTVKAELPEGRGLAGPAEPELE

EELEADHTPHYPEQETEPPLGSCSDVMLSVEEEGKEDPLPTAASGK.

In some cases, the co-stimulatory domain is derived from an intracellular portion of the transmembrane protein GITR (also known as TNFRSF18, RP5-902P8.2, AITR, CD357, and GITR-D). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 9)
HIWQLRSQCMWPRETQLLLEVPPSTEDARSCQFPEEERGERSAEEKG
RLGDLWV.

In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 10)
CVKRRKPRGDVVKVIVSVQRKRQEAEGEATVIEALQAPPDVTTVAVE
ETIPSFTGRSPNH.

In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Linker

In some cases, the engineered signaling polypeptide includes a linker between any two adjacent domains. For example, a linker can be between the transmembrane domain and the first co-stimulatory domain. As another example, the ASTR can be an antibody and a linker can be between the heavy chain and the light chain. As another example, a linker can be between the ASTR and the transmembrane domain and a co-stimulatory domain. As another example, a linker can be between the co-stimulatory domain and the intracellular activating domain of the second polypeptide. As another example, the linker can be between the ASTR and the intracellular signaling domain.

The linker peptide may have any of a variety of amino acid sequences. Proteins can be joined by a spacer peptide, generally of a flexible nature, although other chemical linkages are not excluded. A linker can be a peptide of between about 1 and about 100 amino acids in length, or between about 1 and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$, $GGGS_n$, and $GGGGS_n$ where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGGGSGGGGSGGGGS (SEQ ID NO:53), GGGGSGGGGSGGGGSGGGGSGGGGSGGGGS (SEQ ID NO:54), GGGGSGGGSGGGGS (SEQ ID NO:55), GGSG (SEQ ID NO:56), GGSGG (SEQ ID NO:57), GSGSG (SEQ ID NO:58), GSGGG (SEQ ID NO:59), GGGSG (SEQ ID NO:60), GSSSG (SEQ ID NO:61), and the like. The ordinarily skilled artisan will recognize that design of a peptide conjugated to any elements described above can include linkers that are all or partially flexible, such that the linker can include a flexible linker as well as one or more portions that confer less flexible structure.

Chimeric Antigen Receptor

In some aspects of the present invention, an engineered signaling polypeptide is a chimeric antigen receptor (CAR) or a polynucleotide encoding a CAR, which, for simplicity, is referred to herein as "CAR." In some embodiments, a CAR of the present disclosure includes: a) at least one antigen-specific targeting region (ASTR); b) a transmembrane domain; and c) an intracellular activating domain. In illustrative embodiments, the antigen-specific targeting region of the CAR is a scFv portion of an antibody to the target antigen.

A CAR of the present disclosure can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell, an NK-T cell, and a macrophage. When present in the plasma membrane of a eukaryotic cell, a CAR of the present disclosure is active in the presence of one or more target antigens that, in certain conditions, binds the ASTR. The target antigen is the second member of the specific binding pair. The target antigen of the specific binding pair can be a soluble (e.g., not bound to a cell) factor; a factor present on the surface of a cell such as a target cell; a factor presented on a solid surface; a factor present in a lipid bilayer; and the like. Where the ASTR is an antibody, and the second member of the specific binding pair is an antigen, the antigen can be a soluble (e.g., not bound to a cell) antigen; an antigen present on the surface of a cell such as a target cell; an antigen presented on a solid surface; an antigen present in a lipid bilayer; and the like.

In some instances, a CAR of the present disclosure, when present in the plasma membrane of a eukaryotic cell, and when activated by one or more target antigens, increases expression of at least one nucleic acid in the cell. For example, in some cases, a CAR of the present disclosure, when present in the plasma membrane of a eukaryotic cell, and when activated by the one or more target antigens, increases expression of at least one nucleic acid in the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the level of transcription of the nucleic acid in the absence of the one or more target antigens.

As an example, the CAR of the present disclosure can include an immunoreceptor tyrosine-based activation motif (ITAM)-containing intracellular signaling polypeptide.

A CAR of the present disclosure, when present in the plasma membrane of a eukaryotic cell, and when activated by one or more target antigens, can, in some instances, result in increased production of one or more cytokines by the cell. For example, a CAR of the present disclosure, when present in the plasma membrane of a eukaryotic cell, and when activated by the one or more target antigens, can increase production of a cytokine by the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the cell in the absence of the one or more target antigens. Cytokines whose production can be increased include, but are not limited to interferon gamma (IFN-γ), tumor necrosis factor-alpha (TNF-α), IL-2, IL-15, IL-12, IL-4, IL-5, IL-10; a chemokine; a growth factor; and the like.

In some cases, a CAR of the present disclosure, when present in the plasma membrane of a eukaryotic cell, and when activated by one or more target antigens, can result in both an increase in transcription of a nucleic acid in the cell and an increase in production of a cytokine by the cell.

In some instances, a CAR of the present disclosure, when present in the plasma membrane of a eukaryotic cell, and when activated by one or more target antigens, results in cytotoxic activity by the cell toward a target cell that expresses on its cell surface an antigen to which the antigen-binding domain of the first polypeptide of the CAR binds. For example, where the eukaryotic cell is a cytotoxic cell (e.g., an NK cell or a cytotoxic T lymphocyte), a CAR of the present disclosure, when present in the plasma membrane of the cell, and when activated by the one or more target antigens, increases cytotoxic activity of the cell toward a target cell that expresses on its cell surface the one or more target antigens. For example, where the eukaryotic cell is an NK cell or a T lymphocyte, a CAR of the present disclosure, when present in the plasma membrane of the cell, and when activated by the one or more target antigens, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of the one or more target antigens.

In some cases, a CAR of the present disclosure, when present in the plasma membrane of a eukaryotic cell, and when activated by one or more target antigens, can result in other CAR activation related events such as proliferation and expansion (either due to increased cellular division or anti-apoptotic responses).

In some cases, a CAR of the present disclosure, when present in the plasma membrane of a eukaryotic cell, and when activated by one or more target antigens, can result in other CAR activation related events such as intracellular signaling modulation, cellular differentiation, or cell death.

A CAR of the present disclosure can be present in a eukaryotic cell membrane, where the first and second polypeptides of the CAR are not covalently linked to one another. A CAR of the present disclosure can be present in a eukaryotic cell membrane as a single heterodimer that is not covalently linked to any other polypeptide in the membrane. Alternatively, a first CAR of the present disclosure can be present in a eukaryotic cell membrane as a heterodimer that is covalently or non-covalently linked to a second CAR of the present disclosure. In some cases, the first and the second CAR are covalently linked via a disulfide bond formed between cysteines present in a stalk present in both the first polypeptide of the first CAR and the first polypeptide of the second CAR.

In some cases, a CAR of the present disclosure can be present in a eukaryotic cell membrane, where the first polypeptides of the CAR include an antibody fragment and the second polypeptides of the CAR include a signal transducing domain derived from a cytokine receptor, such that, upon dimerization, the CAR may represent a heterodimeric-signalobody CAR, e.g., a signalobody composed of at least two independent polypeptides. A "signalobody", as it is known in the art, is a single chimeric macromolecule composed of an antibody fragment and a signal transduction domain derived from a cytokine receptor. In certain instances, a heterodimeric-signalobody CAR of the present disclosure, when present in the cell membrane of a eukaryotic cell, dimerized by a dimerizer, and activated by an antigen, e.g., an oligomerized antigen, may induce the oligomerization of the heterodimeric-signalobody CAR. Such ligand-induced oligomerization of a heterodimeric-signalobody CAR may activate, e.g., increase, or perpetuate, e.g., maintain, signal transduction, e.g., ligand-induced oligomerization of a heterodimeric-signalobody CAR may transmit a signal eliciting a cellular response. In some instances, a plurality of heterodimeric-signalobody CARs may be utilized combinatorially to elicit a desired cellular response.

In some embodiments, CARs of the present disclosure are microenvironment restricted. This property is typically the result of the microenvironment restricted nature of the ASTR domain of the CAR. Thus, CARs of the present disclosure can have a lower binding affinity or, in illustrative embodiments, can have a higher binding affinity to one or more target antigens under a condition(s) in a microenvironment than under a condition in a normal physiological environment.

Recombination of Sequences

In certain instances, sequences of the engineered signaling polypeptides, which can be referred to herein as recombinant polypeptides, may be rearranged or deleted in a cell through the use of site-specific recombination technology. In certain embodiments, the cellular activation-related response to a particular engineered signaling polypeptide can be changed by site-specific recombination, e.g., a first intracellular activating domain of an engineered signaling polypeptide eliciting a first activation-related response may be exchanged for a second intracellular activating domain eliciting a second activation-related response. As will be clear to one skilled in the art, site-specific recombination can be used in a cell to exchange any domain or sequence of an engineered signaling polypeptide with any other domain or sequence as disclosed herein. As will also be clear to one skilled in the art, site-specific recombination can be used in a cell to delete any domain or sequence of an engineered signaling polypeptide. Such exchange and excision of sequences and domains is known in the art, see, e.g., domain switching in signalobodies as described in Tone et al. (2013) *Biotechnology and Bioengineering*, 3219-3226, the disclosure of which is disclosed herein by reference. Mechanisms and requirements for performing site-specific recombination in vivo are also well known in the art, see, e.g., Grindley et al. (2006) *Annual Review of Biochemistry*, 567-605 and Tropp (2012) *Molecular Biology* (Jones & Bartlett Publishers, Sudbury, Mass.), the disclosures of which are incorporated herein by reference.

In some embodiments, the engineered signaling polypeptides are generated by fusing all the different domains discussed above together to form a fusion protein. The engineered signaling polypeptide is typically generated by a transcriptional unit comprising polynucleotide sequences that encode the different domains of the engineered signaling polypeptides as discussed herein. In some embodiments, the ASTR of the present invention, which functions to recognize and bind with an antigen on target cells, is microenvironment restricted.

The wild-type or native protein that is suitable to be used in whole or in part for at least its binding domain for the target antigen, as an ASTR in the present invention may be discovered by generating a protein library and screening the library for a protein with a desired binding affinity to the target antigen. The wild-type protein may be discovered by screening a cDNA library. A cDNA library is a combination of cloned cDNA (complementary DNA) fragments inserted into a collection of host cells, which together constitute some portion of the transcriptome of the organism. cDNA is produced from fully transcribed mRNA and therefore contains the coding sequence for expressed proteins of an organism. The information in cDNA libraries is a powerful and useful tool for discovery of proteins with desired properties by screening the libraries for proteins with the desired binding affinity to the target antigen.

Combinations

In some embodiments, a polynucleotide provided by the recombinant retroviruses has one or more transcriptional units that encode certain combinations of the one or more engineered signaling polypeptides. In some methods and compositions provided herein, genetically modified T cells include the combinations of the one or more engineered signaling polypeptides after transduction of T cells by the recombinant retroviruses. It will be understood that the reference of a first polypeptide, a second polypeptide, a third polypeptide, etc. is for convenience and elements on a "first polypeptide" and those on a "second polypeptide" means that the elements are on different polypeptides that are referenced as first or second for reference and convention only, typically in further elements or steps to that specific polypeptide.

In some embodiments, the first engineered signaling polypeptide includes an extracellular antigen binding domain, which is capable of binding an antigen, and an intracellular signaling domain. In other embodiments, the first engineered signaling polypeptide also includes a T cell survival motif and/or a transmembrane domain. In some embodiments, the first engineered signaling polypeptide does not include a co-stimulatory domain, while in other embodiments, the first engineered signaling polypeptide does include a co-stimulatory domain.

In some embodiments, a second engineered signaling polypeptide includes a lymphoproliferative gene product and optionally an extracellular antigen binding domain. In some embodiments, the second engineered signaling polypeptide also includes one or more of the following: a T cell survival motif, an intracellular signaling domain, and one or more co-stimulatory domains. In other embodiments, when two engineered signaling polypeptides are used, at least one is a CAR.

In one embodiment, the one or more engineered signaling polypeptides are expressed under a T cell specific promoter or a general promoter under the same transcript wherein in the transcript, nucleic acids encoding the engineered signaling polypeptides are separated by nucleic acids that encode one or more internal ribosomal entry sites (IREs) or one or more protease cleavage peptides.

In certain embodiments, the polynucleotide encodes two engineered signaling polypeptides wherein the first engineered signaling polypeptide includes a first extracellular antigen binding domain, which is capable of binding to a first antigen, and a first intracellular signaling domain but not a co-stimulatory domain, and the second polypeptide includes a second extracellular antigen binding domain, which is capable of binding VEGF, and a second intracellular signaling domain, such as for example, the signaling domain of a co-stimulatory molecule. In a certain embodiment, the first antigen is PSCA, PSMA, or BCMA. In a certain embodiment, the first extracellular antigen binding domain comprises an antibody or fragment thereof (e.g., scFv), e.g., an antibody or fragment thereof specific to PSCA, PSMA, or BCMA. In a certain embodiment, the second extracellular antigen binding domain that binds VEGF is a receptor for VEGF, i.e., VEGFR. In certain embodiments, the VEGFR is VEGFR1, VEGFR2, or VEGFR3. In a certain embodiment, the VEGFR is VEGFR2.

In certain embodiments, the polynucleotide encodes two engineered signaling polypeptides wherein the first engineered signaling polypeptide includes an extracellular tumor antigen binding domain and a CD3 signaling domain, and the second engineered signaling polypeptide includes an antigen-binding domain, wherein the antigen is an angiogenic or vasculogenic factor, and one or more co-stimulatory molecule signaling domains. The angiogenic factor can be, e.g., VEGF. The one or more co-stimulatory molecule signaling motifs can comprise, e.g., co-stimulatory signaling domains from each of CD27, CD28, OX40, ICOS, and 4-1BB.

In certain embodiments, the polynucleotide encodes two engineered signaling polypeptides wherein the first engineered signaling polypeptide includes an extracellular tumor antigen-binding domain and a CD3 signaling domain, the second polypeptide comprises an antigen-binding domain, which is capable of binding to VEGF, and co-stimulatory signaling domains from each of CD27, CD28, OX40, ICOS, and 4-1BB. In a further embodiment, the first signaling polypeptide or second signaling polypeptide also has a T cell survival motif. In some embodiments, the T cell survival motif is, or is derived from, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor or the TGFβ decoy receptor (TGF-β-dominant-negative receptor II (DNRII)).

In certain embodiments, the polynucleotide encodes two engineered signaling polypeptides wherein the first engineered signaling polypeptide includes an extracellular tumor antigen-binding domain and a CD3 signaling domain, and the second engineered signaling polypeptide includes an antigen-binding domain, which is capable of binding to VEGF, an IL-7 receptor intracellular T cell survival motif, and co-stimulatory signaling domains from each of CD27, CD28, OX40, ICOS, and 4-1BB.

In some embodiments, more than two signaling polypeptides are encoded by the polynucleotide. In certain embodiments, only one of the engineered signaling polypeptides includes an antigen binding domain that binds to a tumor-associated antigen or a tumor-specific antigen; each of the remainder of the engineered signaling polypeptides comprises an antigen binding domain that binds to an antigen that is not a tumor-associated antigen or a tumor-specific antigen. In other embodiments, two or more of the engineered signaling polypeptides include antigen binding domains that bind to one or more tumor-associated antigens or tumor-specific antigens, wherein at least one of the engineered signaling polypeptides comprises an antigen binding domain that does not bind to a tumor-associated antigen or a tumor-specific antigen.

In some embodiments, the tumor-associated antigen or tumor-specific antigen is Her2, prostate stem cell antigen (PSCA), PSMA (prostate-specific membrane antigen), B cell maturation antigen (BCMA), alpha-fetoprotein (AFP), carcinoembryonic antigen (CEA), cancer antigen-125 (CA-125), CA19-9, calretinin, MUC-1, epithelial membrane protein (EMA), epithelial tumor antigen (ETA), tyrosinase, melanoma-associated antigen (MAGE), CD34, CD45, CD99, CD117, chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-1), myo-D1, muscle-specific actin (MSA), neurofilament, neuron-specific enolase (NSE), placental alkaline phosphatase, synaptophysin, thyroglobulin, thyroid transcription factor-1, the dimeric form of the pyruvate kinase isoenzyme type M2 (tumor M2-PK), CD19, CD22, CD27, CD30, CD70, GD2 (ganglioside G2), EphA2, CSPG4, CD138, FAP (Fibroblast Activation Protein), CD171, kappa, lambda, 5T4, αvβ6 integrin, integrin αvβ3 (CD61), galactin, K-Ras (V-Ki-ras2 Kirsten rat sarcoma viral oncogene), Ral-B, B7-H3, B7-H6, CAIX, CD20, CD33, CD44, CD44v6, CD44v7/8, CD123, EGFR, EGP2, EGP40, EpCAM, fetal AchR, FRα, GD3, HLA-A1+MAGE1, HLA-A1+NY-ESO-1, IL-11Rα, IL-13Rα2, Lewis-Y, Muc16, NCAM, NKG2D Ligands, NY-ESO-1, PRAME, ROR1, Survivin, TAG72, TEMs, VEGFR2, EGFRvIII (epidermal growth factor variant III), sperm protein 17 (Sp17), mesothelin, PAP (prostatic acid phosphatase), prostein, TARP (T cell receptor gamma alternate reading frame protein), Trp-p8, STEAP1 (six-transmembrane epithelial antigen of the prostate 1), an abnormal ras protein, or an abnormal p53 protein.

In some embodiments, the first engineered signaling polypeptide includes a first extracellular antigen binding domain that binds a first antigen, and a first intracellular signaling domain; and a second engineered signaling polypeptide includes a second extracellular antigen binding domain that binds a second antigen, or a receptor that binds the second antigen; and a second intracellular signaling domain, wherein the second engineered signaling polypeptide does not comprise a co-stimulatory domain. In a certain embodiment, the first antigen-binding domain and the second antigen-binding domain are independently an antigen-binding portion of a receptor or an antigen-binding portion of an antibody. In a certain embodiment, either or both of the first antigen binding domain or the second antigen binding domain are scFv antibody fragments. In certain embodiments, the first engineered signaling polypeptide and/or the second engineered signaling polypeptide additionally comprises a transmembrane domain. In a certain embodiment, the first engineered signaling polypeptide or the second engineered signaling polypeptide comprises a T cell survival motif, e.g., any of the T cell survival motifs described herein.

In another embodiment, the first engineered signaling polypeptide includes a first extracellular antigen binding domain that binds HER2 and the second engineered signaling polypeptide includes a second extracellular antigen binding domain that binds MUC-1.

In another embodiment, the second extracellular antigen binding domain of the second engineered signaling polypeptide binds an interleukin.

In another embodiment, the second extracellular antigen binding domain of the second engineered signaling polypeptide binds a damage associated molecular pattern molecule (DAMP; also known as an alarmin). In other embodiments, a DAMP is a heat shock protein, chromatin-associated protein high mobility group box 1 (HMGB1), S100A8 (also known as MRP8, or calgranulin A), S100A9 (also known as MRP14, or calgranulin B), serum amyloid A (SAA), deoxyribonucleic acid, adenosine triphosphate, uric acid, or heparin sulfate.

In certain embodiments, said second antigen is an antigen on an antibody that binds to an antigen presented by a tumor cell.

In some embodiments, signal transduction activation through the second engineered signaling polypeptide is non-antigenic, but is associated with hypoxia. In certain embodiments, hypoxia is induced by activation of hypoxia-inducible factor-1α (HIF-1α), HIF-1β, HIF-2α, HIF-2β, HIF-3α, or HIF-3β.

In some embodiments, expression of the one or more engineered signaling polypeptides is regulated by an in vivo control element, which is disclosed in more detail herein.

Additional Sequences

The engineered signaling polypeptides, such as CARs, can further include one or more additional polypeptide domains, where such domains include, but are not limited to, a signal sequence; an epitope tag; an affinity domain; and a polypeptide that produces a detectable signal. Non-limiting examples of additional domains for any of the aspects or embodiments provided herein, include a domain with at least 50%, 60%, 70%, 75%, 80%, 85%, 90%, 95%, 96%, 97%, 98%, 99% or 100% sequence identity to any of the following sequences as described below: a signal sequence, an epitope tag, an affinity domain, or a polypeptide that produces a detectable signal.

Signal sequences that are suitable for use in a subject CAR, e.g., in the first polypeptide of a subject CAR, include any eukaryotic signal sequence, including a naturally-occurring signal sequence, a synthetic (e.g., man-made) signal sequence, etc. In some embodiments, for example, the signal sequence can be the CD8 signal sequence MALPVTALLL-PLALLLHAARP (SEQ ID NO:74).

Suitable epitope tags include, but are not limited to, hemagglutinin (HA; e.g., YPYDVPDYA; SEQ ID NO:37); FLAG (e.g., DYKDDDDK; SEQ ID NO:38); c-myc (e.g., EQKLISEEDL; SEQ ID NO:39), and the like.

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include HisS (HHHHH; SEQ ID NO:40), HisX6 (HHHHHH; SEQ ID NO:41), c-myc (EQKLISEEDL; SEQ ID NO:39), Flag (DYKDDDDK; SEQ ID NO:38), Strep Tag (WSHPQFEK; SEQ ID NO:42), hemagglutinin, e.g., HA Tag (YPYDVP-DYA; SEQ ID NO:37), GST, thioredoxin, cellulose binding domain, RYIRS (SEQ ID NO:43), Phe-His-His-Thr (SEQ ID NO:44), chitin binding domain, S-peptide, T7 peptide, SH2 domain, C-end RNA tag, WEAAAREACCRECCARA (SEQ ID NO:45), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100proteins, parvalbumin, calbindin D9K, calbindin D28K, and calretinin, inteins, biotin, streptavidin, MyoD, Id, leucine zipper sequences, and maltose binding protein.

Suitable detectable signal-producing proteins include, e.g., fluorescent proteins; enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, *Renilla* GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrapel, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Recognition and/or Elimination Domain

Any of the recombinant retroviruses provided herein can include nucleic acids that encode a recognition or elimination domain as part of, or separate from, nucleic acids encoding any of the engineered signaling polypeptides provided herein. Thus, any of the engineered signaling polypeptides provided herein, can include a recognition or elimination domain. For example, any of the CARs disclosed herein can include a recognition or elimination domain. Moreover, a recognition or elimination domain can be expressed together with, or even fused with any of the lymphoproliferative elements disclosed herein. The recognition or elimination domains are expressed on the T cell and/or NK cell but are not expressed on the retrovirus.

In some embodiments, the recognition or elimination domain can be derived from herpes simplex virus-derived enzyme thymidine kinase (HSV-tk) or inducible caspase-9. In some embodiments, the recognition or elimination domain can include a modified endogenous cell-surface molecule, for example as disclosed in U.S. Pat. No. 8,802, 374. The modified endogenous cell-surface molecule can be any cell-surface related receptor, ligand, glycoprotein, cell adhesion molecule, antigen, integrin, or cluster of differentiation (CD) that is modified. In some embodiments, the modified endogenous cell-surface molecule is a truncated tyrosine kinase receptor. In one aspect, the truncated tyrosine kinase receptor is a member of the epidermal growth factor receptor (EGFR) family (e.g., ErbB1, ErbB2, ErbB3, ErbB4. In some embodiments, the recognition domain can be a polypeptide that is recognized by an antibody that recognizes the extracellular domain of an EGFR member. In some embodiments, the recognition domain can be at least 20 contiguous amino acids of an EGFR family member, or for example, between 20 and 50 contiguous amino acids of an EGFR family member. For example, SEQ ID NO:78, is an exemplary polypeptide that is recognized by, and under the appropriate conditions bound by an antibody that recognizes the extracellular domain of an EGFR member. Such extracellular EGFR epitopes are sometimes referred to herein as eTags. In illustrative embodiments, such epitopes are recognized by commercially available anti-EGFR monoclonal antibodies.

Epidermal growth factor receptor, also known as EGFR, ErbB1 and HER1, is a cell-surface receptor for members of the epidermal growth factor family of extracellular ligands. Alterations in EGFR activity have been implicated in certain cancers. In some embodiments, a gene encoding an EGFR polypeptide including human epidermal growth factor receptor (EGFR) is constructed by removal of nucleic acid sequences that encode polypeptides including the membrane distal EGF-binding domain and the cytoplasmic signaling tail, but retains the extracellular membrane proximal epitope recognized by an anti-EGFR antibody. Preferably, the antibody is a known, commercially available anti-EGFR monoclonal antibody, such as cetuximab, matuzumab, necitumumab or panitumumab.

Others have shown that application of biotinylated-cetuximab to immunomagnetic selection in combination with anti-biotin microbeads successfully enriches T cells that have been lentivirally transduced with EGFRt-containing constructs from as low as 2% of the population to greater than 90% purity without observable toxicity to the cell preparation. Furthermore, others have shown that constitutive expression of this inert EGFR molecule does not affect T cell phenotype or effector function as directed by the coordinately expressed chimeric antigen receptor (CAR), CD19R. In addition, others have shown that through flow cytometric analysis, EGFR was successfully utilized as an in vivo tracking marker for T cell engraftment in mice. Furthermore, EGFR was demonstrated to have suicide gene potential through Erbitux® mediated antibody dependent cellular cytotoxicity (ADCC) pathways. The inventors of the present disclosure have successfully expressed eTag in PBMCs using lentiviral vectors, and have found that expression of eTag in vitro by PBMCs exposed to Cetuximab, provided an effective elimination mechanism for PBMCs. Thus, EGFR may be used as a non-immunogenic selection tool, tracking marker, and suicide gene for transduced T cells that have immunotherapeutic potential. The EGFR nucleic acid may also be detected by means well known in the art.

In some embodiments provided herein, EGFR is expressed as part of a single polypeptide that also includes the CAR or as part of a single polypeptide that includes the lymphoproliferative element. In some embodiments, the amino acid sequence encoding the EGFR recognition domain can be separated from the amino acid sequence encoding the chimeric antigen receptor by a cleavage signal and/or a ribosomal skip sequence. The ribosomal skip and/or cleavage signal can be any ribosomal skip and/or cleavage signal known in the art. Not to be limited by theory, the ribosomal skip sequence can be, for example 2A-1 with amino acid sequence GSGEGRGSLLTCGDVEENPGP (SEQ ID NO:77). Not to be limited by theory, other examples of cleavage signals and ribosomal skip sequences include FMDV 2A (F2A); equine rhinitis A virus 2A (abbreviated as E2A); porcine teschovirus-1 2A (P2A); and *Thoseaasigna* virus 2A (T2A). In some embodiments, the polynucleotide sequence encoding the recognition domain can be on the same transcript as the CAR or lymphoproliferative element but separated from the polynucleotide sequence encoding the CAR or lymphoproliferative element by an internal ribosome entry site.

In other embodiments as exemplified empirically herein, a recognition domain can be expressed as part of a fusion polypeptide, fused to a lymphoproliferative element. Such constructs provide the advantage, especially in combination with other "space saving" elements provided herein, of taking up less genomic space on an RNA genome compared to separate polypeptides. In one illustrative embodiment, an eTag is expressed as a fusion polypeptide, fused to an IL7Rα mutant, as experimentally demonstrated herein.

Pseudotyping Elements

Many of the methods and compositions provided herein include pseudotyping elements. The pseudotyping of retroviruses with heterologous envelope glycoproteins typically alters the tropism of a virus and facilitates the transduction of host cells. A pseudotyping element as used herein can include a "binding polypeptide" that includes one or more polypeptides, typically glycoproteins, that identify and bind the target host cell, and one or more "fusogenic polypeptides" that mediate fusion of the retroviral and target host cell membranes, thereby allowing a retroviral genome to enter the target host cell. In some embodiments provided herein, pseudotyping elements are provided as polypeptide(s)/protein(s), or as nucleic acid sequences encoding the polypeptide(s)/protein(s).

In some embodiments, the pseudotyping element is the feline endogenous virus (RD114) envelope protein, the oncoretroviral amphotropic envelope protein, the oncoretroviral ecotropic envelope protein, the vesicular stomatitis virus (VSV-G) envelope protein, and/or the paramyxovirus Measles envelope proteins H and F.

In some embodiments, the pseudotyping elements include a binding polypeptide and a fusogenic polypeptide derived from different proteins. For example, the recombinant retroviruses of the methods and compositions disclosed herein can be pseudotyped with the fusion (F) and hemagglutinin (H) polypeptides of the measles virus (MV), as non-limiting examples, clinical wildtype strains of MV, and vaccine strains including the Edmonston strain (MV-Edm) or fragments thereof. Not to be limited by theory, both hemagglutinin (H) and fusion (F) polypeptides are believed to play a role in entry into host cells wherein the H protein binds MV to receptors CD46, SLAM, and Nectin-4 on target cells and F mediates fusion of the retroviral and host cell membranes. In an illustrative embodiment, especially where the target cell is a T cell and/or NK cell, the binding polypeptide is a Measles Virus H polypeptide and the fusogenic polypeptide is a Measles Virus F polypeptide.

In some studies, lentiviral particles pseudotyped with truncated F and H polypeptides had a significant increase in titers and transduction efficiency (Funke et al. 2008. *Molecular Therapy.* 16(8):1427-1436), (Frecha et al. 2008. *Blood.* 112(13):4843-4852). The highest titers were obtained when the F cytoplasmic tail was truncated by 30 residues (referred to as MV(Ed)-FΔ30 (SEQ ID NO:105)). For the H variants, optimal truncation occurred when 18 or 19 residues were deleted (MV(Ed)-HΔ18 (SEQ ID NO:106) or MV(Ed)-HΔ19), although variants with a truncation of 24 residues with and without replacement of deleted residues with alanine (MV(Ed)-HΔ24 (SEQ ID NO:235) and MV(Ed)-HΔ24+A) also resulted in optimal titers.

In some embodiments, including those directed to transducing T cells and/or NK cells, the recombinant retroviruses of the methods and compositions disclosed herein are pseudotyped with mutated or variant versions of the measles virus fusion (F) and hemagglutinin (H) polypeptides, in illustrative examples, cytoplasmic domain deletion variants of measles virus F and H polypeptides. In some embodiments, the mutated F and H polypeptides are "truncated H" or "truncated F" polypeptides, whose cytoplasmic portion has been truncated, i.e. amino acid residues (or coding nucleic acids of the corresponding nucleic acid molecule encoding the protein) have been deleted. "HΔY" and "FΔX" designate such truncated H and F polypeptide, respectively, wherein "Y" refers to 1-34 residues that have been deleted from the amino termini and "X" refers to 1-35 residues that have been deleted from the carboxy termini of the cytoplasmic domains. In a further embodiment, the "truncated F polypeptide" is FΔ24 or FΔ30 and/or the "truncated H protein" is selected from the group consisting of HΔ14, HΔ15, HΔ16, HΔ17, HΔ18, HΔ19, HΔ20, HΔ21+A, HΔ24 and HΔ24+4A, more preferably HΔ18 or HΔ24. In an illustrative embodiment, the truncated F polypeptide is MV(Ed)-FΔ30 and the truncated H polypeptide is MV(Ed)-HΔ18.

In some embodiments, the fusogenic polypeptide includes multiple elements expressed as one polypeptide. In some embodiments, the binding polypeptide and fusogenic polypeptide are translated from the same transcript but from separate ribosome binding sites; in other embodiments, the binding polypeptide and fusogenic polypeptide are separated by a cleavage peptide site, which not to be bound by theory, is cleaved after translation, as is common in the literature, or a ribosomal skip sequence. In some embodiments, the translation of the binding polypeptide and fusogenic polypeptide from separate ribosome binding sites results in a higher amount of the fusogenic polypeptide as compared to the binding polypeptide. In some embodiments, the ratio of the fusogenic polypeptide to the binding polypeptide is at least 2:1, at least 3:1, at least 4:1, at least 5:1, at least 6:1, at least 7:1, or at least 8:1. In some embodiments, the ratio of the fusogenic polypeptide to the binding polypeptide is between 1.5:1, 2:1, or 3:1, on the low end of the range, and 3:1, 4:1, 5:1, 6:1, 7:1, 8:1. 9:1 or 10:1 on the high end of the range.

Activation Elements

Many of the methods and composition aspects of the present disclosure include an activation element, or a nucleic acid encoding an activation element. The restrictions associated with lentiviral (LV) transduction into resting T cells are attributed to a series of pre-entry and post-entry barriers as well as cellular restrictive factors (Strebel et al 2009. *BMC Medicine* 7:48). One restriction is the inability for the envelope pseudotyped-LV particles to recognize potential receptors and mediate fusion with the cellular membrane. However, under certain conditions, the transduction of resting T cells with HIV-1-based lentiviral vectors is possible mostly upon T cell receptor (TCR) CD3 complex and CD28 co-stimulation (Korin & Zack. 1998. *Journal of Virology.* 72:3161-8, Maurice et al. 2002. *Blood* 99:2342-50), as well as through exposure to cytokines (Cavalieri et al 2003).

Cells of the immune system such as T lymphocytes recognize and interact with specific antigens through receptors or receptor complexes which, upon recognition or an interaction with such antigens, cause activation of the cell and expansion in the body. An example of such a receptor is the antigen-specific T lymphocyte receptor complex (TCR/CD3). The T cell receptor (TCR) is expressed on the surface of T lymphocytes. One component, CD3, is responsible for intracellular signaling following occupancy of the TCR by ligand. The T lymphocyte receptor for antigen-CD3 complex (TCR/CD3) recognizes antigenic peptides that are presented to it by the proteins of the major histocompatibility complex (MHC). Complexes of MHC and peptide are expressed on the surface of antigen presenting cells and other T lymphocyte targets. Stimulation of the TCR/CD3 complex results in activation of the T lymphocyte and a consequent antigen-specific immune response. The TCR/CD3 complex plays a central role in the effector function and regulation of the immune system.

T lymphocytes also require a second, co-stimulatory signal to become fully active. Without such a signal, T lymphocytes are either non-responsive to antigen binding to the TCR, or become anergic. Such a co-stimulatory signal, for example, is provided by CD28, a T lymphocyte protein, which interacts with CD80 and CD86 on antigen-producing cells. ICOS (Inducible COStimulator), another T lymphocyte protein, provides a co-stimulatory signal when bound to ICOS ligand.

Activation of the T cell receptor (TCR) CD3 complex and co-stimulation with CD28 can occur by ex vivo exposure to solid surfaces (e.g. beads) coated with anti-CD3 and anti-CD28. In some embodiments of the methods and compositions disclosed herein, resting T cells are activated by exposure to solid surfaces coated with anti-CD3 and anti-CD28 ex vivo.

In certain illustrative embodiments of the methods and compositions provided herein, polypeptides that are capable of binding CD3 and/or CD28, are presented as "activation elements" on the surface of recombinant retroviruses of the methods and compositions disclosed herein, which are also aspects of the invention. Polypeptides that bind CD3 and/or CD28 are referred to as "activation elements" because of their ability to activate resting T cells.

In some embodiments, the activation element is a polypeptide capable of binding to CD3. In some embodiments, the polypeptide capable of binding to CD3 is an anti-CD3 antibody, or a fragment thereof that retains the ability to bind to CD3. In illustrative embodiments, the anti-CD3 antibody or fragment thereof is a single chain anti-CD3 antibody, such as but not limited to, an anti-CD3 scFv. In another illustrative embodiment, the polypeptide capable of binding to CD3 is anti-CD3scFvFc.

A number of anti-human CD3 monoclonal antibodies and antibody fragments thereof are available, and can be used in the present invention, including but not limited to UCHT1, OKT-3, HIT3A, TRX4, X35-3, VIT3, BMA030 (BW264/56), CLB-T3/3, CRIS7, YTH12.5, F111409, CLB-T3.4.2, TR-66, WT31, WT32, SPv-T3b, 11D8, XIII-141, XII146, XIII-87, 12F6, T3/RW2-8C8, T3/RW24B6, OKT3D, M-T301, SMC2 and F101.01.

In some embodiments, the activation element is a polypeptide capable of binding to CD28. In some embodiments, the polypeptide capable of binding to CD28 is an anti-CD28 antibody, or a fragment thereof that retains the ability to bind to CD28. In other embodiments, the polypeptide capable of binding to CD28 is CD80, CD86, or a functional fragment thereof that is capable of CD28 and inducing CD28-mediated activation of Akt, such as an external fragment of CD80. In illustrative embodiments, the anti-CD28 antibody or fragment thereof is a single chain anti-CD28 antibody, such as, but not limited to, an anti-CD28 scFv. In another illustrative embodiment, the polypeptide capable of binding to CD28 is CD80, or a fragment of CD80 such as an external fragment of CD80.

Anti-CD28 antibodies are known in the art and can include, as non-limiting examples, monoclonal antibody 9.3, an IgG2a antibody (Dr. Jeffery Ledbetter, Bristol Myers Squibb Corporation, Seattle, Wash.), monoclonal antibody KOLT-2, an IgG1 antibody, 15E8, an IgG1 antibody, 248.23.2, an IgM antibody and EX5.3D10, an IgG2a antibody.

In an illustrative embodiment, an activation element includes two polypeptides, a polypeptide capable of binding to CD3 and a polypeptide capable of binding to CD28.

In certain embodiments, the polypeptide capable of binding to CD3 or CD28 is an antibody, a single chain monoclonal antibody or an antibody fragment, for example a single chain antibody fragment. Accordingly, the antibody fragment can be, for example, a single chain fragment variable region (scFv), a antibody binding (Fab) fragment of an antibody, a single chain antigen-binding fragment (scFab), a single chain antigen-binding fragment without cysteines (scFabAC), a fragment variable region (Fv), a construct specific to adjacent epitopes of an antigen (CRAb), or a single domain antibody (VH or VL).

In some embodiments, an activation element is fused to a heterologous signal sequence and/or a heterologous membrane attachment sequence, both of which help direct the activation element to the membrane. The heterologous signal sequence targets the activation element to the endoplasmic reticulum, where the heterologous membrane attachment sequence covalently attaches to one or several fatty acids (also known as posttranslational lipid modification) such that the activation elements that are fused to the heterologous membrane attachment sequence are anchored in the lipid rafts of the plasma membrane. In some embodiments, posttranslational lipid modification can occur via myristoylation, palmitoylation, or GPI anchorage. Myristoylation is a post-translational protein modification which corresponds to the covalent linkage of a 14-carbon saturated fatty acid, the myristic acid, to the N-terminal glycine of a eukaryotic or viral protein. Palmitoylation is a post-translational protein modification which corresponds to the covalent linkage of a C16 acyl chain to cysteines, and less frequently to serine and threonine residues, of proteins. GPI anchorage refers to the attachment of glycosylphosphatidylinositol, or GPI, to the C-terminus of a protein during posttranslational modification.

In some embodiments, the heterologous membrane attachment sequence is a GPI anchor attachment sequence. The heterologous GPI anchor attachment sequence can be derived from any known GPI-anchored protein (reviewed in Ferguson M A J, Kinoshita T, Hart G W. Glycosylphosphatidylinositol Anchors. In: Varki A, Cummings R D, Esko J D, et al., editors. *Essentials of Glycobiology.* 2nd edition. Cold Spring Harbor (N.Y.): Cold Spring Harbor Laboratory Press; 2009. Chapter 11). In some embodiments, the heterologous GPI anchor attachment sequence is the GPI anchor attachment sequence from CD14, CD16, CD48, CD55 (DAF), CD59, CD80, and CD87. In some embodiments, the heterologous GPI anchor attachment sequence is derived from CD16. In illustrative embodiments, the heterologous GPI anchor attachment sequence is derived from Fc receptor FcγRIIIb (CD16b) or decay accelerating factor (DAF), otherwise known as complement decay-accelerating factor or CD55.

In some embodiments, one or both of the activation elements include a heterologous signal sequence to help direct expression of the activation element to the cell membrane. Any signal sequence that is active in the packaging cell line can be used. In some embodiments, the signal sequence is a DAF signal sequence. In illustrative embodiments, an activation element is fused to a DAF signal sequence at its N terminus and a GPI anchor attachment sequence at its C terminus.

In an illustrative embodiment, the activation element includes anti-CD3 scFvFc fused to a GPI anchor attachment sequence derived from CD14 and CD80 fused to a GPI anchor attachment sequence derived from CD16b; and both are expressed on the surface of a recombinant retrovirus provided herein. In some embodiments, the anti-CD3 scFvFc is fused to a DAF signal sequence at its N terminus and a GPI anchor attachment sequence derived from CD14 at its C terminus and the CD80 is fused to a DAF signal sequence at its N terminus and a GPI anchor attachment sequence derived from CD16b at its C terminus; and both are expressed on the surface of a recombinant retrovirus provided herein. In some embodiments, the DAF signal sequence includes amino acid residues 1-30 of the DAF protein.

Membrane-Bound Cytokines

Some embodiments of the method and composition aspects provided herein, include a membrane-bound cytokine, or polynucleotides encoding a membrane-bound cytokine. Cytokines are typically, but not always, secreted proteins. Cytokines that are naturally secreted can be engineered as fusion proteins to be membrane-bound. Membrane-bound cytokine fusion polypeptides are included in methods and compositions disclosed herein, and are also an aspect of the invention. In some embodiments, recombinant retroviruses have a membrane-bound cytokine fusion polypeptide on their surface that is capable of binding a T cell and/or NK cell and promoting proliferation and/or survival thereof. Typically, membrane-bound polypeptides are incorporated into the membranes of recombinant retroviruses, and when a cell is transduced by the recombinant retrovirus, the fusion of the retroviral and host cell membranes results in the polypeptide being bound to the membrane of the transduced cell.

In some embodiments, the cytokine fusion polypeptide includes IL-7, IL-15, or an active fragment thereof. The membrane-bound cytokine fusion polypeptides are typically a cytokine fused to heterologous signal sequence and/or a heterologous membrane attachment sequence. In some embodiments, the heterologous membrane attachment sequence is a GPI anchor attachment sequence. The heterologous GPI anchor attachment sequence can be derived from any known GPI-anchored protein (reviewed in Ferguson M A J, Kinoshita T, Hart G W. Glycosylphosphatidylinositol Anchors. In: Varki A, Cummings R D, Esko J D, et al., editors. *Essentials of Glycobiology.* 2nd edition. Cold Spring Harbor (N.Y.): Cold Spring Harbor Laboratory Press; 2009. Chapter 11). In some embodiments, the heterologous GPI anchor attachment sequence is the GPI anchor attachment sequence from CD14, CD16, CD48, CD55 (DAF), CD59, CD80, and CD87. In some embodiments, the heterologous GPI anchor attachment sequence is derived from CD16. In an illustrative embodiment, the heterologous GPI anchor attachment sequence is derived from Fc receptor FcγRIIIb (CD16b). In some embodiments, the GPI anchor is the GPI anchor of DAF.

In illustrative embodiments, the membrane-bound cytokine is a fusion polypeptide of a cytokine fused to DAF. DAF is known to accumulate in lipid rafts that are incorporated into the membranes of retroviruses budding from packaging cells. Accordingly, not to be limited by theory, it is believed that DAF fusion proteins are preferentially targeted to portions of membranes of packaging cells that will become part of a recombinant retroviral membrane.

In non-limiting illustrative embodiments, the cytokine fusion polypeptide is an IL-7, or an active fragment thereof, fused to DAF. In a specific non-limiting illustrative embodiment, the fusion cytokine polypeptide includes in order: the DAF signal sequence (residues 1-31 of DAF), IL-7 without its signal sequence, and residues 36-525 of DAF.

In Vivo Control Element
Riboswitches

Some of the compositions and methods provided herein include one or more riboswitches or polynucleotides that include one or more riboswitch, which themselves form distinct aspects of the present disclosure. Riboswitches are a common feature in bacteria to regulate gene expression and are a means to achieve RNA control of biological functions. Riboswitches are polynucleotides that can be present in the 5'-untranslated region of mRNAs and allow for regulatory control over gene expression through binding of a small molecule ligand that induces or suppresses a riboswitch activity. Typically, the riboswitch controls a gene product involved in the generation of the small molecule ligand, thus forming a feedback loop. Riboswitches typically act in a cis-fashion, although riboswitches have been identified that act in a trans-fashion. Natural riboswitches consist of two domains: an aptamer domain that binds the ligand through a three-dimensional folded RNA structure and a function switching domain that induces or suppresses an activity in the riboswitch based on the absence or presence of the ligand. Thus, there are two ligand sensitive conformations achieved by the riboswitch, representing on and off states (Garst et al., 2011). The function switching domain can affect the expression of a polynucleotide by regulating: an internal ribosome entry site, pre-mRNA splice donor accessibility in the retroviral gene construct, translation, termination of transcription, transcript degradation, miRNA expression, or shRNA expression (Dambach and Winkler 2009). The aptamer and function switching domains can be used as modular components allowing for synthetic RNA devices to control gene expression either as native aptamers, mutated/evolved native aptamers, or totally synthetic aptamers that are identified from screening random RNA libraries (McKeague et al 2016).

The purine riboswitch family represents one of the largest families with over 500 sequences found (Mandal et al 2003; US20080269258; and WO2006055351). The purine riboswitches share a similar structure consisting of three conserved helical elements/stem structures (P1, P2, P3) with intervening loop/junction elements (J1-2, L2, J2-3, L3, J3-1). The aptamer domains of the purine family of riboswitches naturally vary in their affinity/regulation by various purine compounds such as adenine, guanine, adenosine, guanosine, deoxyadenosine, deoxyguanosine (FIG. 5), etc. due to sequence variation (Kim et al. 2007).

In one aspect, provided herein is an isolated polynucleotide for regulating expression of a target polynucleotide, including: a polynucleotide encoding the target polynucleotide operably linked to a promoter and a riboswitch, wherein the riboswitch includes: a.) an aptamer domain capable of binding a nucleoside analogue antiviral drug and having reduced binding to guanine or 2'-deoxyguanosine relative to the nucleoside analogue antiviral drug; and b.) a function switching domain capable of regulating expression of the target polynucleotide, wherein binding of the nucleoside analogue by the aptamer domain induces or suppresses the expression regulating activity of the function switching domain, thereby regulating expression of the target gene. In some embodiments, the target polynucleotide can be a polypeptide encoding region, an miRNA, or an shRNA. In a non-limiting example, the riboswitch is operably linked to a nucleic acid encoding a polypeptide, miRNA, or shRNA with in vivo activity, for example that is effective at treating a disease. For example, in such a non-limiting example, the riboswitch is operably linked to a nucleic acid encoding a chimeric antigen receptor. In non-limiting illustrative examples provided herein, the target polynucleotide encodes one or more engineered signaling polypeptides included in various other aspects of the present disclosure. In these non-limiting illustrative examples, the riboswitch and the target polynucleotide encoding one or more engineered signaling polypeptides can be found in the genome of a packaging cell, a recombinant retrovirus, a T cell and/or an NK cell.

Figure 5A:
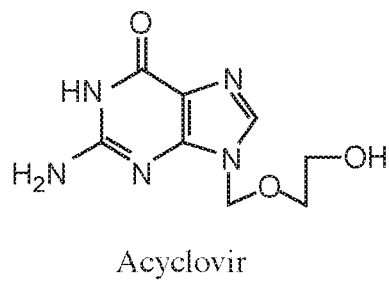
FIG. 5A-5C show molecular structures of acyclovir (FIG. 5A), penciclovir (FIG. 5B), and 2'-deoxyguanonsine (FIG. 5C) as representative nucleoside analogues for selective riboswitch control.
Figure 5B:
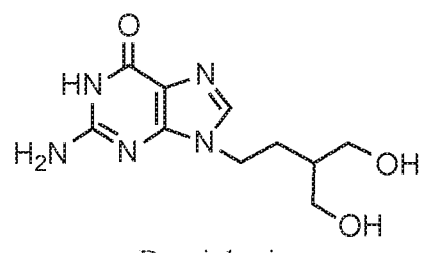
Figure 5C:
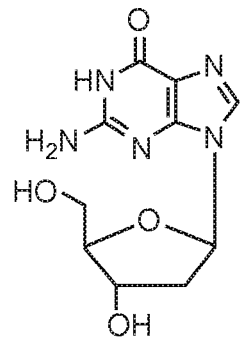

In some embodiments, the aptamer domain can be between 30, 35, 40, 45, 50, 55, 60, 65, and 70 nucleotides in length on the low end of the range and 35, 40, 45, 50, 55, 60, 65, 70, 75, 80, 85, 90, 95, and 100 nucleotides in length on the high end of the range, for example between 45 and 80 nucleotides in length, between 45 and 60 nucleotides in length, or between 45 and 58 nucleotides in length. In illustrative embodiments, the nucleoside analogue antiviral drug can be the pharmaceutical ligand acyclovir (also known as aciclovir and acycloguanosine) or penciclovir (FIG. 5). In some embodiments, the aptamer domain can have a binding affinity to the nucleoside analogue antiviral drug greater than, for example at least 2, 3, 4, 5, 6, 7, 8, 9, 10, 20, 30, 40, 50, 60, 70, 80, 90, or 100-fold greater than the binding affinity to the nucleoside or nucleotide.

The in vivo control element promotes expansion of transduced T cells in vivo. In some embodiments, expansion is dependent on the presence of the control element. However, in other embodiments, expansion of the transduced T cells can be at least partially driven by other factors such as the presence of interleukins within the subject and binding of the ASTR of a CAR on the recombinant T cell to its ligand.

In some embodiments, a nucleoside analogue antiviral drug, for example acyclovir or penciclovir, is administered to a subject before, during, and/or after PBLs are isolated from the blood and before T cells and/or NK cells are contacted with a recombinant retrovirus that includes an in vivo control element, which in illustrative non-limiting examples is a riboswitch, that binds to the nucleoside analogue antiviral drug and regulates expression of one or more target polynucleotides. The one or more target polynucleotides can encode one or more polypeptides that in non-limiting illustrative examples are one or more engineered signaling polypeptides, at least one of which encodes a lymphoproliferative element. In some embodiments, the nucleoside analogue antiviral drug, for example acyclovir or penciclovir, is administered to the subject for between 5, 10, 15, 30, and 60 minutes on the low end of the range, and 1.5, 2, 3, 4, 5, 6, 8, 12, 24, 48, or 72 hours on the high end of the range, before PBLs are isolated from the blood or before T cells and/or NK cells are contacted with a recombinant retrovirus. In some embodiments, the nucleoside analogue antiviral drug, for example acyclovir or penciclovir, is administered to the subject for between 1.5, 2, 3, 4, 5, 6, 8, 12, or 24 hours on the low end of the range, ½, 1, 2, 3, 4, 5, 6, 7, 10, 14, 21, or 28 days on the high end of the range, after PBLs are isolated from the blood or after T cells and/or NK cells are contacted with a recombinant retrovirus in methods provided herein. In some embodiments, the nucleoside analogue antiviral drug, for example acyclovir or penciclovir, is administered to the subject for at least 1.5, 2, 3, 4, 5, 6, 8, 12, or 24 hours, or at least 2, 3, 4, 5, 6, 7, 10, 14, 21, or 28 days after PBLs are isolated from the blood or after T cells and/or NK cells are contacted with a recombinant retrovirus in methods provided herein. In some embodiments, the nucleoside analogue antiviral drug, for example acyclovir or penciclovir, is administered to the subject for at least 1, 2, 3, 4, 5, 7, 10, 14, 21, 28, 30, 60, 90, or 120 days or 5, 6, 9, 12, 24, 36, 48, 60, 72, 84, 96, 120 months or indefinitely after the PBLs have been reinfused into the subject. In any of the embodiments disclosed herein, the nucleoside analogue antiviral drug can be administered before and/or during the reinfusion of the PBLs and/or after the PBLs have been reinfused. In some embodiments, the nucleoside analogue antiviral drug is administered until a subject no longer experiences symptoms of, or is afflicted by, a disease for which the target polynucleotide is related.

In some embodiments, the aptamer domain can preferentially bind penciclovir over acyclovir or alternatively another antiviral agent, such that concomitant antiviral therapy may be utilized without affecting the riboswitch. In some embodiments, the aptamer domain can bind penciclovir with a binding affinity greater than, for example at least 2, 3, 4, 5, 6, 7, 8, 9, 10, 20, 30, 40, 50, 60, 70, 80, 90, or 100-fold greater than the aptamer domain binds acyclovir or another antiviral agent. In some embodiments, the aptamer domain can preferentially bind acyclovir over penciclovir or alternatively another antiviral agent, such that concomitant antiviral therapy may be utilized without affecting the riboswitch. In some embodiments, the aptamer domain can bind acyclovir with a binding affinity greater than, for example at least 2, 3, 4, 5, 6, 7, 8, 9, 10, 20, 30, 40, 50, 60, 70, 80, 90, or 100-fold greater than the aptamer domain binds penciclovir or another antiviral agent. In some embodiments, the oral prodrugs of penciclovir (famciclovir) and acyclovir (valaciclovir) can be given to a subject.

In some embodiments, the aptamer domain of an isolated polynucleotide can share at least 80%, 85%, 90%, 91%, 92%, 93%, 94%, 95%, 96%, 97%, 98%, or 99% sequence identity or be identical to any one of the sequences of SEQ ID NOs:87-93 and retain the ability to bind acyclovir and a reduced ability to bind to guanine or 2'-deoxyguanosine relative to the nucleoside analogue antiviral drug, and wherein the aptamer domain retains the ability to induce or suppress the expression regulating activity of the function switching domain when bound by acyclovir. In some embodiments, the aptamer domain of an isolated polynucleotide can share at least 80%, 85%, 90%, 91%, 92%, 93%, 94%, 95%, 96%, 97%, 98%, or 99% sequence identity or be identical to the aptamer domain of SEQ ID NOs:94-100 and retain the ability to bind penciclovir and a reduced ability to bind to guanine or 2'-deoxyguanosine relative to the nucleoside analogue antiviral drug, and wherein the aptamer domain retains the ability to induce or suppress the expression regulating activity of the function switching domain when bound by penciclovir. In some embodiments, a region of an isolated polynucleotide or a region of a riboswitch can share at least 80%, 85%, 90%, 91%, 92%, 93%, 94%, 95%, 96%, 97%, 98%, or 99% sequence identity or be identical to any one of the sequences of SEQ ID NOs:87-100.

In some embodiments, a DNA sequence containing a region of an aptamer domain of an isolated polynucleotide can share at least 80%, 85%, 90%, 91%, 92%, 93%, 94%, 95%, 96%, 97%, 98%, or 99% sequence identity or be identical to any one of the sequences of SEQ ID NOs:108-221. In some embodiments, a region of an isolated polynucleotide can share at least 80%, 85%, 90%, 91%, 92%, 93%, 94%, 95%, 96%, 97%, 98%, or 99% sequence identity or be identical to any one of the sequences of SEQ ID NOs:108-221.

In some embodiments, a DNA sequence containing a region of an aptamer domain of an isolated polynucleotide can share at least 80%, 85%, 90%, 91%, 91.84%, 92%, 93%, 94%, 95%, 96%, 97%, 98%, or 99% sequence identity or be identical to SEQ ID NO:108. In some embodiments, a DNA sequence containing a region of an aptamer domain of an isolated polynucleotide can share at least 80%, 85%, 90%, 91%, 92%, 93%, 94%, 95%, 95.83%, 96%, 97%, 98%, or 99% sequence identity or be identical to SEQ ID NO:147. In some embodiments, a DNA sequence containing a region of an aptamer domain of an isolated polynucleotide can share at least 80%, 85%, 90%, 91%, 92%, 93%, 93.88%, 94%, 95%, 96%, 97%, 98%, or 99% sequence identity or be identical to SEQ ID NO:164. In some embodiments, a DNA sequence containing a region of an aptamer domain of an isolated polynucleotide can share at least 80%, 85%, 90%, 91%, 92%, 93%, 94%, 95%, 95.83%96%, 97%, 98%, or 99% sequence identity or be identical to SEQ ID NO:183. In some embodiments, a DNA sequence containing a region of an aptamer domain of an isolated polynucleotide can share at least 80%, 85%, 90%, 91%, 91.84%, 92%, 93%, 94%, 95%, 95.83%96%, 97%, 98%, or 99% sequence identity or be identical to SEQ ID NO:198.

In some embodiments, a region of an isolated polynucleotide can include any one of the consensus sequences of SEQ ID NOs:222-226. In some embodiments, a region of an isolated polynucleotide can share at least 80%, 85%, 90%, 91%, 92%, 93%, 94%, 95%, 95.83%, 96%, 97%, 98%, or 99% sequence identity or be identical to any one of the sequences of SEQ ID NOs:222-226.

In any of the embodiments disclosed herein, the isolated polynucleotide can retain the ability to bind acyclovir and/or penciclovir. In any of the embodiments disclosed herein, an isolated polynucleotide can be the reverse complement of any one of the sequences of SEQ ID NOs: 87-100 or SEQ ID NOs:108-221. In any of the embodiments disclosed herein, an isolated polynucleotide can be a transcription or RNA version of either the DNA sequences of SEQ ID NOs:108-221 or the DNA sequences complementary to SEQ ID NOs:108-221. In any of the embodiments disclosed herein, an isolated polynucleotide can be a reverse transcription or DNA version of any one of the RNA sequences of SEQ ID NOs:87-100 or the DNA strand complementary to a reverse transcription of any one of the RNA sequences of SEQ ID NOs:87-100.

In some embodiments provided herein, riboswitch scaffolds can be used for mutational analysis or molecular evolution. The riboswitches selected for mutational analysis or molecular evolution can be from any known organism, for example, bacteria. In some embodiments, the type I-A deoxyguanosine riboswitch from *Mesoplasma florum* can be used for molecular evolution. In some embodiments, the derived aptamer domain can be at least 50%, 60%, 70%, 75%, 80%, 85%, 90%, or 95% identical to the aptamer domain from the type I-A deoxyguanosine riboswitch from

*Mesoplasma florum* (SEQ ID NO:237). In other embodiments, the xpt riboswitch from *Bacillus subtilis* can be used. In some embodiments, the derived aptamer domain can be at least 50%, 60%, 70%, 75%, 80%, 85%, 90%, or 95% identical to the aptamer domain from the xpt riboswitch from *Bacillus subtilis* (SEQ ID NO:243).

The aptamer domains can be used as modular components and combined with any of the function switching domains to affect the RNA transcript. In any of the embodiments disclosed herein, the riboswitch can affect the RNA transcript by regulating any of the following activities: internal ribosomal entry site (IRES), pre-mRNA splice donor accessibility, translation, termination of transcription, transcript degradation, miRNA expression, or shRNA expression. In some embodiments, the function switching domain can control binding of an anti-IRES to an IRES (see, e.g. Ogawa, *RNA* (2011), 17:478-488, the disclosure of which is incorporated by reference herein in its entirety). In any of the embodiments disclosed herein, the presence or absence of the small molecule ligand can cause the riboswitch to affect the RNA transcript. In some embodiments, the riboswitch can include a ribozyme. Riboswitches with ribozymes can inhibit or enhance transcript degradation of target polynucleotides in the presence of the small molecule ligand. In some embodiments, the ribozyme can be a pistol class of ribozyme, a hammerhead class of ribozyme, a twisted class of ribozyme, a hatchet class of ribozyme, or the HDV (hepatitis delta virus) ribozyme.

In any of the embodiments disclosed herein, the riboswitch can be located in various positions relative to the target polynucleotide, as is known generally for riboswitches. In some embodiments, the riboswitch can regulate pre-mRNA splice donor accessibility and be located before the target polynucleotide. In some embodiments, the riboswitch can regulate the inclusion of a poly(A) tail and be located after the target polynucleotide. In some embodiments, the riboswitch can regulate an anti-IRES and be located upstream of an IRES. In non-limiting illustrative embodiments, a riboswitch provided herein can be located in any of these positions relative to a nucleic acid encoding one or more engineered signaling polypeptides provided herein.

In some embodiments, the riboswitch can be destabilized at temperatures above 37.5° C., 38° C., 38.5° C., 39° C., 39.5° C., or 40° C. such that the riboswitch is no longer responsive to the ligand. In some embodiments, molecular evolution can be used to select riboswitches that are destabilized at temperatures above 37.5° C., 38° C., 38.5° C., 39° C., 39.5° C., or 40° C.

In some embodiments, the target polynucleotide can encode a miRNA, shRNA, and/or a polypeptide, wherein the target polynucleotide is operably linked to a promoter. In some embodiments, the target polynucleotide can encode a lymphoproliferative element. In some embodiments, the target polynucleotide can be an miRNA or shRNA. In some embodiments, the miRNA or shRNA can potentiate the STAT5 pathway or inhibit the SOCS pathway. In some embodiments, the miRNA or shRNA can target transcripts from SOCS1, SMAD2, TGFb, or PD-1. In some embodiments, the miRNA is miR-155. In some embodiments, the target polynucleotide encodes a polypeptide and the polypeptide can include a CAR including an antigen-specific targeting region, a transmembrane domain, and an intracellular activating domain.

In another aspect, provided herein is an isolated polynucleotide for regulating expression of a target polynucleotide, including: a polynucleotide encoding the target polynucleotide operably linked to a promoter and a riboswitch, wherein the riboswitch includes: a.) an aptamer domain capable of binding a nucleoside analogue antiviral drug with a binding affinity at least two-fold greater affinity than the aptamer domain binds guanine or 2'-deoxyguanosine; and b.) a function switching domain capable of regulating expression of the target polynucleotide, wherein binding of the nucleoside analogue by the aptamer domain induces or suppresses the expression regulating activity of the function switching domain. In some embodiments, the aptamer domain can bind the nucleoside analogue antiviral drug with a binding affinity at least 3, 4, 5, 6, 7, 8, 9, 10, 20, 30, 40, 50, 60, 70, 80, 90, or 100-fold greater affinity than the aptamer domain binds guanine or 2'-deoxyguanosine. In some embodiments, the aptamer domain can be between 30, 35, 40, 45, 50, 55, 60, 65, and 70 nucleotides in length on the low end of the range and 35, 40, 45, 50, 55, 60, 65, 70, 75, 80, 85, 90, 95, and 100 nucleotides in length on the high end of the range, for example between 45 and 80 nucleotides in length or between 45 and 58 nucleotides in length. In illustrative embodiments, the nucleoside analogue antiviral drug can be the pharmaceutical ligand acyclovir (also known as aciclovir and acycloguanosine) or penciclovir. In some embodiments, the aptamer domain can have a binding affinity to the nucleoside analogue antiviral drug that is greater than, for example at least 2, 3, 4, 5, 6, 7, 8, 9, 10, 20, 30, 40, 50, 60, 70, 80, 90, or 100-fold greater than the binding affinity to the nucleoside or nucleotide. In some embodiments, binding of the nucleoside analogue by the aptamer domain can induce an activity in the riboswitch.

In some embodiments, the aptamer domain can be specific for penciclovir and lack reactivity to acyclovir or alternatively another antiviral agent, such that concomitant antiviral therapy may be utilized without affecting the riboswitch. In some embodiments, the aptamer domain can bind penciclovir with a binding affinity at least 2, 3, 4, 5, 6, 7, 8, 9, 10, 20, 30, 40, 50, 60, 70, 80, 90, or 100-fold greater than the aptamer domain binds acyclovir or another antiviral agent. In some embodiments, the aptamer domain can be specific for acyclovir and lack reactivity to penciclovir or alternatively another antiviral agent, such that concomitant antiviral therapy may be utilized without affecting the riboswitch. In some embodiments, the aptamer domain can bind acyclovir with a binding affinity at least 2, 3, 4, 5, 6, 7, 8, 9, 10, 20, 30, 40, 50, 60, 70, 80, 90, or 100-fold greater than the aptamer domain binds penciclovir or another antiviral agent. In some embodiments, the oral prodrugs of penciclovir (famciclovir) and acyclovir (valaciclovir) can be given to a subject. In some embodiments, the derived aptamer domain can be at least 50%, 60%, 70%, 75%, 80%, 85%, 90%, or 95% identical to the aptamer domain from the type I-A deoxyguanosine riboswitch from *Mesoplasma florum*. In some embodiments, the derived aptamer domain can be at least 50%, 60%, 70%, 75%, 80%, 85%, 90%, or 95% identical to the aptamer domain from the xpt riboswitch from *Bacillus subtilis*. In any of the embodiments disclosed herein, the riboswitch can affect the RNA transcript by regulating any of the following activities: internal ribosomal entry site, pre-mRNA splice donor accessibility in the retroviral gene construct, translation, termination of transcription, transcript degradation, miRNA expression, or shRNA expression. In some embodiments, the function switching domain can control binding of an anti-IRES to an IRES. In any of the embodiments disclosed herein, the presence or absence of the small molecule ligand can cause the riboswitch to affect the RNA transcript. In some embodiments, the riboswitch can include a ribozyme. Riboswitches with ribozymes can inhibit or enhance transcript degradation of genes of interest in the presence of the small molecule ligand. In some embodiments, the ribozyme can be a pistol class of ribozyme, a hammerhead class of ribozyme, a twisted class of ribozyme, a hatchet class of ribozyme, or the HDV (hepatitis delta virus) ribozyme. In some embodiments, the riboswitch can be destabilized at temperatures above 37.5° C., 38° C., 38.5° C., 39° C., 39.5° C., or 40° C. such that the riboswitch is no longer responsive to the ligand. In some embodiments, molecular evolution can be used to select riboswitches that are destabilized at temperatures above 37.5° C., 38° C., 38.5° C., 39° C., 39.5° C., or 40° C. In some embodiments, the target polynucleotide can encode a miRNA, shRNA, and/or a polypeptide, wherein the target polynucleotide is operably linked to a promoter. In some embodiments, the target polynucleotide can encode a lymphoproliferative element. In some embodiments, the target polynucleotide can be an miRNA and, optionally, the miRNA can stimulate the STAT5 pathway or inhibit the SOCS pathway. In some embodiments, the miRNA can target transcripts from SOCS1, SHP, SMAD2, TGFb, or PD-1. In these embodiments, the miRNA can be miR-155. In some embodiments, the target polynucleotide encodes a polypeptide and the polypeptide can include a CAR including an antigen-specific targeting region, a transmembrane domain, and an intracellular activating domain. Further embodiments of CARs are disclosed elsewhere herein.

In some embodiments, the evolution of aptamers can be performed via aptamer selection from randomized native purine or guanine aptamer libraries using SELEX (Systematic Evolution of Ligands by EXponential enrichment) methods including, but not limited to, those methods that employ graphene oxide in the selection process and screening. In other embodiments, random mutagenesis methodology such as error prone PCR can be used to evolve aptamer constructs or riboswitch constructs where the aptamer is incorporated in the context of any of the riboswitch activities described herein by screening in vitro or in mammalian cells. In other embodiments, random libraries of nucleotides can be used in the evolution of the riboswitch. In any of the embodiments disclosed herein, riboswitches can be identified from screening such libraries in vitro or in mammalian cells.

In some embodiments, the evolved or derived aptamer domain can have increased binding to analogues of the native ligand and decreased binding to the native ligand. In some embodiments, the aptamer domain can be configured to have increased binding to analogues of the native ligand and decreased binding to the native ligand. In some embodiments, the aptamer domain can be derived from the purine riboswitch family. In some embodiments, the native ligand can be a nucleoside or nucleotide and the analogue can be a nucleoside analogue or nucleotide analogue. In some embodiments, the nucleoside analogue is an antiviral drug. In illustrative embodiments, the aptamer domains can be derived from 2'-deoxyguanosine and guanine riboswitch scaffolds and the derived aptamer domains can show reduced binding to 2'-deoxyguanosine and guanine relative to the wild-type riboswitch.

In some embodiments, the riboswitch can regulate pre-mRNA splice donor accessibility in the retroviral gene construct, wherein the retroviral construct drives the CAR genes or other genes of interest from the reverse strand under a general promoter or a T cell specific promoter. In other embodiments, the riboswitch can regulate an IRES in the retroviral gene construct, wherein the retroviral construct drives the translation of CAR genes or other genes of interest. In other embodiments, the riboswitch can control transcription termination of the RNA, miRNA, or gene transcripts or can control translation of the transcript. In other embodiments, the nucleoside analogue riboswitch can be integrated with a ribozyme to inhibit or enhance transcript degradation of the CAR genes or other genes of interest in the presence of the nucleoside analogue.

In some embodiments, the isolated polynucleotide for regulating expression of a target polynucleotide that includes a polynucleotide encoding the target polynucleotide operably linked to a promoter and a riboswitch that binds a nucleoside analogue antiviral drug, is a molecular cloning vector. The molecular cloning vector can be any type of molecular cloning vector known in the art. As non-limiting examples, the vector can be a plasmid, a virus, or a retrovirus, any of which can be an expression vector. Such an expression vector can encode any of the target polynucleotides provided hereinabove. One or more restriction and/or multiple cloning sites can be included on a molecular cloning vector 5' or 3' to a riboswitch provided herein such that the riboswitch is operably linked to a target polynucleotide inserted into the restriction and/or multiple cloning site.

Molecular Chaperones

In one aspect, provided herein is a method for genetically modifying and expanding lymphocytes of a subject, comprising:

A. contacting resting T cells and/or NK cells of the subject ex vivo, typically without requiring prior ex vivo stimulation, with recombinant retroviruses comprising:
  i. a pseudotyping element on its surface that is capable of binding to a T cell and/or NK cell and facilitating membrane fusion of the recombinant retrovirus thereto; and
  ii. a polynucleotide comprising one or more transcriptional units operatively linked to a promoter active in T cells and/or NK cells, wherein the one or more transcriptional units encode a first engineered signaling polypeptide regulated by an in vivo control element, wherein said first engineered signaling polypeptide comprises a lymphoproliferative element and/or a chimeric antigen receptor,
  wherein said contacting facilitates transduction of at least some of the resting T cells and/or NK cells by the recombinant retroviruses, thereby producing genetically modified T cells and/or NK cells;

B. introducing the genetically modified T cells and/or NK cells into the subject; and C. exposing the genetically modified T cells and/or NK cells in vivo to a compound that acts as the in vivo control element to affect expression of the first engineered signaling polypeptide and promote expansion of the lymphocytes in vivo, thereby genetically modifying and expanding lymphocytes of the subject.

In illustrative embodiments, the transduction is carried out without ex vivo stimulation. In illustrative embodiments, the compound is a molecular chaperone, such as a small molecule molecular chaperone. In illustrative embodiments, binding of the molecular chaperone to the lymphoproliferative element and/or CAR component increases the proliferative activity of the lymphoproliferative element and/or the CAR. The molecular chaperone can be administered to the subject before the blood is collected, during the contacting, and/or after the T cells and/or NK cells are introduced into the subject. Some embodiments of this aspect include collecting blood from the subject. In these embodiments, the introducing is a reintroducing of the cells that were collected and genetically modified before reintroduction. The entire process, in illustrative embodiments, is a shorter process than prior art methods, as for other aspects herein. For example, the entire process can be completed in less than 48 hours, less than 24 hours, or less than 12 hours. The entire process in other embodiments, can be completed in 2, 4, 6, or 8 hours on the low end of the range, and 12, 24, 36, or 48 hours on the high end of the range.

Accordingly, in some embodiments of the methods and compositions provided herein, the in vivo control element is a molecular chaperone. As compared to other embodiments herein with other in vivo control elements, such as riboswitches that typically bind a compound to affect expression of a lymphoproliferative element or other component of a first or second engineered signaling polypeptide herein, the molecular chaperones are compounds that are the in vivo control elements and as such, directly affect activity of, typically by binding to, a lymphoproliferative element or other component of a first or second engineered signaling polypeptide herein. In illustrative examples of such embodiments of methods herein that include the administration of molecular chaperones, a lymphoproliferative element, membrane-bound cytokine, and/or CAR component, can be a less active or inactive lymphoproliferative element, membrane-bound cytokine, and/or CAR component, that is bound by the molecular chaperone to increase its activity. Thus, the target bound by a molecular chaperone is typically a target polypeptide. In some embodiments, as indicated the polypeptide can be a first and/or a second engineered signaling polypeptide, or a polypeptide component thereof, whose activity is affected by binding to the molecular chaperone, which in illustrative embodiments is a small molecule molecular chaperone. In some embodiments, the polypeptide can include a lymphoproliferative element whose activity is regulated, in illustrative embodiments, up-regulated by a molecular chaperone, preferably a small molecule molecular chaperone. The molecular chaperone in the methods provided herein can be a compound that binds to the mutant lymphoproliferative element and/or inactive CAR component, thus rendering them active.

In other embodiments, a lymphoproliferative element or other signaling domain has been mutated to permit transit to the plasma membrane only in the presence of a small molecular synthetic chaperone. In other embodiments, the chaperone promotes stability of the lymphoproliferative element or other signaling domain or protein and half-life as a potentiator.

It will be understood that aspects and embodiments of the present invention include many of the same steps and compositions provided in detail herein. Accordingly, it will be understood that the teachings throughout this specification that relate to these common elements apply to aspects and embodiments that utilize a molecular chaperone as the in vivo control element, which typically binds a lymphoproliferative element or other target molecule directly, in addition to, or instead of other in vivo control elements provided herein, such as riboswitches, which typically utilize a molecule, such as a drug, that binds the riboswitch.

In some embodiments, the molecular chaperone is a compound that can regulate sub-cellular localization of a target, for example, the proper folding and transit of a target protein, such as a lymphoproliferative element and/or a component of a CAR, from the endoplasmic reticulum to the plasma membrane or its half-life on the surface. In other embodiments, the molecular chaperone can promote the functional conformation of a dysfunctional target, thus acting as a potentiator. Examples of molecules that act as chaperones or potentiators to naturally mutated proteins include lumacaftor and ivacaftor. These proteins act upon the mutant CFTR chloride channel variants such as G551D or F508del. Ivacaftor potentiates the activity of the G551D or F508del mutated ion channel, whereas lumacaftor promotes stabilization of mutant chloride channels and subsequent potentiation by ivacaftor. Such chaperone dependent proteins can be generated from naturally functional proteins and screening for functional activity only in the presence of the molecular chaperones. Thus, such proteins are only active when the chaperone is present. Examples of such molecules which can be screened for specific chaperone activity include small molecule antivirals or anti-infectives that show no activity to normal human proteins. Accordingly, in one embodiment, the molecular chaperone used in methods herein is a small molecule antiviral or anti-infective compound that shows no activity to normal human proteins.

In some embodiments, genetically modified lymphocytes can be exposed and/or a subject can be administered the molecular chaperone. In some embodiments, the compound is administered to the subject before, during, and/or after PBLs are isolated from the blood and before T cells and/or NK cells are contacted with a recombinant retrovirus. The recombinant retrovirus in such embodiments includes a less active or inactive lymphoproliferative element and/or CAR component that binds to, and is regulated by, the molecular chaperone compound.

For any of the embodiments provided herein for modifying and expanding lymphocytes, which can be part of methods of adoptive cell therapy, the compound can be administered to the subject for between 5, 10, 15, 30, and 60 minutes on the low end of the range, and 1.5, 2, 3, 4, 5, 6, 8, 12, or 24 hours on the high end of the range, before PBLs are isolated from the blood or before T cells and/or NK cells are contacted with a recombinant retrovirus. In some embodiments, the compound is administered to the subject for between 1.5, 2, 3, 4, 5, 6, 8, 12, or 24 hours on the low end of the range, ½, 1, 2, 3, 4, 5, 6, 7, 10, 14, 21, or 28 days on the high end of the range, after PBLs are isolated from the blood or after T cells and/or NK cells are contacted with a recombinant retrovirus in methods provided herein. In some embodiments, the compound is administered to the subject for at least 1.5, 2, 3, 4, 5, 6, 8, 12, or 24 hours, or at least 2, 3, 4, 5, 6, 7, 10, 14, 21, or 28 days after PBLs are isolated from the blood or after T cells and/or NK cells are contacted with a recombinant retrovirus in methods provided herein. In some embodiments, the compound is administered to the subject for at least 1, 2, 3, 4, 5, 7, 10, 14, 21, 28, 30, 60, 90, or 120 days or 5, 6, 9, 12, 24, 36, 48, 60, 72, 84, 96, 120 months or indefinitely after the PBLs have been reinfused into the subject. In any of the embodiments disclosed herein, the compound can be administered before and/or during the reinfusion of the PBLs and/or after the PBLs have been reinfused.

For any of the embodiments herein, molecular chaperones are not in the in vivo control elements that are bound by compounds that regulate and/or activate them. Molecular chaperones are compounds, preferably small molecule compounds, that are the in vivo control elements and regulate the activity of lymphoproliferative elements and/or functional components of CARs.

Packaging Cell Lines/Methods of Making Recombinant Retroviruses

In one aspect, provided herein is a retroviral packaging system including: a mammalian cell including: a) a first transactivator expressed from a constitutive promoter and capable of binding a first ligand and a first inducible promoter for affecting expression of a nucleic acid sequence operably linked thereto in the presence versus absence of the first ligand; b) a second transactivator capable of binding a second ligand and a second inducible promoter, and affecting expression of a nucleic acid sequence operably linked thereto in the presence versus absence of a second ligand; and c) a packagable RNA genome for a retroviral particle, wherein the first transactivator regulates expression of the second transactivator, and wherein the second transactivator regulates expression of retroviral polypeptides involved in viral packaging, such as, for example, a gag polypeptide, a pol polypeptide, and/or a pseudotyping element, and optionally other polypeptides that will become incorporated in or on the recombinant retrovirus and are believed to be toxic to packaging cell lines, such as, for example, HEK-293. In certain aspects, the second transactivator itself is cytotoxic to packaging cell lines. Pseudotyping elements are typically capable of binding to a cell membrane of a target cell and facilitating fusion thereto, as discussed in detail herein. Thus, not to be limited by theory, the system provides the ability to accumulate certain polypeptides/proteins that do not inhibit, or do not substantially inhibit, or are not believed to inhibit proliferation or survival of the mammalian cells, for example, non-toxic proteins, while culturing a population of the mammalian cells for days or indefinitely, and controlling induction of polypeptides that are desired for retroviral product but that are inhibitory or can be inhibitory or have been reported to be inhibitory to the survival and/or proliferation of the mammalian cell, for example toxic polypeptides, until a later time closer to the time of when retroviruses will be produced and harvested. The packagable RNA genome is typically encoded by a polynucleotide operably linked to a promoter, sometimes referred to herein as a third promoter for convenience, wherein said third promoter is typically inducible by either the first transactivator or the second transactivator. In illustrative embodiments, the packagable RNA genome is encoded by a polynucleotide operably linked to a third promoter, wherein said third promoter is inducible by the second transactivator. As such, the packagable RNA genome can be produced at the later time point, closer to when the retrovirus will be harvested.

A skilled artisan will appreciate many different transactivators, ligands, and inducible promoters can be used in the retroviral packaging system. Such inducible promoters can be isolated and derived from many organisms, e.g., eukaryotes and prokaryotes. Modification of inducible promoters derived from a first organism for use in a second organism, e.g., a first prokaryote and a second a eukaryote, a first eukaryote and a second a prokaryote, etc., is well known in the art. Such inducible promoters, and systems based on such inducible promoters but also including additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like. In some embodiments, a mifepristone-regulated system can be used. In some embodiments, a mifepristone-inducible system with an autoregulatory feedback loop can be used. In some embodiments, a GAL4 regulatory fusion protein is expressed from one construct that also contains the transposon terminal repeats and lox and FRT sites. In some embodiments, the GAL4 regulatory fusion protein controls expression of a reverse tet transactivator (rtTA) and BiTRE. In some embodiments, another construct with lox and FRT sites contains a GAL4 upstream activating sequences (UAS) and an E1b TATA box promoter driving a reporter like mCherry. In some embodiments, a GAL4 regulatory fusion protein binds to GAL4 upstream activating sequences (UAS) in both the promoter controlling expression of the GAL4 regulatory fusion protein and the promoter controlling expression of a target polynucleotide. In some embodiments, mifepristone, doxycycline, and puromycin will be used for induction and selection of packaging cell line.

In some embodiments, either or both transactivators can be split into two or more polypeptides. In some embodiments, the two or more polypeptides can include a DNA binding domain and an activation domain capable of stimulating transcription on separate polypeptides. This "activation domain" is not to be confused with an "activation element," such as a polypeptide that binds CD3, which is capable of activating a T cell and/or NK cell, and typically does activate such T cell and/or NK cell when contacted with it, as discussed in detail herein. The separate polypeptides can further include fusions with polypeptides capable of dimerization through the addition of a ligand. In some embodiments, the activation domain can be the p65 activation domain or a functional fragment thereof. In illustrative embodiments of the packaging systems herein, the DNA binding domain can be the DNA binding domain from ZFHD1 or a functional fragment thereof. In some embodiments, one polypeptide can be a fusion with FKBP, or functional mutants and/or fragments thereof, or multiple FKBPs and another polypeptide can be a fusion with the FRB domain of mTOR, or functional mutants and/or fragments thereof, and the ligand can be rapamycin or a functional rapalog. In some embodiments, the FRB contains the mutations K2095P, T2098L, and/or W2101F. In some embodiments, the separate polypeptides can be FKBP, or functional fragments thereof, and CalcineurinA, or functional fragments thereof, and the dimerizing agent can be FK506. In some embodiments, the separate polypeptides can be FKBP, or functional fragments thereof, and CyP-Fas, or functional fragments thereof, and the dimerizing agent can be FKCsA. In some embodiments, the separate polypeptides can be GAI, or functional fragments thereof, and GID1, or functional fragments thereof, and the dimerizing agent can be gibberellin. In some embodiments, the separate polypeptides can be Snap-tag and HaloTag, or functional fragments thereof, and the dimerizing agent can be HaXS. In some embodiments, the separate polypeptides can include the same polypeptide. For example, the DNA binding domain and activation domain can be expressed as fusion proteins with FKBP or GyrB and the dimerizing agent can be FK1012 or coumermycin, respectively. In some embodiments, the inducible promoter can be the DNA sequence where the DNA binding domain typically binds. In some embodiments, the inducible promoter can vary from the DNA sequence where the DNA binding domain typically binds. In some embodiments, either transactivator can be an rtTA, the ligand can be tetracycline or doxycycline, and the inducible promoter can be a TRE. In illustrative embodiments, the first transactivator is the p65 activation domain fused to FRB and the ZFHD1 DNA binding domain fused to three FKBP polypeptides and the first ligand is rapamycin. In further illustrative embodiments, the second transactivator can be an rtTA, the second ligand can be tetracycline or doxycycline, and the inducible promoter can be a TRE.

In some embodiments, the first transactivator can regulate expression of an element to control the nuclear export of transcripts containing a consensus sequence, such as an HIV Rev and the consensus sequence can be the Rev response element. In illustrative embodiments, the target cell is a T cell.

In some embodiments, the pseudotyping element is a retroviral envelope polypeptide. The pseudotyping element typically includes a binding polypeptide and a fusogenic polypeptide for binding to and facilitating membrane fusion of the target cell and viral membranes, as discussed in more detail herein. In some embodiments, the pseudotyping element is the feline endogenous virus (RD114) envelope protein, the oncoretroviral amphotropic envelope protein, the oncoretroviral ecotropic envelope protein, and/or vesicular stomatitis virus (VSV-G) envelope protein. In illustrative embodiments, the pseudotyping element includes a binding polypeptide and a fusogenic polypeptide derived from different proteins, as discussed in further detail herein. For example, in an illustrative embodiment, especially where the target cell is a T cell and/or NK cell, the binding polypeptide is a hemagglutinin (H) polypeptide of a Measles Virus (such as the Edmonston strain of the Measles Virus), or a cytoplasmic domain deletion variant thereof, and the fusogenic polypeptide other is a fusion (F) polypeptide of a Measles Virus (such as the Edmonston strain of the Measles Virus), or a cytoplasmic domain deletion variant thereof. In some embodiments, the fusogenic polypeptide can include multiple elements expressed as one polypeptide. In some embodiments, the binding polypeptide and the fusogenic polypeptide can be translated from the same transcript but from separate ribosome binding sites, or the polypeptide is cleaved after translation using a peptide cleavage signal or a ribosomal skip sequence, as disclosed elsewhere herein, to generate the binding polypeptide and the fusogenic polypeptide. In some embodiments, where the binding polypeptide is a Measles Virus H polypeptide, or a cytoplasmic domain deletion thereof, and the fusogenic polypeptide is a Measles Virus F polypeptide, or a cytoplasmic domain deletion thereof, translation of the F and H polypeptides from separate ribosome binding sites results in a higher amount of the F polypeptide as compared to the H polypeptide. In some embodiments, the ratio of the F polypeptides (or cytoplasmic domain deletions thereof) to H polypeptides (or cytoplasmic domain deletions thereof) is at least 2:1, at least 3:1, at least 4:1, at least 5:1, at least 6:1, at least 7:1, or at least 8:1.

In some embodiments, the first transactivator can regulate the expression of an activation element capable of binding to and activating a target cell, such as a T cell. Any of the activation elements disclosed herein can be expressed. For example, in these embodiments, the activation element can include: a.) a membrane-bound polypeptide capable of binding to and activating CD3: and/or b.) a membrane-bound polypeptide capable of binding to and activating CD28. In some embodiments, the membrane-bound polypeptide capable of binding to and activating CD28 is CD80, CD86, or functional fragments thereof, such as the extracellular domain of CD80.

In some embodiments, the second transactivator can regulate the expression of an RNA that encodes one or more target polypeptides, including as a non-limiting example, any of the engineered signaling polypeptides disclosed herein. It should be noted that it is envisioned that the retroviral packaging system aspect, and the method of making a recombinant retrovirus aspect, are not limited to making recombinant retroviruses for transduction of T cell and/or NK cells, but rather for any cell type that can be transduced by recombinant retroviruses. The RNA, in certain illustrative embodiments, includes in opposite orientation (e.g., encoding on the opposite strand and in the opposite orientation), retroviral components such as gag and pol. For example, the RNA can include from 5' to 3': a 5' long terminal repeat, or active truncated fragment thereof; a nucleic acid sequence encoding a retroviral cis-acting RNA packaging element; a nucleic acid sequence encoding a first and optionally second target polypeptide, such as, but not limited to, an engineered signaling polypeptide(s), which can be driven off a promoter, which in some embodiments is called a "fourth" promoter for convenience only; a promoter that is active in a target cell; and a 3' long terminal repeat, or active truncated fragment thereof. In some embodiments, the RNA can include a central polypurine tract (cPPT)/central termination sequence (CTS) element. In some embodiments, the retroviral cis-acting RNA packaging element can be HIV Psi. In some embodiments, the retroviral cis-acting RNA packaging element can be the Rev Response Element. The engineered signaling polypeptide in illustrative embodiments, is one or more of the engineered signaling polypeptides disclosed herein.

It will be understood that promoter number, such as a first, second, third, fourth, etc. promoter is for convenience only. A promoter that is called a "fourth" promoter should not be taken to imply that there are any additional promoters, such as first, second or third promoters, unless such other promoters are explicitly recited.

In some embodiments, the engineered signaling polypeptide can include a first lymphoproliferative element. Suitable lymphoproliferative elements are disclosed in other sections herein. As a non-limiting example, the lymphoproliferative element can be expressed as a fusion with a recognition domain, such as an eTag, as disclosed herein. In some embodiments, the packagable RNA genome can further include a nucleic acid sequence encoding a second engineered polypeptide including a chimeric antigen receptor, encoding any CAR embodiment provided herein. For example, the second engineered polypeptide can include a first antigen-specific targeting region, a first transmembrane domain, and a first intracellular activating domain. Examples of antigen-specific targeting regions, transmembrane domains, and intracellular activating domains are disclosed elsewhere herein. In some embodiments where the target cell is a T cell, the promoter that is active in a target cell is active in a T cell, as disclosed elsewhere herein.

In some embodiments, the packagable RNA genome can further include a riboswitch, as discussed in other sections herein. In some embodiments, the nucleic acid sequence encoding the engineered signaling polypeptide can be in reverse orientation. In further embodiments, the packagable RNA genome can further include a riboswitch and, optionally, the riboswitch can be in reverse orientation. In any of the embodiments disclosed herein, a polynucleotide including any of the elements can include a primer binding site. In illustrative embodiments, transcription blockers or polyA sequences can be placed near genes to prevent or reduce unregulated transcription. In any of the embodiments disclosed herein, a nucleic acid sequence encoding Vpx can be on the second or an optional third transcriptional unit, or on an additional transcriptional unit that is operably linked to the first inducible promoter.

In another aspect, provided herein is a method for making a recombinant retrovirus, including: culturing a population of packaging cells to accumulate a first transactivator, wherein the packaging cells include the first transactivator expressed from a constitutive promoter, wherein the first transactivator is capable of binding a first ligand and a first inducible promoter for affecting expression of a nucleic acid sequence operably linked thereto in the presence versus absence of the first ligand, and wherein expression of a second transactivator is regulated by the first transactivator; incubating the population of packaging cells including accumulated first transactivator in the presence of the first ligand to accumulate the second transactivator, wherein the second transactivator is capable of binding a second ligand and a second inducible promoter for affecting expression of a nucleic acid sequence operably linked thereto in the presence versus absence of the second ligand; and incubating the population of packaging cells including accumulated second transactivator in the presence of the second ligand thereby inducing expression of retroviral polypeptides involved in viral packaging, such as, for example, a gag polypeptide, a pol polypeptide, and/or a pseudotyping element, and optionally other polypeptides that are believed to inhibit mammalian cell proliferation or survival that will become incorporated in or on the recombinant retrovirus, thereby making the recombinant retrovirus. In illustrative embodiments, a packagable RNA genome is encoded by a polynucleotide operably linked to a promoter, sometimes referred to for convenience as a "third" promoter wherein said third promoter is either constitutively active or inducible by either the first transactivator or, in illustrative embodiments, the second transactivator, thereby making the recombinant retrovirus. The pseudotyping elements are typically capable of binding to a cell membrane of a target cell and facilitating fusion of the target cell membrane to the recombinant retrovirus membrane. The pseudotyping elements can be any envelope proteins known in the art. In some embodiments, the envelope protein can be vesicular stomatitis virus (VSV-G) envelope protein, feline endogenous virus (RD114) envelope protein, oncoretroviral amphotropic envelope protein, and/or oncoretroviral ecotropic envelope protein. A skilled artisan will appreciate many different transactivators, ligands, and inducible promoters can be used in the method for making a recombinant retrovirus. Suitable transactivators, ligands, and inducible promoters are disclosed elsewhere herein, including above. A skilled artisan will further appreciate that the teachings hereinabove related to a retroviral packaging system aspect provided herein, apply to method of making recombinant retrovirus aspects as well, and the reverse.

In some embodiments, the first transactivator can regulate expression of an element to control the nuclear export of transcripts containing a consensus sequence, such as an HIV Rev and the consensus sequence can be the Rev Response Element (RRE). In illustrative embodiments, the target cell is typically a T cell. In some embodiments, the HIV RREs and the polynucleotide region encoding HIV Rev can be replaced with HIV-2 RREs and a polynucleotide region encoding the HIV-2 Rev, respectively. In some embodiments, the HIV RREs and the polynucleotide region encoding HIV Rev can be replaced with SIV RREs and a polynucleotide region encoding the SIV Rev, respectively. In some embodiments, the HIV RREs and the polynucleotide region encoding HIV Rev can be replaced with RemREs and a polynucleotide region encoding a betaretrovirus Rem, respectively. In some embodiments, the HIV RREs and the polynucleotide region encoding HIV Rev can be replaced with a deltaretrovirus RexRRE and a polynucleotide region encoding a deltaretrovirus Rex, respectively. In some embodiments, a Rev-like protein is not required and the RREs can be replaced with cis-acting RNA elements, such as the constitutive transport element (CTE).

In some embodiments, the pseudotyping element is a viral envelope protein. The pseudotyping element typically includes a binding polypeptide and a fusogenic polypeptide for binding to and facilitating membrane fusion of viral and target cell membranes. In some embodiments, the pseudotyping element can be the feline endogenous virus (RD114) envelope protein, the oncoretroviral amphotropic envelope protein, the oncoretroviral ecotropic envelope protein, and/or vesicular stomatitis virus (VSV-G) envelope protein. In illustrative embodiments, the pseudotyping element includes a binding polypeptide and a fusogenic polypeptide derived from different proteins, as discussed in further detail herein. For example, in an illustrative embodiment, especially where the target cell is a T cell and/or NK cell, the binding polypeptide can be a cytoplasmic domain deletion variant of a Measles Virus H polypeptide and the fusogenic polypeptide can be the cytoplasmic domain deletion variant of a Measles Virus F polypeptide. In some embodiments, the fusogenic polypeptide can include multiple elements expressed as one polypeptide. In some embodiments, the binding polypeptide and fusogenic polypeptide can be translated from the same transcript and translated from separate ribosome binding sites, or the polypeptide can be cleaved after translation using a peptide cleavage signal or a ribosomal skip sequence, as disclosed elsewhere herein, to generate the binding polypeptide and the fusogenic polypeptide. In some embodiments, the translation of the binding polypeptide and fusogenic polypeptide from separate ribosome binding sites results in a higher amount of the fusogenic polypeptide as compared to the binding polypeptide. In some embodiments, the ratio of the fusogenic polypeptide to the binding polypeptide is at least 2:1, at least 3:1, at least 4:1, at least 5:1, at least 6:1, at least 7:1, or at least 8:1.

In some embodiments, the first transactivator can regulate the expression of an activation element capable of binding to and activating a target cell, such as a T cell. In these embodiments, the activation element can include: a.) aa membrane-bound polypeptide capable of binding to and activating CD3: and/or b.) a membrane-bound polypeptide capable of binding to and activating CD28. In some embodiments, the membrane-bound polypeptide capable of binding to and activating CD28 is CD80, CD86, or functional fragments thereof. In some embodiments, the recombinant retrovirus can include the activation element on a retroviral membrane and the retroviral RNA within a nucleocapsid, thereby making a recombinant retrovirus.

In some embodiments, the second transactivator can regulate the expression of an RNA including from 5' to 3': a 5' long terminal repeat, or active truncated fragment thereof; a nucleic acid sequence encoding a retroviral cis-acting RNA packaging element; a nucleic acid sequence encoding a first target polypeptide and optional second target polypeptide, as non-limiting example, one or two engineered signaling polypeptides; a promoter that is active in a target cell; and a 3' long terminal repeat, or active truncated fragment thereof. In some embodiments, the RNA can include a cPPT/CTS element. In some embodiments, the RNA can include a primer binding site. In some embodiments, the retroviral cis-acting RNA packaging element can be HIV Psi. In some embodiments, the retroviral cis-acting RNA packaging element can be the Rev Response Element. In any of the embodiments disclosed herein, retroviral components on the RNA, including RRE and Psi, can be located in any position, as a skilled artisan will understand. The engineered signaling polypeptide in illustrative embodiments, is one or more of the engineered signaling polypeptides disclosed herein.

In some embodiments, the engineered signaling polypeptide can include a first lymphoproliferative element. Suitable lymphoproliferative elements are disclosed in other sections herein. In some illustrative embodiments, the lymphoproliferative element is an IL-7 receptor mutant fused to a recognition domain, such as an eTag. In some embodiments, the packagable RNA genome can further include a nucleic acid sequence encoding a second engineered polypeptide including a chimeric antigen receptor, encoding any CAR embodiment provided herein. For example, the second engineered polypeptide can include a first antigen-specific targeting region, a first transmembrane domain, and a first intracellular activating domain. Examples of antigen-specific targeting regions, transmembrane domains, and intracellular activating domains are disclosed elsewhere herein. In some embodiments where the target cell is a T cell, the promoter that is active in a target cell is active in a T cell, as disclosed elsewhere herein.

In some embodiments, the packagable RNA genome can further include a riboswitch, as discussed in other sections herein. In some embodiments, the nucleic acid sequence encoding the engineered signaling polypeptide can be in reverse orientation. In further embodiments, the packagable RNA genome can further include a riboswitch and, optionally, the riboswitch can be in reverse orientation. In any of the embodiments disclosed herein, a polynucleotide including any of the elements can include a primer binding site. In illustrative embodiments, transcription blockers or polyA sequences can be placed near genes to prevent or reduce unregulated transcription. In any of the embodiments disclosed herein, a nucleic acid sequence encoding Vpx can be on the second or an optional third transcriptional unit, or on an additional transcriptional unit that is operably linked to the first inducible promoter.

In some embodiments of the packaging system or methods for making retrovirus aspects, the encoded RNA can include an intron, which can be transcribed, for example, from the same promoter for expressing the target polypeptide(s). Such intron can encode 1, 2, 3, or 4 miRNAs, in certain illustrative embodiments. In these and other embodiments of the packaging system or methods for making retrovirus aspects, the packagable RNA genome is 11,000 KB or less and in some instances 10,000 KB or less in size.

In some embodiments, the first transactivator can affect the expression of one or more polypeptides that are non-toxic. In some embodiments, the second transactivator can affect the expression of one or more polypeptides that are toxic. For example, the first transactivator can induce expression of the retroviral proteins Rev and Vpx in addition to polypeptides that will be transported to the cell membrane of the packaging cell and the second transactivator can induce expression of the retroviral proteins GAG, POL, MV(Ed)-FΔ30, and either MV(Ed)-HΔ18 or MV(Ed)-HΔ24 and expression of the lentiviral genome. In some embodiments, the first transactivator can affect the expression of one or more polypeptides that are toxic and/or the second transactivator can affect the expression of one or more polypeptides that are non-toxic.

In another aspect, provided herein is a mammalian packaging cell, including: a.) a first transcriptional unit in the genome of the mammalian packaging cell, including a nucleic acid sequence encoding a first transactivator, wherein said first transcriptional unit is operably linked to a constitutive promoter and wherein said transactivator is capable of binding a first inducible promoter and affecting expression of a nucleic acid sequence operably linked thereto in the presence versus absence of a first ligand, and wherein said first transactivator is capable of binding said first ligand; b.) a second and optional third transcriptional unit in the genome of the mammalian packaging cell, including a nucleic acid sequence encoding a retroviral REV protein and a nucleic acid sequence encoding a second transactivator capable of binding a second inducible promoter and affecting expression of a nucleic acid sequence operably linked thereto in the presence versus absence of a second ligand, wherein the second transactivator is capable of binding the second ligand, and wherein the second and optional third transcriptional units are operably linked to the first inducible promoter; c.) a fourth and optional fifth transcriptional unit in the genome of the mammalian packaging cell, including a nucleic acid sequence encoding a retroviral gag polypeptide and a retroviral pol polypeptide, and a binding polypeptide and a fusogenic polypeptide that are capable of binding to and facilitating fusion of a target cell membrane and the retroviral membrane, wherein the fourth and optional fifth transcriptional unit are operably linked to the second inducible promoter; and d) a sixth transcriptional unit in the genome of the mammalian packaging cell, including, from 5' to 3', a 5' LTR, or active truncated fragment thereof, a nucleic acid sequence encoding a retroviral cis-acting RNA packaging element, a cPPT/CTS element, a reverse complement of a nucleic acid sequence encoding an engineered signaling polypeptide, an intron, a promoter that is active in a target cell, and a 3' LTR, or active truncated fragment thereof, wherein the sixth transcriptional unit is operably linked to the second inducible promoter.

In another aspect, provided herein is a method for making a recombinant retrovirus, including: 1.) culturing a population of packaging cells to accumulate a first transactivator, wherein the packaging cells include: a.) a first transcriptional unit in the genome of the mammalian packaging cell, including a nucleic acid sequence encoding a first transactivator, wherein said first transcriptional unit is operably linked to a constitutive promoter and wherein said transactivator is capable of binding a first inducible promoter and affecting expression of a nucleic acid sequence operably linked thereto in the presence versus absence of a first ligand, and wherein said first transactivator is capable of binding said first ligand; b.) a second and optional third transcriptional unit in the genome of the mammalian packaging cell, including a nucleic acid sequence encoding a retroviral REV protein and a nucleic acid sequence encoding a second transactivator capable of binding a second inducible promoter and affecting expression of a nucleic acid sequence operably linked thereto in the presence versus absence of a second ligand, wherein the second transactivator is capable of binding the second ligand, and wherein the second and optional third transcriptional units are operably linked to the first inducible promoter; c.) a fourth and optional fifth transcriptional unit in the genome of the mammalian packaging cell, including a nucleic acid sequence encoding a retroviral gag polypeptide and a retroviral pol polypeptide, and a binding polypeptide and a fusogenic polypeptide that are capable of binding to and facilitating fusion of the retroviral membrane with a target cell membrane, wherein the fourth and optional fifth transcriptional unit are operably linked to the second inducible promoter; and d.) a sixth transcriptional unit in the genome of the mammalian packaging cell, including from 5' to 3', a 5' LTR, or active truncated fragment thereof, a primer binding site (PBS), a nucleic acid sequence encoding a retroviral cis-acting RNA packaging element, a cPPT/CTS element, a reverse complement of a nucleic acid sequence encoding an engineered signaling polypeptide, an intron, a target cell promoter that is active in a target cell, a 3' LTR, or active truncated fragment thereof, wherein the fifth transcriptional unit is operably linked to the second inducible promoter; and 2.) incubating the population of packaging cells including the first transactivator in the presence of the first ligand to accumulate the second transactivator and the retroviral REV protein; and 3.) incubating the population of packaging cells including the second transactivator and the retroviral REV protein in the presence of the second ligand thereby inducing expression of the retroviral gag polypeptide, the retroviral pol polypeptide, the binding polypeptide, the fusogenic polypeptide, and a retroviral RNA including from 5' to 3', a 5' LTR, or active fragment thereof, the PBS, the retroviral cis-acting RNA packaging element, the reverse complement of the nucleic acid sequence encoding the engineered signaling polypeptide, the target cell promoter, and a 3' LTR, or active truncated fragment thereof, wherein recombinant retroviruses are formed and release from the packaging cells, and wherein the recombinant retroviruses include the binding polypeptide and/or the fusogenic polypeptide on a retroviral membrane and the retroviral RNA within a nucleocapsid, thereby making recombinant retroviruses.

In one aspect provided herein, the retroviral packaging system can include a mammalian cell including: 1.) a first transactivator expressed from a constitutive promoter and capable of binding a first ligand and a first inducible promoter for affecting expression of a nucleic acid sequence operably linked thereto in the presence versus absence of the first ligand; 2.) a second transactivator capable of binding a second ligand and a second inducible promoter and affecting expression of a nucleic acid sequence operably linked thereto in the presence versus absence of a second ligand; and 3.) a packagable RNA genome for a retroviral particle, wherein the first transactivator regulates expression of the second transactivator, HIV REV, an IL7 GPI DAF, and an activation element, and wherein the second transactivator regulates expression of a gag polypeptide, a pol polypeptide, a retroviral cis-acting RNA packaging element, and one or more envelope polypeptides. In illustrative embodiments, the first transactivator can be an FRB domain fused to a p65 activation domain and one or more FKBP domains fused to a ZFHD1 DNA binding domain, the first ligand can be rapamycin, and the first inducible promoter can be one or more ZFHD1 binding sites. In illustrative embodiments, the second transactivator can be an rtTA protein, the second ligand can be tetracycline or doxycycline, and the second inducible promoter can be a TRE promoter or a bi-directional TRE promoter. In illustrative embodiments, the retroviral cis-acting RNA packaging element can be HIV Psi. In illustrative embodiments, the one or more envelope proteins include the cytoplasmic domain deletion variants of F and H polypeptides of a Measles Virus. In illustrative embodiments, transcription blockers or polyA sequences can be placed near genes to prevent or reduce unregulated transcription. In some embodiments, a rapamycin-doxycycline inducible lentiviral genome with riboswitch can be used (SEQ ID NO:83). In some embodiments, a rapamycin-doxycycline inducible GAG POL ENV can be used (SEQ ID NO:84). In some embodiments, a rapamycin-inducible TET activator can be used (SEQ ID NO:85). In some embodiments, a rapamycin inducer inducible REV srcVpx can be used (SEQ ID NO:86).

Some aspects of the present disclosure include or are cells, in illustrative examples, mammalian cells, that are used as packaging cells to make retroviruses, such as lentiviruses, for transduction of T cells and/or NK cells. Any of a wide variety of cells can be selected for in vitro production of a virus, such as a redirected retrovirus, according to the invention. Eukaryotic cells are typically used, particularly mammalian cells including human, simian, canine, feline, equine and rodent cells. In illustrative examples, the cells are human cells. In further illustrative embodiments, the cells reproduce indefinitely, and are therefore immortal. Examples of cells that can be advantageously used in the present invention include NIH 3T3 cells, COS cells, Madin-Darby canine kidney cells, human embryonic 293T cells and any cells derived from such cells, such as gpnlslacZ φNX cells, which are derived from 293T cells. Highly transfectable cells, such as human embryonic kidney 293T cells, can be used. By "highly transfectable" it is meant that at least about 50%, more preferably at least about 70% and most preferably at least about 80% of the cells can express the genes of the introduced DNA.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL1O), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

In any of the embodiments disclosed herein, the methods of making a recombinant retrovirus can include growing a mammalian packaging cells to 50%, 60%, 70%, 80%, 90% or 95% confluence or confluence or to 25%, 30%, 40%, 50%, 60%, 70%, 80%, 90% or 95% peak cell density or peak cell density and then splitting or diluting the cells. In some embodiments, a stirred tank reactor can be used to grow the cells. In some embodiments, the cells can be split at least about 1:2, 1:3, 1:4, 1:5, 1:6, 1:7, 1:8, 1:9, 1:10, 1:12, 1:15, or 1:20 using methods a skilled artisan will understand. In some embodiments, the cells can be diluted to 25%, 30%, 40%, 50%, 60%, 70%, 80%, 90% or 95% peak cell density. In some embodiments, after splitting or diluting the cells the cells can be grown for 1, 2, 3, 4, 5, 6, 7, 8, 10, or 16 hours or 1, 2, 3, 4, 5, 6, or 7 days before adding the first ligand. In some embodiments, the cells are grown in the presence of the first ligand for 1, 2, 3, 4, 5, 6, 7, 8, 9, 10, 11, 12, 13, 14, 21, or 28 days in the presence of the first ligand, which in illustrative embodiments can be rapamycin or a rapalog. In some embodiments, the second ligand can be added and the cells can be grown for at least 1, 2, 3, 4, 5, 6, 7, 8, 9, 10, 11, 12, 13, 14, 21, or 28 days which in illustrative embodiments can be tetracycline or doxyciline. Conditions for culturing will depend on the cells and ligands used and the methods are known in the art. A specific example of conditions for culturing and inducing HEK293S cells is shown in Example 8.

As disclosed herein, recombinant retroviruses are a common tool for gene delivery (Miller, Nature (1992) 357:455-460). The ability of recombinant retroviruses to deliver an unrearranged nucleic acid sequence into a broad range of rodent, primate and human somatic cells makes recombinant retroviruses well suited for transferring genes to a cell. In some embodiments, the recombinant retrovirus can be derived from the Alpharetrovirus genus, the Betaretrovirus genus, the Gammaretrovirus genus, the Deltaretrovirus genus, the Epsilonretrovirus genus, the Lentivirus genus, or the Spumavirus genus. There are many retroviruses suitable for use in the methods disclosed herein. For example, murine leukemia virus (MLV), human immunodeficiency virus (HIV), equine infectious anaemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) can be used. A detailed list of retroviruses may be found in Coffin et al ("Retroviruses" 1997 Cold Spring Harbor Laboratory Press Eds: J M Coffin, S M Hughes, H E Varmus pp 758-763). Details on the genomic structure of some retroviruses may be found in the art. By way of example, details on HIV may be found from the NCBI Genbank (i.e. Genome Accession No. AF033819).

In illustrative embodiments, the recombinant retrovirus can be derived from the Lentivirus genus. In some embodiments, the recombinant retrovirus can be derived from HIV, SIV, or FIV. In further illustrative embodiments, the recombinant retrovirus can be derived from the human immunodeficiency virus (HIV) in the Lentivirus genus. Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages.

In illustrative embodiments, recombinant retroviruses provided herein contain Vpx polypeptide. Vpx polypeptide can be expressed in a packaging cell line, after integration of a Vpx coding nucleic acid in its genome, for example as a cell membrane hound protein that gets incorporated into a retrovirus membrane (Durand et al., *J. Virol.* (2013) 87: 234-242). A retroviral membrane bound Vpx can be constructed with a processing sequence for a viral protease such that free Vpx is released once incorporated in a viral particle. Such an example of a Vpx fusion with this functionality is Src-Hag-which includes a membrane-targeting domain (MGSSKSKPKDP) (SEQ ID NO:227) of the first 11 amino acids of c-Src followed by a viral protease cleavage domain KARVLAEA (SEQ NO:228) followed by Flag-tagged Vpx.

Not to be limited by theory, Vpx polypeptide aids in transduction of resting cells by stimulating the efficiency of the process of reverse transcription by degrading the restriction factor SAMHD1. Accordingly, it is believed that in the methods provided herein where Vpx is present in a. recombinant retrovirus used to transduce T cells and/or NK cells, Vpx is released into the cytoplasm of a resting T cell or a resting NK cell upon transduction of the cell by a recombinant retrovirus that contains Vpx. Vpx then degrades SAMHD1, which causes an increase in free dNTPs, which in turn, stimulates reverse transcription of the retroviral genome.

Retroviral Genome Size

In the methods and compositions provided herein, the recombinant retroviral genomes, in non-limiting illustrative examples, lentiviral genomes, have a limitation to the number of polynucleotides that can be packaged into the viral particle. In some embodiments provided herein, the polypeptides encoded by the polynucleotide encoding region can be truncations or other deletions that retain a functional activity such that the polynucleotide encoding region is encoded by less nucleotides than the polynucleotide encoding region for the wild-type polypeptide. In some embodiments, the polypeptides encoded by the polynucleotide encoding region can be fusion polypeptides that can be expressed from one promoter. In some embodiments, the fusion polypeptide can have a cleavage signal to generate two or more functional polypeptides from one fusion polypeptide and one promoter. Furthermore, some functions that are not required after initial ex vivo transduction are not included in the retroviral genome, but rather are present on the surface of the virus or retrovirus via the packaging cell membrane. These various strategies are used herein to maximize the functional elements that packaged within the retrovirus.

In some embodiments, the recombinant retroviral genome to be packaged can be between 1,000, 2,000, 3,000, 4,000, 5,000, 6,000, 7,000, and 8,000 nucleotides on the low end of the range and 2,000, 3,000, 4,000, 5,000, 6,000, 7,000, 8,000, 9,000, 10,000, and 11,000 nucleotides on the high end of the range. The retroviral genome to be packaged includes one or more polynucleotide regions encoding a first and second engineering signaling polypeptide as disclosed in detail herein. In some embodiments, the recombinant retroviral genome to be packaged can be less than 5,000, 6,000, 7,000, 8,000, 9,000, 10,000, or 11,000 nucleotides. Functions discussed elsewhere herein that can be packaged include required retroviral sequences for retroviral assembly and packaging, such as a retroviral rev, gag, and pol coding regions, as well as a 5' LTR and a 3' LTR, or an active truncated fragment thereof, a nucleic acid sequence encoding a retroviral cis-acting RNA packaging element, and a cPPT/CTS element. Furthermore, in illustrative embodiments a recombinant virus or retrovirus herein can include any one or more or all of the following, in some embodiments in reverse orientation of these retroviral functional regions: one or more polynucleotide regions encoding a first and second engineering signaling polypeptide, at least one of which includes a lymphoproliferative element and can further include an ASTR; a second engineered signaling polypeptide that can include a chimeric antigen receptor; an in vivo control element, such as a riboswitch, which typically regulates expression of the first and/or the second engineering signaling polypeptide; a recognition domain, an intron, a promoter that is active in a target cell, such as a T cell, a 2A cleavage signal and/or an IRES.

Recombinant Retroviruses

Recombinant retroviruses are disclosed in methods and compositions provided herein, for example, to transduce T cells and/or NK cells to make genetically modified T cells and/or NK cells. The recombinant retroviruses are themselves aspects of the present invention. In some embodiments, the recombinant retroviruses are replication incompetent, meaning that a retrovirus cannot replicate once it leaves the packaging cell. In some embodiments, the recombinant retroviruses can be adenoviruses, adeno-associated viruses, herpesviruses, cytomegaloviruses, poxviruses, avipox viruses, influenza viruses, vesicular stomatitis virus (VSV), or Sindbis virus. A skilled artisan will appreciate how to modify the methods disclosed herein for use with different retroviruses. For example, in some embodiments, the HIV RREs and the polynucleotide region encoding HIV Rev can be replaced with N-terminal RGG box RNA binding motifs and a polynucleotide region encoding ICP27. In some embodiments, the polynucleotide region encoding HIV Rev can be replaced with one or more polynucleotide regions encoding adenovirus E1B 55-kDa and E4 Orf6.

Accordingly, provided herein in some embodiments, is a recombinant retrovirus that includes (i) a pseudotyping element capable of binding to a T cell and/or NK cell and facilitating membrane fusion of the recombinant retrovirus thereto; (ii) a polynucleotide having one or more transcriptional units operatively linked to a promoter active in T cells and/or NK cells, wherein the one or more transcriptional units encode a first engineered signaling polypeptide having a chimeric antigen receptor that includes an antigen-specific targeting region, a transmembrane domain, and an intracellular activating domain, and a second engineered signaling polypeptide that includes a lymphoproliferative element; wherein expression of the first engineered signaling polypeptide and/or the second engineered signaling polypeptide are regulated by an in vivo control element; and (iii) an activation element on its surface, wherein the activation element is capable of binding to a T cell and/or NK cell and is not encoded by a polynucleotide in the recombinant retrovirus. In some embodiments, the active in T cells and/or NK cells is not active in the packaging cell line. In any of the embodiments disclosed herein, either of the first and second engineered signaling polypeptides can have a chimeric antigen receptor and the other engineered signaling polypeptide can have a lymphoproliferative element.

Genetically Modified T Cells and NK Cells

In embodiments of the methods and compositions herein, genetically modified lymphocytes are produced, which themselves are a separate aspect of the invention. In some embodiments, genetically modified lymphocytes are lymphocytes such as T cells and/or NK cells that have been genetically modified to express a first engineered signaling polypeptide comprising a lymphoproliferative element and/or a second engineered signaling polypeptide comprising a chimeric antigen receptor, which includes an antigen-specific targeting region (ASTR), a transmembrane domain, and an intracellular activating domain.

In the methods and compositions disclosed herein, expression of one or both of the engineered signaling polypeptides is typically regulated by an in vivo control element, and in some embodiments, the in vivo control element is a polynucleotide comprising a riboswitch. In certain embodiments, the riboswitch is capable of binding a nucleoside analog and when the nucleoside analog is present, one or both of the engineered signaling polypeptides are expressed.

The genetically modified lymphocytes disclosed herein can also have polypeptides expressed on their surface, such as one or more polypeptides that function as an activation element, one or more polypeptides that function as a pseudotyping element, and/or one or more fusion polypeptides that include a cytokine. In some embodiments, the genetically modified lymphocytes have an activation element on their surface. The activation element can have a membrane-bound polypeptide capable of binding to CD3 and/or a membrane-bound polypeptide capable of binding to CD28. In some embodiments, the activation element is anti-CD3 scFvFc fused to a heterologous GPI anchor attachment sequence and/or CD80 fused to a heterologous GPI anchor attachment sequence. In some embodiments, the genetically modified lymphocytes have a pseudotyping element on their surface. In some embodiments, the genetically modified lymphocytes have a fusion polypeptide on their surface in which the fusion polypeptide is a cytokine covalently attached to DAF. In some embodiments, the cytokine is IL-7 or IL-15. In illustrative embodiments, the cytokine is IL-7. In some embodiments, the cytokine is without its signal sequence. In illustrative embodiments, the cytokine is inserted into DAF behind its signal sequence.

Nucleic Acids

The present disclosure provides nucleic acid encoding polypeptides of the present disclosure. A nucleic acid will in some embodiments be DNA, including, e.g., a recombinant expression vector. A nucleic acid will in some embodiments be RNA, e.g., in vitro synthesized RNA.

In some cases, a nucleic acid provides for production of a polypeptide of the present disclosure, e.g., in a mammalian cell. In other cases, a subject nucleic acid provides for amplification of the nucleic acid encoding a polypeptide of the present disclosure.

A nucleotide sequence encoding a polypeptide of the present disclosure can be operably linked to a transcriptional control element, e.g., a promoter, and enhancer, etc.

Suitable promoter and enhancer elements are known in the art. For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some instances, the locus or construct or trans gene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *PNAS* (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) *Annual Review of Biochemistry*, 567-605 and Tropp (2012) Molecular Biology (Jones & Bartlett Publishers, Sudbury, Mass.), the disclosures of which are incorporated herein by reference.

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90:7739; and Marodon et al. (2003) *Blood* 101:3416. As another example, a CD8 gene promoter can be used. NK cell-specific expression can be achieved by use of an Neri (p46) promoter; see, e.g., Eckelhart et al. (2011) *Blood* 117:1565.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PH05 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacterial.*, 1991: 173(1): 86-93; Alpuche-Aranda et al., *PNAS*, 1992; 89(21): 10079-83), a nirB promoter (Harborne et al. (1992) *Mal. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mal. Microbial.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and PLambda Non-limiting examples of operators for use in bacterial host cells include a lactose promoter operator (Laci repressor protein changes conformation when contacted with lactose, thereby preventing the Laci repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a polypeptide of the disclosure can be present in an expression vector and/or a cloning vector. Nucleotide sequences encoding two separate polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant constructs. The following bacterial vectors are provided by way of example: pBs, phagescript, PsiX174, pBluescript SK, pBs KS, pNH8a, pNH16a, pNH18a, pNHΔ6a (Stratagene, La Jolla, Calif., USA); pTrc99A, pKK223-3, pKK233-3, pDR540, and pRIT5 (Pharmacia, Uppsala, Sweden). The following eukaryotic vectors are provided by way of example: pWLneo, pSV2cat, pOG44, PXR1, pSG (Stratagene) pSVK3, pBPV, pMSG, and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90: 10613-10617); SV40; herpes simplex virus; gamma retrovirus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid encoding a polypeptide of the present disclosure will in some embodiments be RNA, e.g., in vitro synthesized RNA. Methods for in vitro synthesis of RNA are known in the art; any known method can be used to synthesize RNA including a nucleotide sequence encoding a polypeptide of the present disclosure. Methods for introducing RNA into a host cell are known in the art. See, e.g., Zhao et al. (2010) Cancer Res. 15:9053. Introducing RNA including a nucleotide sequence encoding a polypeptide of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding a polypeptide of the present disclosure.

Cells

The present disclosure provides mammalian cell lines that produce recombinant retroviruses that genetically modify target mammalian cells and the target mammalian cells themselves.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual or an ex vivo cell. For example, in some cases, the cell is an immune cell obtained from an individual. As another example, the cell is a stem cell or progenitor cell obtained from an individual.

Methods of Activating an Immune Cell

The present disclosure provides methods of activating an immune cell in vitro, in vivo, or ex vivo. The methods generally involve contacting an immune cell (in vitro, in vivo, or ex vivo) with one or more target antigens, where the immune cell has been genetically modified to produce a microenvironment restricted CAR of the present disclosure. In the presence of the one or more target antigens, the microenvironment restricted CAR activates the immune cell, thereby producing an activated immune cell. Immune cells include, e.g., a cytotoxic T lymphocyte, an NK cell, a $CD4^+$ T cell, a T regulatory (Treg) cell, a γδ T cell, an NK-T cell, neutrophils, etc.

Contacting the genetically modified immune cell (e.g., a T lymphocyte, an NK cell) with one or more target antigens can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of the one or more target antigens. Cytokines whose production can be increased include, but are not limited to, IL-2 and IFN-γ.

Contacting a genetically modified cytotoxic cell (e.g., cytotoxic T lymphocyte) with AAR can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the one or more target antigens.

Contacting a genetically modified cytotoxic cell (e.g., cytotoxic T lymphocyte) with one or more target antigens can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of the one or more target antigens.

In other embodiments, e.g., depending on the host immune cell, contacting a genetically modified host cell with an antigen can increase or decrease cell proliferation, cell survival, cell death, and the like.

Methods for Making a Microenvironment Restricted Antigen-Specific Targeting Region In some embodiments, antigen binding domains (also referred to herein as "antigen-specific target regions" or "ASTRs") of CARs constitutively bind their cognate antigens. In other embodiments, the ASTRs can be microenvironment restricted, preferentially or only binding their cognate antigen under certain aberrant conditions, such as those that exist in the tumor microenvironment, as disclosed in more detail herein. Microenvironment restricted ASTRs that bind preferentially or exclusively under aberrant conditions of a tumor microenvironment, can provide a reduction in on-target off-tumor effects as binding to the antigen in normal physiological conditions is reduced, in some situations to levels below detection by immunoassays. In certain aspects, CARs provided herein include a microenvironment restricted ASTR that specifically binds to a target protein, wherein the ASTR is an scFv fragment that includes a heavy chain variable region and a light chain variable region.

Certain illustrative embodiments of the aspects disclosed herein, for example the methods, cells, cells lines, retroviruses, polynucleotides, or vectors disclosed herein, include CARs that include microenvironment restricted antigen-specific targeting regions.

Accordingly, in one aspect, provided herein is a chimeric antigen receptor for binding a target antigen, that includes:
  a) a microenvironment restricted antigen-specific targeting region that exhibits an increase in binding to the target antigen in an aberrant condition compared to a normal physiological environment, wherein the antigen-specific targeting region binds to the target;
  b) a transmembrane domain; and
  c) an intracellular activating domain.

In another aspect, provided herein is a chimeric antigen receptor for binding a target antigen, that includes:
  a) at least one microenvironment restricted antigen specific targeting region selected by panning a polypeptide library and having an increase in activity in a target antigen binding assay at an aberrant condition compared to a normal physiological condition;
  b) a transmembrane domain; and
  c). an intracellular activating domain.

In some embodiments of any aspect disclosed herein, any of the chimeric antigen receptors can be microenvironment restricted such that they exhibit an increase in binding activity at an aberrant condition compared to a normal physiological condition. In some illustrative embodiments of any aspect disclosed herein, the microenvironment restricted ASTR is identified from an initial polypeptide library without mutating/evolving members of the library before screening/evolving and/or without mutating during or between optional repeated rounds of screening. Exemplary transmembrane domains and intracellular activating domains can be any of those disclosed herein for CARs.

In one aspect, provided herein is a method for selecting a microenvironment restricted ASTR, comprising panning a polypeptide display library by:
a. subjecting polypeptides of the polypeptide display library to a target antigen binding assay under a normal physiological condition and a target antigen binding assay under an aberrant condition; and
b. selecting a polypeptide which exhibits an increase in target antigen binding activity at the aberrant condition compared to the physiological condition, thereby selecting the microenvironment restricted antigen specific targeting region.

In another aspect, provided herein is a method for isolating a microenvironment restricted ASTR, that includes panning a polypeptide library by:
contacting the polypeptide library under aberrant conditions with a target antigen bound to a solid support, wherein clones expressing polypeptides that bind the target antigen remain bound to the solid support through the target antigen;
incubating the solid supports with bound polypeptides under physiological conditions; and
collecting clones that elute from the solid support under the physiological conditions, thereby isolating the microenvironment restricted antigen-specific targeting region.

In some illustrative embodiments of any aspect disclosed herein, the microenvironment restricted antigen-specific targeting region is identified from an initial polypeptide library screen without mutating/evolving members of the library before screening and/or without mutating/evolving during or between optional repeated rounds of screening or panning.

Normal physiological conditions can include those of temperature, pH, osmotic pressure, osmolality, oxidative stress, and electrolyte concentration that would be considered within a normal range at the site of administration, or at the tissue or organ at the site of action, to a subject. An aberrant condition is that which deviates from the normally acceptable range for that condition. In one aspect, a microenvironment restricted antigen-specific targeting region (i.e. polypeptide) is virtually inactive at normal conditions but is active at other than normal conditions at a level that is equal or better than at normal conditions. For example, in one aspect, the microenvironment restricted antigen-specific targeting region is virtually inactive at body temperature, but is active at lower temperatures. In another aspect, the microenvironment restricted antigen-specific targeting region is reversibly or irreversibly inactivated at the normal conditions. In a further aspect, the microenvironment restricted antigen-specific targeting region is a therapeutic protein. In another aspect, the microenvironment restricted antigen-specific targeting region is used as a drug, or therapeutic agent. In yet another aspect, the microenvironment restricted antigen-specific targeting region is more or less active in highly oxygenated blood, such as, for example, after passage through the lung or in the lower pH environments found in the kidney.

In some embodiments, a single round of selection is performed to obtain the microenvironment restricted antigen-specific targeting region. In certain embodiments, the screening or panning method is repeated after identifying free polypeptides that bound antigen under aberrant conditions and did not bind under physiological conditions, or cells expressing a test polypeptide that had these properties, or phage coated with a test polypeptide that has such properties in an initial or previous round. In some methods, phage that are collected are used to infect cells, which can be infected with helper phage as well, in order to amplify the collected phage. In other methods where polypeptides on the surface of cells are tested, collected cells can be grown to "amplify" the polypeptides expressed by the cells by amplifying polynucleotides in the cells that encode the polypeptides. In some embodiments, the amplifying is done by growing cells that express the identified polypeptides without performing a process to mutate the polynucleotides encoding the identified polypeptides between rounds. Thus, polypeptides that were collected in a previous round are enriched by amplifying cells that contain polynucleotides encoding these collected polypeptides.

The panning or screening method can be performed a single time, or repeated for 1 to 1000 times. In illustrative embodiments, the panning is repeated 1 to 20 times or 2 to 10 times or 2 to 5 times.

In other methods, microenvironment restricted ASTRs against an antigen of interest (i.e. target antigen) are performed using one or more rounds of mutation/evolution between rounds of panning. In one method, a wild-type protein is identified for example by generating a polypeptide or protein library and screening the polypeptide or protein library for a polypeptide or protein with a desired binding affinity to a target antigen. In some embodiments where the wild-type proteins are antibodies, the wild-type antibodies can be discovered by generating and screening polyclonal or monoclonal antibody libraries, including phage display antibody libraries, for example phage display humanized antibody libraries.

Evolved ASTRs can be generated by subjecting the wild-type protein, or a nucleic acid sequence encoding the wild-type protein, to a process of mutagenesis to produce a population of mutant polypeptides that can be screened to identify a mutant ASTR with an increased activity (e.g. enhanced binding affinity to the target antigen) in a tumor environment and/or in an in vitro tumor surrogate assay condition, compared to a normal physiological environment. Examples of such methods are provided in WO2016033331 ("CONDITIONALLY ACTIVE CHIMERIC ANTIGEN RECEPTORS FOR MODIFIED T CELLS") or U.S. Pat. No. 8,709,755, both herein incorporated by reference in their entirety. This method of generating a microenvironment restricted antibody is hereby incorporated by reference in its entirety herein.

In other embodiments, microenvironment restricted antigen-specific polypeptides (i.e. targeting regions, e.g. antibodies) can be identified by screening an initial polypeptide library under aberrant versus physiological conditions and identifying a test polypeptide from the initial polypeptide library, that binds preferentially or exclusively under aberrant vs. physiological conditions. In some examples, the identified and isolated microenvironment restricted antigen-specific polypeptides (i.e. targeting regions, e.g. antibodies) identified from an initial polypeptide library in an initial polypeptide library screen, bind their cognate antigen preferentially or exclusively under aberrant vs. physiological conditions. In such instances, no rounds of mutating/evolving are performed. Accordingly, the method in illustrative embodiments is performed without mutating polynucleotides encoding the isolated microenvironment restricted antigen-specific targeting region between rounds of screening (e.g. rounds of panning), or performed for only a single binding assay under aberrant versus physiological conditions to isolate and identify the microenvironment restricted antigen-specific polypeptide (i.e. targeting region, e.g. antibody). The method can be performed by culturing, high fidelity amplifying, and/or diluting polynucleotides encoding antigen-specific targeting regions, or host organisms including the same, between rounds of screening and/or panning, without any mutating/evolving. Furthermore, the method can be performed without repeating the screening and/or panning and can be performed without mutating/evolving a polynucleotide encoding the isolated microenvironment restricted antigen-specific targeting region, after the microenvironment restricted antigen-specific polypeptide (i.e. target region, e.g. antibody) is isolated.

Assays for use in the methods provided herein to detect binding of a polypeptide to a cognate binding partner include cell based assays, and in particular assays performed using cell surface display systems, such as mammalian cell surface display systems. In an exemplary method, nucleic acids encoding a polypeptide or a library of variant polypeptides, including a library of modified polypeptides, can be introduced into a vector suitable for expression in cells, such as mammalian cells. Cells are then transfected with the vector, and the polypeptide(s) is/are expressed by the cells. The library of cells containing surface-expressed polypeptides can be contacted with a solution containing a soluble or surface-bound cognate binding partner. Binding activity can be detected using any assay that can detect the binding to the surface of the cells. Activity also can be assessed by assessing a functional activity of the polypeptide or polypeptide. Any cell based assay known to the skilled artisan is contemplated for use in the methods provided herein, including cell proliferation assays, cell death assays, flow cytometry, cell separation techniques, fluorescence activated cell sorting (FACS), phase microscopy, fluorescence microscopy, receptor binding assays, cell signaling assays, immunocytochemistry and reporter gene assays. In some examples, the assays are fluorescence activated cell sorting (FACS) assays.

Polypeptides or proteins can be expressed by mammalian cells as secreted, soluble molecules, cell surface molecules, or intracellular antibodies. In an exemplary method, cells can be transfected with a library of proteins under conditions whereby most or all of the cells display a member of the protein library anchored on the cell surface. Optionally, an expression system can be used in which most of mammalian cell transfectants have only one plasmid integrated in their genome. Therefore, most (i.e., at least about 70% or about 80% or about 90%) of the transfectants express one or more molecules of one polypeptide. This can be verified, for example, by isolating and culturing individual transfectants; and amplifying and sequencing the expressed sequences to determine whether they have a single sequence.

In some examples of the methods provided herein, the polypeptides are antibodies displayed on the surface of mammalian cells. Any antibody described herein can be expressed on the surface of mammalian cells, including full length, bivalent, functional antibodies, such as IgG antibodies. The antibody can be a fragment, for example, Fab fragments or scFv fragments. Antibodies can include an Fc region, such as an scFv-Fc or a full length antibody, which comprises two heavy and two light chains. The skilled artisan can select a suitable antibody fragment. For example, an ScFv-Fcs and full length antibodies made in mammalian cells can have several advantages over scFv's or Fab fragments.

Solid supports that can be used in the binding assays provided herein include any carrier that is capable of being affixed with a binding partner of a polypeptide such as a ligand, receptor or antigen. Typically, to facilitate high throughput screening a cognate binding partner is affixed to the solid support. Examples of carriers for use as solid supports in the methods provided herein include, but are not limited to, glass, polystyrene, polypropylene, polyethylene, dextran, nylon, amyloses, natural and modified celluloses, polyacrylamides, agaroses and magnetic solid supports, such as solid supports that include magnetite. The solid support can be one or more beads or particles, microspheres, a surface of a tube or plate, a filter membrane, and other solid supports known in the art. Exemplary solid support systems include, but are not limited to, a flat surface constructed, for example, of glass, silicon, metal, nylon, cellulose, plastic or a composite, including multiwell plates or membranes; or can be in the form of a bead such as a silica gel, a controlled pore glass, a magnetic or cellulose bead. Further, such methods can be adapted for use in suspension or in the form of a column. In some embodiments, the microenvironment restricted antigen-specific polypeptide (i.e. target region, e.g. antibody) is identified and isolated by biopanning a phage display or yeast surface display (Colby et al., "Engineering Antibody Affinity by Yeast Surface Display," *Meth. Enzym.* 388, 26 (2004)) antibody (e.g. humanized antibody) library with an immobilized target antigen. For example, either a naïve humanized antibody library or a synthetic humanized antibody library can be panned using the phage display or yeast surface display methods herein. In some embodiments, an initial phage display process, phage clones can be transferred to a mammalian vector and used to a mammalian cell surface screening method (See e.g., Yoon et al., *BMC Biotechnology* 12:62; 1472-6750 (2012)). An exemplary method for performing phage display to isolate a microenvironment restricted antigen-specific target region is provided in Example 2.

A microenvironment restricted ASTR identified using methods provided herein, can be an antibody, an antigen, a ligand, a receptor binding domain of a ligand, a receptor, a ligand binding domain of a receptor, or an affibody. In embodiments where the microenvironment restricted ASTR is an antibody, it can be a full-length antibody, a single-chain antibody, an Fab fragment, an Fab' fragment, an (Fab')2 fragment, an Fv fragment, and a divalent single-chain antibody or a diabody. wherein the antigen-specific targeting region comprises a heavy chain and a light chain from an antibody. In some embodiments, the microenvironment restricted ASTR is a single-chain variable fragment. Such single-chain variable fragment can have heavy and light chains separated by a linker, wherein the linker is between 6 and 100 amino acids in length. In some embodiments the heavy chain is positioned N-terminal to the light chain on the chimeric antigen receptor. In other embodiments, the light chain is positioned N-terminal to the heavy chain. The microenvironment restricted ASTR can be a bispecific ASTR.

Microenvironment restricted ASTRs identified using methods provided herein are typically polypeptides and more specifically polypeptide antibodies, and in illustrative embodiments, single chain antibodies. These polypeptides can bind to their cognate antigens with higher or lower affinity under aberrant conditions vs. normal conditions, but in illustrative embodiments, bind with higher affinity under aberrant conditions than normal conditions. In some embodiments, these polypeptides can bind to their cognate antigen with a 10%, 20%, 25%, 50%, 75%, 90%, 95% or 99% greater affinity under aberrant conditions than physiological (i.e. normal) conditions. In some embodiments, the ASTRs identifying using methods provided herein do not bind to their cognate antigens under normal physiological conditions to any detectable level above background levels obtained using negative controls, such as negative control antibodies.

The nucleotide sequence encoding a microenvironment restricted ASTR isolated by the method provided herein, can be determined by sequencing nucleotides of the collected cell expressing the microenvironment restricted antigen-specific targeting. This nucleotide sequence information can then be used to make a microenvironment restricted biologic chimeric antigen receptor (MRB-CAR) by generating a polynucleotide that encodes a polypeptide comprising the microenvironment restricted antigen-specific targeting region, a transmembrane domain, and an intracellular activating domain. Microenvironment restricted antigen-specific targeting regions can be cloned into a CAR construct expression system, which can be used to generate recombinant lentiviruses that include the CAR in their genome, and then the recombinant lentiviruses can be used to transduce T cells for testing for CAR-mediated tumor antigen expressing target cell killing in a tumor-selective environment compared to physiologic conditions.

Conditions for Conditional Activity

In the methods provided herein, the activity of one or more polypeptides, such as, for example, single chain antibodies, is screened or tested under two different sets of conditions that simulate a condition or conditions in two different physiologic environments such as, for example, a diseased microenvironment and the normal physiologic condition of a non-diseased microenvironment. Typically, the conditions are conditions that can be simulated or replicated in vitro. A set of conditions can include one or more conditions to simulate a microenvironment associated with a disease. Disease can alter intracellular and extracellular homeostasis. For example, the diseased microenvironment can simulate one or more conditions in a tumor microenvironment or a cancer microenvironment. Typically, the difference or differences in activity under the two sets of conditions can result in the conditional activity of the molecule. Thus, a molecule that exhibits greater activity under the first set of conditions (e.g. simulating conditions in a tumor microenvironment) compared to the second set of conditions (e.g. simulating conditions in a normal or non-diseased environment) is identified as a candidate molecule that is microenvironment restricted.

The two sets of conditions can be selected to vary by one or more parameters that differ in two physiologic environments, such as described herein or known to one of skill in the art, including but not limited to chemical conditions, biological conditions, or physical conditions. Parameters that can be varied between the two sets of conditions can include one or more conditions selected from among pressure, temperature, pH, ionic strength, osmotic pressure, osmolality, oxidative stress, turbidity, exposure to light (including UV, infrared or visible light), concentration of one or more solutes, such as electrolytes, concentration of glucose, concentration of hyaluronan, concentration of lactic acid or lactate, concentration of albumin, levels of adenosine, levels of R-2-hydroxyglutarate, concentration of pyruvate, concentration of oxygen, and/or presence of oxidants, reductants, or co-factors. By varying the electrolyte and buffer systems in the calibration solutions, physiological conditions such as pH, buffer capacity, ionic environment, temperature, glucose concentration, and ionic strength can be adjusted to those of the biological environment to be simulated. The set of conditions that simulate a normal physiologic environment can be selected to be different from the set of conditions that simulate a diseased microenvironment, such as a tumor microenvironment, by one or more conditions described herein.

For example, as discussed below, various parameters of the tumor microenvironment differ compared to a non-tumor microenvironment, including, but not limited to, oxygen concentration, pressure, presence of co-factors, pH, hyaluronan concentration, lactate concentration, albumin concentration, levels of adenosine, levels of R-2-hydroxyglutarate, and pyruvate concentration. Any of these parameters can be replicated in vitro to simulate one or more conditions that exist in a tumor or cancer environment compared to conditions that exist in a non-tumor or a normal environment. The normal physiologic conditions that can be simulated include environments found in healthy or nondiseased tissue at any location of the body such as the GI tract, the skin, the vasculature, the blood, and extracellular matrix. Typically, in the assays herein, physiologic conditions can be simulated in vitro by the choice of buffer that is used to assess the activity of the protein. For example, any one or more conditions of a diseased microenvironment (such as a tumor microenvironment) and a non-diseased environment can be simulated by differences in the assay buffer used to assess activity in the assay. Hence, in the methods herein to identify a microenvironment restricted polypeptide, a component or components or characteristic or characteristics of an assay buffer are altered or made to be different in a first assay to test activity under a first condition and in a second assay to test activity under a second condition. For example, as discussed herein, various parameters of the tumor microenvironment are different compared to a non-tumor environment including, but not limited to, oxygen, pressure, presence of co-factors, pH, hyaluronan concentration (such as increased or decreased hyaluronan concentration), lactate concentration (such as increased or decreased lactate concentration), albumin concentration (such as increased or decreased albumin concentration), levels of adenosine (such as increased or decreased adenosine levels), levels of R-2-hydroxyglutarate (such as increased or decreased R-2-hydroxyglutarate levels) and pyruvate concentration (including increased or decreased pyruvate concentration). More specifically, conditions in a tumor microenvironment can include lower pH, higher concentrations of hyaluronan, higher concentrations of lactate and pyruvate, higher concentrations of albumin, increased levels of adenosine, increased levels of R-2-hydroxyglutarate, hypoxia, lower concentration of glucose, and slightly higher temperature in comparison with non-tumor microenvironment. For example, a microenvironment restricted ASTR is virtually inactive at normal body temperature, but is active at a higher temperature in a tumor microenvironment. In yet another aspect, the microenvironment restricted antibody is less active in normal oxygenated blood, but more active under a less oxygenated environment that exists in a tumor. In yet another aspect, the microenvironment restricted antibody is less active in normal physiological pH 7.2-7.8, but more active under an acidic pH 5.8-7.0, or 6.0-6.8 that exists in a tumor microenvironment. For example, the microenvironment restricted antibody is more active at a pH of 6.7 than at pH 7.4. There are other conditions in the tumor microenvironment known to a person skilled in the field that may also be used as the condition in the present invention under which the conditionally active ASTRs have different binding affinities. In vitro assay conditions that mimic these in vivo tumor conditions are referred to herein as in vitro tumor surrogate assay conditions.

Any one or more of these conditions can be simulated in vitro by choice of the particular assay buffer. The composition of the assay buffer that simulates a diseased microenvironment can be selected to be identical to the composition of the assay buffer that simulate a normal environment, with the exception of one or more conditions known or described herein that is altered in the diseased microenvironment. Further, in screening or identifying the activity of one or more polypeptides under two different sets of conditions, generally the only conditions that are varied in the assay relate to the buffer conditions simulating the in vivo microenvironment. The other conditions of the assay, such as time, temperature and incubation conditions, can be the same for both sets of conditions. Typically, the same base buffer is used in the set of conditions that simulate a diseased microenvironment and conditions that simulate a normal microenvironment, but the design of the buffer composition can be made to differ in one or more parameters such as pH, oxygen, pressure, presence of co-factors, pH, hyaluronan concentration (such as increased or decreased hyaluronan concentration), lactate concentration (such as increased or decreased lactate concentration), albumin concentration (such as increased or decreased hyaluronan concentration) and/or pyruvate concentration (including increased or decreased pyruvate concentration). In the conditions that simulate a diseased microenvironment and the conditions that simulate a normal microenvironment, any base buffer known to one of skill in the art that can be used Methods of Generating a Microenvironment Restricted Cell The present disclosure provides a method of generating a microenvironment restricted cell. The method generally involves genetically modifying a mammalian cell with an expression vector (e.g. a plasmid or a retrovirus), or an RNA (e.g., in vitro transcribed RNA), including nucleotide sequences encoding microenvironment restricted CARs of the present disclosure. The genetically modified cell is microenvironment restricted in the presence of one or more target antigens. The genetic modification can be carried out in vivo, in vitro, or ex vivo. The cell can be an immune cell (e.g., a T lymphocyte, a T-helper cell, or an NK cell), a stem cell, a progenitor cell, etc.

In some cases, the genetic modification is carried out ex vivo. For example, a T lymphocyte, a stem cell, a T-helper cell, or an NK cell is obtained from an individual; and the cell obtained from the individual is genetically modified to express a CAR of the present disclosure. The genetically modified cell is microenvironment restrictable in the presence of one or more target antigens. In some cases, the genetically modified cell is activated ex vivo. In other cases, the genetically modified cell is introduced into an individual (e.g., the individual from whom the cell was obtained); and the genetically modified cell is activated in vivo. For example, where the one or more target antigens are present on the surface of a cell in the individual, there is no need to administer the antigen. The genetically modified cell comes into contact with the antigen present on the surface of a cell in the individual and the genetically modified cell is activated. For example, where the genetically modified cell is a T lymphocyte, the genetically modified cell can exhibit cytotoxicity toward a cell that expresses the one or more target antigens on its surface to which the CAR binds.

Methods of Transient Reduction of Tumor Microenvironment Sensitive CAR-T Target Binding Provided herein is a method of transient reduction of tumor microenvironment sensitive CAR-T target binding through pharmacologic modification of vascular and tissue pH. Microenvironmentally controlled scFvs in CAR-T cells provide an additional level of protection against on-target off tumor toxicity, requiring tumor local environmental conditions to enable T cell engagement. While attractive for some monoclonal antibody therapies, adoptive cellular therapy may create local environments that are transiently permissive for their CAR-T targets. For example, CAR-T cells activated in local tissues may further reduce local pH, depending on cytoplasmic domains present in the CAR construct. In other instances, cytokine release syndrome and other morbidity associated with adoptive cellular therapy may result in loss of bicarbonate buffering capacity of blood, leading to lactic acidosis. It is established that adoptive cellular therapies administered by intravenous infusion result in temporary pulmonary entrapment. For some cellular therapies, infusion rate requires constant monitoring of dissolved oxygen (Fischer et al. *Stem Cells Dev.* 2009 June; 18(5): 683-691). The extent of pulmonary entrapment is dependent upon cell size, activation state, cell dose and infusion rate. Cruz et al (*Cytotherapy.* 2010 October; 12(6): 743-749) report the adverse findings from over 300 T cell infusions, that low doses and slow infusion may reduce pulmonary entrapment. However, with certain high potency CAR-T cells, targets present even in low levels on lung endothelium, such as Her2 (Morgan et al. *Mol Ther.* 2010 April; 18(4): 843-851), can result in immediate toxicity that cannot be controlled, and results in rapid patient deterioration due to the initial high CAR-T cellular concentration in the lung following infusion and the presence of the T cell target in these tissues. In other cases, the presence of T cell targets in other off target tissues such as bile duct may create on target off tumor toxicities that cannot be controlled (Lamers *Mol Ther.* 2013 April; 21(4):904-12) and result in severe organ toxicity before other agents such as steroids or cell elimination epitopes can be utilized. While venous and arterial plasma have strong buffering capacity against acidosis, conditions of respiratory acidosis, shock, metabolic acidosis and ischemic acidosis can occur in patients with cancer treated with adoptive cellular therapy.

In some embodiments, methods for transiently increasing vascular pH at certain conditions to reduce affinity of microenvironmentally controlled scFvs for their antigens are provided. A 0.4 U shift in blood pH can reduce affinity of certain scFvs by greater than 10-fold. In some embodiments, therapeutic pH control can be achieved via IV or oral administration routes. In some embodiments, inactivation of binding affinity can be achieved with bicarbonate. In other embodiments, Tris-hydroxylmethyl aminomethane (also known as tromethamine, trometamol, and THAM) and Carbicarb™ (and equimolar hypertonic solution of sodium bicarbonate and sodium carbonate) are utilized to increase blood pH in a sufficient amount to alleviate on target off tumor toxicities. In still other embodiments, small molecule proton pump inhibitors can also be utilized to increase blood pH and/or tissue pH in a sufficient amount to alleviate on target off tumor toxicities. Proton pump inhibitors include, but are not limited to, esomeprazole (Nexium), esomeprazole and naproxen (Vimovo), lansoprazole (Prevacid), omeprazole (Prilosec and Zegerid), and rabeprazole (Aciphex). Administration of proton pump inhibitors can be used effectively over longer time periods to modulate the binding affinity of the antigen biding domain to its cognate antigen for days, weeks, months, or years. In other embodiments, the affinity of the antigen binding domain for its cognate antigen can also be modulated by altering the blood pH and/or tissue pH by controlling the transcription, translation, membrane expression, and stability of transporters and pumps. Examples of such transporters and pumps to modulate pH include, but are not limited to, proton pumps, members of the sodium proton exchange family (NHE), bicarbonate transporter family (BCT), and monocarboxylate transporter family. In certain embodiments, bicarbonate, THAM, or Caricarb™ may be administered prior to or concurrent with infusion of patients CAR-T cells expressing pH controlled scFvs. Such treatment will alleviate the immediate cytotoxicity that is otherwise associated with the temporary pulmonary entrapment of CAR-T cell infusions.

Further Embodiments

In certain embodiments, methods provided herein for the present disclosure include inhibiting expression of one or more endogenous genes expressed in T cell and/or NK cells. Methods provided herein illustrate the ability to make recombinant retroviruses that express miRNA or shRNA, for example, that can be used for such methods. In fact, the methods provided herein illustrate that such miRNA or shRNA can be encoded within introns, including for example, an Ef1a intron. This takes advantage of the present teachings of methods to maximize the functional elements that can be included in a packagable retroviral genome to overcome shortcomings of prior teachings and maximize the effectiveness of such recombinant retroviruses in adoptive T cell therapy.

In some embodiments, 1, 2, 3, 4, 5, 6, 7, 8, 9, or 10 miRNAs, in illustrative embodiments between 2 and 5, for example 4 miRNAs, that bind nucleic acids encoding one or more of the following target endogenous T cell expressed genes, can be included in the recombinant retroviral genome and delivered to T cells and/or NK cells using methods provided herein. In fact, as provided herein 1, 2, 3, or 4 miRNAs can be delivered in a single intron such as the EF1a intron. The target endogenous genes expressed on T cells can include the following, with a non-limiting expected benefit of such inactivation in parentheses: PD-1 (prevent inactivation); CTLA4 (prevent inactivation); TCRa (safety—prevent autoimmunity); TCRb (safety—prevent autoimmunity); CD3Z (safety—prevent autoimmunity); SOCS (prevent inactivation); SMAD2 (prevent inactivation); miR-155 (promote activation); IFN gamma (reduce CRS); cCBL (prolong signaling); TRAIL2 (prevent death); PP2A (prolong signaling); ABCG1 (increase cholesterol microdomain content by limiting clearance of cholesterol).

In certain embodiments, miRNA against target genes with similar expected utilities can be combined. In other embodiments, miRNA against target genes with complementary utilities can be combined. In some embodiments, the combinations can include CD3Z, PD1, SOCS1, and/or IFN gamma.

Treatment Methods

The present disclosure provides various treatment methods using a CAR. A CAR of the present disclosure, when present in a T lymphocyte or an NK cell, can mediate cytotoxicity toward a target cell. A CAR of the present disclosure binds to an antigen present on a target cell, thereby mediating killing of a target cell by a T lymphocyte or an NK cell genetically modified to produce the CAR. The ASTR of the CAR binds to an antigen present on the surface of a target cell.

The present disclosure provides methods of killing, or inhibiting the growth of, a target cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cell, and mediates killing of the target cell.

The present disclosure provides a method of treating a disease or disorder in an individual having the disease or disorder, the method including: a. introducing an expression vector including a polynucleotide sequence encoding a CAR into peripheral blood cells obtained from the subject to produce a genetically engineered cytotoxic cell; and b. administering the genetically engineered cytotoxic cell to the subject.

Subjects Suitable for Treatment

A variety of subjects are suitable for treatment with the methods and compositions presented herein. Suitable subjects include any individual, e.g., a human or non-human animal who has a disease or disorder, who has been diagnosed with a disease or disorder, who is at risk for developing a disease or disorder, who has had a disease or disorder and is at risk for recurrence of the disease or disorder, who has been treated with an agent for the disease or disorder and failed to respond to such treatment, or who has been treated with an agent for the disease or disorder but relapsed after initial response to such treatment.

Subjects suitable for treatment with an immunomodulatory method include individuals who have an autoimmune disorder; individuals who are organ or tissue transplant recipients; and the like; individuals who are immunocompromised; and individuals who are infected with a pathogen.

The following non-limiting examples are provided purely by way of illustration of exemplary embodiments, and in no way limit the scope and spirit of the present disclosure. Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

EXAMPLES

Example 1. Generation of Riboswitches that Respond Specifically to Nucleoside Analogue Antiviral Drugs This example provides a method to screen libraries based on natural structural riboswitches that bind guanosine and deoxyguanosine. These riboswitches were used as scaffolds to develop biased libraries for the selection of aptamers that bind specifically to a ligand nucleoside analogue. Previously, isothermal titration calorimetry has been used to show these natural riboswitches bind to their native ligands. Additional tests showed a deoxyguanosine switch also interacted weakly with the nucleoside analogues acyclovir and penciclovir, leading to the re-design of this sequence into a new library. The single-stranded regions of the riboswitch were targeted for mutation and variant sequences that specifically respond to acyclovir or penciclovir were selected for.

Materials

Selection components guanine, guanosine, deoxyguanosine, acyclovir, and penciclovir were ordered from Sigma-Aldrich (St. Louis, Mo.). Acyclovir was the initial target while penciclovir was a special interest analyte used in latter rounds and guanine, guanosine, and deoxyguanosine were used as counter-targets. Graphene oxide (GrO), to be used as the partitioning medium, was purchased from Angstron Materials (Dayton, Ohio). HEPES (pH 7.3) and $MgCl_2$ were purchased from Amersco LLC. (Solon, Ohio). KCl was purchased from Teknova (Hollister, Calif.). Selection buffer was prepared at 5× (1× as 50 mM HEPES, 100 mM KCl, 20 mM $MgCl_2$, pH 7.3). Targets, counter-targets, and oligos were reconstituted in nuclease-free water for preliminary analysis and aptamer screening. Aliquots were prepared for all targets and stored at −20° C. to maximize shelf life.

Generation of the Aptamer Library

Figure 14:
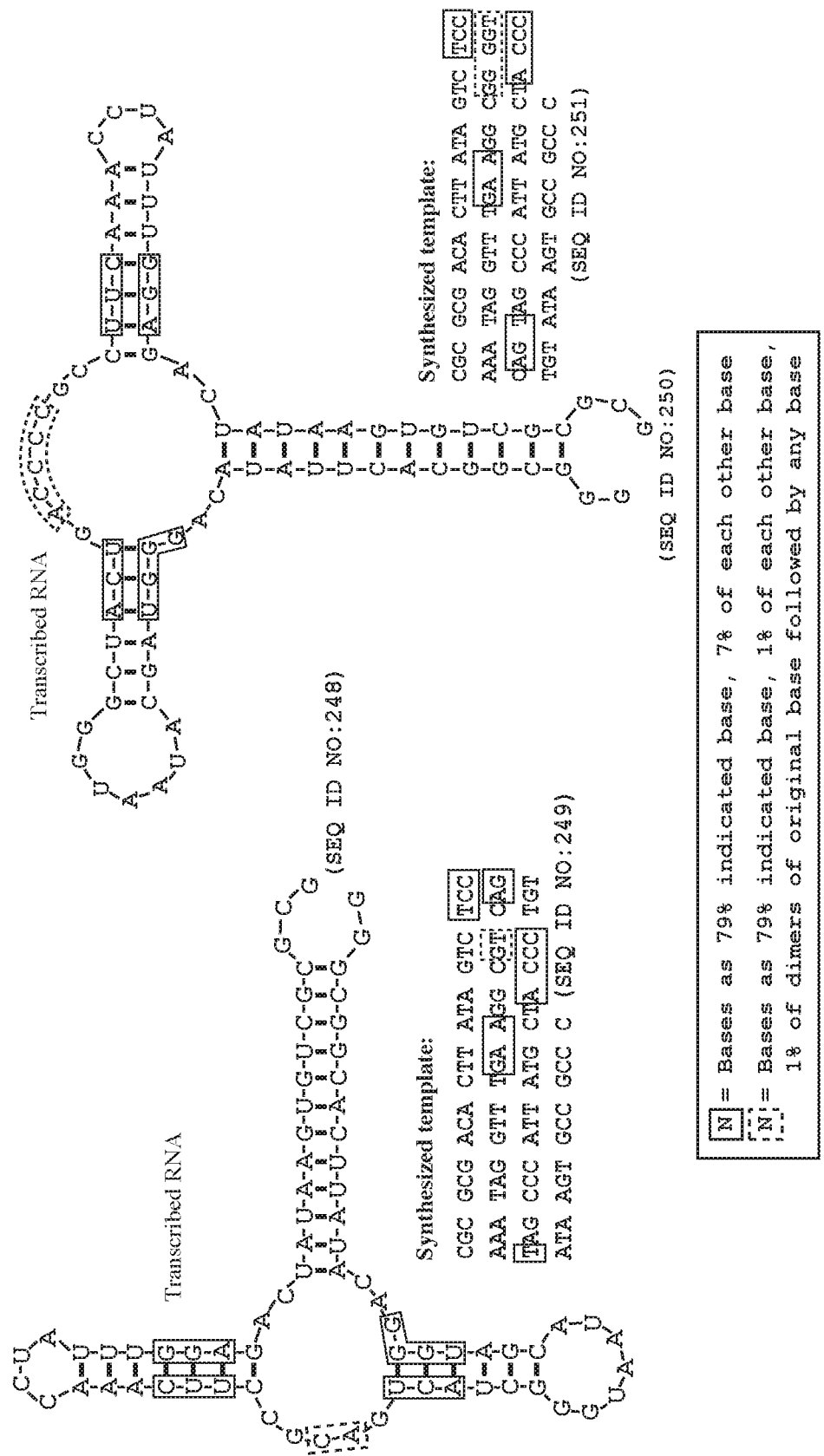
FIG. 14 shows the selection library construction. The library was constructed on the basis of known guanosine- and deoxyguanosine-binding RNA (Pikovskaya, 2013).

The initial aptamer library template was synthesized by IBA GmbH (Gottingen, Germany) as the reverse complement of the sequences in FIG. 14. In FIG. 14, the nucleotides in boxes are single-stranded in the known sequences, with "mutations" introduced during synthesis to allow for better binding to analogues of the original targets. For nucleotides within the boxes outlined with solid lines, substitution mutations were allowed; for nucleotides within the boxes outlined with dashed lines, substitution mutations as well as insertions or deletions were allowed. Primers were synthesized by IDT (Coralville, Iowa) as single-stranded DNA. T7 primer (SEQ ID NO:240) was combined with library template sequences for primer extension with Titanium Taq DNA polymerase (Clontech; Mountain View, Calif.). Primer-extended material was transcribed using the Ampliscribe T7 High Yield Transcription Kit (Epicentre; Madison, Wis.) and then purified on 10% denaturing polyacrylamide gel electrophoresis (PAGE) with 8 M urea before use in selection. During selection, the library was reverse-transcribed using SuperScript IV Reverse Transcriptase (Invitrogen; Carlsbad, Calif.) using reverse primer (SEQ ID NO:241) and amplified using Titanium Taq DNA polymerase (Clontech; Mountain View, Calif.). The aptamer with SEQ ID NO:248 had a J2-3 loop variation of −3 to −1 and a diversity of $\sim2.25\times10^{10}$. The aptamer with SEQ ID NO:250 had a J2-3 loop variation of 0 (native) to +5 and a diversity of $\sim9.38\times10^{14}$. The two oligonucleotides (SEQ ID NOs:249 and 250) were mixed at a ratio of 1:4160 to produce equimolar diversity in the combined library pool, with a total diversity of $\sim9.38\times10^{13}$.

Library Screening

Figure 15:
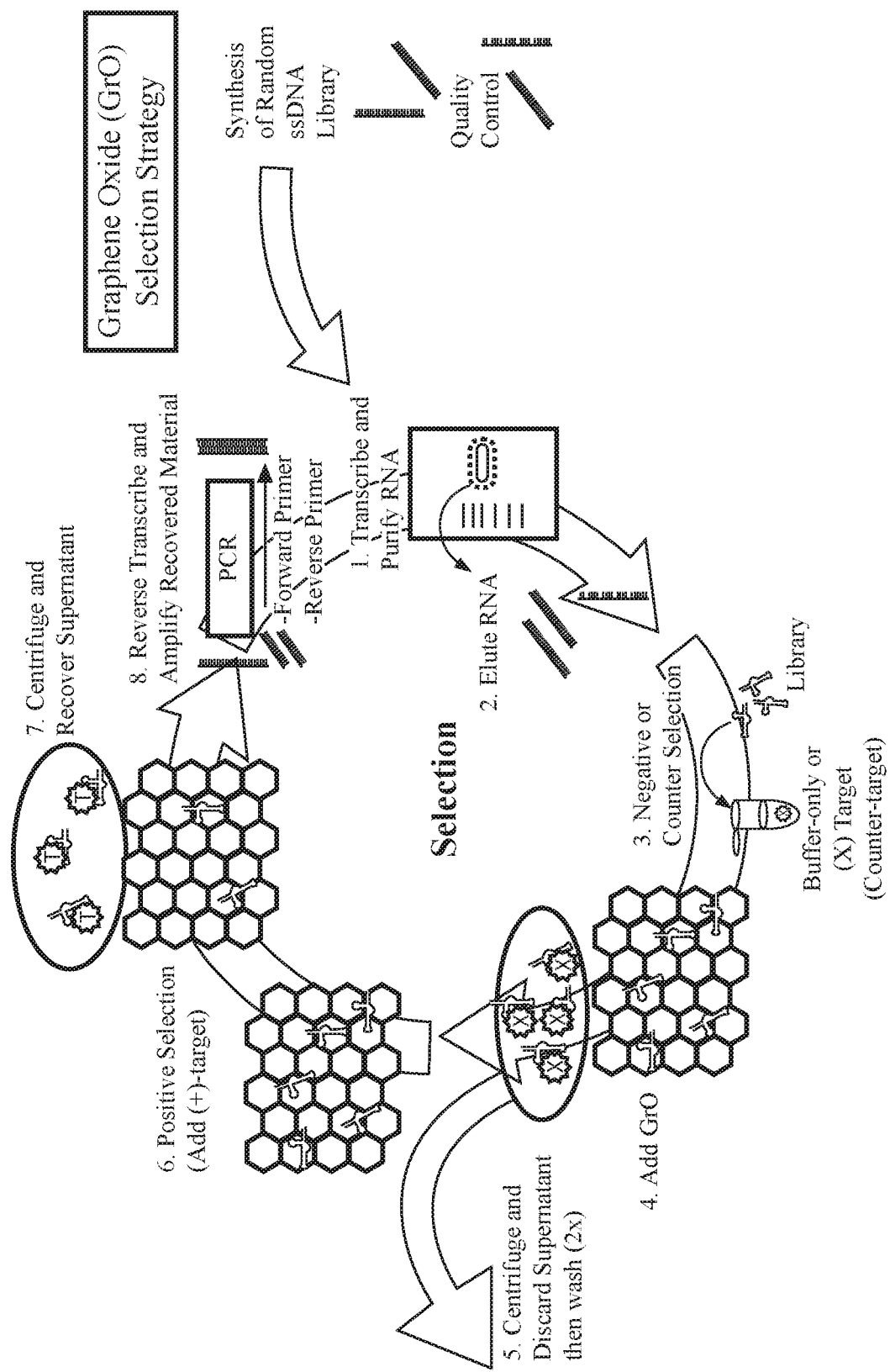
FIG. 15 shows an illustration of graphene oxide (GrO) aptamer selection. In step (1), RNA was transcribed and purified. In step (2), purified RNA was eluted. In step (3), aptamers were incubated with counter-targets and buffer. In step (4), sequences bound to counter-targets or buffer components were removed with graphene oxide. In step (5), centrifugation partitioned the non-specifically-responsive species within the supernatant, which is then discarded. Two additional 5-minute washes removed most of the residual counter-target-binding and buffer-binding sequences. In step (6), a solution of acyclovir in 1× selection buffer was added to the GrO-bound library for positive selection so potential aptamer sequences desorb from the GrO through interaction with the positive target. In step (7), a final centrifugation step separates the target-binding sequences in the supernatant from the non-responsive sequences still adsorbed to the GrO. In step (8) selected sequences were reverse-transcribed, then the library was amplified through PCR, then transcribed to generate library for the next selection round.

Library screening was conducted using a graphene oxide-Systematic Evolution of Ligands by EXponential enrichment (GO-SELEX) approach (FIG. 15) (Park et al., 2012), taking advantage of the π-π interaction that grants graphene oxide a high affinity for single-stranded nucleic acids (Zeng et al., 2015). The goal was to select sequences that did not interact with the 1× selection buffer or with the counter-targets (guanine, guanosine, and deoxyguanosine) but did bind to the positive target acyclovir.

For each round, a given amount of library was first refolded in 1× selection buffer (5-minute denaturing at 90° C., 5 minutes at 4° C., then room temperature). The counter-targets were then added to refolded libraries and incubated for 30 minutes at 37° C. The exceptions to this were rounds 1 and 2, where the counter-targets were only briefly (<1 minute) included to help load the library onto the GrO. After allowing the library to interact with the counter-targets and buffer components, unbound library was loaded onto GrO (mass equal to 100 times the mass of the library at the start of the round) over the course of a 10-minute incubation at 37° C. The solution was then centrifuged at 7,000×g to sediment the GrO. The supernatant, which contained sequences bound to the counter-targets and/or to the buffer, was removed. The sediment was then washed twice with 200 µL 1× selection buffer, centrifuging at 7,000×g and removing the supernatant after each wash. A positive target-containing solution was then added and allowed to elute library from the GrO under the conditions indicated in Table 1 for up to 60 minutes at 37° C., essentially allowing the target to compete with graphene oxide for library binding. Sequences that bound more strongly to the target would desorb from graphene oxide and remain bound to the target at the end of the incubation. A final centrifugation step separated the released material, located in the supernatant, from the non-responsive library that remained bound to the graphene oxide.

After positive selection, the recovered RNA purified using 10% denaturing PAGE with 8 M Urea, was then quantified using a spectrophotometer reading (Table 1), reverse-transcribed with SuperScript IV, and amplified using PCR with Titanium Taq DNA polymerase. Amplification products were transcribed into RNA for the next round of selection.

Three tiers of stringency were implemented over the course of selection (Table 1). The first two rounds of selection did not include screening against counter-targets to maximize library loading onto GrO. Additionally, a large excess of acyclovir was used in positive incubations to maximize library recovery, thus the low-stringency designation. Counter-target incubations were introduced after library recovery was achieved, as middle-stringency conditions. The ratio of acyclovir to library was also reduced during these three rounds to increase library competition for binding to target. Once greater than 10% recovery was achieved, the final rounds of high-stringency selection were implemented. Counter-targets/library ratio remained high and positive target/library ratio was brought to 1:1 while positive incubation time was reduced, to select for faster binding sequences. Once library recovery was shown to remain over 10% after more than two rounds of the high-stringency conditions, parallel assessments were conducted.

TABLE 1

Selection and Assessment Conditions. Conditions used for each round of selection or incubation, with recovery as the ratio between recovered sample and input library for each round. Library enrichment was monitored over the course of selection.

| Generation (Stringency) | Library:X-Targets (30-min inc.) | Library:(+) Target | (+) Incubation Time (min) | Recovery (%) |
|---|---|---|---|---|
| G0/R1 (low) | 1:1000* | 1:1000 | 60 | 0.43 |
| G1/R2 (low) | 1:1000* | 1:1000 | 60 | 2.00 |
| G2/R3 (middle) | 1:1000 | 1:500 | 60 | 3.60 |

TABLE 1-continued

Selection and Assessment Conditions. Conditions used for each round of selection or incubation, with recovery as the ratio between recovered sample and input library for each round. Library enrichment was monitored over the course of selection.

| Generation (Stringency) | Library:X-Targets (30-min inc.) | Library:(+) Target | (+) Incubation Time (min) | Recovery (%) |
|---|---|---|---|---|
| G3/R4 (middle) | 1:1000 | 1:100 | 60 | 8.73 |
| G4/R5 (middle) | 1:1000 | 1:10 | 60 | 10.20 |
| G5/R6 (high) | 1:1000 | 1:1 | 60 | 12.00 |
| G6/R7 (high) | 1:1000 | 1:1 | 60 | 8.60 |
| G7/R8 (high) | 1:1000 | 1:1 | 60 | 9.72 |
| G8/R9 (high) | 1:1000 | 1:1 | 30 | 20.08 |
| G9/R10 (high) | 1:1000 | 1:1 | 30 | 10.62 |
| G10(−)† (parallel 1) | — | — | 30 | 3.74 |
| G10(X)* (parallel 1) | 1:40 | — | 30 | 3.60 |
| G10(+)† (parallel 1) | — | 1:4 | 30 | 14.14 |
| G10(P)† (parallel 1) | — | 1:4 | 30 | 5.46 |
| G11(−)‡ (parallel 2) | — | — | 30 | 4.60 |
| G11(X)‡ (parallel 2) | 1:40 | — | 30 | 5.26 |
| G11(+)† (parallel 2) | — | 1:2 | 30 | 9.34 |
| G11(P)‡ (parallel 2) | — | 1:4 | 30 | 6.32 |

*Counter-targets used for loading, not extended incubation.
†Pre-loading incubation conducted with pooled counter-targets.
‡Pre-loading incubation conducted with positive target acyclovir. This was done to minimize the recovery of cross-reactive species.
The following abbreviations are used in this table: "X-Targets" are counter-targets; "(+) Target" is acyclovir or penciclovir; "(+) Incubation Time (min)" is the time the "Library:(+) Target" solution was incubated on the GrO. G0 is Generation 0 and so on; R1 is Round 1 and so on. For the parallel assessment (parallel 1 and parallel 2) the incubations were performed with: (−) 1X selection buffer only, (X) counter-targets in 1X selection buffer, (+) acyclovir in 1X selection buffer, and (P) penciclovir in 1X selection buffer.

Figure 16:
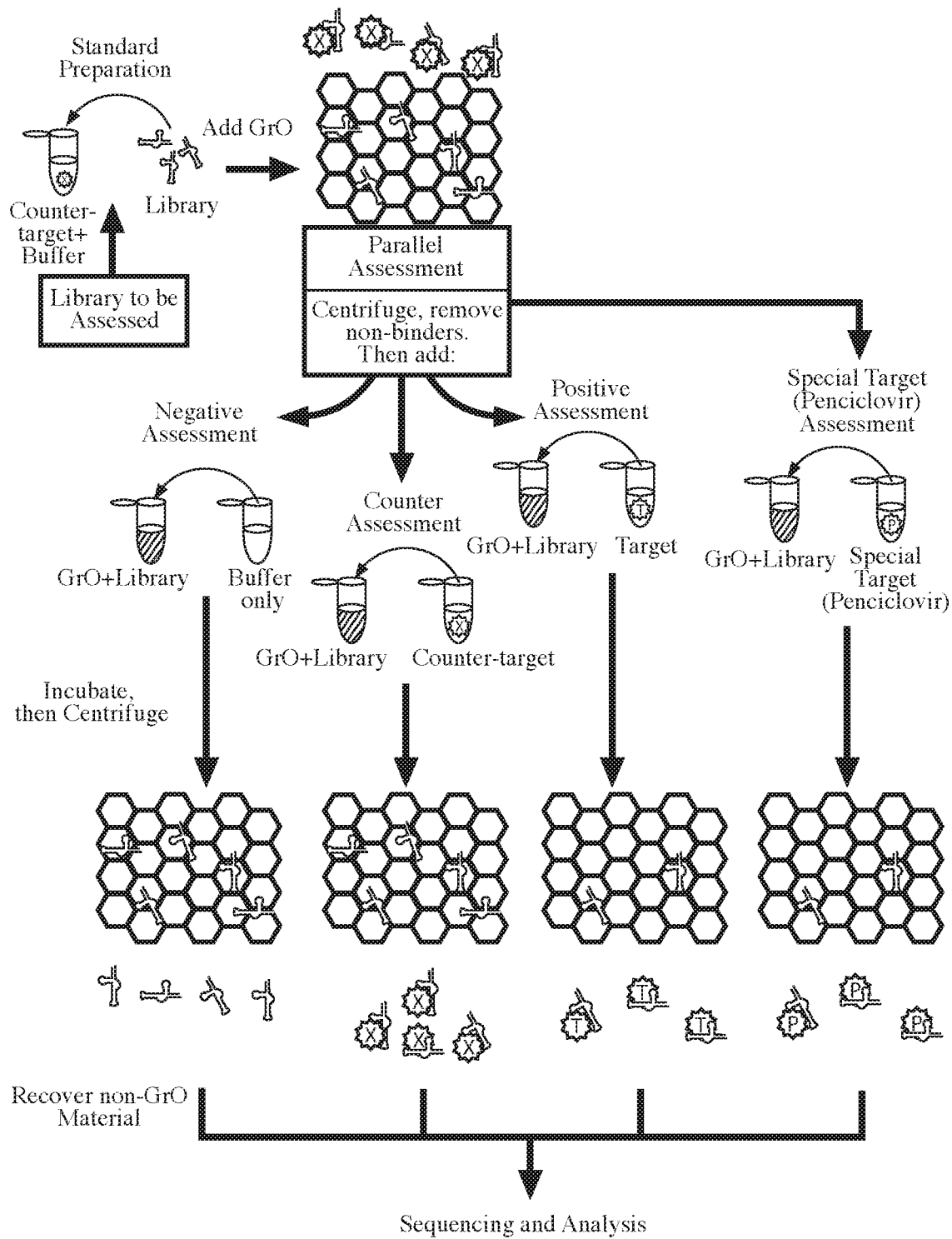
FIG. 16 shows an illustration of graphene oxide parallel assessment. Enriched libraries undergoing parallel assessment were divided into four equal portions. Library samples were then added to graphene oxide and allowed to incubate to load the library on the graphene oxide. Two 5-minute washes were used to remove non-binding material. For the positive (acyclovir) and special target (penciclovir) sample, each target was prepared separately in 1× selection buffer to 1 µM; the counter target replaced the positive target with 10 µM of each counter-target in solution; the negative sample replaced the positive target with an equal volume of nuclease-free water. Samples were then combined with their respective graphene oxide preparations and incubated. Post-incubation, samples were centrifuged to recover their supernatants, and library recovery was determined by NanoDrop-1000 spectrophotometer reading (Thermo Fisher Scientific; Wilmington, Del.). Remaining library sample was analyzed on denaturing PAGE. Images of the gels were taken after staining/destaining with Gel-Star. Bands corresponding to expected library size were recovered for a follow-up round of parallel assessment, with positive target acyclovir replacing counter-targets for the negative, counter, and special target samples' pre-loading incubation. Material recovered from the second parallel assessment was used for sequencing and analysis.

For the two parallel assessments, library to be assessed was divided into four equal amounts for preparation and refolding as above (FIG. 16). For each condition, 50 pmoles of library were combined with 1× selection buffer, refolded (90° C. for 5 minutes, 4° C. for 5 minutes), and then incubated with 200 μL of 10 μM combined counter-targets in 1× selection buffer for 30 minutes at 37° C. These samples were then loaded onto an amount of graphene oxide equal to 100 times the mass of library in the sample and incubated for 10 minutes at 37° C. and then washed twice with 200 μL of 1× selection buffer as before. The loaded graphene oxide samples were then incubated in parallel with 200 μL of the appropriate assessment condition (1× selection buffer only, 10 μM pooled counter-targets, 1 μM penciclovir, 1 μM acyclovir for the first parallel assessment, or 0.5 μM acyclovir for the second parallel assessment; in Table 1 these conditions are shown as: (−); (X); (P); (+); and (+), respectively) in 1× selection buffer for 30 minutes at 37° C. A final centrifugation step separated desorbed responsive library from non-responsive graphene oxide-bound library. The responsive libraries were quantified using spectrophotometric reading (Table 1), verified using 10% denaturing PAGE with 8 M urea, and prepared for a second parallel assessment. This follow-up assessment continued to use counter-targets for the positive sample's pre-loading incubation, but utilized positive target acyclovir for each other samples' pre-incubation. This was done to minimize representation of cross-reactive sequences in a given sample (i.e. responsive to counter-targets in the positive sample, responsive to acyclovir in the negative, counter-targets, or penciclovir samples). Material recovered from the second parallel assessment was quantified using spectrophotometric reading (Table 1), verified using 10% denaturing PAGE with 8 M urea, and prepared for sequencing by reverse transcription and PCR to generate double-stranded DNA.

Sequencing

The initial library was subjected to over 10 rounds of GrO-based selection and parallel assessment (Table 1). The GO-SELEX process is designed to enrich for sequences over multiple rounds of selection that bind to the given targets of interest and remove sequences that bind to the non-target compounds or buffer components. As a result, the populations to be sequenced are expected to contain multiple copies of potential aptamer candidates.

The Illumina MiSeq system (San Diego, Calif.) was implemented to sequence the aptamer libraries after parallel assessment using a single-end read technique. Deep sequencing and subsequent data analysis reduces the large number of screening rounds traditional SELEX requires, which may introduce error and bias due to the screening process (Schütze et al., 2011). Five samples were sequenced: the final generation library that responded to acyclovir, the final generation library that responded to the counter-targets, the final generation library that responded to 1× selection buffer (negative condition), the penultimate generation library that responded to acyclovir, and the final generation library that responded to the additional target of interest, penciclovir. From these sets of data, sequence families were constructed at 95% homology (sequence similarity considering mutations, deletions, and insertion) for aptamer candidate identification. There were 1,711,535 raw sequences (124,600 unique sequences) from the library that responded to acyclovir and 2,074,832 raw sequences (110,149 unique sequences) from the library that responded to penciclovir.

Aptamer Candidate Selection

Sequence family construction focused primarily on sequence similarity. This means that a sequence's frequency in the positive target population was factored in, but greater emphasis was placed on the degree of variation between similar sequences, with 95% homology being the minimum requirement (100% match over the entire sequence is not necessary to join a family, up to 2 bases can be mismatched, inserted, or deleted). One would therefore expect families with the greatest number of members to rank highly as aptamer candidates. After families are constructed, consideration can be given to the relative presence of a family in a given population—families that occur frequently in the negative and counter-target populations are considered weaker candidates, as they demonstrate a degree on non-specific interaction in binding to buffer or counter-target components. Additionally, families that demonstrate a high rate of enrichment (i.e. large ratio between the final positive population and penultimate positive population) improve their candidacy, as enrichment rate has been linked to the binding affinity of a candidate relative to the rest of the population (Levay et al., 2015; Wang et al., 2014). Under these conditions, several candidate families appeared to be strong candidates for binding acyclovir (Table 2) and penciclovir.

TABLE 2

DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild-type sequence.

| Candidate Family-Sequence Number | SEQ ID NO: | Sequence | Length | % Identity Consensus | Wildtype |
|---|---|---|---|---|---|
| 582-1 | 108 | ACAGCTTAGCGTAATGGCTACTGACGCCGTCCAAACCTATTTACAGACT | 49 | 100 | 80.77 |
| 582-2 | 109 | ACAGCTTAGGATAATGGCTACTGACGCCGTCCAAACCTATTTACAGACT | 49 | 95.92 | 80.77 |
| 582-3 | 110 | ACAGCTTAGCATAATGGCTACTGACGCCGTCCAAACCTATTCACAGACT | 49 | 95.92 | 80.77 |
| 582-4 | 111 | ACAGCTTAGCATAATGGCTACTGACGCCGTCCAAACCTATTGACAGACT | 49 | 95.92 | 80.77 |
| 582-5 | 112 | ACAGCATAGCATAATGGCTACTGACGCCGTCCAAACCTATTTACAGACT | 49 | 95.92 | 82.69 |
| 582-6 | 113 | ACAGCTTAGCATAATGGCTACTGACGCCGTCCAAACCTATGTACAGACT | 49 | 95.92 | 80.77 |
| 582-7 | 114 | ACAGCTAGCGTAATGGCTACTGACGCCGTCCAAACCTATTTACAGACT | 48 | 97.96 | 80.77 |
| 582-8 | 115 | ACAGCTTAGCATTATGGCTACTGACGCCGTCCAAACCTATTTACAGACT | 49 | 95.92 | 80.77 |
| 582-9 | 116 | ACAGTTAGCATAATGGCTACTGACGCCGTCCAAACCTATTTACAGACT | 48 | 95.92 | 82.69 |
| 582-10 | 117 | ACAGCTTAGCATAATGGCTACTGACGCGGTCCAAACCTATTTACAGACT | 49 | 95.92 | 80.77 |
| 582-11 | 118 | ACAGCTTAGCTTAATGGCTACTGACGCCGTCCAAACCTATTTACAGACT | 49 | 97.96 | 80.77 |
| 582-12 | 119 | ACAGCTTAGCATAATGGCTACTGACGCCGTCCAAACCCATTTACAGACT | 49 | 95.92 | 80.77 |
| 582-13 | 120 | ACAGCTTAGCATAATGGCTACTGACGCCGTCCAAACCAATTTACAGACT | 49 | 95.92 | 80.77 |
| 582-14 | 121 | ACAGCTTAGCATAATGGATACTGACGCCGTCCAAACCTATTTACAGACT | 49 | 95.92 | 80.77 |
| 582-15 | 122 | ACAGCTTAGCATTGTGGCTACTGACGCCGTCCAAACCTATTTACAGACT | 49 | 93.88 | 78.85 |
| 582-16 | 123 | ACAGGTTAGCATAATGGCTACCGACGCCGTCCAAACCTATTTACAGACT | 49 | 93.88 | 82.69 |
| 582-17 | 124 | ACAGCTTAGCGTAATGGCTACTGACGCCGCCCAAACCTATTTACAGACT | 49 | 97.96 | 82.69 |
| 582-18 | 125 | ACAGCTTAGCATAATGGCTACTGACGCCGTCCAAAACTATTTCCAGACT | 49 | 93.88 | 80.77 |

TABLE 2-continued

DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild-type sequence.

| Candidate Family-Sequence Number | SEQ ID NO: | Sequence | Length | % Identity Consensus | % Identity Wildtype |
|---|---|---|---|---|---|
| 582-19 | 126 | ACAGCCTAGCATAAGGGCTACTGACGCCGTCCAAACCTATTTACAGACT | 49 | 93.88 | 82.69 |
| 582-20 | 127 | ACAGCTTAGCATAATGGCTACTGAGGCCGTCCAAACCTATTTACAGACT | 49 | 95.92 | 80.77 |
| 582-21 | 128 | ACAGCTTACCTTAATGGCTACTGACGCCGTCCAAACCTATTTACAGACT | 49 | 95.92 | 78.85 |
| 582-22 | 129 | ACAGCTTAGCATAATGGCTACCGACGCTGTCCAAACCTATTTACAGACT | 49 | 93.88 | 78.85 |
| 582-23 | 130 | ACAGCTTAGCGTAATGGCTACTGGCGCCGTCCAAACCTATTTACAGACT | 49 | 97.96 | 78.85 |
| 582-24 | 131 | ACAGCTTAGCATACTGGCTACTGACGCCGCCCAAACCTATTTACAGACT | 49 | 93.88 | 82.69 |
| 582-25 | 132 | ACAGCTTAGCATAATGGCTACTGACGCCGTCCTAACCTATTTACAGACT | 49 | 95.92 | 80.77 |
| 582-26 | 133 | ACAGGTTAGCATAATGCCTACTGACGCCGTCCAAACCTATTTACAGACT | 49 | 93.88 | 82.69 |
| 582-27 | 134 | ACAGCTTAGCATAATTGCTACTGACGCCGTTCAAACCTATTTACAGACT | 49 | 93.88 | 82.69 |
| 582-28 | 135 | ACAGCTTAGCATAAAGGCTACTGACGCCGTCCAAACCTATTTACAGACT | 49 | 95.92 | 80.77 |
| 582-29 | 136 | ACAGCTTAGCGTAATGGCTACTGACGCCGTCTAAACCTATTTCCAGACT | 49 | 95.92 | 80.77 |
| 582-30 | 137 | ACAGGTTAGCATAATGGCTACTGACGCCGTCCAAACCTATTTAGAGACT | 49 | 93.88 | 86.54 |
| 582-31 | 138 | ACAGGGTAGCGTAATGGCTACTGACGCCGTCCAAACCTATTTACAGACT | 49 | 95.92 | 84.62 |
| 582-32 | 139 | ACAGCGTAGCATAATGGCTACTGACGCCGTTCAAACCTATTTACAGACT | 49 | 93.88 | 86.54 |
| 582-33 | 140 | ACAGCTTAGCATAATGGCTACTGACGCCGTCCAAACTCATTTACAGACT | 49 | 93.88 | 78.85 |
| 582-34 | 141 | ACAGCGTAGCATAGTGGCTACTGACGCCGTCCAAACCTATTTACAGACT | 49 | 93.88 | 82.69 |
| 582-35 | 142 | ACAGCTTAGTGTAATGGCTACTGACGCTGTCCAAACCTATTTACAGACT | 49 | 95.92 | 76.92 |
| 582-36 | 143 | ACAGCTTAGCATAATGGCTACTGACGGCGTTCAAACCTATTTACAGACT | 49 | 93.88 | 82.69 |
| 582-37 | 144 | ACAGGTTAGCATAATGGCTACTGACGCCGTCCAAACCTATTTATAGACT | 49 | 93.88 | 84.62 |
| 582-38 | 145 | ACAGCTTAGCATAATGGCTACTGACGCCGTCCAAACCTATTGTCGACT | 48 | 91.84 | 80.77 |

TABLE 2-continued

DNA sequences corresponding to the non-stem regions of the acyclovir binding RNA riboswitches. Seven families were identified in the screen: 582, 769, 795, 935

TABLE 2-continued

DNA sequences corresponding to the non-stem regions of the acyclovir binding RNA riboswitches. Seven families were identified in the screen: 582, 769, 795

TABLE 2-continued

DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild-type sequence.

| Candidate Family-Sequence Number | SEQ ID NO: | Sequence | Length | % Identity Consensus | Wildtype |
|---|---|---|---|---|---|
| 795 Consensus Sequence | 224 | ACAGNSWRGCATAMTGKCTWCWGA CGSCBKCAAAMCYTANTTVNMGACT Where the N at position 5 can be C or no nucleotide, the N at position 40 can be T or no nucleotide, and the N at position 44 can be C, G, T, or no nucleotide | 49 | — | — |
| 935-1 | 183 | ACAGGGTAGCATAATGGGCTACTTG ACGCCTTCACCTATTTGTAGACT | 48 | 100 | 86.79 |
| 935-2 | 184 | ACAGGGTAGCATAATGGGCTACTTG ACGCCTTCACCTATTTGAGACT | 47 | 97.92 | 86.79 |
| 935-3 | 185 | ACAGGGTAGCATAATGGGCTACTTTA CGCCTTCACCTATTTGTAGACT | 48 | 97.92 | 84.62 |
| 935-4 | 186 | ACAGGGTAGCATAATGGGCTACTTG ACGCCTTCACCTATTTCTAGACT | 48 | 97.92 | 84.91 |
| 935-5 | 187 | ACAGGGTAGCATAATGGGCTACTTG ACGCCTTCACCTATTTGGAGACT | 48 | 97.92 | 88.68 |
| 935-6 | 188 | ACAGGGTAGCATAGTGGGCTACTTG ACGCCTTCACCTATTTGTAGACT | 48 | 97.92 | 84.91 |
| 935-7 | 189 | ACAGGGTAGCATGATGGGCTACTTG ACGCCTTCACCTATTTGTAGACT | 48 | 97.92 | 84.91 |
| 935-8 | 190 | ACAGGGTAGCATAATGGGCTACTTG ACGCCTTCACCTATTAGTAGACT | 48 | 97.92 | 84.91 |
| 935-9 | 191 | ACAGGGTAGCATAATGGGCTATTTGA CGCCTTCACCTATTTGTAGACT | 48 | 97.92 | 84.91 |
| 935-10 | 192 | ACAGGGTAGCATAATGGGCTACTTGC CGCCTTCACCTATTTGTAGACT | 48 | 97.92 | 86.54 |
| 935-11 | 193 | ACAGTGTAGCATAATTGGCTACTTGA CGCCTTCACCTATTTGTAGACT | 48 | 95.83 | 83.02 |
| 935-12 | 194 | ACAGGGTAGCATAATGGGCTACTTG ACGCTTTCACCTTTTTGTAGACT | 48 | 95.83 | 83.02 |
| 935-13 | 195 | ACAGGGTAGCATAAGGGGCTACTTG ACGCCTTCACCTATTTGTAGACT | 48 | 97.92 | 84.91 |
| 935-14 | 196 | ACAGGGTAGCATAATGGACTACTTG ACGCCTCCACCTATTTGTAGACT | 48 | 95.83 | 81.13 |
| 935-15 | 197 | ACAGGGTAGCATAATGGGCTACTTGT CGCCTTCACCTATTTGTAGACT | 48 | 97.92 | 84.62 |
| 935 Consensus Sequence | 225 | ACAGKGTCGCATRRKKGRCTAYTTKH CGCYTYCACCTWTTWSNAGACT Where the N at position 43 can be G, T, or no nucleotide. | 48 | — | — |
| 946-1 | 198 | ACAGCGTAGCATAATGGGCTGCAGA CGCCGTCAAACCTATTTGCAGACT | 49 | 100 | 84.62 |

TABLE 2-continued

DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild-type sequence.

| Candidate Family-Sequence Number | SEQ ID NO: | Sequence | Length | % Identity Consensus | Wildtype |
|---|---|---|---|---|---|
| 946-2 | 199 | ACAGCGTAGCATAATGGGCTGCAGACGCAGTCAAACCTATTTGCAGACT | 49 | 97.96 | 82.69 |
| 946-3 | 200 | ACATGTAGCATAATGGGCTACTGACGCCGTCAAACCTATTTGCAGACT | 48 | 91.84 | 86.54 |
| 946-4 | 201 | ACAGCGTAGCATAGTGGGCTGCAGACGCCGTCAAACCTATTTGCAGACT | 49 | 97.96 | 82.69 |
| 946-5 | 202 | ACAGTGTAGCATAATGGGCTGCAGACGCCTTCAAACCTATTTGGAGACT | 49 | 93.88 | 88.46 |
| 946-6 | 203 | ACAGTGTAGCATAATGGGCTGCTGACGCCGTCAAACCTATTTGAAGACT | 49 | 93.88 | 86.54 |
| 946-7 | 204 | ACAGCGTAGCATAATGGGCTACAGGCGCCGTCAAACCTATTTGCAGACT | 49 | 95.92 | 84.62 |
| 946-8 | 205 | ACAGCGTAGCATAATGGGCTACTGGCGCCGTCAAACCTATTTGCAGACT | 49 | 93.88 | 86.54 |
| 946-9 | 206 | ACAGCGTAGCATAATGGGCTGCAGACGCCGTCAAACCTATTTGAGACT | 48 | 97.96 | 84.62 |
| 946-10 | 207 | ACAGGTAGCATAATGGGCTGCAGACGCCGTCAAACCTATTTGCAGACT | 48 | 97.96 | 84.62 |
| 946-11 | 208 | ACAGGTAGCATAATGGGCTGCTGACGCCGTCAAACCTATTTACAGACT | 48 | 93.88 | 84.62 |
| 946-12 | 209 | ACAGCGTAGCATATTGGGCTGCAGACGCCGTCAAACCTATTTGCAGACT | 49 | 97.96 | 82.69 |
| 946-13 | 210 | ACAGCGTAGCATAATGGGCTGCAGACGCCTTCAAACCTATTTGGAGACT | 49 | 95.92 | 88.46 |
| 946-14 | 211 | ACAGTGTAGCATAATGGGCTGCAGACGCCGTCAAACCTATTTGAGACT | 48 | 95.92 | 84.62 |
| 946-15 | 212 | ACAGCGTAGCATAATGGGCTGCTGACGCCGTCAAACCTATTTGGAGACT | 49 | 95.92 | 88.46 |
| 946-16 | 213 | ACAGCGTAGCATAATGGGCTGCAGACGCCGTCAAACCTATTTACAGACT | 49 | 97.96 | 82.69 |
| 946-17 | 214 | ACAGCGTAGCATAATGGGCTGCTGACGCCGTCAAACCTATTTGCAGACT | 49 | 97.96 | 86.54 |
| 946-18 | 215 | ACAGGGTAGCATAATGGGCTGCAGACGCCGTCAAACCTATTTGGAGACT | 49 | 95.92 | 88.46 |
| 946-19 | 216 | ACAGCGTAGCATAATGGGCTACAGACGCCGTCAAACCTATTTGCAGACT | 49 | 97.96 | 86.54 |
| 946-20 | 217 | ACAGCGTCGCATAATGGGCTGCAGACGCCGTCAAATCTATTTGCAGACT | 49 | 95.92 | 80.77 |
| 946-21 | 218 | ACAGCGTAGCATAATGGGCTTCAGACGCCGTCAAACCTATTTGCAGACT | 49 | 97.96 | 84.62 |

TABLE 2-continued

DNA sequences corresponding to the non-stem regions of the acyclovir binding RNA riboswitches. Seven families were identified in the screen: 582, 769, 795, 935, 946, 961, and 996 with between 1 and 39 sequences in each family. The percent identity for each sequence in the family was compared to the most prevalent sequence within each family (582-1, 769-1, 795-1, 935-1, 946-1, 961-1, and 996-1). The percent identity for each sequence in the family was also compared to the wild-type sequence.

| Candidate Family-Sequence Number | SEQ ID NO: | Sequence | Length | % Identity Consensus | Wildtype |
|---|---|---|---|---|---|
| 946-22 | 219 | ACATGTAGCATAATGGGCTGCAGAC GCCGTCAAACCTATTTGGAGACT | 48 | 93.88 | 84.62 |
| 946 Consensus Sequence | 226 | ACANNGTMGCATADTGGGCTDCWGR CGCMKTCAAAYCTATTTRNAGACT Where the N at position 4 can be G or no nucleotide, the N at position 5 can be C, G, T, or no nucleotide, and the N at position 44 can be A, C, G, or no nucleotide. | 49 | — | — |
| 961-1 | 220 | ACACCGTAGCATAATGGGCTACTGCC GCCGTCGACCTTTTGGAGACT | 47 | 100% | 82.69 |
| 996-1 | 221 | ACAGGGTAGCATAATGGCTTAGGAC GCCTTCAAACCTATCAAGACT | 46 | 100% | 76.92 |

Positive target acyclovir produced seven strong candidates (SEQ ID NOs:87-93; RNA sequences including stem regions) corresponding to 582-1 (SEQ ID NO:108), 769-1 (SEQ ID NO:147), 795-1 (SEQ ID NO:164), 935-1 (SEQ ID NO:183), 946-1 (SEQ ID NO:198), 961-1 (SEQ ID NO:220), and 996-1 (SEQ ID NO:221), each designated F1A (FIG. 17). These sequences were the most prevalent sequences in each family (the DNA sequences of all the members of each family are: 582 (SEQ ID NOs:108-146); 769 (SEQ ID NOs:147-163); 795 (SEQ ID NOs:164-182); 935 (SEQ ID NOs:183-197); 946 (SEQ ID NOs:198-219); 961 (SEQ ID NO:220); and 996 (SEQ ID NO:221)). The consensus sequences show all possible substitutions or gaps at each nucleotide position for each family (SEQ ID NOs: 222-226). As the goal was to identify aptamers from a library based on RNA that is known to bind to deoxyguanosine, strong candidates needed to have minimal presence in the counter-targets population. Candidates F1A-795, F1A-935, and F1A-946 met this criterion very well, as they were not detected in the counter-target population. F1A-996 and F1A-961 are considered the next best candidates in this regard, although they do show up to a small degree in the counter-targets population. In addition, candidates should appear minimally in the negative population, as those sequences desorbed from GrO without the influence of acyclovir and could represent false positives. F1A-935 and F1A-946 performed ideally under this criterion as well, as they were not found in the negative population. Candidate F1A-769 was minimally detected in the negative population, with candidates F1A-961, F1A-795 and F1A-996 performing less well. Enrichment rate was the final condition to be considered, with F1A-935, F1A-946, and F1A-769 performing adequately. Candidate F1A-582 was included because it exhibited the greatest enrichment rate, although it did not perform well under the other criteria. The remaining candidates did not perform well relative to these four, but exhibited acceptable characteristics.

Additional target penciclovir produced seven strong candidates (SEQ ID NOs:94-100), each designated F1P (FIG. 18). As before, the goal was to identify aptamers from a library based on RNA that is known to bind to deoxyguanosine, diverging from libraries enriched for binding to acyclovir (acyclovir) after Round 10. Strong candidates needed to have minimal presence in both the acyclovir and the counter-targets populations to minimize cross-reactivity. Candidate F1P-923 met the first criterion, candidate F1P-710 met the second criterion, and candidate F1P-584 met both criteria to a degree. Candidate F1P-584 also demonstrated moderate favorability for penciclovir over the negative condition, as well as moderate enrichment relative to the previous generation's response to acyclovir. The remaining candidates demonstrated either minimal favoring of penciclovir over acyclovir or minimal favoring of penciclovir over counter-targets (F1P-837 and F1P-932; F1P-991 and F1P-718; respectively). These four candidates demonstrated some favorability for penciclovir over the negative condition which minimizes the chance of a false positive, although this criterion is not as significant if a candidate does not demonstrate selectivity for penciclovir over its analogues. Enrichment rate was the final condition to be considered, with F1P-923, F1P-932, and F1P-584 performing adequately.

Qualitative PAGE assessment of selected aptamers was performed. Individually synthesized and transcribed aptamers were subjected to selection on Graphene Oxide (GrO) under physiological Mg++ (0.5 mM) and elution with either acyclovir (+) or counter-targets (x). The specifically eluted aptamer fractions for each sample were subjected to PAGE for analysis.

100 pmoles of each aptamer candidate (per trial/lane) was resuspended in 1× modified selection buffer (50 mM HEPES, 100 mM KCl, 0.5 mM MgCl$_2$, pH 7.3) and refolded (90° C. for 5 min, then 4° C. for 5 min), then incubated at 37° C. for 30 minutes with 200 pmoles (each) of pooled counter-targets or target. Final library concentration was 0.5 µM, target/counter-targets concentration was 1 µM (incubation volume was 200 µl).

After target/counter-target incubation, 250 m of GrO (Angstron Materials (Dayton, Ohio) was added to adsorb unbound candidate (10-minute incubation at 37° C.).

Samples were centrifuged for 5 minutes at 7,000×g. Supernatant was recovered, denatured using 2× Formamide with 40 mM EDTA, and run on 10% denaturing PAGE with 8 M urea (supplier: American Bioanalytical; catalog #'s AB13021-01000. AB13022-01000). Running buffer was 1×TBE (supplier: Amresco/VWR; catalog #0658-20L, diluted using DI water). DNA ladder was 20/100 DNA ladder (IDT). Gels stained with Gel Star (Lonza, 50535) and imaged on a blue light transilluminator.

Candidates F1A-769, F1A-795, F1A-946, and F1A-996 appear to exhibit selective positive response in this qualitative PAGE assessment (good elution of the Aptamer from GrO with Acyclovir target and relatively lower or minimal elution with counter-targets).

CONCLUSION

Strong candidates for acyclovir were identified after twelve rounds of iterative screening and parallel assessment; reasonable candidates for penciclovir were identified after two rounds of screening and parallel assessment.

Example 2: Isolation of Conditional scFv's

Potential splice site liabilities are removed and tumor antigen specific scFv's are synthesized by overlapping oligo synthesis and cloned into the CAR shuttle construct containing the acyclovir responsive element and the primate CD3 promoter. As an initial prototype, anti-ECD of EPCAM or ERBB2scFv with a CD8-alpha signal peptide, stalk, and transmembrane domain is utilized. Solid tumor microenvironment restricted CAR products are generated either using methods as described in U.S. Pat. No. 8,709,755 and PCT Publication No. WO/2016/033331A1 or by direct selection from human phage libraries under permissive and non-permissive conditions. Briefly, a human V$_H$×V$_L$ library from Creative Biolabs (Shirley, N.Y.) is panned in the following tumor permissive conditions: 100 µg/ml hyaluronan, 100 kDa fraction (Lifecore Biomedical, Chaska, Minn.), 20 mg/ml recombinant HSA (Cyagen, Santa Clara, Calif.), 200 ng/ml recombinant human VEGF in 25 mM sodium bicarbonate buffer, 2 µM adenosine, 10 mM sodium lactate pH 6.7, following clearance with streptavidin magnetic beads (ThermoFisher, Carlsbad, Calif.) bound to biotinylated human IgG. Binding to biotinylated-target receptor ECD of EPCAM and ERBB2 conjugated beads at 37° C. is performed under permissive conditions followed by serial washes in permissive conditions. Phage are released with physiologic conditions (1 µg/ml hyaluronan, 20 mg/ml HSA, 25 mM bicarbonate, 1 mM sodium lactate pH 7.2) followed by elution of tight variants with acid elution and rapid neutralization with 1 M Tris. Phage are expanded and genomic DNA is split for deep sequence analysis of V$_H$×V$_L$ chains using long read sequencing (PacBio, Menlo Park, Calif.) Panning can be repeated for enrichment. V$_H$×V$_L$ sequences showing preferential amplification of reads during the phage culturing process over enrichment to target are excluded for further analysis. Phage with selective binding to the target that are enriched under tumor permissive conditions but released under physiologic conditions are chosen for further characterization by cloning into the CAR construct expression system, generation of lentivirus, and transduction into T cells for testing CAR-mediated tumor antigen expressing target cell killing in a tumor-selective environment compared to physiologic conditions.

Example 3: Generation of MRB-CARs Using Microenvironment Restricted scFv's

Microenvironment restricted ASTRs were obtained that were made by subjecting V$_H$ and V$_L$ sequences with low selectivity for the tumor microenvironment to evolution as described in application WO/2016/033331A1. Chimeric antigen receptors (CARs) for binding either of two tumor antigens, Axl or Ror2, with increased activity at the reduced pH of a tumor environment compared to normal tissue (such microenvironment restricted biologics is sometimes referred to herein as (MRB-CARs) were made by incorporating the heavy chains and light chains of the microenvironment restricted single-chain antibodies into lentiviral expression vectors along with other CAR domains to generate MRB-CARs. These CARs included various combinations of modules from amino to carboxy terminus, which included a CD8 signal peptide (P1) (SEQ ID NO:74); microenvironment restricted anti-Ror2 and Anti-Axl V$_H$ and V$_L$ combinations; a stalk and transmembrane domain from CD8 (SEQ ID NO:75) or CD28 (SEQ ID NO:76) (P5); a co-stimulatory domain from CD 137 (SEQ ID NO:1) or ICA (SEQ ID NO:3) (P6); an activation domain from CD3Z (SEQ ID NO:13) (P7); a 2A-1 ribosomal skip sequence (SEQ ID NO:77) (P8); and an exemplary eTAG (SEQ ID NO:78) (P9).

Pan T cells were transduced with the recombinant lentiviral particles expressing the candidate CARs and the percent transfected cells was determined by determining the percent of cells expressing the eTag using FACS. Pan T cells were successfully transduced with the recombinant lentiviral particles encoding the candidate CARs and displayed conditional activity in these transduced T cell assays at pH 6.7 vs. pH 7.4.

The cytotoxic activity of the candidate CARs against target cells expressing either Axl or Ror2 was analyzed at a pH of 7.4 (physiological pH) or a pH of 6.7 (pH surrogate tumor assay condition). Many of the candidate CARs were more effective at lysing target cells at a pH of 6.7 than a pH of 7.4.

Example 4. Construction of Ligand-Inducible Riboswitches

Figure 7:
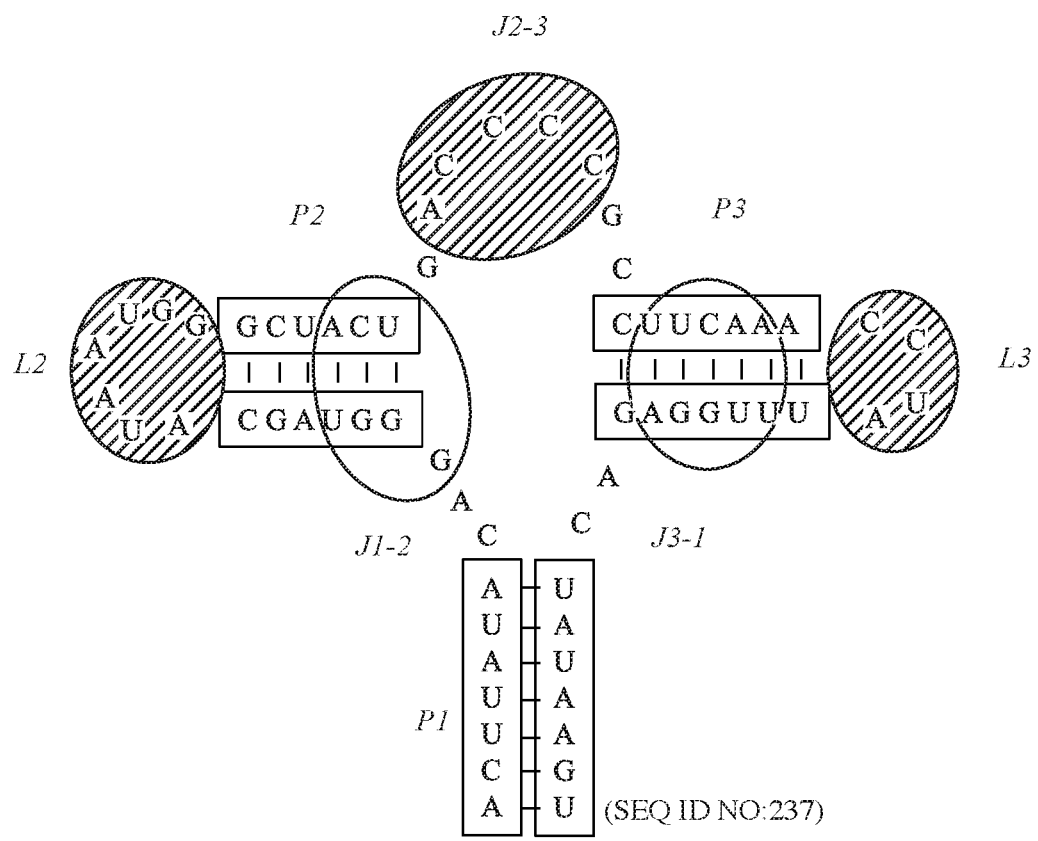
FIG. 7 represents the *M. forum* type I-A deoxyguanosine riboswitch aptamer regions targeted for directed evolution strategy. Nucleotides within empty ovals were targeted for randomization. Nucleotides within striped ovals were targeted for insertion/deletion and randomization.
Figure 8A:
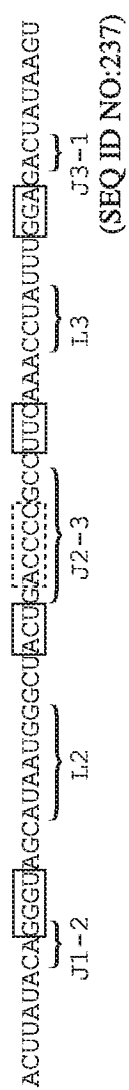
FIGS. 8A and 8B represent the *M. forum* type I-A deoxyguanosine riboswitch aptamer screening library.
Figure 8B:
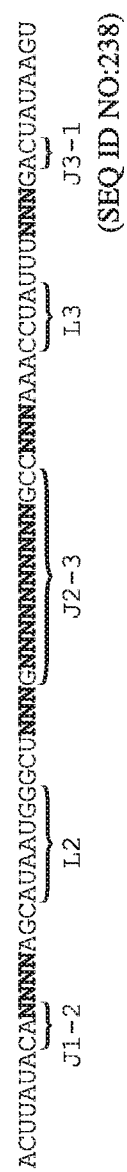
Figure 11:
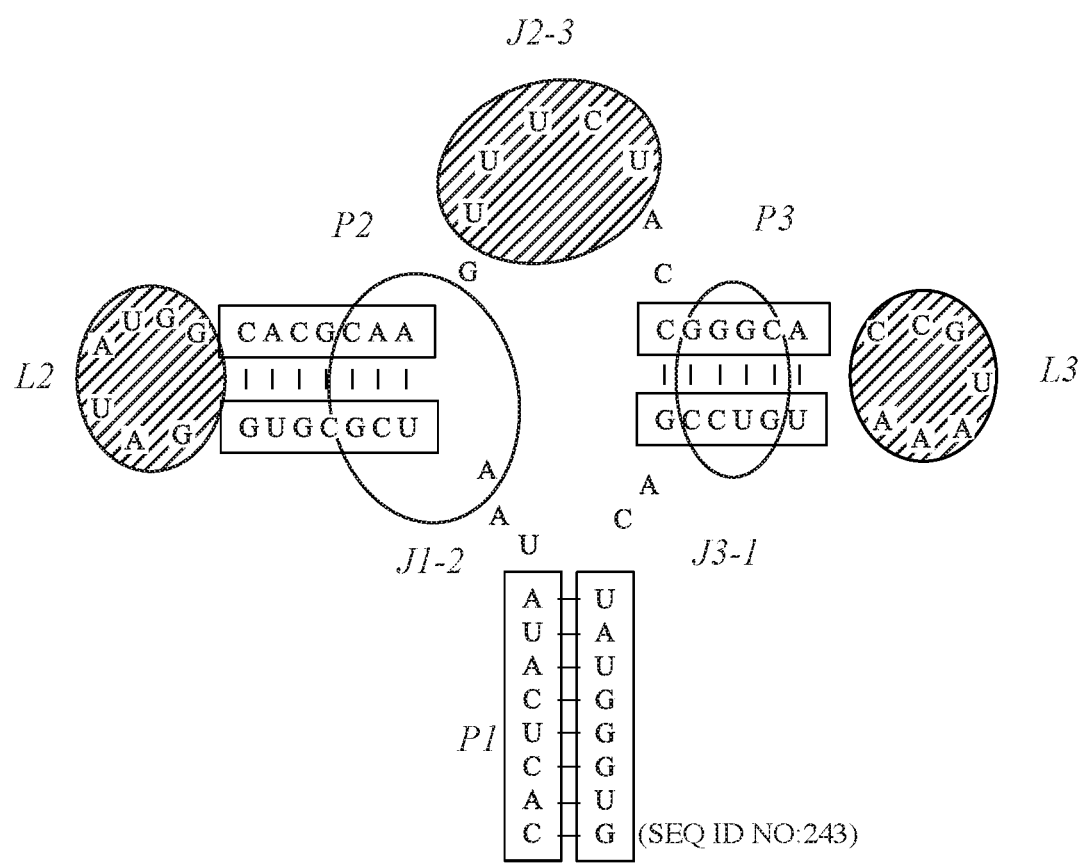
FIG. 11 represents the *B. subtilis* guanosine xpt riboswitch aptamer regions targeted for directed evolution strategy. Nucleotides within empty ovals were targeted for randomization. Nucleotides within striped ovals were targeted for insertion/deletion and randomization
Figure 12A:
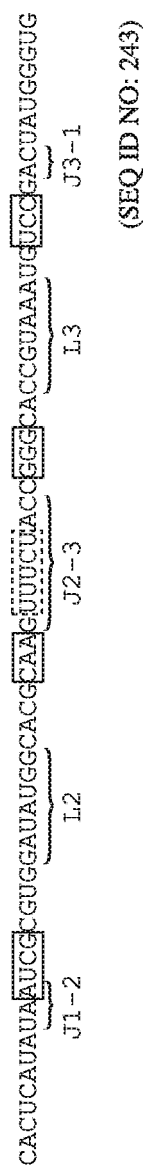
FIGS. 12A and 12B represent the *B. subtilis* guanosine xpt riboswitch aptamer screening library.
Figure 12B:
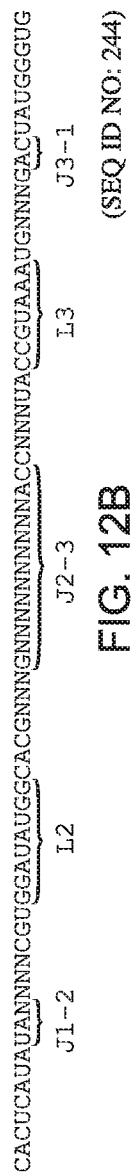

Deoxyguanosine riboswitch aptamer and guanine riboswitch aptamers (Pikovskaya, 2014; Kim, 2007) or other purine riboswitch aptamers are synthesized as oligonucleotides. In one example, the deoxyguanosine IA riboswitch from *Mesoplasma florum* (underlined and in bold in FIG. 6; FIG. 7) is selected for evolution to generate an acyclovir-responsive riboswitch. In another example, the guanine xpt riboswitch from *Bacillus subtilis* (underlined and in bold in FIG. 10; FIG. 11) is selected for evolution to generate an acyclovir-responsive riboswitch. For each of these two examples, a random RNA library is generated with alternate nucleotides at targeted sequence positions in the P2, P3, J1-2, and J2-3 segments (FIGS. 7 and 11). Each segment allows for 3 alternate nucleic acids at each targeted sequence position, or alternatively base deletion and insertion of 4 nucleotides in the +1 site at each targeted sequence position for saturation mutagenesis as indicated in FIGS. 8A-8B and 9 (*M. florum* IA) and FIGS. 12A-12B and 13 (*B. subtilis* xpt). Primer extension and reagent preparation is followed by RNA transcription. The resultant RNA library is negatively selected on graphene oxide in the presence of guanine, guanosine, and deoxyguanosine followed by positive selection with acyclovir or penciclovir. During the negative and positive selection processes, human cell physiologic magnesium levels (0.5 mM to 1.2 mM) are used and the temperature is kept at 37° C. Recovered aptamers are reverse transcribed and PCR amplified followed by transcription and subsequent screening for at least 8 successive rounds of selection. In a parallel approach, aptamers are screened with an additional negative screen at 40° C. Resultant positive pools are examined by NextGen sequencing and analysis. Individual aptamers are synthesized and examined for affinity by isothermal calorimetry at 35-40° C. in human cell physiologic magnesium levels. Following selection for positive acyclovir and penciclovir specific aptamers, aptamers are integrated with ribozyme hammerhead and pistol ribozymes. Positive acyclovir selective aptamers are combined with pistol ribozymes to identify acyclovir regulated ribozymes. (Harris K A RNA. 2015 November; 21(11): 1852-8. doi: 10.1261/rna). Variants are subjected to gel shift based PAGE purification in the presence of acyclovir and absence of penciclovir. Additionally, the acycloguanosine selective riboswitch is placed immediately 3' in a loop to a splice acceptor upstream of the CAR/IL-7 construct. In the absence of acyclovir, the splice site position is bound in the riboswitch complex but in the presence of acyclovir becomes accessible, generating a functional CAR transcript.

Example 5. Construction of In Vivo Propagation Domains

A series of constitutively active IL7 receptor (IL7R) transmembrane mutants from T cell lymphoblastic leukemias (243 InsPPCL (SEQ ID NO:82); 246 InsKCH (SEQ ID NO:101); 241 InsFSCGP (SEQ ID NO:102); 244 InsCHL (SEQ ID NO:103); and 244 InsPPVCSVT (SEQ ID NO:104); all from Shochat et al 2011, J. Exp. Med. Vol. 208 No. 5 901-908) are synthesized by overlapping oligo nucleotide synthesis (DNA2.0, Newark, Calif.). The synthesized constitutively active IL7R transmembrane mutants are inserted into a constitutively expressing lentiviral vector backbone immediately behind a 2A ribosomal skip sequence followed by an anti-CD19 CD3 expression cassette, which includes a CD8A stalk (SEQ ID NO:79) and a leader peptide (SEQ ID NO:74). HEK293 packaging cells are transfected with the IL7R transmembrane mutant lentiviral vectors and lentiviral packaging constructs, grown, and viral supernatants are harvested using methods known in the art. CD3/CD28-stimulated T cells are transduced with the viral supernatants and grown in IL2 deficient AIM V, CTS OpTmizer T Cell Expansion SFM, or X-VIVO 15 media for 4 weeks, supplemented weekly with frozen PBMCs from the same donor. The resulting expanded transduced T cells expressing IL7R variants are cloned by FACS sorting and the sequences of the IL7R constructs are identified by sequencing RT-PCR products. The 243 InsPPCL variant (PPCL) (SEQ ID NO:82) is selected for further evolution to generate a conditionally active CAR.

Example 6. Screening of Accessory Components for CAR-T Activation and Propagation A series of protein-encoding domains (ABCG1, SOCS1, SMAD2, TGFBR2, cCBL, and PD1) and miRNA sequences are constructed for incorporation into a synthetic intron on the reverse strand of a CD3-promoter driven CAR cassette. Each construct containing the CD3-promoter driven CAR cassette and a protein-encoding domain or miRNA sequence includes a unique bar code for deep sequencing and is assembled using Gibson assembly followed by transformation and library expansion in *E. coli*. Viral stocks are produced and used to transduce CD3/CD28-stimulated T cells in AIM V, CTS OpTmizer T Cell Expansion SFM, or X-VIVO 15 media without IL2 and allowed to grow for 4 weeks in culture with serial sampling of DNA for amplification and deep sequencing for code identification. The library is also subject to PACBio full length sequencing to determine library diversity and to decode the bar code components. The miRNA sequences and protein-encoding domains are tested for synergistic activation of CAR CD3 domains.

Example 7. Engineering a Retroviral Packaging and Transducing System to Target Resting T Cells for Selective T Cell Integration and Expression from PBMCs Although producing high-titer lentiviral vectors by transient transfection is possible, this method carries the risk of generating replication competent retroviruses (RCRs) and is not scalable for clinical applications. Herein, a stable retroviral packaging cell line is generated by the simultaneous introduction of multiple constructs encoding inducible promoters and their regulators into HEK293 suspension-adapted cells (HEK293S) to stably produce the viral components, CAR genes, and their regulatory components. Two distinct inducible systems can be used to temporally control the expression of genes. One system is based on rapamycin- or rapalog-induced dimerization of two transcription factors. One transcription factor consists of three copies of the FKPB protein fused to a ZFHD1 DNA binding domain and the other transcription factor consists of a FRB protein fused to a p65 activation domain. Rapamycin or a rapalog dimerizes the transcription factors to form ZFHD1/p65 AD and can activate gene transcription at 12xZFHD1 binding sites.

A series of vectors as shown in FIGS. 3A-3E are generated with flanking transposon sequences for integration into the HEK293S genome. Once integrated into the genome of a cell, these sequences function as regulatory components and lox and/or FRT sites for subsequent integration using Cre and/or flp recombinases, herein referred to as landing pads. The initial 5 constructs contain polynucleotide sequences encoding puromycin resistance, GFP, RFP, and an extracellular MYC tag that is targeted to the cell membrane through an N-terminal PLss (bovine prolactin signal peptide) and anchored to the cell membrane through a platelet-derived growth factor receptor (PDGFR)C-terminal transmembrane anchoring domain. The initial 5 constructs can also include constitutive minimal CMV and minimal IL-2 promoters, a rapamycin-regulated ZFHD1-based promoter, a tetracycline-responsive element (TRE) promoter, or a bidirectional TRE (BiTRE) promoter. The construct in FIG. 3A contains a polynucleotide sequence encoding FRB domain fused to the NFκB p65 activator domain (p65 AD) and ZFHD1 DNA binding domain fused to three FKBP repeats that is constitutively expressed. The construct in FIG. 3A also includes HIV1 REV and HSV VP65 domain SrcFlagVpx under the rapamycin-inducible ZFHD1/p65 AD promoter. The construct in FIG. 3B includes a polynucleotide encoding an rtTA sequence under the control of the ZFHD1/p65 AD promoter. The construct in FIG. 3C includes a polynucleotide encoding a puromycin resistance gene flanked by loxP sites and the extracellular MYC tag flanked by lox2272 sites. Both of these selectable markers are under the control of a BiTRE promoter, which is flanked by FRT sites. The construct in FIG. 3D includes a polynucleotide encoding GFP flanked by loxP sites that is under the control of a TRE promoter. The construct in FIG. 3D also includes a single FRT site between the TRE promoter and the 5' loxP site of GFP. The construct in FIG. 3E includes a polynucleotide encoding RFP flanked by loxP sites that is under the control of the ZFHD1/p65 AD promoter. The construct in FIG. 3E also includes a single FRT site between the ZFHD1/p65 AD promoter and the 5' loxP site of RFP The constructs in FIGS. 3C-3E function as landing pads for other polynucleotide sequences to insert into the genome of the packaging cell line. The polynucleotide sequences to be inserted can be flanked by lox sites and inserted into the genome using Cre recombinase and the loxP sites. This results in insertion and simultaneous removal of the genomic regions encoding puromycin resistance, the extracellular MYC tag, GFP, and RFP. Alternatively, the polynucleotide sequences can be flanked by FRT sites and inserted into the genome using flp recombinase and the FRT sites followed by removal of the polynucleotide sequences encoding puromycin resistance, the extracellular MYC tag, GFP, and RFP using Cre recombinase.

To generate the packaging cell line with landing pads integrated into the genome, HEK293S cells are co-transfected with equimolar concentrations of the 5 plasmids (FIGS. 3A-3E) plus 5 µg of in vitro-transcribed piggybac transposase mRNA or 5 µg of a plasmid with a promoter for expressing piggybac transposase in the presence of PEI at a ratio of 2:1 or 3:1 PEI to DNA (w/w) or 2-5 µg piggybac transposase protein using a cationic peptide mixture. The transfected cells are selected with puromycin in the presence of 100 nm rapamycin and 1 ug/mL doxycycline for 2-5 days followed by fluorescence-activated cell sorting to collect cells expressing GFP and RFP. The sorted cells are grown 5 days in the absence of puromycin, rapamycin, and doxycycline and cells expressing GFP and RFP are removed also myc positive cells are removed with myc beads. Individual clones from negatively sorted cells are then screened for induction of GFP and RFP by rapamycin and doxycycline and single cell cloned. The DNA from clones is harvested and sequenced for integration analysis. Clones positive for strong inducible expression of GFP and RFP in the presence of rapamycin and doxycycline with limited background expression in the absence of rapamycin and doxycycline are expanded and banked.

Figure 4C:
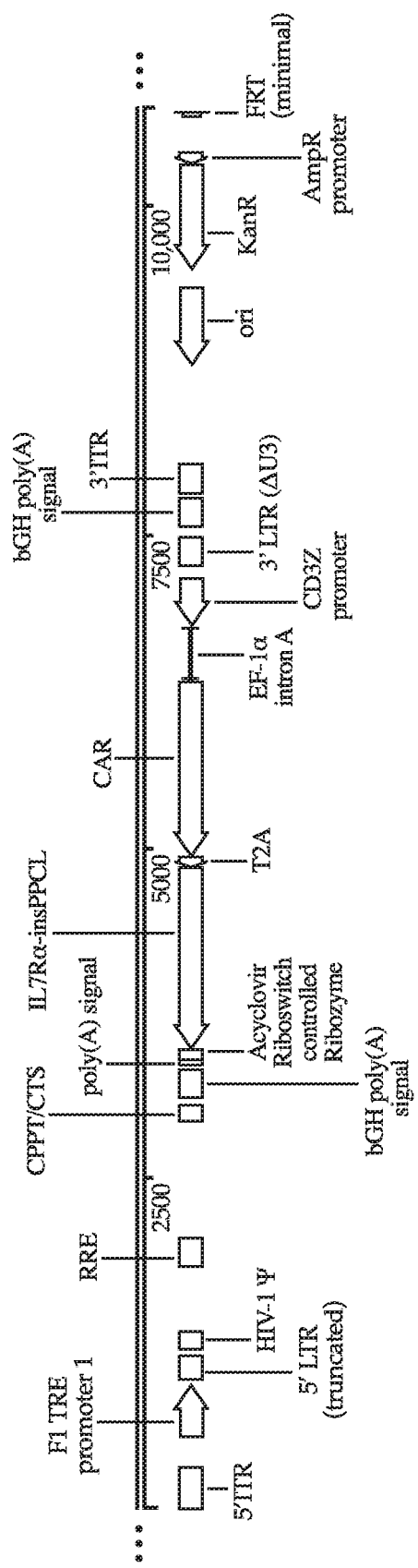

The HEK293S cells with the constructs from FIGS. 3A-3E integrated into the genome are then transfected with a construct containing a tricistronic polynucleotide encoding a DAF signal sequence/anti-CD3 scFvFc (UCHT1)/CD14 GPI anchor attachment site (SEQ ID NO:252), a DAF signal sequence/CD80 extra-cellular domain capable of binding CD28/CD16B GPI anchor attachment site (SEQ ID NO:253), and a DAF signal sequence/IL-7/DAF (SEQ ID NO:107) and transposon sequences flanking the polynucleotide region for integration into the HEK293S genome (FIG. 4A). After transfection, cells are expanded for 2 days in the absence of rapamycin and doxycycline and colonies that are constitutively red are selected. Positive colonies are then transiently transfected with a construct for expressing Cre recombinase to remove remaining genomic DNA, and the RFP encoding region. Another construct (FIG. 4B) containing a polynucleotide with a BiTRE promoter and a polynucleotide region encoding the gag and pol polypeptides in one direction and a polynucleotide region encoding the measles virus F and H proteins in the other direction is transfected at the same time. The Cre recombinase integrates the construct into the genome to generate the integrated sequence shown in FIG. 4B. Resultant colonies are evaluated for protein expression in the presence of doxycycline and rapamycin and analyzed by deep sequencing for genomic integration. The remaining TRE responsive GFP site is retained for the lentiviral genome insertion.

Example 8. Generation of Lentivirus Vector and Retroviral Packaging

The retroviral packaging stable cell line generated in Example 7 is transfected with a construct (FIG. 4C) for expressing Flp recombinase and a construct containing a polynucleotide sequence encoding a CAR and the lymphoproliferative element IL7Rα-insPPCL under the control of a CD3Z promoter that is not active in HEK293S cells, wherein the CAR and IL7Rα-insPPCL are separated by a polynucleotide sequence encoding a T2A ribosomal skip sequence and the IL7Rα-insPPCL has an acyclovir riboswitch controlled ribozyme. The CAR-containing construct further includes cPPT/CTS and RRE sequences and a polynucleotide sequence encoding HIV-1 Psi. The entire polynucleotide sequence on the CAR-containing construct to be integrated into the genome is flanked by FRT sites. Successful integration of the CAR-containing construct causes constitutive expression of GFP that is consequently removed by transient transfection with a construct for expressing Cre recombinase. The HEK293S line is grown in serum free media. Following growth to peak cell density in a stirred tank reactor, the cells are diluted to 70% peak cell density and treated with 100 nM rapamycin for 2 days to induce expression of early genes REV, Vpx, and aCD3 scFv CD16B GPI, aCD28 scFv CD16B GPI, and IL-7 SD GPI DAF followed by the addition of 1 ug/mL doxycycline in the media to induce expression of structural elements like Gag Pol, MV(Ed)-FΔ30, MV(Ed)-HΔ18, and lentiviral genome including the therapeutic target. Levels of virus production are examined by qPCR of the packaging sequence and p24 ELISA. Virus is harvested by depth filtration of cells, and concentration/diafiltration using a TFF cartridge followed by flash freezing for vialing.

Example 9. Peripheral Blood Mononuclear Cell (PBMC) Isolation, Transduction, and Expansion The following example illustrates the use of a closed system for ex vivo processing of PBMCs before in vivo expansion. As an example, 30 to 200 ml of human blood is drawn from a subject with Acid Citrate Dextrose Solution (ACD) as an anticoagulant into a blood collection bag. Alternatively, blood is drawn into Vacutainer tubes, a syringe, or an equivalent and is transferred to an empty blood collection or IV bag. The whole blood is processed using a Neat Cell kit (Cat # CS-900.2, Omniamed) on a Sepax 2 cell processing system (BioSafe) according to the manufacturers' instructions. The peripheral blood mononuclear cells (PBMCs) are collected either into a culture bag, or alternatively a syringe. An aliquot is taken aseptically for cell counting to determine the number of viable cells. The PBMCs are transferred to a G-Rex100MCS Gas Permeable Cell Culture System device (Wilson Wolf) at a final concentration of 0.1-1.0×10$^6$ viable cells/ml in X-VIVO 15 (Cat #08-879H, Lonza) or CTS OpTmizer Cell Expansion SFM (Cat # A1048501, Thermo Fisher Scientific) media with 10-300 IU/ml IL-2 (Cat #202-IL-010, R&D Systems) in up to 200 ml final volume. In addition to IL-2, CTS Immune Cell SR (Cat # A2596101, Thermo Fisher Scientific) can be added to the media. The closed G-Rex Gas Permeable Cell Culture System device can be pre-coated with Retronectin (Cat # CH-296, Takara), or a similar fibronectin-derived equivalent, according to the manufacturer's instructions.

The PBMCs isolated from peripheral blood are loaded onto a PALL PBMC filter, washed once through the filter with 10 ml of AIM V (Thermo Fisher Scientific) or X-VIVO 15 media followed by perfusion with 10-60 ml of lentivirus stock (as prepared in Example 8) at 37° C. at 5 ml/hr. The PBMCs are then washed again with AIM V, CTS OpTmizer T Cell Expansion SFM, or X-VIVO 15 media containing recombinant human DNase (Pulmozyme, Genentech) followed by a wash with DNase-free Lactated Ringers (Cat # L7500, Braun). The PBMCs are then reverse perfused through the filter into a syringe. The cells (target levels of cells are 5×10$^5$ to 1×10$^6$ cells/kg) are then reinfused into the subject through intravenous infusion.

Depending upon the riboswitch contained within the retroviral genome, the subject is given the respective nucleoside analogue antiviral drug or nucleoside analogue antiviral prodrug (acyclovir, valaciclovir, penciclovir, or famciclovir). Subjects can be given any therapeutically effective dose, such as 500 mg of the nucleoside analogue antiviral drug or prodrug orally three times/day. Treatment with the nucleoside analogue antiviral drug or prodrug preferably begins before reinfusion, such as 2 hours before, and can also begin at the time of reinfusion or at some time after reinfusion. The treatment can continue for at least 1, 2, 3, 4, 5, 7, 10, 14, 21, 28, 30, 60, 90, 120 days or 5, 6, 9, 12, 24, 36, or 48 months or longer. The treatment can include administration of the nucleoside analogue antiviral drug or prodrug once, twice, three, or four times daily. After reinfusion and treatment is begun, the number of infected cells is determined through blood counts on days 2, 5, 7, 11, 13, 18, 28, and 56 post-reinfusion using qPCR to quantitate the amount of viral genome. A subject experiencing fever or cytokine release syndrome may have the dose or frequency of the nucleoside analogue antiviral drug or prodrug reduced or halted. If the infected T cells fail to amplify 10,000-100,000 fold by day 18, the dose or frequency of the nucleoside analogue antiviral drug or prodrug may be increased. The clinical response of the subject can be measured through FDG PET imaging and serial CT scan. Oral dosing of the nucleoside analogue antiviral drug or prodrug can be reduced or halted following prolonged remission or in the event of excessive T cell propagation beyond 30% of total peripheral T cell counts.

Example 10. Therapeutic Intervention to Raise Vascular or Tissue pH

To reduce the binding of an antigen binding domain to its cognate antigen, NaHCO$_3$ is administered as an IV bolus or by IV infusion. The standard dosage is 1 mg/kg of body weight as the initial dose followed by 0.5 mg/kg every 10 minutes. A 50-milliliter bolus of NaHCO$_3$ will raise the serum pH approximately 0.1 of a pH unit. If the pH is 7.0, it requires four 50 mEq ampules of HCO$_3$ to correct the pH to 7.40

Example 11. Testing Activity of IL-7 Receptor Lymphoproliferative/Survival Elements in PBMCs To test IL-7Rα variants for their ability to mediate antigen-independent survival of T cells, thirty milliliters of human blood were drawn with acid citrate dextrose (ACD) as an anticoagulant into Vacutainer tubes. The whole blood was processed using density gradient centrifugation with Ficoll-Pacque™ (General Electric) following manufacturer's instruction, to obtain peripheral blood mononuclear cells (PBMCs). Aliquots of the PBMCs were transferred aseptically to wells of a 12 well tissue culture plate, along with X-Vivo™ 15 media (Lonza) to a final concentration of 0.5 million viable cells/mL in a final volume of 1 mL. Recombinant human interleukin-2 (IL-2) (Novoprotein) was also added to a concentration of 100 IU/ml in some samples. Activating anti-CD3 Ab (OKT3, Novoprotein) was added at a concentration of 50 ng/ml, to activate the PBMC for viral transduction. The plates were incubated overnight in a standard humidified tissue culture incubator at 37 degrees C. and 5% Carbon Dioxide. After overnight incubation, lentivirus particle preparations containing the desired test constructs (FIG. 19A) were added to individual wells at a multiplicity of infection (MOI) of 5. The plate was incubated overnight in a standard humidified tissue culture incubator at 37 degrees C. and 5% Carbon Dioxide. Following the overnight incubation, the contents of each of the wells of the 12 well plate were collected and centrifuged to obtain a pellet. The samples were washed once with D-PBS+2% Human Serum Albumin (HSA), resuspended in X-Vivo15™ media, and transferred to wells of G-Rex® 6-well gas permeable cell culture devices (Wilson Wolf). Additional X-Vivo™ 15 media was added to bring the final volume of each well to 30 ml. Matching control samples for each of the constructs were transferred to wells of G-Rex® 6-well gas permeable cell culture devices (Wilson Wolf) and additional media was added to bring the final volume to 30 ml with 100 IU/ml IL-2 for some control samples. The G-Rex® device was incubated in a standard humidified tissue culture incubator at 37 degrees C. and 5% Carbon Dioxide for 7 days. Fresh IL-2 was added to the control samples containing IL-2 during the culture every 2-3 days. Matched test samples without IL-2 were not supplemented. Samples were removed for tracking cell numbers and viability during expansion (Countess, Thermo Fisher) at day 7.

Figure 19A:
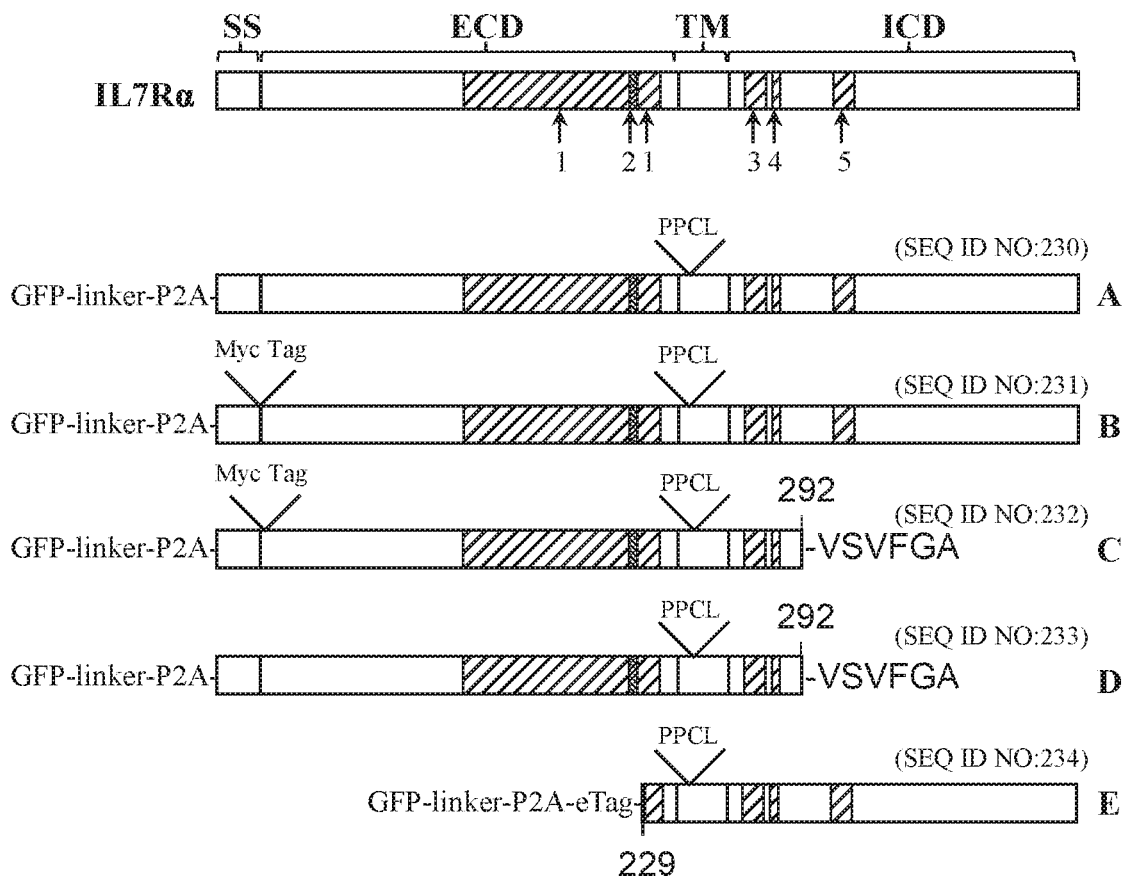
FIG. 19A provides a schematic of IL7Rα variants tested for lymphoproliferative/survival activity when expressed in PBMCs.

FIG. 19A provides a schematic of the IL7Rα constructs that were tested. These constructs were inserted into a recombinant lentiviral genome. The recombinant retroviruses were used to transduce PBMCs. FIG. 19A shows a schematic of wild-type IL7Rα (SEQ ID NO:229), which consists of a signal sequence (SS), an extracellular domain (ECD), a transmembrane (TM), and an intracellular domain (ICD). "1" indicates the site of a fibronectin type III domain; "2" indicates the site of a WSXWS motif"; "3" indicates a Box 1 site, "4" indicates the site of a protein kinase C (PKC) phosphorylation site, and "5" indicates a Box 2 site.

Variant "A" is the IL-7Rα with an InsPPCL at position 243 (Shochat et al 2011, *J. Exp. Med.* Vol. 208 No. 5 901-908) but without the S185C mutation, expressed on a transcript with a GFP polypeptide, a GSG linker, and a P2A ribosomal skip sequence fused to its N-terminus. Variant "B" is the IL-7Rα InsPPCL with a GFP polypeptide, a GSG linker, and a P2A ribosomal skip sequence fused to its N-terminus as well as a Myc Tag between the signal sequence and the extracellular domain. Variant "C" is similar to variant "B" except its intracellular domain is truncated at position 292. Variant "D" is similar to variant "A" except its intracellular domain is truncated at position 292. Variant "E" is the IL-7Rα InsPPCL variant truncated at its N terminus such that the signal sequence and most of the extracellular domain (residues 1-228) are not present; variant "E" also has a GFP polypeptide, a GSG linker, a P2A ribosomal skip sequence, and an eTag fused to the N terminus, in that order from the amino terminus. Numbering of the amino acid residues is based on IL7Rα (NCBI GI No. 002176.2). T cells containing each of the variants were tested for viability in the presence or absence of IL-2 using Trypan Blue exclusion.

Figure 19B:
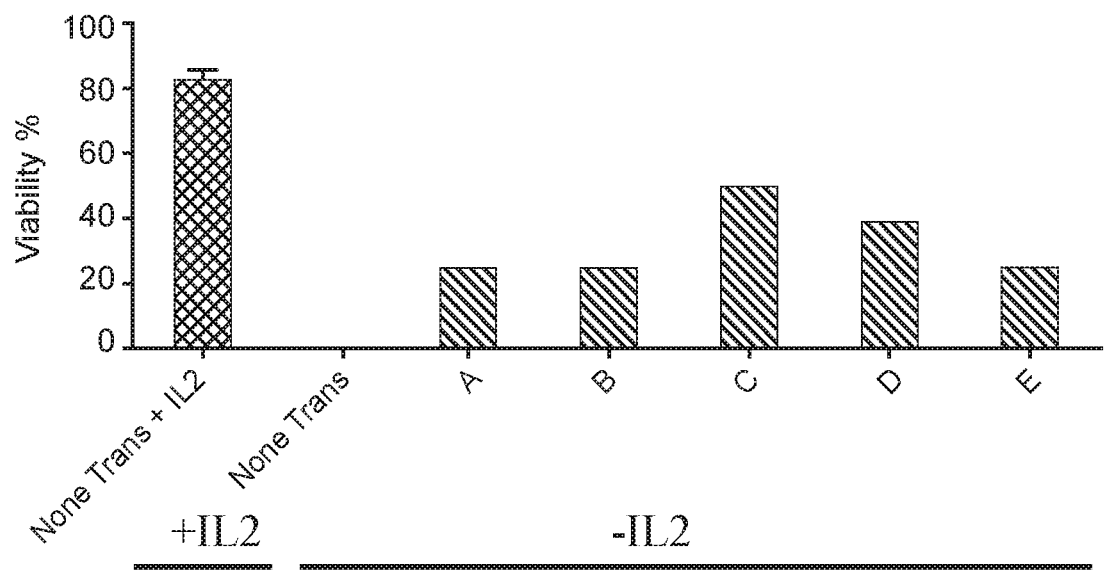
FIG. 19B provides a bar graph showing percent viability of PBMCs in the presence and absence of IL-2.

As shown in FIG. 19B, PBMCs require IL-2 for survival in vitro. As illustrated in FIG. 19B, untransfected PBMCs have about 80% viability in the presence of IL-2 and 0% viability in the absence of IL-2. PBMCs having the full-length versions of IL-7Rα InsPPCL (IL-7Rα variants A and B in FIG. 19A) had over 20% viability in the absence of IL-2, indicating that expression of the constitutively active IL-7Rα InsPPCL receptor has survival activity in these cells. Furthermore, T cells expressing the IL-7Rα InsPPCL variants with a truncated intracellular domain (ICD) (IL-7Rα variants C and D in FIG. 19A) had increased viability compared to the wild-type IL-7 receptor. Finally, the N-terminal IL-7 receptor mutant (IL-7Rα variant E in FIG. 19A) as shown in FIG. 19B had survival activity in these cells. Accordingly, this example illustrates that IL-7 receptor has survival activity when expressed in PBMCs.

Example 12. Transduction Efficiency of Freshly Isolated Unstimulated Human T Cells by MeVpp Lentiviruses were produced by transient transfection of 293T cells (Lenti-X 293T, Clontech) with the lentiviral expression vectors. The cells were adapted to suspension culture by serial growth in Freestyle 293 Expression Medium (ThermoFisher Scientific). The cells in suspension were seeded at $1 \times 10^6$ cells/mL (30 mL) in a 125 mL Erlenmeyer flask, and immediately transfected using PEI (Polysciences) dissolved in weak acid.

Plasmid DNA was diluted in 1.5 ml Optimem media for 30 mL of cells. For the VSV-G pseudo-particles, the total DNA (1 µg/mL of culture volume) was a mixture of 4 plasmids with the following molar ratios: 2× genomic plasmid, 1× Rev-containing plasmid, 1×VSVg-containing plasmid, and 1× Gagpol-containing plasmid. For the MV(Ed)-FΔ30/HΔ18 pseudo-particles, the total DNA (1 µg/mL of culture volume) was a mixture of 5 plasmids with the following molar ratios: 2× genomic plasmid, 1× Rev-containing plasmid, (⅔, two thirds)×MV(Ed)-FΔ30-containing plasmid, (⅓, one third)×MV(Ed)-HΔ18-containing plasmid, and 1× Gagpol-containing plasmid. For the MV(Ed)-FΔ30/HΔ24 pseudo-particles, the total DNA (1 µg/mL of culture volume) was a mixture of 5 plasmids with the following molar ratios: 2× genomic plasmid, 1× Rev-containing plasmid, (⅔, two third)×MV(Ed)-FΔ30-containing plasmid, (⅓, one third)×MV(Ed)-HΔ24-containing plasmid, and 1× Gagpol-containing plasmid. Separately, the PEI was diluted in 1.5 ml Optimem to 2 µg/mL (culture volume, 2:1 ratio to DNA). After a 5-minute room temperature incubation, the two solutions were mixed together thoroughly, and incubated at room temperature for 20 more minutes. The final volume (3 ml) was added to the cells. The cells were then incubated at 37° C. for 48 hours with rotation at 120 rpm and with 5-8% $CO_2$.

After 48 hours, the supernatants were harvested by centrifugation at 1,000 g for 10 minutes. The supernatants were decanted to a fresh tube and ¼ of the supernatants volume in PEG solution (PEG-IT, System Biosciences) was added. The lentiviral pseudotypes were precipitated by incubation overnight at 4° C. followed by centrifugation at 1,500 g for 20 minutes at 4° C. The supernatant was removed, and the virus was resuspended in 1:100 volume of PBS. Viruses were titered by serial dilution and GFP expression on Raji cells, which express both CD46 and SLAM, 48 hours post-transduction, by flow cytometry.

Enriched peripheral blood T cells were first isolated from a fresh buffy coat of blood collected and distributed by the San Diego Blood Bank, CA. Briefly, SepMate™ (Stemcell™)-based gradient density separation of PBMCs on Ficoll-Paque PLUS® (GE Healthcare Life Sciences) was performed per manufacturers' instructions. Untouched T cells were then further enriched by negative selection from the freshly isolated total PBMCs, using the untouched T cells Dynabeads® kit (Invitrogen) and manufacturer's instructions. After isolation, 2.6E5 of enriched and freshly isolated and unstimulated peripheral blood T lymphocytes were transduced, in duplicate, with the different vectors, at various multiplicities of infection (MOI). The transductions were conducted for 14 h, at 37° C., in 100 uL RPMI-2% HIFCS final, in a 96 wells plate format. After incubation with the vectors for 14 h, the cells were washed three times with PBS-2% HIFCS, and finally incubated at a cell density of 0.5E6/mL in RPMI-10% HIFCS at 37° C. until day 3.

Three days post-transduction with the VSV-Gpp or MeVpp, 1E5 cells were collected and analyzed by flow cytometry for expression of GFP in the $CD3^+$ cell population. FIG. 20 shows a plot of transduction efficiency against MOI for negatively selected and unstimulated T cells. Symbols are staggered for improved clarity. Unstimulated T cells were more efficiently transduced using MV(Ed)-FΔ30/MV(Ed)-HΔ18 pseudo-particles (~70-80%) as compared to VSV-Gpp (~0-5%) at an MOI of 1. Unstimulated T cells were also more efficiently transduced using MV(Ed)-FΔ30/MV(Ed)-HΔ24 pseudotyping particles at an MOI of 5 (~70-80%) as compared to VSV-Gpp at an MOI of 6 (~5-10%). Transduction efficiency of freshly isolated unstimulated human T cells by pseudotyped lentivectors is much higher when truncated MeV-envelope polypeptides are used for pseudotyping than when VSV-G is used.

Example 13. Demonstrating Functionality of miRNAs Inserted into the EF-1Alpha Promoter Intron Four separate gBlocks® Gene Fragments were designed, each containing the miR-155 framework. For each gBlock®, a unique miRNA targeting the CD3zeta mRNA transcript was used to replace the miR-155 target sequence. Each gBlock® contained a 40 bp overlap sequence designed to facilitate assembly of all four gBlocks® as a single chain into the EF-1alpha promoter intron. The gBlocks® were assembled using a commercial kit for performing Gibson® assembly ultra (NEBuilder, New England Biolabs, Inc.).

The EF-1alpha promoter and intron A (SEQ ID NO:255) was part of a transgene expression cassette driving expression of GFP and eTag contained in a lentivirus vector backbone (the lentivirus vector backbone with the GFP and exemplary eTag recognized by cetuximab is referred to herein as F02). The nucleotide positions of each gBlock® and its respective components in SEQ ID NO:255 are denoted in Table 3. Proper assembly of four miRNA into the lentivirus vector backbone was confirmed by comprehensive sequencing of the EF-1alpha promoter.

TABLE 3

Nucleotide positions of features in SEQ ID NO: 255

| Feature | Nucleotide positions in SEQ ID NO: 255 |
|---|---|
| gBlock ® 1 | 927-1138 |
| EF1alpha overlap | 927-966 |
| miR155 framework - 5' arm | 967-994 |
| siRNA1 | 995-1015 |
| miR terminal loop | 1016-1034 |
| siRNA1 | 1035-1042 |
| siRNA1 | 1043-1053 |
| miR155 framework - 3' arm | 1054-1098 |
| gBlock ® 2 | 1099-1310 |
| 40bp 50% GC Linker 1 | 1099-1138 |
| miR155 framework - 5' arm | 1139-1166 |
| siRNA2 | 1167-1187 |
| miR terminal loop | 1188-1206 |
| siRNA2 | 1207-1214 |
| siRNA2 | 1215-1225 |
| miR155 framework - 3' arm | 1226-1270 |
| gBlock ® 3 | 1271-1482 |
| 40bp 50% GC Linker 2 | 1271-1310 |
| miR155 framework - 5' arm | 1311-1338 |
| siRNA3 | 1339-1359 |
| miR terminal loop | 1360-1378 |
| siRNA3 | 1379-1386 |
| siRNA3 | 1387-1397 |
| miR155 framework - 3' arm | 1398-1442 |
| gBlock ® 4 | 1443-1654 |
| 40bp 50% GC Linker 4 | 1443-1482 |
| miR155 framework - 5' arm | 1483-1510 |
| siRNA4 | 1511-1531 |
| miR terminal loop | 1532-1550 |
| siRNA4 | 1551-1558 |
| siRNA4 | 1559-1569 |
| miR155 framework - 3' arm | 1570-1614 |
| EF-1alpha overlap | 1615-1654 |

Lentiviruses containing the four miRNAs directed against CD3zeta were produced by transient co-transfection of four plasmids into suspension HEK293 cells: the plasmid containing the four miRNAs targeting the CD3zeta mRNA transcript, a plasmid containing VSV-G, a plasmid containing REV, and a plasmid containing GAG-POL. Viral supernatant was harvested after 48 hours and PEG-precipitated for 24 hours. Supernatants were centrifuged, and pelleted virus was re-suspended in complete PBMC growth media without IL-2. Viral titers were calculated by 48 hour transduction of Jurkat cells.

For transduction, PBMCs were thawed on Day 0 and incubated for 24 hours with 100 U/mL of hrIL-2. On Day 1, PBMCs were activated via CD3/CD28 conjugated beads. On Day 2, activated PBMCs were transduced with the lentivirus containing the miRNAs at an MOI of 10. Cells were expanded until Day 11, with fresh hrIL-2 added every two days. On days 7, 9, and 11, 1 million cells were harvested for FACS analysis.

Figure 21:
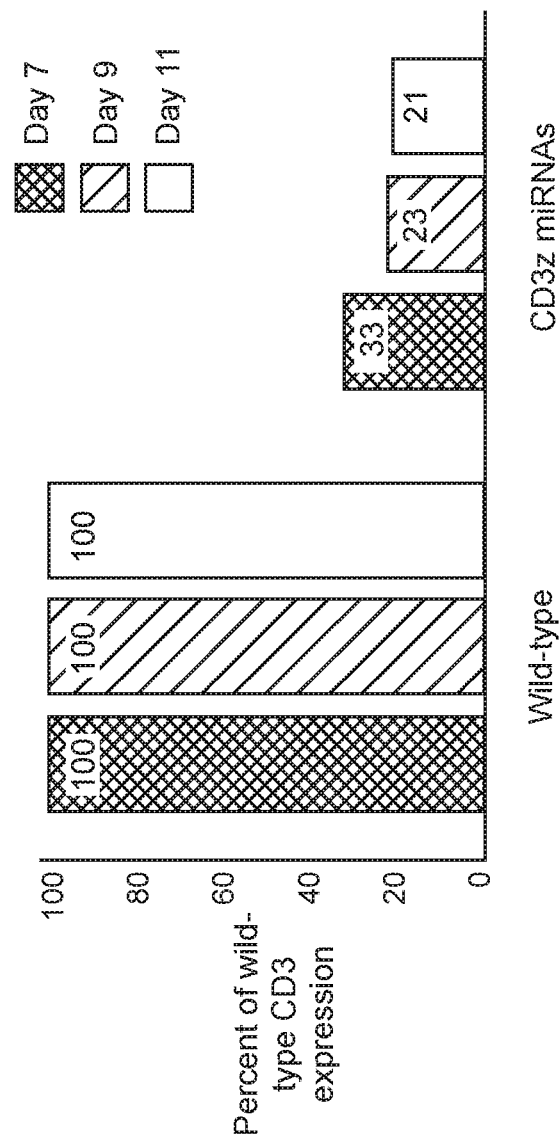
FIG. 21 is a graph showing that the miRNAs targeting CD3zeta that are in the EF-1alpha promoter intron are able to knockdown expression of the CD3 complex.

Cells were stained for CD3 Epsilon surface expression, using PE conjugated OKT-3 antibody (Biolegend). Expression levels were determined by the mean fluorescence intensity (MF) of PE in the GFP positive population (transduced cells). Expression levels of transduced cells were compared between wild-type (F02) virus and F02 virus containing the CD3z miRNAs. FIG. 21 shows that the miRNAs targeting CD3zeta that are in the EF-1alpha promoter intron are able to knockdown expression of the CD3 complex.

The disclosed embodiments, examples and experiments are not intended to limit the scope of the disclosure or to represent that the experiments below are all or the only experiments performed. Efforts have been made to ensure accuracy with respect to numbers used (e.g., amounts, temperature, etc.) but some experimental errors and deviations should be accounted for. It should be understood that variations in the methods as described may be made without changing the fundamental aspects that the experiments are meant to illustrate.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

What is claimed is:

1. An isolated polynucleotide, comprising:
   a) an aptamer RNA comprising an aptamer domain capable of binding acyclovir;
   b) a reverse complement of the aptamer RNA;
   c) a coding DNA encoding the aptamer RNA; or
   d) a reverse complement DNA encoding the reverse complement of the aptamer RNA,
   wherein the aptamer domain comprises from 5' to 3', ACUUAU followed by an RNA version of the nucleotide sequence of any one of SEQ ID NOs: 108-221 followed by AUAAGU.

2. The isolated polynucleotide of claim 1, wherein the isolated polynucleotide comprises the aptamer RNA or the coding DNA and further comprises a target polynucleotide encoding at least one of a target polypeptide, an miRNA, or an shRNA, or
   wherein the isolated polynucleotide comprises the reverse complement of the aptamer RNA or the reverse complement DNA and further comprises the reverse complement of the target polynucleotide.

3. The isolated polynucleotide of claim 2, wherein the isolated polynucleotide is within a T cell or a packaging cell.

4. The isolated polynucleotide of claim 2, wherein the isolated polynucleotide is DNA, and wherein the DNA is within the genome of a T cell or a packaging cell.

5. The isolated polynucleotide of claim 2, wherein the isolated polynucleotide further comprises a promoter operably linked to the target polynucleotide, or the reverse complement of the promoter operably linked to the reverse complement of the target polynucleotide.

6. The isolated polynucleotide of claim 5, wherein the target polynucleotide encodes the target polypeptide, and wherein the target polypeptide is a chimeric antigen receptor.

7. The isolated polynucleotide of claim 5, wherein the target polynucleotide encodes the target polypeptide, and wherein the target polypeptide is a lymphoproliferative element.

8. The isolated polynucleotide of claim 2, wherein the isolated polynucleotide further comprises a function switching domain.

9. The isolated polynucleotide of claim 1, wherein the isolated polynucleotide comprises the aptamer RNA.

10. The isolated polynucleotide of claim 1, wherein the isolated polynucleotide comprises the reverse complement of the aptamer RNA.

11. The isolated polynucleotide of claim 10, wherein the isolated polynucleotide further comprises a reverse complement of a target polynucleotide encoding at least one of a target polypeptide, an miRNA, or an shRNA.

12. The isolated polynucleotide of claim 11, wherein the isolated polynucleotide is within a solution comprising a buffer.

13. The isolated polynucleotide of claim 1, wherein the isolated polynucleotide comprises the coding DNA.

14. The isolated polynucleotide of claim 1, wherein the isolated polynucleotide comprises the reverse complement DNA.

15. The isolated polynucleotide of claim 1, wherein the isolated polynucleotide is a vector.

16. The isolated polynucleotide of claim 15, wherein the isolated polynucleotide is RNA, and wherein the vector is a retroviral vector.

17. The isolated polynucleotide of claim 16, wherein the vector is a lentiviral vector.

18. The isolated polynucleotide of claim 1, wherein the isolated polynucleotide comprises the RNA version of any one of the nucleotide sequences of SEQ ID NOs:108-146.

19. The isolated polynucleotide of claim 1, wherein the isolated polynucleotide comprises the RNA version of any one of the nucleotide sequences of SEQ ID NOs:147-163.

20. The isolated polynucleotide of claim 1, wherein the isolated polynucleotide comprises the RNA version of any one of the nucleotide sequences of SEQ ID NOs:164-182.

21. The isolated polynucleotide of claim 1, wherein the isolated polynucleotide comprises the RNA version of any one of the nucleotide sequences of SEQ ID NOs:183-197.

22. The isolated polynucleotide of claim 1, wherein the isolated polynucleotide comprises the RNA version of any one of the nucleotide sequences of SEQ ID NOs:198-219.

23. The isolated polynucleotide of claim 1, wherein the isolated polynucleotide comprises the RNA version of the nucleotide sequence of SEQ ID NO:220.

24. The isolated polynucleotide of claim 1, wherein the isolated polynucleotide comprises the RNA version of the nucleotide sequence of SEQ ID NO:221.

* * * * *

SEQUENCE LISTING

```
<160> NUMBER OF SEQ ID NOS: 255

<210> SEQ ID NO 1
<211> LENGTH: 42
<212> TYPE: PRT
<213> ORGANISM: Homo sapiens

<400> SEQUENCE: 1

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

-continued

<210> SEQ ID NO 2
<211> LENGTH: 41
<212> TYPE: PRT
<213> ORGANISM: Homo sapiens

<400> SEQUENCE: 2

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 3
<211> LENGTH: 41
<212> TYPE: PRT
<213> ORGANISM: Homo sapiens

<400> SEQUENCE: 3

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Ala Tyr Ala Ala
            20                  25                  30

Ala Arg Asp Phe Ala Ala Tyr Arg Ser
        35                  40

<210> SEQ ID NO 4
<211> LENGTH: 35
<212> TYPE: PRT
<213> ORGANISM: Homo sapiens

<400> SEQUENCE: 4

Thr Lys Lys Lys Tyr Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 5
<211> LENGTH: 37
<212> TYPE: PRT
<213> ORGANISM: Homo sapiens

<400> SEQUENCE: 5

Arg Arg Asp Gln Arg Leu Pro Pro Asp Ala His Lys Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35

<210> SEQ ID NO 6
<211> LENGTH: 49
<212> TYPE: PRT
<213> ORGANISM: Homo sapiens

<400> SEQUENCE: 6

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Gly Ser
                20                  25                  30

Thr Ile Pro Ile Gln Glu Asp Tyr Arg Lys Pro Glu Pro Ala Cys Ser
            35                  40                  45

Pro

<210> SEQ ID NO 7
<211> LENGTH: 114
<212> TYPE: PRT
<213> ORGANISM: Homo sapiens

<400> SEQUENCE: 7

Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45

Gly Ile Tyr Asp Asn Asp Pro Asp Leu Cys Phe Arg Met Gln Glu Gly
50                  55                  60

Ser Glu Val Tyr Ser Asn Pro Cys Leu Glu Glu Asn Lys Pro Gly Ile
65                  70                  75                  80

Val Tyr Ala Ser Leu Asn His Ser Val Ile Gly Pro Asn Ser Arg Leu
                85                  90                  95

Ala Arg Asn Val Lys Glu Ala Pro Thr Glu Tyr Ala Ser Ile Cys Val
            100                 105                 110

Arg Ser

<210> SEQ ID NO 8
<211> LENGTH: 187
<212> TYPE: PRT
<213> ORGANISM: Homo sapiens

<400> SEQUENCE: 8

Arg Arg Ala Cys Arg Lys Arg Ile Arg Gln Lys Leu His Leu Cys Tyr
1               5                   10                  15

Pro Val Gln Thr Ser Gln Pro Lys Leu Glu Leu Val Asp Ser Arg Pro
            20                  25                  30

Arg Arg Ser Ser Thr Gln Leu Arg Ser Gly Ala Ser Val Thr Glu Pro
        35                  40                  45

Val Ala Glu Glu Arg Gly Leu Met Ser Gln Pro Leu Met Glu Thr Cys
50                  55                  60

His Ser Val Gly Ala Ala Tyr Leu Glu Ser Leu Pro Leu Gln Asp Ala
65                  70                  75                  80

Ser Pro Ala Gly Gly Pro Ser Ser Pro Arg Asp Leu Pro Glu Pro Arg
                85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
        115                 120                 125

Gly Arg Gly Leu Ala Gly Pro Ala Glu Pro Glu Leu Glu Glu Glu Leu
130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Glu Gly Lys

```
                165                 170                 175

Glu Asp Pro Leu Pro Thr Ala Ala Ser Gly Lys
            180                 185

<210> SEQ ID NO 9
<211> LENGTH: 54
<212> TYPE: PRT
<213> ORGANISM: Homo sapiens

<400> SEQUENCE: 9

His Ile Trp Gln Leu Arg Ser Gln Cys Met Trp Pro Arg Glu Thr Gln
1               5                   10                  15

Leu Leu Leu Glu Val Pro Pro Ser Thr Glu Asp Ala Arg Ser Cys Gln
            20                  25                  30

Phe Pro Glu Glu Glu Arg Gly Glu Arg Ser Ala Glu Glu Lys Gly Arg
        35                  40                  45

Leu Gly Asp Leu Trp Val
    50

<210> SEQ ID NO 10
<211> LENGTH: 60
<212> TYPE: PRT
<213> ORGANISM: Homo sapiens

<400> SEQUENCE: 10

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 11
<211> LENGTH: 163
<212> TYPE: PRT
<213> ORGANISM: Homo sapiens

<400> SEQUENCE: 11

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140
```

Ser Thr Ala Thr Lys Asp Thr Tyr Asp Ala Leu His Met Gln Ala Leu
145                 150                 155                 160

Pro Pro Arg

<210> SEQ ID NO 12
<211> LENGTH: 164
<212> TYPE: PRT
<213> ORGANISM: Homo sapiens

<400> SEQUENCE: 12

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
                20                  25                  30

Tyr Leu Leu Asp Gly Ile Leu Phe Ile Tyr Gly Val Ile Leu Thr Ala
            35                  40                  45

Leu Phe Leu Arg Val Lys Phe Ser Arg Ser Ala Asp Ala Pro Ala Tyr
        50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 13
<211> LENGTH: 112
<212> TYPE: PRT
<213> ORGANISM: Homo sapiens

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 21
<212> TYPE: PRT

<213> ORGANISM: Homo sapiens

<400> SEQUENCE: 14

Asn Gln Leu Tyr Asn Glu Leu Asn Leu Gly Arg Arg Glu Glu Tyr Asp
1               5                   10                  15

Val Leu Asp Lys Arg
            20

<210> SEQ ID NO 15
<211> LENGTH: 22
<212> TYPE: PRT
<213> ORGANISM: Homo sapiens

<400> SEQUENCE: 15

Glu Gly Leu Tyr Asn Glu Leu Gln Lys Asp Lys Met Ala Glu Ala Tyr
1               5                   10                  15

Ser Glu Ile Gly Met Lys
            20

<210> SEQ ID NO 16
<211> LENGTH: 21
<212> TYPE: PRT
<213> ORGANISM: Homo sapiens

<400> SEQUENCE: 16

Asp Gly Leu Tyr Gln Gly Leu Ser Thr Ala Thr Lys Asp Thr Tyr Asp
1               5                   10                  15

Ala Leu His Met Gln
            20

<210> SEQ ID NO 17
<211> LENGTH: 171
<212> TYPE: PRT
<213> ORGANISM: Homo sapiens

<400> SEQUENCE: 17

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
                35                  40                  45

Gly Thr Leu Leu Ser Asp Ile Thr Arg Leu Asp Leu Gly Lys Arg Ile
            50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
            115                 120                 125

Glu Thr Gly Arg Leu Ser Gly Ala Ala Asp Thr Gln Ala Leu Leu Arg
        130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 18
<211> LENGTH: 127
<212> TYPE: PRT
<213> ORGANISM: Homo sapiens

<400> SEQUENCE: 18

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys
            115                 120                 125

<210> SEQ ID NO 19
<211> LENGTH: 21
<212> TYPE: PRT
<213> ORGANISM: Homo sapiens

<400> SEQUENCE: 19

Asp Gln Val Tyr Gln Pro Leu Arg Asp Arg Asp Asp Ala Gln Tyr Ser
1               5                   10                  15

His Leu Gly Gly Asn
            20

<210> SEQ ID NO 20
<211> LENGTH: 206
<212> TYPE: PRT
<213> ORGANISM: Homo sapiens

<400> SEQUENCE: 20

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Met Ser
            115                 120                 125

Val Ala Thr Ile Val Ile Val Asp Ile Cys Ile Thr Gly Gly Leu Leu

```
                130                 135                 140
Leu Leu Val Tyr Tyr Trp Ser Lys Asn Arg Lys Ala Lys Ala Lys Pro
145                 150                 155                 160

Val Thr Arg Gly Ala Gly Ala Gly Gly Arg Gln Arg Gly Gln Asn Lys
                165                 170                 175

Glu Arg Pro Pro Pro Val Pro Asn Pro Asp Tyr Glu Pro Ile Arg Lys
                180                 185                 190

Gly Gln Arg Asp Leu Tyr Ser Gly Leu Asn Gln Arg Ile
                195                 200                 205

<210> SEQ ID NO 21
<211> LENGTH: 21
<212> TYPE: PRT
<213> ORGANISM: Homo sapiens

<400> SEQUENCE: 21

Asn Pro Asp Tyr Glu Pro Ile Arg Lys Gly Gln Arg Asp Leu Tyr Ser
1               5                   10                  15

Gly Leu Asn Gln Arg
            20

<210> SEQ ID NO 22
<211> LENGTH: 182
<212> TYPE: PRT
<213> ORGANISM: Homo sapiens

<400> SEQUENCE: 22

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
                20                  25                  30

Val Tyr Asp Tyr Gln Glu Asp Gly Ser Val Leu Leu Thr Cys Asp Ala
                35                  40                  45

Glu Ala Lys Asn Ile Thr Trp Phe Lys Asp Gly Lys Met Ile Gly Phe
50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
                100                 105                 110

Ala Thr Ile Ser Gly Phe Leu Phe Ala Glu Ile Val Ser Ile Phe Val
                115                 120                 125

Leu Ala Val Gly Val Tyr Phe Ile Ala Gly Gln Asp Gly Val Arg Gln
                130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 23
<211> LENGTH: 21
<212> TYPE: PRT
<213> ORGANISM: Homo sapiens

<400> SEQUENCE: 23
```

```
Asp Gln Leu Tyr Gln Pro Leu Lys Asp Arg Glu Asp Gln Tyr Ser
1               5                   10                  15

His Leu Gln Gly Asn
            20

<210> SEQ ID NO 24
<211> LENGTH: 226
<212> TYPE: PRT
<213> ORGANISM: Homo sapiens

<400> SEQUENCE: 24

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
    130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
    210                 215                 220

Lys Pro
225

<210> SEQ ID NO 25
<211> LENGTH: 188
<212> TYPE: PRT
<213> ORGANISM: Homo sapiens

<400> SEQUENCE: 25

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60
```

```
Thr Trp Trp Arg Val Leu His Gly Asn Tyr Thr Trp Pro Pro Glu Phe
 65                  70                  75                  80

Leu Gly Pro Gly Glu Asp Pro Asn Glu Pro Pro Arg Pro Phe Leu
                 85                  90                  95

Asp Met Gly Glu Gly Thr Lys Asn Arg Ile Ile Thr Ala Glu Gly Ile
            100                 105                 110

Ile Leu Leu Phe Cys Ala Val Val Pro Gly Thr Leu Leu Leu Phe Arg
            115                 120                 125

Lys Arg Trp Gln Asn Glu Lys Leu Gly Leu Asp Ala Gly Asp Glu Tyr
            130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185
```

<210> SEQ ID NO 26
<211> LENGTH: 21
<212> TYPE: PRT
<213> ORGANISM: Homo sapiens

<400> SEQUENCE: 26

```
Glu Asn Leu Tyr Glu Gly Leu Asn Leu Asp Asp Cys Ser Met Tyr Glu
1               5                   10                  15

Asp Ile Ser Arg Gly
            20
```

<210> SEQ ID NO 27
<211> LENGTH: 113
<212> TYPE: PRT
<213> ORGANISM: Homo sapiens

<400> SEQUENCE: 27

```
Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
                20                  25                  30

Cys Ser Cys Ser Thr Val Ser Pro Gly Val Leu Ala Gly Ile Val Met
            35                  40                  45

Gly Asp Leu Val Leu Thr Val Leu Ile Ala Leu Ala Val Tyr Phe Leu
        50                  55                  60

Gly Arg Leu Val Pro Arg Gly Arg Gly Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys
```

<210> SEQ ID NO 28
<211> LENGTH: 107
<212> TYPE: PRT
<213> ORGANISM: Homo sapiens

<400> SEQUENCE: 28

```
Met Gly Gly Leu Glu Pro Cys Ser Arg Leu Leu Leu Leu Pro Leu Leu
```

```
                1               5                      10                      15
Leu Ala Val Ser Gly Leu Arg Pro Val Gln Ala Gln Ala Gln Ser Asp
                20                      25                      30

Cys Ser Cys Ser Thr Val Ser Pro Gly Val Leu Ala Gly Ile Val Met
                35                      40                      45

Gly Asp Leu Val Leu Thr Val Leu Ile Ala Leu Ala Val Tyr Phe Leu
                50                      55                      60

Gly Arg Leu Val Pro Arg Gly Arg Gly Ala Ala Glu Ala Thr Arg Lys
 65                     70                      75                      80

Gln Arg Ile Thr Glu Thr Glu Ser Pro Tyr Gln Glu Leu Gln Gly Gln
                        85                      90                      95

Arg Ser Asp Val Tyr Ser Asp Leu Asn Thr Gln
                100                     105
```

<210> SEQ ID NO 29
<211> LENGTH: 102
<212> TYPE: PRT
<213> ORGANISM: Homo sapiens

<400> SEQUENCE: 29

```
Met Gly Gly Leu Glu Pro Cys Ser Arg Leu Leu Leu Leu Pro Leu Leu
 1               5                      10                      15

Leu Ala Val Ser Asp Cys Ser Cys Ser Thr Val Ser Pro Gly Val Leu
                20                      25                      30

Ala Gly Ile Val Met Gly Asp Leu Val Leu Thr Val Leu Ile Ala Leu
                35                      40                      45

Ala Val Tyr Phe Leu Gly Arg Leu Val Pro Arg Gly Arg Gly Ala Ala
                50                      55                      60

Glu Ala Ala Thr Arg Lys Gln Arg Ile Thr Glu Thr Glu Ser Pro Tyr
 65                     70                      75                      80

Gln Glu Leu Gln Gly Gln Arg Ser Asp Val Tyr Ser Asp Leu Asn Thr
                        85                      90                      95

Gln Arg Pro Tyr Tyr Lys
                100
```

<210> SEQ ID NO 30
<211> LENGTH: 101
<212> TYPE: PRT
<213> ORGANISM: Homo sapiens

<400> SEQUENCE: 30

```
Met Gly Gly Leu Glu Pro Cys Ser Arg Leu Leu Leu Leu Pro Leu Leu
 1               5                      10                      15

Leu Ala Val Ser Asp Cys Ser Cys Ser Thr Val Ser Pro Gly Val Leu
                20                      25                      30

Ala Gly Ile Val Met Gly Asp Leu Val Leu Thr Val Leu Ile Ala Leu
                35                      40                      45

Ala Val Tyr Phe Leu Gly Arg Leu Val Pro Arg Gly Arg Gly Ala Ala
                50                      55                      60

Glu Ala Thr Arg Lys Gln Arg Ile Thr Glu Thr Glu Ser Pro Tyr Gln
 65                     70                      75                      80

Glu Leu Gln Gly Gln Arg Ser Asp Val Tyr Ser Asp Leu Asn Thr Gln
                        85                      90                      95

Arg Pro Tyr Tyr Lys
                100
```

```
<210> SEQ ID NO 31
<211> LENGTH: 21
<212> TYPE: PRT
<213> ORGANISM: Homo sapiens

<400> SEQUENCE: 31

Glu Ser Pro Tyr Gln Glu Leu Gln Gly Gln Arg Ser Asp Val Tyr Ser
1               5                   10                  15

Asp Leu Asn Thr Gln
            20

<210> SEQ ID NO 32
<211> LENGTH: 86
<212> TYPE: PRT
<213> ORGANISM: Homo sapiens

<400> SEQUENCE: 32

Met Ile Pro Ala Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85

<210> SEQ ID NO 33
<211> LENGTH: 21
<212> TYPE: PRT
<213> ORGANISM: Homo sapiens

<400> SEQUENCE: 33

Asp Gly Val Tyr Thr Gly Leu Ser Thr Arg Asn Gln Glu Thr Tyr Glu
1               5                   10                  15

Thr Leu Lys His Glu
            20

<210> SEQ ID NO 34
<211> LENGTH: 20
<212> TYPE: PRT
<213> ORGANISM: Homo sapiens

<400> SEQUENCE: 34

Arg Pro Arg Arg Ser Pro Ala Gln Asp Gly Lys Val Tyr Ile Asn Met
1               5                   10                  15

Pro Gly Arg Gly
            20

<210> SEQ ID NO 35
<211> LENGTH: 68
<212> TYPE: PRT
<213> ORGANISM: Homo sapiens

<400> SEQUENCE: 35

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
```

```
                  20                  25                  30
Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
        50                  55                  60

Ala Tyr Arg Ser
65

<210> SEQ ID NO 36
<211> LENGTH: 619
<212> TYPE: PRT
<213> ORGANISM: Homo sapiens

<400> SEQUENCE: 36

Met Pro Asp Pro Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
        50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
130                 135                 140

Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
290                 295                 300

Pro Arg Pro Met Pro Met Asp Thr Ser Val Tyr Glu Ser Pro Tyr Ser
305                 310                 315                 320
```

```
Asp Pro Glu Glu Leu Lys Asp Lys Lys Leu Phe Leu Lys Arg Asp Asn
            325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Gln Ile Asp Val Ala Ile
            355                 360             365

Lys Val Leu Lys Gln Gly Thr Glu Lys Ala Asp Thr Glu Glu Met Met
            370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                    405                 410                 415

Ala Gly Gly Gly Pro Leu His Lys Phe Leu Val Gly Lys Arg Glu Glu
                420                 425                 430

Ile Pro Val Ser Asn Val Ala Glu Leu Leu His Gln Val Ser Met Gly
                435                 440                 445

Met Lys Tyr Leu Glu Glu Lys Asn Phe Val His Arg Asp Leu Ala Ala
            450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                    485                 490                 495

Ser Ala Gly Lys Trp Pro Leu Lys Trp Tyr Ala Pro Glu Cys Ile Asn
                500                 505                 510

Phe Arg Lys Phe Ser Ser Arg Ser Asp Val Trp Ser Tyr Gly Val Thr
            515                 520                 525

Met Trp Glu Ala Leu Ser Tyr Gly Gln Lys Pro Tyr Lys Lys Met Lys
            530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                    565                 570                 575

Ile Tyr Lys Trp Glu Asp Arg Pro Asp Phe Leu Thr Val Glu Gln Arg
                580                 585                 590

Met Arg Ala Cys Tyr Tyr Ser Leu Ala Ser Lys Val Glu Gly Pro Pro
            595                 600                 605

Gly Ser Thr Gln Lys Ala Glu Ala Ala Cys Ala
        610                 615

<210> SEQ ID NO 37
<211> LENGTH: 9
<212> TYPE: PRT
<213> ORGANISM: Artificial sequence
<220> FEATURE:
<223> OTHER INFORMATION: synthetic HA Epitope

<400> SEQUENCE: 37

Tyr Pro Tyr Asp Val Pro Asp Tyr Ala
1               5

<210> SEQ ID NO 38
<211> LENGTH: 8
<212> TYPE: PRT
<213> ORGANISM: Artificial sequence
<220> FEATURE:
<223> OTHER INFORMATION: synthetic FLAG Epitope

<400> SEQUENCE: 38
```

```
Asp Tyr Lys Asp Asp Asp Lys
1               5

<210> SEQ ID NO 39
<211> LENGTH: 10
<212> TYPE: PRT
<213> ORGANISM: Artificial sequence
<220> FEATURE:
<223> OTHER INFORMATION: synthetic c-myc Epitope

<400> SEQUENCE: 39

Glu Gln Lys Leu Ile Ser Glu Glu Asp Leu
1               5                   10

<210> SEQ ID NO 40
<211> LENGTH: 5
<212> TYPE: PRT
<213> ORGANISM: Artificial sequence
<220> FEATURE:
<223> OTHER INFORMATION: synthetic His5 Affinity

<400> SEQUENCE: 40

His His His His His
1               5

<210> SEQ ID NO 41
<211> LENGTH: 6
<212> TYPE: PRT
<213> ORGANISM: Artificial sequence
<220> FEATURE:
<223> OTHER INFORMATION: synthetic HisX6 Affinity

<400> SEQUENCE: 41

His His His His His His
1               5

<210> SEQ ID NO 42
<211> LENGTH: 8
<212> TYPE: PRT
<213> ORGANISM: Artificial sequence
<220> FEATURE:
<223> OTHER INFORMATION: synthetic Strep Tag Affinity

<400> SEQUENCE: 42

Trp Ser His Pro Gln Phe Glu Lys
1               5

<210> SEQ ID NO 43
<211> LENGTH: 5
<212> TYPE: PRT
<213> ORGANISM: Artificial sequence
<220> FEATURE:
<223> OTHER INFORMATION: synthetic HisX6 Affinity

<400> SEQUENCE: 43

Arg Tyr Ile Arg Ser
1               5

<210> SEQ ID NO 44
<211> LENGTH: 4
<212> TYPE: PRT
<213> ORGANISM: Artificial sequence
<220> FEATURE:
<223> OTHER INFORMATION: synthetic Affinity

<400> SEQUENCE: 44
```

Phe His His Thr
1

<210> SEQ ID NO 45
<211> LENGTH: 17
<212> TYPE: PRT
<213> ORGANISM: Artificial sequence
<220> FEATURE:
<223> OTHER INFORMATION: synthetic Affinity

<400> SEQUENCE: 45

Trp Glu Ala Ala Ala Arg Glu Ala Cys Cys Arg Glu Cys Cys Ala Arg
1               5                   10                  15

Ala

<210> SEQ ID NO 46
<211> LENGTH: 24
<212> TYPE: PRT
<213> ORGANISM: Homo sapiens

<400> SEQUENCE: 46

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 47
<211> LENGTH: 23
<212> TYPE: PRT
<213> ORGANISM: Homo sapiens

<400> SEQUENCE: 47

Leu Gly Leu Leu Val Ala Gly Val Leu Val Leu Val Ser Leu Gly
1               5                   10                  15

Val Ala Ile His Leu Cys Cys
            20

<210> SEQ ID NO 48
<211> LENGTH: 25
<212> TYPE: PRT
<213> ORGANISM: Homo sapiens

<400> SEQUENCE: 48

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25

<210> SEQ ID NO 49
<211> LENGTH: 23
<212> TYPE: PRT
<213> ORGANISM: Homo sapiens

<400> SEQUENCE: 49

Leu Cys Tyr Leu Leu Asp Gly Ile Leu Phe Ile Tyr Gly Val Ile Leu
1               5                   10                  15

Thr Ala Leu Phe Leu Arg Val
            20

<210> SEQ ID NO 50
<211> LENGTH: 27
<212> TYPE: PRT
<213> ORGANISM: Homo sapiens

```
<400> SEQUENCE: 50

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 51
<211> LENGTH: 26
<212> TYPE: PRT
<213> ORGANISM: Homo sapiens

<400> SEQUENCE: 51

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 52
<211> LENGTH: 24
<212> TYPE: PRT
<213> ORGANISM: Homo sapiens

<400> SEQUENCE: 52

Ala Leu Pro Ala Ala Leu Ala Val Ile Ser Phe Leu Leu Gly Leu Gly
1               5                   10                  15

Leu Gly Val Ala Cys Val Leu Ala
            20

<210> SEQ ID NO 53
<211> LENGTH: 15
<212> TYPE: PRT
<213> ORGANISM: Artificial sequence
<220> FEATURE:
<223> OTHER INFORMATION: synthetic Linker 1

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 30
<212> TYPE: PRT
<213> ORGANISM: Artificial sequence
<220> FEATURE:
<223> OTHER INFORMATION: synthetic Linker 2

<400> SEQUENCE: 54

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 55
<211> LENGTH: 14
<212> TYPE: PRT
<213> ORGANISM: Artificial sequence
<220> FEATURE:
<223> OTHER INFORMATION: synthetic Linker 3

<400> SEQUENCE: 55

Gly Gly Gly Gly Ser Gly Gly Gly Ser Gly Gly Gly Gly Ser
1               5                   10
```

```
<210> SEQ ID NO 56
<211> LENGTH: 4
<212> TYPE: PRT
<213> ORGANISM: Artificial sequence
<220> FEATURE:
<223> OTHER INFORMATION: synthetic Linker 4

<400> SEQUENCE: 56

Gly Gly Ser Gly
1

<210> SEQ ID NO 57
<211> LENGTH: 5
<212> TYPE: PRT
<213> ORGANISM: Artificial sequence
<220> FEATURE:
<223> OTHER INFORMATION: synthetic Linker 5

<400> SEQUENCE: 57

Gly Gly Ser Gly Gly
1               5

<210> SEQ ID NO 58
<211> LENGTH: 5
<212> TYPE: PRT
<213> ORGANISM: Artificial sequence
<220> FEATURE:
<223> OTHER INFORMATION: synthetic Linker 6

<400> SEQUENCE: 58

Gly Ser Gly Ser Gly
1               5

<210> SEQ ID NO 59
<211> LENGTH: 5
<212> TYPE: PRT
<213> ORGANISM: Artificial sequence
<220> FEATURE:
<223> OTHER INFORMATION: synthetic Linker 7

<400> SEQUENCE: 59

Gly Ser Gly Gly Gly
1               5

<210> SEQ ID NO 60
<211> LENGTH: 5
<212> TYPE: PRT
<213> ORGANISM: Artificial sequence
<220> FEATURE:
<223> OTHER INFORMATION: synthetic Linker 8

<400> SEQUENCE: 60

Gly Gly Gly Ser Gly
1               5

<210> SEQ ID NO 61
<211> LENGTH: 5
<212> TYPE: PRT
<213> ORGANISM: Artificial sequence
<220> FEATURE:
<223> OTHER INFORMATION: synthetic Linker 9

<400> SEQUENCE: 61

Gly Ser Ser Ser Gly
1               5
```

```
<210> SEQ ID NO 62
<211> LENGTH: 4
<212> TYPE: PRT
<213> ORGANISM: Artificial sequence
<220> FEATURE:
<223> OTHER INFORMATION: synthetic Hinge 1

<400> SEQUENCE: 62

Cys Pro Pro Cys
1

<210> SEQ ID NO 63
<211> LENGTH: 5
<212> TYPE: PRT
<213> ORGANISM: Artificial sequence
<220> FEATURE:
<223> OTHER INFORMATION: synthetic Hinge 2

<400> SEQUENCE: 63

Asp Lys Thr His Thr
1               5

<210> SEQ ID NO 64
<211> LENGTH: 15
<212> TYPE: PRT
<213> ORGANISM: Artificial sequence
<220> FEATURE:
<223> OTHER INFORMATION: synthetic Hinge 3

<400> SEQUENCE: 64

Cys Pro Glu Pro Lys Ser Cys Asp Thr Pro Pro Cys Pro Arg
1               5                   10                  15

<210> SEQ ID NO 65
<211> LENGTH: 12
<212> TYPE: PRT
<213> ORGANISM: Artificial sequence
<220> FEATURE:
<223> OTHER INFORMATION: synthetic Hinge 4

<400> SEQUENCE: 65

Glu Leu Lys Thr Pro Leu Gly Asp Thr Thr His Thr
1               5                   10

<210> SEQ ID NO 66
<211> LENGTH: 10
<212> TYPE: PRT
<213> ORGANISM: Artificial sequence
<220> FEATURE:
<223> OTHER INFORMATION: synthetic Hinge 5

<400> SEQUENCE: 66

Lys Ser Cys Asp Lys Thr His Thr Cys Pro
1               5                   10

<210> SEQ ID NO 67
<211> LENGTH: 7
<212> TYPE: PRT
<213> ORGANISM: Artificial sequence
<220> FEATURE:
<223> OTHER INFORMATION: synthetic Hinge 6

<400> SEQUENCE: 67

Lys Cys Cys Val Asp Cys Pro
1               5

<210> SEQ ID NO 68
```

```
<211> LENGTH: 7
<212> TYPE: PRT
<213> ORGANISM: Artificial sequence
<220> FEATURE:
<223> OTHER INFORMATION: synthetic Hinge 7

<400> SEQUENCE: 68

Lys Tyr Gly Pro Pro Cys Pro
1               5

<210> SEQ ID NO 69
<211> LENGTH: 15
<212> TYPE: PRT
<213> ORGANISM: Artificial sequence
<220> FEATURE:
<223> OTHER INFORMATION: synthetic Hinge 8

<400> SEQUENCE: 69

Glu Pro Lys Ser Cys Asp Lys Thr His Thr Cys Pro Pro Cys Pro
1               5                   10                  15

<210> SEQ ID NO 70
<211> LENGTH: 12
<212> TYPE: PRT
<213> ORGANISM: Artificial sequence
<220> FEATURE:
<223> OTHER INFORMATION: synthetic Hinge 9

<400> SEQUENCE: 70

Glu Arg Lys Cys Cys Val Glu Cys Pro Pro Cys Pro
1               5                   10

<210> SEQ ID NO 71
<211> LENGTH: 17
<212> TYPE: PRT
<213> ORGANISM: Artificial sequence
<220> FEATURE:
<223> OTHER INFORMATION: synthetic Hinge 10

<400> SEQUENCE: 71

Glu Leu Lys Thr Pro Leu Gly Asp Thr Thr His Thr Cys Pro Arg Cys
1               5                   10                  15

Pro

<210> SEQ ID NO 72
<211> LENGTH: 12
<212> TYPE: PRT
<213> ORGANISM: Artificial sequence
<220> FEATURE:
<223> OTHER INFORMATION: synthetic Hinge 11

<400> SEQUENCE: 72

Ser Pro Asn Met Val Pro His Ala His His Ala Gln
1               5                   10

<210> SEQ ID NO 73
<211> LENGTH: 45
<212> TYPE: PRT
<213> ORGANISM: Artificial sequence
<220> FEATURE:
<223> OTHER INFORMATION: synthetic Hinge 12

<400> SEQUENCE: 73

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
```

```
                20                  25                  30
Gly Ala Val His Thr Arg Gly Leu Asp Phe Ala Cys Asp
            35                  40                  45

<210> SEQ ID NO 74
<211> LENGTH: 21
<212> TYPE: PRT
<213> ORGANISM: Homo sapiens

<400> SEQUENCE: 74

Met Ala Leu Pro Val Thr Ala Leu Leu Leu Pro Leu Ala Leu Leu Leu
1               5                   10                  15

His Ala Ala Arg Pro
            20

<210> SEQ ID NO 75
<211> LENGTH: 24
<212> TYPE: PRT
<213> ORGANISM: Homo sapiens

<400> SEQUENCE: 75

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 76
<211> LENGTH: 27
<212> TYPE: PRT
<213> ORGANISM: Homo sapiens

<400> SEQUENCE: 76

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 77
<211> LENGTH: 21
<212> TYPE: PRT
<213> ORGANISM: Artificial sequence
<220> FEATURE:
<223> OTHER INFORMATION: synthetic 2A-1 Cleavage signal

<400> SEQUENCE: 77

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 78
<211> LENGTH: 357
<212> TYPE: PRT
<213> ORGANISM: Homo sapiens

<400> SEQUENCE: 78

Met Leu Leu Leu Val Thr Ser Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
            35                  40                  45
```

Lys Asn Cys Thr Ser Ile Ser Gly Asp Leu His Ile Leu Pro Val Ala
 50                  55                  60

Phe Arg Gly Asp Ser Phe Thr His Thr Pro Pro Leu Asp Pro Gln Glu
 65                  70                  75                  80

Leu Asp Ile Leu Lys Thr Val Lys Glu Ile Thr Gly Phe Leu Leu Ile
                 85                  90                  95

Gln Ala Trp Pro Glu Asn Arg Thr Asp Leu His Ala Phe Glu Asn Leu
             100                 105                 110

Glu Ile Ile Arg Gly Arg Thr Lys Gln His Gly Gln Phe Ser Leu Ala
         115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                 165                 170                 175

Thr Lys Ile Ile Ser Asn Arg Gly Glu Asn Ser Cys Lys Ala Thr Gly
             180                 185                 190

Gln Val Cys His Ala Leu Cys Ser Pro Glu Gly Cys Trp Gly Pro Glu
         195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                 245                 250                 255

Asn Ile Thr Cys Thr Gly Arg Gly Pro Asp Asn Cys Ile Gln Cys Ala
             260                 265                 270

His Tyr Ile Asp Gly Pro His Cys Val Lys Thr Cys Pro Ala Gly Val
         275                 280                 285

Met Gly Glu Asn Asn Thr Leu Val Trp Lys Tyr Ala Asp Ala Gly His
290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                 325                 330                 335

Thr Gly Met Val Gly Ala Leu Leu Leu Leu Val Val Ala Leu Gly
             340                 345                 350

Ile Gly Leu Phe Met
        355

<210> SEQ ID NO 79
<211> LENGTH: 45
<212> TYPE: PRT
<213> ORGANISM: Homo sapiens

<400> SEQUENCE: 79

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

```
<210> SEQ ID NO 80
<211> LENGTH: 39
<212> TYPE: PRT
<213> ORGANISM: Homo sapiens

<400> SEQUENCE: 80

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
            35

<210> SEQ ID NO 81
<211> LENGTH: 113
<212> TYPE: PRT
<213> ORGANISM: Homo sapiens

<400> SEQUENCE: 81

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 82
<211> LENGTH: 463
<212> TYPE: PRT
<213> ORGANISM: Homo sapiens

<400> SEQUENCE: 82

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
            115                 120                 125
```

```
Pro Glu Ala Pro Phe Asp Leu Ser Val Ile Tyr Arg Glu Gly Ala Asn
        130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Pro Pro Cys Leu Thr Ile Ser Ile Leu Ser Phe Phe Ser
                245                 250                 255

Val Ala Leu Leu Val Ile Leu Ala Cys Val Leu Trp Lys Lys Arg Ile
                260                 265                 270

Lys Pro Ile Val Trp Pro Ser Leu Pro Asp His Lys Lys Thr Leu Glu
        275                 280                 285

His Leu Cys Lys Lys Pro Arg Lys Asn Leu Asn Val Ser Phe Asn Pro
    290                 295                 300

Glu Ser Phe Leu Asp Cys Gln Ile His Arg Val Asp Asp Ile Gln Ala
305                 310                 315                 320

Arg Asp Glu Val Glu Gly Phe Leu Gln Asp Thr Phe Pro Gln Gln Leu
                325                 330                 335

Glu Glu Ser Glu Lys Gln Arg Leu Gly Gly Asp Val Gln Ser Pro Asn
                340                 345                 350

Cys Pro Ser Glu Asp Val Val Val Thr Pro Glu Ser Phe Gly Arg Asp
            355                 360                 365

Ser Ser Leu Thr Cys Leu Ala Gly Asn Val Ser Ala Cys Asp Ala Pro
        370                 375                 380

Ile Leu Ser Ser Ser Arg Ser Leu Asp Cys Arg Glu Ser Gly Lys Asn
385                 390                 395                 400

Gly Pro His Val Tyr Gln Asp Leu Leu Leu Ser Leu Gly Thr Thr Asn
                405                 410                 415

Ser Thr Leu Pro Pro Pro Phe Ser Leu Gln Ser Gly Ile Leu Thr Leu
                420                 425                 430

Asn Pro Val Ala Gln Gly Gln Pro Ile Leu Thr Ser Leu Gly Ser Asn
            435                 440                 445

Gln Glu Glu Ala Tyr Val Thr Met Ser Ser Phe Tyr Gln Asn Gln
450                 455                 460

<210> SEQ ID NO 83
<211> LENGTH: 13673
<212> TYPE: DNA
<213> ORGANISM: Artificial sequence
<220> FEATURE:
<223> OTHER INFORMATION: synthetic Dox-rapamycin inducible lentiviral
      genome with riboswitch

<400> SEQUENCE: 83
gatatctata acaagaaaat atatatataa taagttatca cgtaagtaga acatgaaata      60
acaatataat tatcgtatga gttaaatctt aaaagtcacg taaaagataa tcatgcgtca     120
ttttgactca cgcggtcgtt atagttcaaa atcagtgaca cttaccgcat tgacaagcac     180
```

```
gcctcacggg agctccaagc ggcgactgag atgtcctaaa tgcacagcga cggattcgcg    240
ctatttagaa agagagagca atatttcaag aatgcatgcg tcaattttac gcagactatc    300
tttctagggt taagacggat cgggagatct cccgatcccc tatggtgcac tctcagtaca    360
atctgctctg atgccgcata gttaagccag tatctgctcc ctgcttgtgt gttggaggtc    420
gctgagtagt gcgcgagcaa aatttaagct acaacaaggc aaggcttgac cgacaattgc    480
atgaagaatc tgcttagggt taggcgtttt gcgctgcttc gcgatgtacg ggccagatat    540
acgcgttgac attgattatt gactagttat taatagtaat caattacggg gtcattagtt    600
catagcccat atatggagtt ccgcgttaca aacttacgg taaatggccc gcctggctga    660
ccgcccaacg accccgccc attgacgtca ataatgacgt atgttcccat agtaacgcca    720
atagggactt tccattgacg tcaatgggtg gagtatttac ggtaaactgc ccacttggca    780
gtacatcaag tgtatcatat gccaagtacg cccctattg acgtcaatga cggtaaatgg    840
cccgcctggc attatgccca gtacatgacc ttatgggact ttcctacttg gcagtacatc    900
tacgtattag tcatcgctat taccatggtg atgcggtttt ggcagtacat caatgggcgt    960
ggatagcggt ttgactcacg gggatttcca agtctccacc ccattgacgt caatgggagt   1020
ttgttttgga accaaaatca acgggacttt ccaaaatgtc gtaacaactc cgccccattg   1080
acgcaaatgg gcggtaggcg tgtacggtgg gaggtctata taagcagagc tctccctatc   1140
agtgatagag atctccctat cagtgataga gatcgtcgac gagctcgttt agtgaaccgt   1200
cagatcgcct ggagacgccc tcgaagccgc ggtgcgggtg ccagggcgtg ccctgggtct   1260
ctctggttag accagatctg agcctgggag ctctctggct aactagggaa cccactgctt   1320
aagcctcaat aaagcttgcc ttgagtgctt caagtagtgt gtgcccgtct gttgtgtgac   1380
tctggtaact agagatccct cagacccttt tagtcagtgt ggaaaatctc tagcagtggc   1440
gcccgaacag ggacttgaaa gcgaaaggga accagagga gctctctcga cgcaggactc   1500
ggcttgctga agcgcgcacg gcaagaggcg aggggcggcg actggtgagt acgccaaaaa   1560
ttttgactag cggaggctag aaggagagag atgggtgcga gagcgtcagt attaagcggg   1620
ggagaattag atcgcgatgg gaaaaaattc ggttaaggcc agggggaaag aaaaaatata   1680
aattaaaaca tatagtatgg gcaagcaggg agctagaacg attcgcagtt aatcctggcc   1740
tgttagaaac atcagaaggc tgtagacaaa tactgggaca gctacaacca tcccttcaga   1800
caggatcaga agaacttaga tcattatata atacagtagc aaccctctat tgtgtgcatc   1860
aaaggataga gataaaagac accaaggaag ctttagacaa gatagaggaa gagcaaaaca   1920
aaagtaagac caccgcacag caagcggccg ctgatcttca gacctggagg aggagatatg   1980
agggacaatt ggagaagtga attatataaa tataaagtag taaaaattga accattagga   2040
gtagcaccca ccaaggcaaa gagaagagtg gtgcagagag aaaaaagagc agtgggaata   2100
ggagctttgt tccttgggtt cttgggagca gcaggaagca ctatgggcgc agcgtcaatg   2160
acgctgacgg tacaggccag acaattattg tctggtatag tgcagcagca gaacaatttg   2220
ctgagggcta ttgaggcgca acagcatctg ttgcaactca cagtctgggg catcaagcag   2280
ctccaggcaa gaatcctggc tgtggaaaga tacctaaagg atcaacagct cctgggattt   2340
tggggttgct ctggaaaact catttgcacc actgctgtgc cttggaatgc tagttggagt   2400
aataaatctc tggaacagat ttggaatcac acgacctgga tggagtggga cagagaaatt   2460
aacaattaca caagcttaat acactcctta attgaagaat cgcaaaacca gcaagaaaag   2520
```

```
aatgaacaag aattattgga attagataaa tgggcaagtt tgtggaattg gtttaacata    2580
acaaattggc tgtggtatat aaaattattc ataatgatag taggaggctt ggtaggttta    2640
agaatagttt ttgctgtact ttctatagtg aatagagtta ggcagggata ttcaccatta    2700
tcgtttcaga cccacctccc aaccccgagg ggaccgaca ggcccgaagg aatagaagaa     2760
gaaggtggag agagagacag agacagatcc attcgattag tgaacggatc tcgacggtat    2820
cgattagact gtagcccagg aatatggcag ctagattgta cacatttaga aggaaaagtt    2880
atcttggtag cagttcatgt agccagtgga tatatagaag cagaagtaat tccagcagag    2940
acagggcaag aaacagcata cttcctctta aaattagcag gaagatggcc agtaaaaaca    3000
gtacatacag acaatggcag caatttcacc agtactacag ttaaggccgc ctgttggtgg    3060
gcggggatca agcaggaatt tggcattccc tacaatcccc aaagtcaagg agtaatagaa    3120
tctatgaata aagaattaaa gaaaattata ggacaggtaa gagatcaggc tgaacatctt    3180
aagacagcag tacaaatggc agtattcatc cacaattta aaagaaaagg ggggattggg     3240
gggtacagtg caggggaaag aatagtagac ataatagcaa cagacataca aactaaagaa    3300
ttacaaaaac aaattacaaa aattcaaaat tttcgggttt attacaggga cagcagagat    3360
ccagtttggc tgcattgatc acgtgagggg ctctagactc tagacacaca aaaaaccaac    3420
acacagatct aatgaaaata aagatctttt attgagaaac ttatacaggg tagcataatg    3480
ggctactgac cccgccttca aacctatttg gagactataa gtgaaaatta tcactggttt    3540
tggtagaagc tggacatggt gacatatgct tcttcttgat ttgatcccag ggaagtaaga    3600
atgggctgac cctgagcaac tgggttcaat gtcaggattc cagattggag agaaaatgga    3660
gggggcagcg tgctgtttgt agtcccaagg ctaagcagga ggtcctggta cacatgaggc    3720
ccattcttgc cactctccct gcagtctagg gacctggaag aggagagaat aggggcgtca    3780
catgcactga cattcccagc caggcatgtg agggatgaat ctcttccaaa gctttctgga    3840
gtgacgacta catcctcaga tgggcagttg gggctctgca catcccctcc aagcctctgc    3900
ttctcagatt cttctagttg ctgaggaaac gtatcttgca gaaaaccttc cacttcatct    3960
ctagcttgaa tgtcatccac cctatgaatc tggcagtcca ggaaactttc aggattgaaa    4020
ctcacattta aatttttct tggtttctta caaagatgtt ccagagtctt cttatgatcg       4080
gggagactgg gccatacgat aggcttaatc cttttttcc ataacacaca ggccaagatg      4140
accaacagag cgacagagaa aaaactcaaa atgctgatgg tcaggcatgg tggtagtaag    4200
ataggatcca tctccctga gctattattg atctctggag ttctgaagta ataacttgga     4260
ctccattcac tccagaagcc tttaaaatag tgatcaggga tggatcgaac tttaatctca    4320
tacattgctg ccggttggag ctttctctgc aggagtgtca gctttgtgct ggataaattc    4380
acatgcgtcc atttgttttc atccttttcc tggcggtaag ctacatcatg cattaaaact    4440
tttacatact tcttttgcaa gtgtgatgta ttaaatgtca ccacaaagtc attggctcct    4500
tcccgataga tgacactcag gtcaaaagga gcctcaggtt taactatagt ggttaggtct    4560
atttttttgc aggttagact cttttctcca accttcacac atatattgct ctttccaatc    4620
agtaagaatt tctttgtctc gatgaaatat atctcttgta gtttcctgaa attcaggcac    4680
tttacctcca cgagggcccc acatatttca aattccagat tggtggtgtt gacatctggg    4740
tcctcaaaag cacatgtcag tgaatgctgc gatccattca cttccaactg gctatagcat    4800
gagaatgagt agtcatccag ttctgcatct tccaagtctc catttgagc ataccactt      4860
tctccagaaa cgacttgaag taaagaaaaa accatgccaa aagttgtacc tagaattgtc    4920
```

```
attgggccgg gattttcctc cacgtccccg catgttagta gacttcccct gccctcgccg    4980
gagcgagggg gcagggcctg catgtgaagg gcgtcgtagg tgtccttggt ggctgtactg    5040
agaccctggt aaaggccatc gtgccccttg ccctccggc gctcgccttt catcccaatc    5100
tcactgtagg cctccgccat cttatctttc tgcagttcat tgtacaggcc ttcctgaggg    5160
ttcttccttc tcggctttcc ccccatctca gggtcccggc cacgtctctt gtccaaaaca    5220
tcgtactcct ctcttcgtcc tagattgagc tcgttataga gctggttctg gccctgcttg    5280
tacgcgggg cgtctgcgct cctgctgaac ttcactctca gttcacatcc tccttcttct    5340
tcttctggaa atcggcagct acagccatct tcctcttgag tagtttgtac tggtctcata    5400
aatggttgtt tgaatatata caggagtttc tttctgcccc gtttgcagta aagggtgata    5460
accagtgaca ggagaaggac cccacaagtc ccggccaagg gcgcccagat gtagatatca    5520
caggcgaagt ccagcccct cgtgtgcact gcgccccccg ccgctggccg gcacgcctct    5580
gggcgcaggg acaggggctg cgacgcgatg gtgggcgccg gtgttggtgg tcgcggcgct    5640
ggcgtcgtgg ttgaggagac ggtgactgag gttccttggc cccagtagtc catagcatag    5700
ctaccaccgt agtaataatg tttggcacag tagtaaatgg ctgtgtcatc agtttgcaga    5760
ctgttcattt ttaagaaaac ttggctcttg gagttgtcct tgatgatggt cagtctggat    5820
ttgagagctg aattatagta tgtggtttca ctaccccata ttactcccag ccactccaga    5880
ccctttcgtg gaggctggcg aatccagctt acaccatagt cgggtaatga daccctgag    5940
acagtgcatg tgacggacag gctctgtgag ggcgccacca ggccaggtcc tgactcctgc    6000
agtttcacct cagatccgcc gccacccgac ccaccaccgc ccgagccacc gccacctgtg    6060
atctccagct tggtccccc tccgaacgtg tacggaagcg tattaccctg ttggcgaagt    6120
aggtggcaat atcttcttgc tccaggttgc taattgtcag agaataatct gttccagacc    6180
cactgccact gaaccttgat gggactcctg agtgtaatct tgatgtatgg tagatcagga    6240
gtttaacagt tccatctggt ttctgctgat accaatttaa atatttacta atgtcctgac    6300
ttgccctgca actgatggtg actctgtctc ccagagaggc agacaggag gatgtagtct    6360
gtgtcatctg gatgtccggc ctggcggcgt ggagcagcaa ggcagcggc aggagcaagg    6420
cggtcactgg taaggccatg gatcctctag atcacgacac ctgaaatgga agaaaaaaac    6480
tttgaaccac tgtctgaggc ttgagaatga accaagatcc aaactcaaaa agggcaaatt    6540
ccaaggagaa ttacatcaag tgccaagctg gcctaacttc agtctccacc cactcagtgt    6600
ggggaaactc catcgcataa aacccctccc cccaacctaa agacgacgta ctccaaaagc    6660
tcgagaacta atcgaggtgc ctggacggcg cccggtactc agtggagtca catgaagcga    6720
cggctgagga cggaaaggcc ctttccttt gtgtgggaga aacttataca gggtagcata    6780
atgggctact gaccccgcct tcaaacctat ttggagacta aagtgaaaa tgactcaccc    6840
gcccgctctc ccggcacctt catcttgtcc tttccctcag aaagaggctg ggaggcagag    6900
gctgaggcag cggtggccgg gacggttagg agaaaaggag tctctgctgg ttttattctg    6960
cagctacctc cccaggaagt ggaggactgt ggggcctttg agaagcacct gccgacaggg    7020
ccaagaaatt cgcactcccc ctttcggttc acaggcagga agccctggag gtttgagggt    7080
ttggggtgtg tgtatgtatc tgtctgtctg aattttgctt tttctctcat ttgaccattg    7140
ttttaatgct cctttttta aaaaaaataa ttcttatcta attcctatct tgattggtaa    7200
agtccatctc taggcaaata caagttctcg atggaaaaca ataagtaatg taaaatacag    7260
```

```
catagcaaaa ctttaacctc caaatcaagc ctctacttga atccttttct gagggatgaa    7320
taaggcatag gcatcagggg ctgttgccaa tgtgcattag ctgtttgcag cctcaccttc    7380
tttcatggag tttaagatat agtgtatttt cccaaggttt gaactagctc ttcatttctt    7440
tatgttttaa atgcactgac ctcccacatt ccctttttag taaaatattc agaaataatt    7500
taaatacatc attgcaatga aaataaatgt tttttattag gcagaatcca gatgctcaag    7560
gcccttcata atatcccca gtttagtagt tggacttagg gaacaaagga acctttaata    7620
gaaattggac agcaagaaag cgagcttagt gatacttgtg atcctctaga tcacgacacc    7680
tgaaatggaa gaaaaaaact gcaccttcat cttgtccttt ccctcagaaa gaggctggga    7740
ggcagaggct gaggcagcgg tggccgggac ggttaggaga aaaggagtct ctgctggttt    7800
tattctgcag ctacctcccc aggaagtgga ggactgtggg gcctttgaga agcacctgcc    7860
gacagggcca agaaattcgc actccccctt tcggttcaca ggcaggaagc cctggaggtt    7920
tgagggtttg gggtgtgtgt atgtatctgt ctgtctgaat tttgcttttt ctctcatttg    7980
accattgttt taatgctcct ttttttaaaa aaaataattc ttatctaatt cctatcttga    8040
ttggtaaagt ccatctctag gcaaatacaa gttctcgatg gaaaacaata agtaatgtaa    8100
aatacagcat agcaaaactt taacctccaa atcaagcctc tacttgaatc cttttctgag    8160
ggatgaataa ggcataggca tcaggggctg ttgccaatgt gcattagctg tttgcagcct    8220
caccttcttt catggagttt aagatatagt gtattttccc aaggtttgaa ctagctcttc    8280
atttctttat gttttaaatg cactgacctc ccacattccc tttttagtaa aatattcaga    8340
aataatttaa atacatcatt gcaatgaaaa taaatgtttt ttattaggca gaatccagat    8400
gctcaaggcc cttcataata tcccccagtt tagtagttgg acttagggaa caaaggaacc    8460
tttaatagaa attggacagc aagaaagcga gcttagtgat acttgtaaaa agagacgcgt    8520
ctctaaaagt cctttccatg gctgctcgcc tgtgttgcca cctggattct gcgcgggacg    8580
tccttctgct acgtcccttc ggccctcaat ccagcggacc ttccttcccg cggcctgctg    8640
ccggctctgc ggcctcttcc gcgtcttcgc cttcgccctc agacgagtcg gatctccctt    8700
tgggccgcct ccccgcctgg aattcgagct cggtaccttt aagaccaatg acttacaagg    8760
cagctgtaga tcttagccac ttttttaaaag aaaaggggg actggaaggg ctaattcact    8820
cccaacgaag acaagatctg cttttttgctt gtactgggtc tctctggtta gaccagatct    8880
gagcctggga gctctctggc taactaggga acccactgct taagcctcaa taaagcttgc    8940
cttgagtgct tcaagtagtg tgtgcccgtc tgttgtgtga ctctggtaac tagagatccc    9000
tcagaccctt ttagtcagtg tggaaaatct ctagcagtag tagttcatgt catcttatta    9060
ttcagtattt ataacttgca aagaaatgaa tatcagagag tgagaggaac ttgtttattg    9120
cagcttataa tggttacaaa taaagcaata gcatcacaaa tttcacaaat aaagcatttt    9180
tttcactgca ttctagttgt ggtttgtcca aactcatcaa tgtatcttat catgtctggc    9240
tctagctatc ccgcccctaa ctccgcccat cccgccccta actccgccca gttccgccca    9300
ttctccgccc catggctgac taatttttttt tatttatgca gaggccgagg ccgcctcggc    9360
ctctgagcta ttccagaagt agtgaggagg cttttttgga ggcctaggga cgtatggcca    9420
caacctgggc tcccgggcg cgtactccac ctcacccatc atccacgctg ttttatgagt    9480
aaaggagaag aacttttcac tggagttgtc ccaattcttg ttgaattaga tggtgatgtt    9540
aatgggcaca aattttctgt cagtggagag ggtgaaggtg atgcaacata cggaaaactt    9600
acccttaaat ttatttgcac tactggaaaa ctacctgttc catggccaac acttgtcact    9660
```

```
actttctctt atggtgttca atgcttttca agatacccag atcatatgaa acggcatgac    9720
tttttcaaga gtgccatgcc cgaaggttat gtacaggaaa gaactatatt tttcaaagat    9780
gacgggaact acaagacacg tgctgaagtc aagtttgaag gtgataccct tgttaataga    9840
atcgagttaa aaggtattga ttttaaagaa gatggaaaca ttcttggaca caaattggaa    9900
tacaactata actcacacaa tgtatacatc atggcagaca acaaaagaa tggaatcaaa     9960 gttaacttca aaattagaca caacattgaa gatggaagcg ttcaactagc agaccattat   10020
caacaaaata ctccaattgg cgatggccct gtccttttac cagacaacca ttacctgtcc   10080
acacaatctg cccttcgaa agatcccaac gaaaagagag accacatggt ccttcttgag    10140
tttgtaacag ctgctgggat tacacatggc atggatgaac tatacaaata ggacctccat   10200
agaagacacc gggaccgatc caataacttc gtatagcata cattatacga agttatgcct   10260
ccggactcta gcgtttaaac ttaagcttgg gaagttccta ttccgaagtt cctattctct   10320
agaaagtata ggaacttcta ccgagctcgg atccactagt ccagtgtggt ggaattctgc   10380
agatatccag cacagtggcg gccgctcgag tctagagggc ccgtttaaac ccgctgatca   10440
gcctcgactg tgccttctag ttgccagcca tctgttgttt gcccctcccc cgtgccttcc   10500
ttgaccctgg aaggtgccac tcccactgtc ctttcctaat aaaatgagga aattgcatcg   10560
cattgtctga gtaggtgtca ttctattctg gggggtgggg tggggcagga cagcaagggg   10620
gaggattggg aagacaatag caggcatgct ggggatgcgg tgggctctat ggcttctgag   10680
gcggaaagtt aaccctagaa agataatcat attgtgacgt acgttaaaga taatcatgcg   10740
taaaattgac gcatgtgttt tatcggtctg tatatcgagg tttatttatt aatttgaata   10800
gatattaagt tttattatat ttacacttac atactaataa taaattcaac aaacaattta   10860
tttatgttta tttatttatt aaaaaaaaac aaaaactcaa aatttcttct ataaagtaac   10920
aaaaaccagc tggggctcga agttcctata ctttctagag aataggaact tctatagtga   10980
gtcgaataag ggcgacacaa aatttattct aaatgcataa taaatactga taacatctta   11040
tagtttgtat tatattttgt attatcgttg acatgtataa ttttgatatc aaaaactgat   11100
tttcccttta ttattttcga gatttatttt cttaattctc tttaacaaac tagaaatatt   11160
gtatatacaa aaaatcataa ataatagatg aatagtttaa ttataggtgt tcatcaatcg   11220
aaaaagcaac gtatcttatt taaagtgcgt tgcttttttc tcatttataa ggttaaataa   11280
ttctcatata tcaagcaaag tgacaggcgc ccttaaatat tctgacaaat gctctttccc   11340
taaactcccc ccataaaaaa acccgccgaa gcgggttttt acgttatttg cggattaacg   11400
attactcgtt atcagaaccg cccagggggc ccgagcttaa gactggccgt cgttttacaa   11460
cacagaaaga gtttgtagaa acgcaaaaag gccatccgtc aggggccttc tgcttagttt   11520
gatgcctggc agttccctac tctcgccttc cgcttcctcg ctcactgact cgctgcgctc   11580
ggtcgttcgg ctgcggcgag cggtatcagc tcactcaaag gcggtaatac ggttatccac   11640
agaatcaggg gataacgcag gaaagaacat gtgagcaaaa ggccagcaaa aggccaggaa   11700
ccgtaaaaag gccgcgttgc tggcgttttt ccataggctc cgcccccctg acgagcatca   11760
caaaaatcga cgctcaagtc agaggtggcg aaacccgaca ggactataaa gataccaggc   11820
gtttccccct ggaagctccc tcgtgcgctc tcctgttccg accctgccgc ttaccggata   11880
cctgtccgcc tttctccctt cgggaagcgt ggcgctttct catagctcac gctgtaggta   11940
tctcagttcg gtgtaggtcg ttcgctccaa gctgggctgt gtgcacgaac cccccgttca   12000
```

```
gcccgaccgc tgcgccttat ccggtaacta tcgtcttgag tccaacccgg taagacacga    12060
cttatcgcca ctggcagcag ccactggtaa caggattagc agagcgaggt atgtaggcgg    12120
tgctacagag ttcttgaagt ggtgggctaa ctacggctac actagaagaa cagtatttgg    12180
tatctgcgct ctgctgaagc cagttacctt cggaaaaaga gttggtagct cttgatccgg    12240
caaacaaacc accgctggta gcggtggttt ttttgtttgc aagcagcaga ttacgcgcag    12300
aaaaaaagga tctcaagaag atcctttgat cttttctacg gggtctgacg ctcagtggaa    12360
cgacgcgcgc gtaactcacg ttaagggatt ttggtcatga gcttgcgccg tcccgtcaag    12420
tcagcgtaat gctctgcttt tagaaaaact catcgagcat caaatgaaac tgcaattttat    12480 tcatatcagg attatcaata ccatattttt gaaaaagccg tttctgtaat gaaggagaaa    12540
actcaccgag gcagttccat aggatggcaa gatcctggta tcggtctgcg attccgactc    12600
gtccaacatc aatacaacct attaatttcc cctcgtcaaa aataaggtta tcaagtgaga    12660
aatcaccatg agtgacgact gaatccggtg agaatggcaa aagtttatgc atttctttcc    12720
agacttgttc aacaggccag ccattacgct cgtcatcaaa atcactcgca tcaaccaaac    12780
cgttattcat tcgtgattgc gcctgagcga ggcgaaatac gcgatcgctg ttaaaaggac    12840
aattacaaac aggaatcgag tgcaaccggc gcaggaacac tgccagcgca tcaacaatat    12900
tttcacctga atcaggatat tcttctaata cctggaacgc tgtttttccg gggatcgcag    12960
tggtgagtaa ccatgcatca tcaggagtac ggataaaatg cttgatgtc ggaagtggca    13020 taaattccgt cagccagttt agtctgacca tctcatctgt aacatcattg gcaacgctac    13080
ctttgccatg tttcagaaac aactctggcg catcgggctt cccatacaag cgatagattg    13140
tcgcacctga ttgcccgaca ttatcgcgag cccatttata cccatataaa tcagcatcca    13200
tgttggaatt taatcgcggc ctcgacgttt ccgttgaat atggctcata ttcttccttt    13260
ttcaatatta ttgaagcatt tatcagggtt attgtctcat gagcggatac atatttgaat    13320
gtatttagaa aaataaacaa ataggggtca gtgttacaac caattaacca attctgaaca    13380
ttatcgcgag cccatttata cctgaatatg gctcataaca ccccttgttt gcctggcggc    13440
agtagcgcgg tggtcccacc tgaccccatg ccgaactcag aagtgaaacg ccgtagcgcc    13500
gatggtagtg tggggactcc ccatgcgaga gtagggaact gccaggcatc aaataaaacg    13560
aaaggctcag tcgaaagact gggcctttcg cccgggctaa ttaggggtg tcgcccttat    13620 tcgactctat agtgaagttc ctattctcta gaaagtatag gaacttctga agt          13673

<210> SEQ ID NO 84
<211> LENGTH: 15025
<212> TYPE: DNA
<213> ORGANISM: Artificial sequence
<220> FEATURE:
<223> OTHER INFORMATION: synthetic Dox-rapamycin inducible GAG POL ENV

<400> SEQUENCE: 84
gatatctata acaagaaaat atatatataa taagttatca cgtaagtaga acatgaaata     60
acaatataat tatcgtatga gttaaatctt aaaagtcacg taaaagataa tcatgcgtca    120
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaattttac gcagactatc    300
tttctagggt taagacggat cgggagatct cccgatcccc tatggtgcac tctcagtaca    360
atctgctctg atgccgcata gttaagccag tatctgctcc ctgcttgtgt gttggaggtc    420
```

```
gctgagtagt gcgcgagcaa aatttaagct acaacaaggc aaggcttgac cgacaattgc    480
atgaagaatc tgcttagggt taggcgtttt gaagttccta tactttctag agaataggaa    540
cttcggaata ggaacttcgg atgcaatttc ctcattttat taggaaagga cagtgggagt    600
ggcaccttcc agggtcaagg aaggcacggg ggaggggcaa acaacagatg gctggcaact    660
agaaggcaca gcgttagtga tacttgtggg ccagggcatt agccacacca gccaccactt    720
tctgataggc agcctgcact ggtggggtga attccgcgga agcttgtgta attgttaatt    780
tctctgtccc actccatcca ggtcgtgtga ttccaaatct gttccagaga tttattactc    840
caactagcat tccaaggcac agcagtggtg caaatgagtt ttccagagca accccaaatc    900
cccaggagct gttgatcctt taggtatctt tccacagcca ggattcttgc ctggagctgc    960
ttgatgcccc agactgtgag ttgcaacaga tgctgttgcg cctcaatagc cctcagcaaa   1020
ttgttctgct gctgcactat accagacaat aattgtctgg cctgtaccgt cagcgtcatt   1080
gacgctgcgc ccatagtgct tcctgctgct cccaagaacc caaggaacaa agctcctgcg   1140
gccgctccgg aattccatgt gttaatcctc atcctgtcta cttgccacac aatcatcacc   1200
tgccatctgt tttccataat ccctgatgat cttgcttt cttcttggca ctactttat   1260 gtcactatta tcttgtatta ctactgcccc ttcacctttc cagaggagct ttgctggtcc   1320
tttccaaact ggatctctgc tgtccctgta ataaacccga aaattttgaa tttttgtaat   1380
ttgtttttgt aattctttag tttgtatgtc tgttgctatt atgtctacta ttctttcccc   1440
tgcactgtac cccccaatcc cccctttct tttaaaattg tggatgaata ctgccatttg   1500
tactgctgtc ttaagatgtt cagcctgatc tcttacctgt cctataattt tcttaattc   1560 tttattcata gattctatta ctccttgact ttggggattg tagggaatgc caaattcctg   1620
cttgatcccc gcccaccaac aggcggcctt aactgtagta ctggtgaaat tgctgccatt   1680
gtctgtatgt actgttttta ctggccatct tcctgctaat tttaagagga agtatgctgt   1740
ttcttgccct gtctctgctg gaattacttc tgcttctata tatccactgg ctacatgaac   1800
tgctaccaag ataactttc cttctaaatg tgtacaatct agctgccata ttcctgggct   1860
acagtctact tgtccatgca tggcttcccc ttttagctga catttatcac agctggctac   1920
tatttctttt gctactacag gtggtaggtt aaaatcacta gccattgctc tccaattact   1980
gtgatatttc tcatgttctt cttgggcctt atctattcca tctaaaaata gtactttcct   2040
gattccagca ctgaccaatt tatctacttg ttcatttcct ccaattcctt tgtgtgctgg   2100
tacccatgcc aggtagactt ttttcctttt tattaactgc tctattattt gactgactaa   2160
ctctgattca ctcttatctg gttgtgcttg aatgattccc aatgcatatt gtgagtctgt   2220
cactatgttt acttctaatc ccgaatcctg caaagctaga tgaattgctt gtaactcagt   2280
cttctgattt gttgtgtccg ttaggggac aacttttttgt cttcctctgt cagttacata   2340
tcctgctttt cctaatttag tttccctatt ggctgcccca tctacataga aagtttctgc   2400
tcctattatg ggttctttct ctaactggta ccataacttc actaagggag gggtattgac   2460
aaactcccac tcaggaatcc aggtggcttg ccaatactct gtccaccatg cttcccatgt   2520 ttcctttgt atgggtaatt taaatttagg agtctttccc catattacta tgctttctgt   2580
ggctattttt tgtactgcct ctgttaattg tttcacatca ttagtgtggg caccctttcat   2640 tcttgcatac tttcctgttt tcagattttt aaatggctct tgataaattt gatatgtcca   2700
ttggccttgc ccctgcttct gtatttctgc tattaagtct tttgatgggt cataatacac   2760
```

```
tccatgtacc ggttctttta gaatctccct gttttctgcc agttctagct ctgcttcttc    2820
tgttagtggt actacttctg ttagtgcttt ggttccccta agaagtttac ataattgcct    2880
tactttaatc cctgcataaa tctgacttgc ccaattcaat tttcccacta atttctgtat    2940
gtcattgaca gtccagctgt cctttctgg cagcactata ggctgtactg tccatttatc    3000
aggatggagt tcataaccca tccaaaggaa tggaggttct ttctgatgtt ttttgtctgg    3060
tgtggtaaat ccccacctca acagatgttg tctcagttcc tctattttg ttctatgctg    3120 ccctatttct aagtcagatc ctacatacaa atcatccatg tattgataga tgactatgtc    3180
tggattttgt tttctaaaag gctctaagat ttttgtcatg ctacactgga atattgctgg    3240
tgatcctttc catccctgtg gaagcacatt gtactgatat ctaatccctg gtgtctcatt    3300
gtttatacta ggtatggtaa atgcagtata cttcctgaag tctttatcta agggaactga    3360
aaaatatgca tcgcccacat ccagtactgt tactgatttt ttctgtttta accctgcagg    3420
atgtggtatt cctaattgaa cttcccagaa atcttgagtt ctcttattaa gttctctgaa    3480
atctactaat tttctccatt tagtactgtc ttttttcttt atggcaaata ctggagtatt    3540
gtatggattt tcaggcccaa ttttgaaat ttttccttcc ttttccattt ctgtacaaat    3600
ttctactaat gcttttattt tttcttctgt caatggccat tgtttaactt tgggccatc    3660 cattcctggc tttaattta ctggtacagt ctcaatagga ctaatgggaa aatttaaagt    3720
gcagccaatc tgagtcaaca gatttcttcc aattatgttg acaggtgtag gtcctactaa    3780
tactgtacct atagctttat gtccgcagat ttctatgagt atctgatcat actgtcttac    3840
tttgataaaa cctccaattc ccctatcat ttttggtttc catcttcctg gcaaattcat    3900
ttcttctaat actgtatcat ctgctcctgt atctaataga gcttccttta attgcccccc    3960
tatctttatt gtgacgaggg gtcgctgcca aagagtgatc tgagggaagc taaaggatac    4020
agttccttgt ctatcggctc ctgcttctga gagggagttg ttgtctcttc cccaaacctg    4080
aagctctctt ctggtgggc tgttggctct ggtctgctct gaagaaaatt ccctggcctt    4140
cccttgtggg aaggccagat cttccctaaa aaattagcct gtctctcagt acaatctttc    4200
atttggtgtc cttcctttcc acatttccaa cagcccttt tcctagggc cctgcaattt    4260 ttggctatgt gcccttcttt gccacaattg aaacacttaa cagtcttct ttggttccta    4320 aaattgcctt tctgtatcat tatggtagct ggatttgtta cttggctcat tgcttcagcc    4380
aaaactcttg ctttatggcc gggtccccc actccctgac atgctgtcat catttcttct    4440
agtgtcgctc ctggtcccaa tgcttttaaa atagtcttac aatctgggtt cgcattttgg    4500
accaacaagg tttctgtcat ccaatttttt acctcttgtg aagcttgctc ggctcttaga    4560
gttttataga atcggtctac atagtctcta aagggttcct ttggtccttg tcttatgtcc    4620
agaatgctgg tagggctata cattcttact attttattta atcccaggat tatccatctt    4680
ttatagattt ctcctactgg gataggtgga ttatgtgtca tccatcctat ttgttcctga    4740
agggtactag tagttcctgc tatgtcactt ccccttggtt ctctcatctg gcctggtgca    4800
ataggccctg catgcactgg atgcactcta tcccattctg cagcttcctc attgatggtc    4860
tcttttaaca tttgcatggc tgcttgatgt cccccactg tgtttagcat ggtgtttaaa    4920
tcttgtgggg tggctccttc tgataatgct gaaaacatgg gtatcacttc tgggctgaaa    4980
gccttctctt ctactacttt tacccatgca tttaaagttc taggtgatat ggcctgatgt    5040
accatttgcc cctggatgtt ctgcactata gggtaatttt ggctgacctg attgctgtgt    5100
cctgtgtcag ctgctgcttg ctgtgctttt ttcttacttt tgttttgctc ttcctctatc    5160
```

```
ttgtctaaag cttccttggt gtcttttatc tctatccttt gatgcacaca atagagggtt   5220
gctactgtat tatataatga tctaagttct tctgatcctg tctgaaggga tggttgtagc   5280
tgtcccagta tttgtctaca gccttctgat gtttctaaca ggccaggatt aactgcgaat   5340
cgttctagct ccctgcttgc ccatactata tgttttaatt tatattttt ctttccccct   5400 ggccttaacc gaattttttc ccatcgatct aattctcccc cgcttaatac tgacgctctc   5460
gcacccatgg cggcggcaga tctcgaattc agatctcacg tgctttgcca aagtgatggg   5520
ccagcacaca gaccagcacg ttgcccagga gctgtgggag aagataaga ggtatgaaca   5580 tgattagcaa aagggcctag cttggactca gaataatcca gccttatccc aaccataaaa   5640
taaaagcaga atggtagctg gattgtagct gctattagca atatgaaacc tcttacatca   5700
gttacaattt atatgcagaa atatttatat gcagaaatat tgctattgcc ttaacccaga   5760
aattatcact gttattcttt agaatggtgc aaagaggcat gatacattgt atcattattg   5820
ccctgaaaga aagagattag ggaaagtatt agaaataaga taaacaaaaa agtatattaa   5880
aagaagaaag cattttttaa aattacaaat gcaaaattac cctgatttgg tcaatatgtg   5940
taccctgtta cttctcccct tcctatgaca tgaacttaac catagaaaag aaggggaaag   6000
aaaacatcaa gggtcccata gactcaccct gaagttctca ggatccgagc tcggtaccac   6060
atgtaagctt cgaggggagg ctggatcggt cccggtgtct tctatggagg tcaaaacagc   6120
gtggatggcg tctccaggcg atctgacggt tcactaaacg ctgcttcgcg atgtacgggc   6180
cagatatacg cgttgcgatc tgacggttca ctaaacgagc tctgcttata taggcctccc   6240
accgtacacg ccacctcgac atactcgagt ttactcccta tcagtgatag agaacgtatg   6300
aagagtttac tccctatcag tgatagagaa cgtatgcaga cttactccc tatcagtgat   6360 agagaacgta taaggagttt actccctatc agtgatagag aacgtatgac cagtttactc   6420
cctatcagtg atagagaacg tatctacagt ttactcccta tcagtgatag agaacgtata   6480
tccagtttac tccctatcag tgatagagaa cgtataagct ttaggcgtgt acggtgggcg   6540
cctataaaag cagagctcgt ttagtgaacc gtcagatcgc ctggagcaat tccacaacac   6600
ttttgtctta taccaacttt ccgtaccact tcctaccctc gtaaatcgtc gacgagctcg   6660
tttagtgaac cgtcagatcg cctggagacg ccctcgaagc cgcggtgcgg gtgccagggc   6720
gtgcccttgg gctccatgtc catcatgggt ctcaaggtga acgtctctgc catattcatg   6780
gcagtactgt taactctcca aacacccacc ggtcaaatcc attggggcaa tctctctaag   6840
ataggggtga taggaatagg aagtgcaagc tacaaagtta tgactcgttc cagccatcaa   6900
tcattagtca taaaattaat gcccaatata actctcctca ataactgcac gagggtagag   6960
attgcagaat acaggagact actgagaaca gttttggaac caattagaga tgcacttaat   7020
gcaatgaccc agaatataag accggttcag agtgtagctt caagtaggag acacaagaga   7080
tttgcgggag tagtcctggc aggtgcggcc ctaggcgttg ccacagctgc tcagataaca   7140
gccggcattg cacttcacca gtccatgctg aactctcaag ccatcgacaa tctgagagcg   7200
agcctggaaa ctactaatca ggcaattgag gcaatcagac aagcagggca ggagatgata   7260
ttggctgttc agggtgtcca agactacatc aataatgagc tgataccgtc tatgaaccaa   7320
ctatcttgtg atttaatcgg ccagaagctc gggctcaaat tgctcagata ctatacagaa   7380
atcctgtcat tatttggccc cagccttacg gaccccatat ctgcggagat atctatccag   7440
gctttgagct atgcgcttgg aggagacatc aataaggtgt tagaaaagct cggatacagt   7500
```

```
ggaggtgatt tactgggcat cttagagagc agaggaataa aggcccggat aactcacgtc    7560
gacacagagt cctacttcat tgtcctcagt atagcctatc cgacgctgtc cgagattaag    7620
ggggtgattg tccaccggct agaggggtc tcgtacaaca taggctctca agagtggtat    7680
accactgtgc ccaagtatgt tgcaacccaa gggtaccta tctcgaattt tgatgagtca    7740
tcgtgtactt tcatgccaga ggggactgtg tgcagccaaa atgccttgta cccgatgagt    7800
cctctgctcc aagaatgcct ccgggggtcc accaagtcct gtgctcgtac actcgtatcc    7860
gggtcttttg ggaaccggtt cattttatca caagggaacc taatagccaa ttgtgcatca    7920
atcctttgca agtgttacac aacaggaacg atcattaatc aagaccctga caagatccta    7980
acatacattg ctgccgatca ctgcccgta gtcgaggtga acggcgtgac catccaagtc    8040
gggagcagga ggtatccaga cgctgtgtac ttgcacagaa ttgacctcgg tcctcccata    8100
tcattggaga ggttggacgt agggacaaat ctggggaatg caattgctaa gttggaggat    8160
gccaaggaat tgttggagtc atcggaccag atattgagga gtatgaaagg tttatcgagc    8220
actagcatag tctacatcct gattgcagtg tgtcttggag ggttgatagg gatccccgct    8280
ttaatatgtt gctgcagggg gcgttgaccc ctctcccctcc cccccccta acgttactgg    8340 ccgaagccgc ttgaataag gccggtgtgc gttttgtctat atgttatttt ccaccatatt    8400
gccgtctttt ggcaatgtga gggcccggaa acctggccct gtcttcttga cgagcattcc    8460 tagggggtctt tccctctcg ccaaaggaat gcaaggtctg ttgaatgtcg tgaaggaagc    8520
agttcctctg gaagcttctt gaagacaaac aacgtctgta gcgacccttt gcaggcagcg    8580 gaaccccca cctggcgaca ggtgcctctg cggccaaaag ccacgtgtat aagatacacc    8640
tgcaaaggcg gcacaaccc agtgccacgt tgtgagttgg atagttgtgg aaagagtcaa    8700
atggctctcc tcaagcgtat tcaacaaggg gctgaaggat gcccagaagg taccccattg    8760
tatgggatct gatctggggc ctcggtacac atgctttaca tgtgtttagt cgaggttaaa    8820
aaaacgtcta ggccccccga accacgggga cgtggttttc ctttgaaaaa cacgatgata    8880
atatggccac aaccatggga agtaggatag tcattaacag agaacatctt atgattgata    8940
gaccttatgt tttgctggct gttctgtttg tcatgtttct gagcttgatc gggttgctag    9000
ccattgcagg cattagactt catcgggcag ccatctacac cgcagagatc cataaaagcc    9060
tcagcaccaa tctagatgta actaactcaa tcgagcatca ggtcaaggac gtgctgacac    9120
cactcttcaa aatcatcggt gatgaagtgg gcctgaggac acctcagaga ttcactgacc    9180
tagtgaaatt catctctgac aagattaaat tccttaatcc ggatagggag tacgacttca    9240
gagatctcac ttggtgtatc aacccgccag agagaatcaa attggattat gatcaatact    9300
gtgcagatgt ggctgctgaa gagctcatga atgcattggt gaactcaact ctactggaga    9360
ccagaacaac caatcagttc ctagctgtct caaagggaaa ctgctcaggg cccactacaa    9420
tcagaggtca attctcaaac atgtcgctgt ccctgttaga cttgtattta ggtcgaggtt    9480
acaatgtgtc atctatagtc actatgacat cccaggaat gtatggggga acttacctag    9540
tggaaaagcc taatctgagc agcaaaaggt cagagttgtc acaactgagc atgtaccgag    9600
tgtttgaagt aggtgttatc agaaatccgg gtttgggggc tccggtgttc catatgacaa    9660
actatcttga gcaaccagtc agtaatgatc tcagcaactg tatggtggct ttggggagc    9720 tcaaactcgc agccctttgt cacggggaag attctatcac aattccctat cagggatcag    9780
ggaaaggtgt cagcttccag ctcgtcaagc taggtgtctg gaaatcccca accgacatgc    9840
aatcctgggt ccccttatca acggatgatc cagtgataga caggctttac ctctcatctc    9900
```

```
acagaggtgt tatcgctgac aaycaagcaa aatgggctgt cccgacaaca cgaacagatg    9960
acaagttgcg aatggagaca tgcttccaac aggcgtgtaa gggtaaaatc caagcactct   10020
gcgagaatcc cgagtgggca ccattgaagg ataacaggat tccttcatac ggggtcttgt   10080
ctgttgatct gagtctgaca gttgagctta aaatcaaaat tgcttcggga ttcgggccat   10140
tgatcacaca cggttcaggg atggacctat acaaatccaa ccacaacaat gtgtattggc   10200
tgactatccc rccaatgaag aacctagcct taggtgtaat caacacattg gagtggatac   10260
cgagattcaa ggttagtccc tacctcttca mtgtcccaat taaggaagca ggcgaagact   10320
gccatgcccc aacataccta cctgcggagg tggatggtga tgtcaaactc agttccaatc   10380
tggtgattct acctggtcaa gatctccaat atgttttggc aacctacgat acttccaggg   10440
ttgaacatgc tgtggtttat tacgtttaca gcccaagccg ctcatttttct tactttttatc   10500 cttttaggtt gcctataaag ggggtcccca tcgaattaca agtggaatgc ttcacatggg   10560
accaaaaact ctggtgccgt cacttctgtg tgcttgcgga ctcagaatct ggtggacata   10620
tcactcactc tgggatggtg ggcatgggag tcagctgcac agtcacccgg gaagatggaa   10680
ccaatcgcag ataggggctgc tagtgaacya atcwcatgat gtcacccaga catcaggcat   10740
acccactagt gtgaaataga catcagaatt aagaaaaatg ggctccccgg gcgcgtactc   10800
cacctcaccc atcatccacg ctcggcaata aaaagacaga ataaaacgca cgggtgttgg   10860
gtcgtttgtt cgccgggcgc gtactccacc tcacccatca tccacgctgt tttatggata   10920
gcactgagaa cgtcatcaag cccttcatgc gcttcaaggt gcacatggag ggctccgtga   10980
acggccacga gttcgagatc gagggcgagg gcgagggcaa gcccctacgag ggcacccaga   11040 ccgccaagct gcaggtgacc aagggcggcc ccctgcccct cgcctgggac atcctgtccc   11100
cccagttcca gtacggctcc aaggtgtacg tgaagcaccc cgccgacatc cccgactaca   11160
agaagctgtc cttccccgag ggcttcaagt gggagcgcgt gatgaacttc gaggacggcg   11220
gcgtggtgac cgtgacccag gactcctccc tgcaggacgg caccttcatc taccacgtga   11280
agttcatcgg cgtgaacttc ccctccgacg gccccgtaat gcagaagaag actctgggct   11340
gggagccctc caccgagcgc ctgtaccccc gcgacggcgt gctgaagggc gagatccaca   11400
aggcgctgaa gctgaagggc ggcggccact acctggtgga gttcaagtca atctacatgg   11460
ccaagaagcc cgtgaagctg cccggctact actacgtgga ctccaagctg gacatcacct   11520
cccacaacga ggactacacc gtggtggagc agtacgagcg cgccgaggcc cgccaccacc   11580
tgttccagta ggacctccat agaagacacc gggaccgatc caataacttc gtatagcata   11640
cattatacga agttatgcct ccggactcta gcgtttaaac ttaagcttgg taccgagctc   11700
ggatccacta gtccagtgtg gtggaattct gcagatatcc agcacagtgg cggccgctcg   11760
agtctagagg gcccgtttaa acccgctgat cagcctcgac tgtgccttct agttgccagc   11820
catctgttgt ttgcccctcc cccgtgcctt ccttgaccct ggaaggtgcc actcccactg   11880
tcctttccta ataaaatgag gaaattgcat cgcattgtct gagtaggtgt cattctattc   11940
tggggggtgg ggtggggcag gacagcaagg gggaggattg ggaagacaat agcaggcatg   12000
ctggggatgc ggtgggctct atggcttctg aggcggaaag ttaacccctag aaagataatc   12060 atattgtgac gtacgttaaa gataatcatg cgtaaaattg acgcatgtgt tttatcggtc   12120
tgtatatcga ggtttatttta ttaatttgaa tagatattaa gttttattat atttacactt   12180
acatactaat aataaattca acaaacaatt tatttatgtt tatttattta ttaaaaaaaa   12240
```

```
acaaaaactc aaaatttctt ctataaagta acaaaaacca gctggggctc gaagttccta   12300
tactttctag agaataggaa cttctatagt gagtcgaata agggcgacac aaaatttatt   12360
ctaaatgcat aataaatact gataacatct tatagtttgt attatatttt gtattatcgt   12420
tgacatgtat aattttgata tcaaaaactg attttcccctt tattattttc gagatttatt   12480
ttcttaattc tctttaacaa actagaaata ttgtatatac aaaaaatcat aaataataga   12540
tgaatagttt aattataggt gttcatcaat cgaaaaagca acgtatctta tttaaagtgc   12600
gttgcttttt tctcatttat aaggttaaat aattctcata tatcaagcaa agtgacaggc   12660
gcccttaaat attctgacaa atgctctttc cctaaactcc ccccataaaa aaacccgccg   12720
aagcgggttt ttacgttatt tgcggattaa cgattactcg ttatcagaac cgcccagggg   12780
gcccgagctt aagactggcc gtcgttttac aacacagaaa gagtttgtag aaacgcaaaa   12840
aggccatccg tcagggggcct tctgcttagt ttgatgcctg gcagttccct actctcgcct   12900
tccgcttcct cgctcactga ctcgctgcgc tcggtcgttc ggctgcggcg agcggtatca   12960
gctcactcaa aggcggtaat acggttatcc acagaatcag gggataacgc aggaaagaac   13020
atgtgagcaa aaggccagca aaaggccagg aaccgtaaaa aggccgcgtt gctggcgttt   13080
ttccataggc tccgcccccc tgacgagcat cacaaaaatc gacgctcaag tcagaggtgg   13140
cgaaacccga caggactata aagataccag gcgtttcccc ctggaagctc cctcgtgcgc   13200
tctcctgttc cgaccctgcc gcttaccgga tacctgtccg cctttctccc ttcgggaagc   13260
gtggcgcttt ctcatagctc acgctgtagg tatctcagtt cggtgtaggt cgttcgctcc   13320
aagctgggct gtgtgcacga accccccgtt cagcccgacc gctgcgcctt atccggtaac   13380
tatcgtcttg agtccaaccc ggtaagacac gacttatcgc cactggcagc agccactggt   13440
aacaggatta gcagagcgag gtatgtaggc ggtgctacag agttcttgaa gtggtggcct   13500
aactacggct acactagaag aacagtattt ggtatctgcg ctctgctgaa gccagttacc   13560
ttcggaaaaa gagttggtag ctcttgatcc ggcaaacaaa ccaccgctgg tagcggtggt   13620
ttttttgttt gcaagcagca gattacgcgc agaaaaaaag gatctcaaga agatcctttg   13680
atcttttcta cggggtctga cgctcagtgg aacgacgcgc gcgtaactca cgttaaggga   13740
ttttggtcat gagcttgcgc cgtcccgtca agtcagcgta atgctctgct tttagaaaaa   13800
ctcatcgagc atcaaatgaa actgcaattt attcatatca ggattatcaa taccatattt   13860
ttgaaaaagc cgtttctgta atgaaggaga aaactcaccg aggcagttcc ataggatggc   13920
aagatcctgg tatcggtctg cgattccgac tcgtccaaca tcaatacaac ctattaattt   13980
cccctcgtca aaaataaggt tatcaagtga gaaatcacca tgagtgacga ctgaatccgg   14040
tgagaatggc aaaagtttat gcatttcttt ccagacttgt tcaacaggcc agccattacg   14100
ctcgtcatca aaatcactcg catcaaccaa accgttattc attcgtgatt gcgcctgagc   14160
gaggcgaaat acgcgatcgc tgttaaaagg acaattacaa acaggaatcg agtgcaaccg   14220
gcgcaggaac actgccagcg catcaacaat attttcacct gaatcaggat attcttctaa   14280
tacctggaac gctgtttttc cggggatcgc agtggtgagt aaccatgcat catcaggagt   14340
acggataaaa tgcttgatgg tcggaagtgg cataaattcc gtcagccagt ttagtctgac   14400
catctcatct gtaacatcat tggcaacgct acctttgcca tgtttcagaa acaactctgg   14460
cgcatcgggc ttcccataca agcgatagat tgtcgcacct gattgcccga cattatcgcg   14520
agcccattta tacccatata aatcagcatc catgttggaa tttaatcgcg gcctcgacgt   14580
ttcccgttga atatggctca tattcttcct ttttcaatat tattgaagca tttatcaggg   14640
```

```
ttattgtctc atgagcggat acatatttga atgtatttag aaaaataaac aaataggggt    14700
cagtgttaca accaattaac caattctgaa cattatcgcg agcccattta tacctgaata    14760
tggctcataa cacccctttgt ttgcctggcg gcagtagcgc ggtggtccca cctgacccca    14820
tgccgaactc agaagtgaaa cgccgtagcg ccgatggtag tgtggggact ccccatgcga    14880
gagtagggaa ctgccaggca tcaaataaaa cgaaaggctc agtcgaaaga ctgggccttt    14940 cgccccgggct aattagggggg tgtcgccctt attcgactct atagtgaagt tcctattctc    15000
tagaaagtat aggaacttct gaagt                                          15025
```

<210> SEQ ID NO 85
<211> LENGTH: 6584
<212> TYPE: DNA
<213> ORGANISM: Artificial sequence
<220> FEATURE:
<223> OTHER INFORMATION: synthetic Rapamycin-inducible TET activator

<400> SEQUENCE: 85

```
gatatctata acaagaaaat atatatataa taagttatca cgtaagtaga acatgaaata      60
acaatataat tatcgtatga gttaaatctt aaaagtcacg taaaagataa tcatgcgtca     120
ttttgactca cgcggtcgtt atagttcaaa atcagtgaca cttaccgcat tgacaagcac     180
gcctcacggg agctccaagc ggcgactgag atgtcctaaa tgcacagcga cggattcgcg     240
ctatttagaa agagagagca atatttcaag aatgcatgcg tcaattttac gcagactatc     300
tttctagggt taagacggat cgggagatct cccgatcccc tatggtgcac tctcagtaca     360
atctgctctg atgccgcata gttaagccag tatctgctcc ctgcttgtgt gttggaggtc     420
gctgagtagt gcgcgagcaa atttaagct acaacaaggc aaggcttgac cgacaattgc     480
atgaagaatc tgcttagggt taggcgtttt gcgctgcttc gcgatgtacg ggccagatat     540
acgcgttctc catagaagac accgaataaa atatctttat tttcattaca tctgtgtgtt     600
ggttttttgt gtgaatcgat agtactaaca tacgctctcc atcaaaacaa acgaaacaa      660 aacaaactag caaaataggc tgtccccagt gcaagtgcag gtgccagaac atttctctgg     720
accgatccaa taacttcgta tagcatacat tatacgaagt tatgcctccg gactctagcg     780
ttttagttat tactagcgct accggactca gatctcgagc tcaagcttcg aattctgcag     840
tcgacggtac gcgggcttac gcgtgctagc taatgatggg cgctcgagta atgatgggcg     900
gtcgactaat gatgggcgct cgagtaatga tgggcgtcta gctaatgatg ggcgctcgag     960
taatgatggg cggtcgacta atgatgggcg ctcgagtaat gatgggcgtc tagctaatga    1020
tgggcgctcg agtaatgatg ggcggtcgac taatgatggg cgctcgagta atgatgggcg    1080
tctagaacgc gaattaattc aacattttga caccccata atattttttcc agaattaaca    1140 gtataaattg catctcttgt tcaagagttc cctatcactc tctttaatca ctactcacag    1200
taacctcaac tcctgccaca agcttgccct gcagcgggaa ttccaaactt aagcttggta    1260
ccgagctcgg atccactagt ccagtgtggt ggaattctgc agatatccag cacagtggcg    1320
gccgctcgag tctagagggc ccgtttaaac ccgctgatca atgtctagac tggacaagag    1380
caaagtcata aactctgctc tggaattact caatggagtc ggtatcgaag gcctgacgac    1440
aaggaaactc gctcaaaagc tgggagttga gcagcctacc ctgtactggc acgtgaagaa    1500
caagcgggcc ctgctcgatg ccctgccaat cgagatgctg gacaggcatc atacccactc    1560 ctgcccctg gaaggcgagt catggcaaga ctttctgcgg aacaacgcca agtcataccg    1620
```

```
ctgtgctctc ctctcacatc gcgacggggc taaagtgcat ctcggcaccc gcccaacaga    1680
gaaacagtac gaaaccctgg aaaatcagct cgcgttcctg tgtcagcaag gcttctccct    1740
ggagaacgca ctgtacgctc tgtccgccgt gggccacttt acactgggct gcgtattgga    1800
ggaacaggag catcaagtag caaaagagga aagagagaca cctaccaccg attctatgcc    1860
cccacttctg aaacaagcaa ttgagctgtt cgaccggcag ggagccgaac ctgccttcct    1920
tttcggcctg gaactaatca tatgtggcct ggagaaacag ctaaagtgcg aaagcggcgg    1980
gccgaccgac gcccttgacg attttgactt agacatgctc ccagccgatg cccttgacga    2040
cttttgacctt gatatgctgc ctgctgacgc tcttgacgat tttgaccttg acatgctccc    2100
cgggtaagtc cctccccccc ccctaacgtt actggccgaa gccgcttgga ataaggccgg    2160
tgtgcgtttg tctatatgtt attttccacc atattgccgt cttttggcaa tgtgagggcc    2220
cggaaacctg gccctgtctt cttgacgagc attcctaggg gtcttcccc tctcgccaaa     2280
ggaatgcaag gtctgttgaa tgtcgtgaag gaagcagttc ctctggaagc ttcttgaaga    2340
caaacaacgt ctgtagcgac cctttgcagg cagcggaacc ccccacctgg cgacaggtgc    2400
ctctgcggcc aaaagccacg tgtataagat acacctgcaa aggcggcaca accccagtgc    2460
cacgttgtga gttggatagt tgtggaaaga gtcaaatggc tctcctcaag cgtattcaac    2520
aaggggctga aggatgccca gaaggtaccc cattgtatgg gatctgatct ggggcctcgg    2580
tgcacatgct ttacatgtgt ttagtcgagg ttaaaaaacg tctaggcccc ccgaaccacg    2640
gggacgtggt tttcctttga aaaacacgat gataaatgga tagcactgag aacgtcatca    2700
agcccttcat gcgcttcaag gtgcacatgg agggctccgt gaacggccac gagttcgaga    2760
tcgagggcga gggcgagggc aagccctacg agggcaccca gaccgccaag ctgcaggtga    2820
ccaagggcgg ccccctgccc ttcgcctggg acatcctgtc cccccagttc cagtacggct    2880
ccaaggtgta cgtgaagcac cccgccgaca tccccgacta caagaagctg tccttccccg    2940
agggcttcaa gtgggagcgc gtgatgaact tcgaggacgg cggcgtggtg accgtgaccc    3000
aggactcctc cctgcaggac ggcaccttca tctaccacgt gaagttcatc ggcgtgaact    3060
tccccctcga cggccccgta atgcagaaga gactctggg ctgggagccc tccaccgagc     3120
gcctgtaccc ccgcgacggc gtgctgaagg gcgagatcca aaggcgctg aagctgaagg     3180
gcggcggcca ctacctggtg gagttcaagt caatctacat ggccaagaag cccgtgaagc    3240
tgcccggcta ctactacgtg gactccaagc tggacatcac ctcccacaac gaggactaca    3300
ccgtggtgga gcagtacgag cgcgccgagg cccgccacca cctgttccag tagctcgact    3360
gtgccttcta gttgccagcc atctgttgtt tgcccctccc ccgtgccttc cttgaccctg    3420
gaaggtgcca ctcccactgt cctttcctaa taaaatgagg aaattgcatc gcattgtctg    3480
agtaggtgtc attctattct ggggggtggg gtggggcagg acagcaaggg ggaggattgg    3540
gaagacaata gcaggcatgc tggggatgcg gtgggctcta tggcttctga gcggaaagt     3600
taaccctaga aagataatca tattgtgacg tacgttaaag ataatcatgc gtaaaattga    3660
cgcatgtgtt ttatcggtct gtatatcgag gtttatttat taatttgaat agatattaag    3720
ttttattata tttacactta catactaata ataaattcaa caaacaattt atttatgttt    3780
atttatttat taaaaaaaaa caaaaactca aaatttcttc tataaagtaa caaaaccag     3840
ctggggctcg aagttcctat actttctaga aataggaac ttctatagtg agtcgaataa     3900
gggcgacaca aaatttattc taaatgcata ataaatactg ataacatctt atagtttgta    3960
ttatattttg tattatcgtt gacatgtata attttgatat caaaaactga ttttcccttt    4020
```

```
attattttcg agatttattt tcttaattct ctttaacaaa ctagaaatat tgtatataca    4080
aaaaatcata aataatagat gaatagttta attataggtg ttcatcaatc gaaaaagcaa    4140
cgtatcttat ttaaagtgcg ttgctttttt ctcatttata aggttaaata attctcatat    4200
atcaagcaaa gtgacaggcg cccttaaata ttctgacaaa tgctctttcc ctaaactccc    4260
cccataaaaa aacccgccga agcgggtttt tacgttattt gcggattaac gattactcgt    4320
tatcagaacc gcccaggggg cccgagctta agactggccg tcgttttaca acacagaaag    4380
agtttgtaga aacgcaaaaa ggccatccgt caggggcctt ctgcttagtt tgatgcctgg    4440
cagttcccta ctctcgcctt ccgcttcctc gctcactgac tcgctgcgct cggtcgttcg    4500
gctgcggcga gcggtatcag ctcactcaaa ggcggtaata cggttatcca cagaatcagg    4560
ggataacgca ggaaagaaca tgtgagcaaa aggccagcaa aaggccagga accgtaaaaa    4620
ggccgcgttg ctggcgtttt tccataggct ccgcccccct gacgagcatc acaaaaatcg    4680
acgctcaagt cagaggtggc gaaacccgac aggactataa agataccagg cgtttccccc    4740
tggaagctcc ctcgtgcgct ctcctgttcc gaccctgccg cttaccggat acctgtccgc    4800
ctttctccct tcgggaagcg tggcgctttc tcatagctca cgctgtaggt atctcagttc    4860
ggtgtaggtc gttcgctcca agctgggctg tgtgcacgaa ccccccgttc agcccgaccg    4920
ctgcgcctta tccggtaact atcgtcttga gtccaacccg gtaagacacg acttatcgcc    4980
actggcagca gccactggta acaggattag cagagcgagg tatgtaggcg gtgctacaga    5040
gttcttgaag tggtgggcta actacggcta cactagaaga acagtatttg gtatctgcgc    5100
tctgctgaag ccagttacct tcggaaaaag agttggtagc tcttgatccg gcaaacaaac    5160
caccgctggt agcggtggtt tttttgtttg caagcagcag attacgcgca gaaaaaaagg    5220
atctcaagaa gatcctttga tcttttctac ggggtctgac gctcagtgga acgacgcgcg    5280
cgtaactcac gttaagggat tttggtcatg agcttgcgcc gtcccgtcaa gtcagcgtaa    5340
tgctctgctt ttagaaaaac tcatcgagca tcaaatgaaa ctgcaattta ttcatatcag    5400
gattatcaat accatatttt tgaaaaagcc gtttctgtaa tgaaggagaa aactcaccga    5460
ggcagttcca taggatggca agatcctggt atcggtctgc gattccgact cgtccaacat    5520
caatacaacc tattaatttc ccctcgtcaa aataaggtt  atcaagtgag aaatcaccat    5580
gagtgacgac tgaatccggt gagaatggca aaagtttatg catttctttc cagacttgtt    5640
caacaggcca gccattacgc tcgtcatcaa atcactcgc  atcaaccaaa ccgttattca    5700
ttcgtgattg cgcctgagcg aggcgaaata cgcgatcgct gttaaaagga caattacaaa    5760
caggaatcga gtgcaaccgg cgcaggaaca ctgccagcgc atcaacaata ttttcacctg    5820
aatcaggata ttcttctaat acctggaacg ctgtttttcc ggggatcgca gtggtgagta    5880
accatgcatc atcaggagta cggataaaat gcttgatggt cggaagtggc ataaattccg    5940
tcagccagtt tagtctgacc atctcatctg taacatcatt gcaacgcta  cctttgccat    6000 gtttcagaaa caactctggc gcatcgggct tcccatacaa gcgatagatt gtcgcacctg    6060
attgcccgac attatcgcga gcccatttat acccatataa atcagcatcc atgttggaat    6120
ttaatcgcgg cctcgacgtt tcccgttgaa tatggctcat attcttcctt tttcaatatt    6180
attgaagcat ttatcagggt tattgtctca tgagcggata catatttgaa tgtatttaga    6240
aaaataaaca ataggggtc  agtgttcaa  ccaattaacc aattctgaac attatcgcga    6300
gcccatttat acctgaatat ggctcataac accccttgtt tgcctggcgg cagtagcgcg    6360
```

```
gtggtcccac ctgaccccat gccgaactca gaagtgaaac gccgtagcgc cgatggtagt    6420
gtggggactc cccatgcgag agtagggaac tgccaggcat caaataaaac gaaaggctca    6480
gtcgaaagac tgggcctttc gcccgggcta attaggggt gtcgcccta ttcgactcta     6540 tagtgaagtt cctattctct agaaagtata ggaacttctg aagt                    6584
```

<210> SEQ ID NO 86
<211> LENGTH: 11528
<212> TYPE: DNA
<213> ORGANISM: Artificial sequence
<220> FEATURE:
<223> OTHER INFORMATION: synthetic Rapamycin inducer inducible REV srcVpx

<400> SEQUENCE: 86

```
gatatctata caagaaaat atatatataa taagttatca cgtaagtaga acatgaaata      60
acaatataat tatcgtatga gttaaatctt aaaagtcacg taaaagataa tcatgcgtca    120
ttttgactca cgcggtcgtt atagttcaaa atcagtgaca cttaccgcat tgacaagcac    180
gcctcacggg agctccaagc ggcgactgag atgtcctaaa tgcacagcga cggattcgcg    240
ctatttagaa agagagagca atatttcaag aatgcatgcg tcaattttac gcagactatc    300
tttctagggt taagacggat cgggagatct cccgatcccc tatggtgcac tctcagtaca    360
atctgctctg atgccgcata gttaagccag tatctgctcc ctgcttgtgt gttggaggtc    420
gctgagtagt gcgcgagcaa aatttaagct acaacaaggc aaggcttgac cgacaattgc    480
atgaagaatc tgcttagggt taggcgtttt gcgctgcttc gcgatgtacg ggccagatat    540
acgcgttgac attgattatt gactagttat taatagtaat caattacggg gtcattagtt    600
catagcccat atatggagtt ccgcgttaca taacttacgg taaatggccc gcctggctga    660
ccgcccaacg acccccgccc attgacgtca ataatgacgt atgttcccat agtaacgcca    720
atagggactt tccattgacg tcaatgggtg gagtatttac ggtaaactgc ccacttggca    780
gtacatcaag tgtatcatat gccaagtacg cccctattg acgtcaatga cggtaaatgg    840
cccgcctggc attatgccca gtacatgacc ttatgggact ttcctacttg gcagtacatc    900
tacgtattag tcatcgctat taccatggtg atgcggtttt ggcagtacat caatgggcgt    960
ggatagcggt ttgactcacg gggatttcca agtctccacc ccattgacgt caatgggagt   1020
ttgttttgga accaaaatca acgggacttt ccaaaatgtc gtaacaactc cgccccattg   1080
acgcaaatgg gcggtaggcg tgtacggtgg gaggtctata taagcagagc tcggcattga   1140
ttattgacta gttattaata gtaatcaatt acggggtcat tagttcatag cccatatatg   1200
gagttccgcg ttacataact tacggtaaat ggcccgcctg gctgaccgcc caacgacccc   1260
cgcccattga cgtcaataat gacgtatgtt cccatagtaa cgccaatagg gactttccat   1320
tgacgtcaat gggtggagta tttacggtaa actgcccact tggcagtaca tcaagtgtat   1380
catatgccaa gtccgccccc tattgacgtc aatgacggta atggcccgc ctggcattat    1440 gcccagtaca tgaccttacg ggactttcct acttggcagt acatctacgt attagtcatc   1500
gctattacca tggtgatgcg gttttggcag tacaccaatg ggcgtggata gcggtttgac   1560
tcacggggat ttccaagtct ccaccccatt gacgtcaatg ggagtttgtt ttggcaccaa   1620
aatcaacggg actttccaaa atgtcgtaac aactgcgatc gcccgccccg ttgacgcaaa   1680
tgggcggtag gcgtgtacgg tgggaggtct atataagcag agctcgttta gtgaaccgtc   1740
agatcactag aagctttatt gcggtagttt atcacagtta aattgctaac gcagtcagtg   1800
```

```
cttctgacac aacagtctcg aacttaagct gcagtgactc tcttaaggta gccttgcaga   1860
agttggtcgt gaggcactgg gcaggtaagt atcaaggtta caagacaggt ttaaggagac   1920
caatagaaac tgggcttgtc gagacagaga agactcttgc gtttctgata ggcacctatt   1980
ggtcttactg acatccactt tgcctttctc tccacaggtg tccactccca gttcaattac   2040
agctcttaag gctagagtac ttaatacgac tcactatagg ctagcctcga gaattcatgg   2100
cttctagaat cctctggcat gagatgtggc atgaaggcct ggaagaggca tctcgtttgt   2160
actttgggga aaggaacgtg aaaggcatgt ttgaggtgct ggagcccttg catgctatga   2220
tggaacgggg cccccagact ctgaaggaaa catcctttaa tcaggcctat ggtcgagatt   2280
taatggaggc ccaagagtgg tgcaggaagt acatgaaatc agggaatgtc aaggacctcc   2340
tccaagcctg ggacctctat tatcatgtgt tccgacgaat ctcaaagact agagatgagt   2400
ttcccaccat ggtgtttcct tctgggcaga tcagccaggc ctcggccttg gccccggccc   2460
ctccccaagt cctgccccag gctccagccc ctgcccctgc tccagccatg gtatcagctc   2520
tggcccaggc cccagcccct gtcccagtcc tagccccagg ccctcctcag gctgtggccc   2580
cacctgcccc caagcccacc caggctgggg aaggaacgct gtcagaggcc ctgctgcagc   2640
tgcagtttga tgatgaagac ctgggggcct tgcttggcaa cagcacagac ccagctgtgt   2700
tcacagacct ggcatccgtc gacaactccg agtttcagca gctgctgaac cagggcatac   2760
ctgtggcccc ccacacaact gagcccatgc tgatggagta ccctgaggct ataactcgcc   2820
tagtgacagg ggcccagagg cccccgacc cagctcctgc tccactgggg gccccggggc   2880
tccccaatgg cctcctttca ggagatgaag acttctcctc cattgcggac atggacttct   2940
cagccctgct gagtcagatc agctccacta gttattaaga attcacgcgt cgagcatgca   3000
tctagggcgg ccaattccgc ccctctcccc cccccctc tccctccccc cccctaacg   3060 ttactggccg aagccgcttg gaataaggcc ggtgtgcgtt tgtctatatg ttattttcca   3120
ccatattgcc gtcttttggc aatgtgaggg cccggaaacc tggccctgtc ttcttgacga   3180
gcattcctag gggtctttcc cctctcgcca aaggaatgca aggtctgttg aatgtcgtga   3240
aggaagcagt tcctctggaa gcttcttgaa gacaaacaac gtctgtagcg acccttgca   3300 ggcagcggaa ccccccacct ggcgacaggt gcctctgcgg ccaaaagcca cgtgtataag   3360
atacacctgc aaaggcggca caaccccagt gccacgttgt gagttggata gttgtggaaa   3420
gagtcaaatg gctctcctca agcgtattca acaaggggct gaaggatgcc cagaaggtac   3480
cccattgtat gggatctgat ctggggcctc ggtgcacatg ctttacatgt gtttagtcga   3540
ggttaaaaaa acgtctaggc cccccgaacc acggggacgt ggttttcctt tgaaaaacac   3600
gatgataagc ttgccacaac ccgggatcct ctagagtcga catggactat cctgctgcca   3660
agagggtcaa gttggactct agagaacgcc catatgcttg ccctgtcgag tcctgcgatc   3720
gccgcttttc tcgctcggat gagcttaccc gccatatccg catccacaca ggccagaagc   3780
ccttccagtg tcgaatctgc atgcgtaact tcagtcgtag tgaccacctt accacccaca   3840
tccgcaccca cacaggcggc ggccgcagga ggaagaaacg caccagcata gagaccaaca   3900
tccgtgtggc cttagagaag agtttcttgg agaatcaaaa gcctacctcg aagagatca   3960 ctatgattgc tgatcagctc aatatggaaa aagaggtgat tcgtgtttgg ttctgtaacc   4020
gccgccagaa agaaaaaaga atcaacacta gaggagtgca ggtggaaacc atctcccgg   4080 gagacgggcg caccttcccc aagcgcggcc agacctgcgt ggtgcactac accgggatgc   4140
ttgaagatgg aaagaaattt gattcctccc gggacagaaa caagcccttt aagtttatgc   4200
```

```
taggcaagca ggaggtgatc cgaggctggg aagaaggggt tgcccagatg agtgtgggtc    4260
agagagccaa actgactata tctccagatt atgcctatgg tgccactggg cacccaggca    4320
tcatcccacc acatgccact ctcgtcttcg atgtggagct tctaaaactg gaagtcgagg    4380
gcgtgcaggt ggaaaccatc tccccaggag acgggcgcac cttccccaag cgcggccaga    4440
cctgcgtggt gcactacacc gggatgcttg aagatggaaa gaaatttgat tcctcccggg    4500
acagaaacaa gcccctttaag tttatgctag gcaagcagga ggtgatccga ggctgggaag    4560
aaggggttgc ccagatgagt gtgggtcaga gagccaaact gactatatct ccagattatg    4620
cctatggtgc cactgggcac ccaggcatca tcccaccaca tgccactctc gtcttcgatg    4680
tggagcttct aaaactggaa actagaggag tgcaggtgga aaccatctcc ccaggagacg    4740 gcgcacctt ccccaagcgc ggccagacct gcgtggtgca ctacaccggg atgcttgaag    4800
atggaaagaa atttgattcc tcccgggaca gaaacaagcc ctttaagttt atgctaggca    4860
agcaggaggt gatccgaggc tgggaagaag gggttgccca gatgagtgtg gtcagagag    4920 ccaaactgac tatatctcca gattatgcct atggtgccac tgggcaccca ggcatcatcc    4980
caccacatgc cactctcgtc ttcgatgtgg agcttctaaa actggaaact agttattaag    5040
tcgacccggg cggccgcttc cctttagtga gggttaatgc ttcgagcaga catgataaga    5100
tacattgatg agtttggaca aaccacaact agaatgcagt gaaaaaaatg ctttatttgt    5160
gaaatttgtg atgctattgc tttatttgta accattataa gctgcaataa acaagttaac    5220
ctccatagaa gacaccggga ccgatccaat aacttcgtat agcatacatt atacgaagtt    5280
atggctgcta gtgaacyaat cwcatgatgt cacccagaca tcaggcatac ccactagtgt    5340
gaaatagaca tcagaattaa gaaaaatggg ctccccgggc gcgtactcca cctcacccat    5400
catccacgct cggcaataaa aagacagaat aaaacgcacg ggtgttgggt cgtttgttcg    5460
ttttatggat agcactgaga acgtcatcaa gcccttcatg cgcttcaagg tgcacatgga    5520
gggctccgtg aacggccacg agttcgagat cgagggcgag gcgagggca gccctacga    5580 gggcacccag accgccaagc tgcaggtgac caagggcggc cccctgccct tcgcctggga    5640
catcctgtcc ccccagttcc agtacggctc caaggtgtac gtgaagcacc ccgccgacat    5700
ccccgactac aagaagctgt ccttccccga gggcttcaag tgggagcgcg tgatgaactt    5760
cgaggacggc ggcgtggtga ccgtgaccca ggactcctcc ctgcaggacg gcaccttcat    5820
ctaccacgtg aagttcatcg gcgtgaactt ccccgtcgac ggccccgtaa tgcagaagaa    5880
gactctgggc tgggagccct ccaccgagcg cctgtacccc cgcgacggcg tgctgaaggg    5940
cgagatccac aaggcgctga agctgaaggg cggcggccac tacctggtgg agttcaagtc    6000
aatctacatg gccaagaagc ccgtgaagct gcccggctac tactacgtgg actccaagct    6060
ggacatcacc tcccacaacg aggactacac cgtggtggag cagtacgagc gcgccgaggc    6120
ccgccaccac ctgttccagt aggacctcca tagaagacac cgaataaaat atctttattt    6180
tcattacatc tgtgtgttgg ttttttgtgt gaatcgatag tactaacata cgctctccat    6240
caaaacaaaa cgaaacaaaa caaactagca aaataggctg tccccagtgc aagtgcaggt    6300
gccagaacat ttctctggac cgatccaata acttcgtata gcatacatta tacgaagtta    6360
tgcctccgga ctctagcgtt ttagttatta ctagcgctac cggactcaga tctcgagctc    6420
aagcttcgaa ttctgcagtc gacggtaccg cggttacgc gtgctagcta atgatgggcg    6480
ctcgagtaat gatgggcggt cgactaatga tgggcgctcg agtaatgatg ggcgtctagc    6540
```

-continued

```
taatgatggg cgctcgagta atgatgggcg gtcgactaat gatgggcgct cgagtaatga    6600
tgggcgtcta gctaatgatg ggcgctcgag taatgatggg cggtcgacta atgatgggcg    6660
ctcgagtaat gatgggcgtc tagaacgcga attaattcaa cattttgaca cccccataat    6720
attttccag aattaacagt ataaattgca tctcttgttc aagagttccc tatcactctc     6780
tttaatcact actcacagta acctcaactc ctgccacaag cttgccctgc agcgggaatt    6840
ccaaacttaa gcttggtacc gagctcggat ccactagtcc agtgtggtgg aattctgcag    6900
atatccagca cagtggcggc cgctcgagtc tagagggccc gtttaaaccc gctgatcaga    6960
tggcaggaag aagcggagac agcgacgaag acctcctcaa ggcagtcaga ctcatcaagt    7020
ttctctatca aagcaaccca cctcccaacc ccgagggac ccgacaggcc cgaaggaata     7080
gaagaagaag gtggagagag agacagagac agatccattc gattagtgaa cggatcctta    7140
gcacttattt gggacgatct gcggacgctg tgcctcttca gctaccaccg cttgagagac    7200
ttactcttga ttgtgacgag gattgtggaa cttctgggac gcaggggtg ggaagccctc     7260
aaatattggt ggaatctcct acaatattgg agtcaggagc taaagaatag tccctccccc    7320
cccctaacg ttactggccg aagccgcttg gaataaggcc ggtgtgcgtt tgtctatatg     7380
ttatttcca ccatattgcc gtcttttggc aatgtgaggg cccggaaacc tggccctgtc     7440
ttcttgacga gcattcctag gggtctttcc cctctcgcca aaggaatgca aggtctgttg    7500
aatgtcgtga aggaagcagt tcctctggaa gcttcttgaa gacaaacaac gtctgtagcg    7560
acctttgca ggcagcggaa ccccccacct ggcgacaggt gcctctgcgg ccaaaagcca    7620
cgtgtataag atacacctgc aaaggcggca caaccccagt gccacgttgt gagttggata    7680
gttgtggaaa gagtcaaatg gctctcctca agcgtattca acaaggggct gaaggatgcc    7740
cagaaggtac cccattgtat gggatctgat ctggggcctc ggtgcacatg ctttacatgt    7800
gtttagtcga ggttaaaaaa cgtctaggcc ccccgaacca cggggacgtg gttttccttt    7860
gaaaaacacg atgataatgg ggaggaggaa gaggaagccg aaggatccga aggcgagggt    7920
gttggcggag gcggattaca aggacgacga tgacaagatg tcagatccca gggagagaat    7980
cccacctgga aacagtggag aagagacaat aggagaggcc ttcgaatggc taaacagaac    8040
agtagaggag ataaacagag aggcagtaaa ccacctacca agggagctga ttttccaggt    8100
ttggcaaagg tcttgggaat actggcatga tgaacaaggg atgtcacaaa gctatgtaaa    8160
atacagatac ttgtgtttaa tgcaaaaggc tttatttatg cattgcaaga aaggctgtag    8220
atgtctaggg gaaggacacg gggcaggagg atggagacca ggacctcctc ctcctccccc    8280
tccaggacta gcataacctc gactgtgcct tctagttgcc agccatctgt tgtttgcccc    8340
tcccccgtgc cttccttgac cctggaaggt gccactccca ctgtcctttc ctaataaaat    8400
gaggaaattg catcgcattg tctgagtagg tgtcattcta ttctgggggg tggggtgggg    8460
caggacagca agggggagga ttgggaagac aatagcaggc atgctgggga tgcggtgggc    8520
tctatggctt ctgaggcgga aagttaaccc tagaaagata atcatattgt gacgtacgtt    8580
aaagataatc atgcgtaaaa ttgacgcatg tgttttatcg gtctgtatat cgaggtttat    8640
ttattaattt gaatagatat taagttttat tatatttaca cttacatact aataataaat    8700
tcaacaaaca atttatttat gtttatttat ttattaaaaa aaacaaaaa ctcaaaattt     8760
cttctataaa gtaacaaaaa ccagctgggg ctcgaagttc ctatactttc tagagaatag    8820
gaacttctat agtgagtcga ataagggcga cacaaaattt attctaaatg cataataaat    8880
actgataaca tcttatagtt tgtattatat tttgtattat cgttgacatg tataatttg     8940
```

```
atatcaaaaa ctgatttttcc ctttattatt ttcgagattt attttcttaa ttctctttaa    9000
caaactagaa atattgtata tacaaaaaat cataaataat agatgaatag tttaattata    9060
ggtgttcatc aatcgaaaaa gcaacgtatc ttatttaaag tgcgttgctt ttttctcatt    9120
tataaggtta aataattctc atatatcaag caaagtgaca ggcgcccta aatattctga     9180
caaatgctct ttccctaaac tcccccata aaaaacccg ccgaagcggg tttttacgtt      9240
atttgcggat taacgattac tcgttatcag accgcccag ggggcccgag cttaagactg    9300
gccgtcgttt tacaacacag aaagagtttg tagaaacgca aaaaggccat ccgtcagggg    9360
ccttctgctt agtttgatgc ctggcagttc cctactctcg ccttccgctt cctcgctcac    9420
tgactcgctg cgctcggtcg ttcggctgcg gcgagcggta tcagctcact caaaggcggt    9480
aatacggtta tccacagaat caggggataa cgcaggaaag aacatgtgag caaaaggcca    9540
gcaaaaggcc aggaaccgta aaaaggccgc gttgctggcg ttttttccata ggctccgccc   9600
ccctgacgag catcacaaaa atcgacgctc aagtcagagg tggcgaaacc cgacaggact    9660
ataaagatac caggcgtttc ccctggaag ctccctcgtg cgctctcctg ttccgaccct     9720
gccgcttacc ggatacctgt ccgcctttct cccttcggga agcgtggcgc tttctcatag    9780
ctcacgctgt aggtatctca gttcggtgta ggtcgttcgc tccaagctgg gctgtgtgca    9840
cgaaccccc gttcagcccg accgctgcgc cttatccggt aactatcgtc ttgagtccaa     9900
cccggtaaga cacgacttat cgccactggc agcagccact ggtaacagga ttagcagagc    9960
gaggtatgta ggcggtgcta cagagttctt gaagtggtgg ctaactacg gctacactag    10020
aagaacagta tttggtatct gcgctctgct gaagccagtt accttcggaa aaagagttgg    10080
tagctcttga tccggcaaac aaaccaccgc tggtagcggt ggttttttg tttgcaagca     10140
gcagattacg cgcagaaaaa aaggatctca agaagatcct ttgatctttt ctacggggtc    10200
tgacgctcag tggaacgacg cgcgcgtaac tcacgttaag ggattttggt catgagcttg    10260
cgccgtcccg tcaagtcagc gtaatgctct gcttttagaa aaactcatcg agcatcaaat    10320
gaaactgcaa tttattcata tcaggattat caataccata ttttgaaaa agccgttctct    10380
gtaatgaagg agaaaactca ccgaggcagt tccataggat ggcaagatcc tggtatcggt    10440
ctgcgattcc gactcgtcca acatcaatac aacctattaa tttccctcg tcaaaaataa     10500
ggttatcaag tgagaaatca ccatgagtga cgactgaatc cggtgagaat ggcaaaagtt    10560
tatgcatttc tttccagact tgttcaacag gccagccatt acgctcgtca tcaaaatcac    10620
tcgcatcaac caaaccgtta ttcattcgtg attgcgcctg agcgaggcga atacgcgat     10680
cgctgttaaa aggacaatta caaacaggaa tcgagtgcaa ccggcgcagg aacactgcca    10740
gcgcatcaac aatatttca cctgaatcag gatattcttc taatacctgg aacgctgttt     10800
ttccggggat cgcagtggtg agtaaccatg catcatcagg agtacggata aaatgcttga    10860
tggtcggaag tggcataaat tccgtcagcc agtttagtct gaccatctca tctgtaacat    10920
cattggcaac gctacctttg ccatgtttca gaaacaactc tggcgcatcg gcttcccat     10980
acaagcgata gattgtcgca cctgattgcc cgacattatc gcgagcccat ttatacccat    11040
ataaatcagc atccatgttg gaatttaatc gcggcctcga cgtttcccgt tgaatatggc    11100
tcatattctt ccttttcaa tattattgaa gcatttatca gggttattgt ctcatgagcg    11160
gatacatatt tgaatgtatt tagaaaaata acaaataggg gtcagtgtt acaaccaatt      11220
aaccaattct gaacattatc gcgagcccat ttatacctga atatggctca taacacccct    11280
```

```
tgtttgcctg gcggcagtag cgcggtggtc ccacctgacc ccatgccgaa ctcagaagtg    11340
aaacgccgta gcgccgatgg tagtgtgggg actccccatg cgagagtagg gaactgccag    11400
gcatcaaata aaacgaaagg ctcagtcgaa agactgggcc tttcgcccgg gctaattagg    11460
gggtgtcgcc cttattcgac tctatagtga agttcctatt ctctagaaag tataggaact    11520
tctgaagt                                                              11528
```

```
<210> SEQ ID NO 87
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 87
gggcggcacu uauacagcga agcauaaugg cuacugacgc ccucaaaccc uauuugcaga    60
cuauaagugu cgcgcg                                                    76
```

```
<210> SEQ ID NO 88
<211> LENGTH: 73
<212> TYPE: RNA
<213> ORGANISM: Artificial sequence
<220> FEATURE:
<223> OTHER INFORMATION: synthetic Evolved aptamer

<400> SEQUENCE: 88
gggcggcacu uauacagggu agcauaaugg cuuaggacgc cuucaaaccu aucaagacua    60
uaagugucgc gcg                                                       73
```

```
<210> SEQ ID NO 89
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 89
gggcggcacu uauacagggu agcauaaugg gcuacuugac gccuucaccu auuuguagac    60
uauaaguguc gcgcg                                                     75
```

```
<210> SEQ ID NO 90
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 90
gggcggcacu uauacagcgu agcauaaugg gcugcagacg ccgucaaacc uauuugcaga    60
cuauaagugu cgcgcg                                                    76
```

```
<210> SEQ ID NO 91
<211> LENGTH: 74
<212> TYPE: RNA
<213> ORGANISM: Artificial sequence
<220> FEATURE:
<223> OTHER INFORMATION: synthetic Evolved aptamer

<400> SEQUENCE: 91
gggcggcacu uauacaccgu agcauaaugg gcuacugccg ccgucgaccu uuuggagacu    60
auaagugucg cgcg                                                      74
```

<210> SEQ ID NO 92
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 92
gggcggcacu uauacagguc agcauaaugu gcuagugcgc cuucaaaccu auuuagagac    60
uauaaguguc gcgcg    75

<210> SEQ ID NO 93
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 93
gggcggcacu uauacagcuu agcguaaugg cuacugacgc cguccaaacc uauuuacaga    60
cuauaagugu cgcgcg    76

<210> SEQ ID NO 94
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 94
gggcggcacu uauacagggg agcauaaugg gcuacugacg ccuuuaaacc uauuugagga    60
cuauaagugu cgcgcg    76

<210> SEQ ID NO 95
<211> LENGTH: 74
<212> TYPE: RNA
<213> ORGANISM: Artificial sequence
<220> FEATURE:
<223> OTHER INFORMATION: synthetic Evolved aptamer

<400> SEQUENCE: 95
gggcggcacu uauacaugga agcauaaugg gcugccgacg gcccuuaacc uuuggagacu    60
auaagugucg cgcg    74

<210> SEQ ID NO 96
<211> LENGTH: 79
<212> TYPE: RNA
<213> ORGANISM: Artificial sequence
<220> FEATURE:
<223> OTHER INFORMATION: synthetic Evolved aptamer

<400> SEQUENCE: 96
gggcggcacu uauacagauu agcauaaugg gcuacugacc ccgccggcaa accuauuuga    60
agacuauaag ugucgcgcg    79

<210> SEQ ID NO 97
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 97
gggcggcacu uauacagugu agcauaaugg gcuacugucg caucaaaccu auuggagac    60 uauaaguguc gcgcg    75

<210> SEQ ID NO 98
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 98
gggcggcacu uauacaguga agcauaaugg gcuacugaca cccuuaaacc uauuugcaga    60
cuauaagugu cgcgcg    76

<210> SEQ ID NO 99
<211> LENGTH: 76
<212> TYPE: RNA
<213> ORGANISM: Artificial sequence
<220> FEATURE:
<223> OTHER INFORMATION: synthetic Evolved aptamer

<400> SEQUENCE: 99
gggcggcacu uauacagagu agcauaaugg gcuacagacg ccgucaaacc uauuuaccga    60
cuauaagugu cgcgcg    76

<210> SEQ ID NO 100
<211> LENGTH: 75
<212> TYPE: RNA
<213> ORGANISM: Artificial sequence
<220> FEATURE:
<223> OTHER INFORMATION: synthetic Evolved aptamer

<400> SEQUENCE: 100
gggcggcacu uauacagggu gcauaauggg cuagugacgc cuucaaaccu auuguagac    60 uauaaguguc gcgcg    75

<210> SEQ ID NO 101
<211> LENGTH: 461
<212> TYPE: PRT
<213> ORGANISM: Homo sapiens

<400> SEQUENCE: 101

```
Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125
```

Pro Glu Ala Pro Phe Asp Leu Ser Val Ile Tyr Arg Glu Gly Ala Asn
            130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
            195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Lys Cys His Leu Ser Phe Phe Ser Val Ala
                245                 250                 255

Leu Leu Val Ile Leu Ala Cys Val Leu Trp Lys Lys Arg Ile Lys Pro
            260                 265                 270

Ile Val Trp Pro Ser Leu Pro Asp His Lys Lys Thr Leu Glu His Leu
    275                 280                 285

Cys Lys Lys Pro Arg Lys Asn Leu Asn Val Ser Phe Asn Pro Glu Ser
    290                 295                 300

Phe Leu Asp Cys Gln Ile His Arg Val Asp Asp Ile Gln Ala Arg Asp
305                 310                 315                 320

Glu Val Glu Gly Phe Leu Gln Asp Thr Phe Pro Gln Gln Leu Glu Glu
                325                 330                 335

Ser Glu Lys Gln Arg Leu Gly Gly Asp Val Gln Ser Pro Asn Cys Pro
            340                 345                 350

Ser Glu Asp Val Val Val Thr Pro Glu Ser Phe Gly Arg Asp Ser Ser
    355                 360                 365

Leu Thr Cys Leu Ala Gly Asn Val Ser Ala Cys Asp Ala Pro Ile Leu
    370                 375                 380

Ser Ser Ser Arg Ser Leu Asp Cys Arg Glu Ser Gly Lys Asn Gly Pro
385                 390                 395                 400

His Val Tyr Gln Asp Leu Leu Leu Ser Leu Gly Thr Thr Asn Ser Thr
                405                 410                 415

Leu Pro Pro Pro Phe Ser Leu Gln Ser Gly Ile Leu Thr Leu Asn Pro
            420                 425                 430

Val Ala Gln Gly Gln Pro Ile Leu Thr Ser Leu Gly Ser Asn Gln Glu
    435                 440                 445

Glu Ala Tyr Val Thr Met Ser Ser Phe Tyr Gln Asn Gln
    450                 455                 460

<210> SEQ ID NO 102
<211> LENGTH: 463
<212> TYPE: PRT
<213> ORGANISM: Homo sapiens

<400> SEQUENCE: 102

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val

```
                35                  40                  45
Asn Gly Ser Gln His Ser Leu Thr Cys Ala Phe Glu Asp Pro Asp Val
 50                  55                  60

Asn Thr Thr Asn Leu Glu Phe Glu Ile Cys Gly Ala Leu Val Glu Val
 65                  70                  75                  80

Lys Cys Leu Asn Phe Arg Lys Leu Gln Glu Ile Tyr Phe Ile Glu Thr
                 85                  90                  95

Lys Lys Phe Leu Leu Ile Gly Lys Ser Asn Ile Cys Val Lys Val Gly
                100                 105                 110

Glu Lys Ser Leu Thr Cys Lys Lys Ile Asp Leu Thr Thr Ile Val Lys
                115                 120                 125

Pro Glu Ala Pro Phe Asp Leu Ser Val Ile Tyr Arg Glu Gly Ala Asn
                130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
                180                 185                 190

Arg Lys Leu Gln Pro Ala Ala Met Tyr Glu Ile Lys Val Arg Ser Ile
                195                 200                 205

Pro Asp His Tyr Phe Lys Gly Phe Trp Ser Glu Trp Ser Pro Ser Tyr
                210                 215                 220

Tyr Phe Arg Thr Pro Glu Ile Asn Asn Ser Ser Gly Glu Met Asp Pro
225                 230                 235                 240

Ile Phe Ser Cys Gly Pro Leu Thr Ile Ser Ile Leu Ser Phe Phe Ser
                245                 250                 255

Val Ala Leu Leu Val Ile Leu Ala Cys Val Leu Trp Lys Lys Arg Ile
                260                 265                 270

Lys Pro Ile Val Trp Pro Ser Leu Pro Asp His Lys Lys Thr Leu Glu
                275                 280                 285

His Leu Cys Lys Lys Pro Arg Lys Asn Leu Asn Val Ser Phe Asn Pro
                290                 295                 300

Glu Ser Phe Leu Asp Cys Gln Ile His Arg Val Asp Asp Ile Gln Ala
305                 310                 315                 320

Arg Asp Glu Val Glu Gly Phe Leu Gln Asp Thr Phe Pro Gln Gln Leu
                325                 330                 335

Glu Glu Ser Glu Lys Gln Arg Leu Gly Gly Asp Val Gln Ser Pro Asn
                340                 345                 350

Cys Pro Ser Glu Asp Val Val Val Thr Pro Glu Ser Phe Gly Arg Asp
                355                 360                 365

Ser Ser Leu Thr Cys Leu Ala Gly Asn Val Ser Ala Cys Asp Ala Pro
                370                 375                 380

Ile Leu Ser Ser Ser Arg Ser Leu Asp Cys Arg Glu Ser Gly Lys Asn
385                 390                 395                 400

Gly Pro His Val Tyr Gln Asp Leu Leu Leu Ser Leu Gly Thr Thr Asn
                405                 410                 415

Ser Thr Leu Pro Pro Pro Phe Ser Leu Gln Ser Gly Ile Leu Thr Leu
                420                 425                 430

Asn Pro Val Ala Gln Gly Gln Pro Ile Leu Thr Ser Leu Gly Ser Asn
                435                 440                 445

Gln Glu Glu Ala Tyr Val Thr Met Ser Ser Phe Tyr Gln Asn Gln
                450                 455                 460
```

<210> SEQ ID NO 103
<211> LENGTH: 462
<212> TYPE: PRT
<213> ORGANISM: Homo sapiens

<400> SEQUENCE: 103

```
Met Thr Ile Leu Gly Thr Thr Phe Gly Met Val Phe Ser Leu Leu Gln
  1               5                  10                  15

Val Val Ser Gly Glu Ser Gly Tyr Ala Gln Asn Gly Asp Leu Glu Asp
             20                  25                  30

Ala Glu Leu Asp Asp Tyr Ser Phe Ser Cys Tyr Ser Gln Leu Glu Val
         35                  40                  45

Asn Gly Ser Gln His Ser Leu Thr Cys Ala Phe Glu Asp Pro Asp Val
 50                  55                  60

Asn Thr Thr Asn Leu Glu Phe Glu Ile Cys Gly Ala Leu Val Glu Val
 65                  70                  75                  80

Lys Cys Leu Asn Phe Arg Lys Leu Gln Glu Ile Tyr Phe Ile Glu Thr
                 85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
210                 215                 220

Tyr Phe Arg Thr Pro Glu Ile Asn Asn Ser Ser Gly Glu Met Asp Pro
225                 230                 235                 240

Ile Leu Leu Thr Cys His Leu Ile Ser Ile Leu Ser Phe Phe Ser Val
                245                 250                 255

Ala Leu Leu Val Ile Leu Ala Cys Val Leu Trp Lys Lys Arg Ile Lys
            260                 265                 270

Pro Ile Val Trp Pro Ser Leu Pro Asp His Lys Lys Thr Leu Glu His
        275                 280                 285

Leu Cys Lys Lys Pro Arg Lys Asn Leu Asn Val Ser Phe Asn Pro Glu
290                 295                 300

Ser Phe Leu Asp Cys Gln Ile His Arg Val Asp Asp Ile Gln Ala Arg
305                 310                 315                 320

Asp Glu Val Glu Gly Phe Leu Gln Asp Thr Phe Pro Gln Gln Leu Glu
                325                 330                 335

Glu Ser Glu Lys Gln Arg Leu Gly Gly Asp Val Gln Ser Pro Asn Cys
            340                 345                 350

Pro Ser Glu Asp Val Val Val Thr Pro Glu Ser Phe Gly Arg Asp Ser
        355                 360                 365

Ser Leu Thr Cys Leu Ala Gly Asn Val Ser Ala Cys Asp Ala Pro Ile
```

```
                    370                 375                 380
Leu Ser Ser Arg Ser Leu Asp Cys Arg Glu Ser Gly Lys Asn Gly
385                 390                 395                 400

Pro His Val Tyr Gln Asp Leu Leu Ser Leu Gly Thr Thr Asn Ser
                    405                 410                 415

Thr Leu Pro Pro Phe Ser Leu Gln Ser Gly Ile Leu Thr Leu Asn
                420                 425                 430

Pro Val Ala Gln Gly Gln Pro Ile Leu Thr Ser Leu Gly Ser Asn Gln
            435                 440                 445

Glu Glu Ala Tyr Val Thr Met Ser Ser Phe Tyr Gln Asn Gln
    450                 455                 460

<210> SEQ ID NO 104
<211> LENGTH: 466
<212> TYPE: PRT
<213> ORGANISM: Homo sapiens

<400> SEQUENCE: 104

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
            20                  25                  30

Ala Glu Leu Asp Asp Tyr Ser Phe Ser Cys Tyr Ser Gln Leu Glu Val
        35                  40                  45

Asn Gly Ser Gln His Ser Leu Thr Cys Ala Phe Glu Asp Pro Asp Val
    50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Pro Pro Val Cys Ser Val Thr Ile Ser Ile Leu Ser
                245                 250                 255

Phe Phe Ser Val Ala Leu Leu Val Ile Leu Ala Cys Val Leu Trp Lys
            260                 265                 270

Lys Arg Ile Lys Pro Ile Val Trp Pro Ser Leu Pro Asp His Lys Lys
        275                 280                 285
```

```
Thr Leu Glu His Leu Cys Lys Lys Pro Arg Lys Asn Leu Asn Val Ser
    290                 295                 300

Phe Asn Pro Glu Ser Phe Leu Asp Cys Gln Ile His Arg Val Asp Asp
305                 310                 315                 320

Ile Gln Ala Arg Asp Glu Val Glu Gly Phe Leu Gln Asp Thr Phe Pro
                325                 330                 335

Gln Gln Leu Glu Glu Ser Glu Lys Gln Arg Leu Gly Gly Asp Val Gln
            340                 345                 350

Ser Pro Asn Cys Pro Ser Glu Asp Val Val Thr Pro Glu Ser Phe
        355                 360                 365

Gly Arg Asp Ser Ser Leu Thr Cys Leu Ala Gly Asn Val Ser Ala Cys
    370                 375                 380

Asp Ala Pro Ile Leu Ser Ser Arg Ser Leu Asp Cys Arg Glu Ser
385                 390                 395                 400

Gly Lys Asn Gly Pro His Val Tyr Gln Asp Leu Leu Ser Leu Gly
                405                 410                 415

Thr Thr Asn Ser Thr Leu Pro Pro Phe Ser Leu Gln Ser Gly Ile
            420                 425                 430

Leu Thr Leu Asn Pro Val Ala Gln Gly Gln Pro Ile Leu Thr Ser Leu
        435                 440                 445

Gly Ser Asn Gln Glu Glu Ala Tyr Val Thr Met Ser Ser Phe Tyr Gln
    450                 455                 460

Asn Gln
465

<210> SEQ ID NO 105
<211> LENGTH: 523
<212> TYPE: PRT
<213> ORGANISM: Artificial sequence
<220> FEATURE:
<223> OTHER INFORMATION: synthetic Fc-delta-30

<400> SEQUENCE: 105

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
        115                 120                 125

Ala Thr Ala Ala Gln Ile Thr Ala Gly Ile Ala Leu His Gln Ser Met
    130                 135                 140

Leu Asn Ser Gln Ala Ile Asp Asn Leu Arg Ala Ser Leu Glu Thr Thr
145                 150                 155                 160

Asn Gln Ala Ile Glu Ala Ile Arg Gln Ala Gly Gln Glu Met Ile Leu
                165                 170                 175
```

```
Ala Val Gln Gly Val Gln Asp Tyr Ile Asn Asn Glu Leu Ile Pro Ser
            180                 185                 190

Met Asn Gln Leu Ser Cys Asp Leu Ile Gly Lys Leu Gly Leu Lys
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255

Gly Asp Leu Leu Gly Ile Leu Glu Ser Arg Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Ser Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg
        515                 520

<210> SEQ ID NO 106
<211> LENGTH: 599
<212> TYPE: PRT
<213> ORGANISM: Artificial sequence
<220> FEATURE:
<223> OTHER INFORMATION: synthetic Hc-delta-18

<400> SEQUENCE: 106

Met Gly Ser Arg Ile Val Ile Asn Arg Glu His Leu Met Ile Asp Arg
1               5                   10                  15
```

Pro Tyr Val Leu Leu Ala Val Leu Phe Val Met Ser Leu Ser Leu Ile
              20                  25                  30

Gly Leu Leu Ala Ile Ala Gly Ile Arg Leu His Arg Ala Ala Ile Tyr
          35                  40                  45

Thr Ala Glu Ile His Lys Ser Leu Ser Thr Asn Leu Asp Val Thr Asn
    50                  55                  60

Ser Ile Glu His Gln Val Lys Asp Val Leu Thr Pro Leu Phe Lys Ile
65                  70                  75                  80

Ile Gly Asp Glu Val Gly Leu Arg Thr Pro Gln Arg Phe Thr Asp Leu
                85                  90                  95

Val Lys Phe Ile Ser Asp Lys Ile Lys Phe Leu Asn Pro Asp Arg Glu
                100                 105                 110

Tyr Asp Phe Arg Asp Leu Thr Trp Cys Ile Asn Pro Glu Arg Ile
                115                 120                 125

Lys Leu Asp Tyr Asp Gln Tyr Cys Ala Asp Val Ala Ala Glu Glu Leu
                130                 135                 140

Met Asn Ala Leu Val Asn Ser Thr Leu Leu Glu Thr Arg Thr Thr Asn
145                 150                 155                 160

Gln Phe Leu Ala Val Ser Lys Gly Asn Cys Ser Gly Pro Thr Thr Ile
                165                 170                 175

Arg Gly Gln Phe Ser Asn Met Ser Leu Ser Leu Leu Asp Leu Tyr Leu
                180                 185                 190

Ser Arg Gly Tyr Asn Val Ser Ser Ile Val Thr Met Thr Ser Gln Gly
                195                 200                 205

Met Tyr Gly Gly Thr Tyr Leu Val Glu Lys Pro Asn Leu Ser Ser Lys
210                 215                 220

Arg Ser Glu Leu Ser Gln Leu Ser Met Tyr Arg Val Phe Glu Val Gly
225                 230                 235                 240

Val Ile Arg Asn Pro Gly Leu Gly Ala Pro Val Phe His Met Thr Asn
                245                 250                 255

Tyr Leu Glu Gln Pro Val Ser Asn Asp Leu Ser Asn Cys Met Val Ala
                260                 265                 270

Leu Gly Glu Leu Lys Leu Ala Ala Leu Cys His Gly Glu Asp Ser Ile
                275                 280                 285

Thr Ile Pro Tyr Gln Gly Ser Gly Lys Gly Val Ser Phe Gln Leu Val
290                 295                 300

Lys Leu Gly Val Trp Lys Ser Pro Thr Asp Met Gln Ser Trp Val Pro
305                 310                 315                 320

Leu Ser Thr Asp Asp Pro Val Ile Asp Arg Leu Tyr Leu Ser Ser His
                325                 330                 335

Arg Gly Val Ile Ala Asp Asn Gln Ala Lys Trp Ala Val Pro Thr Thr
                340                 345                 350

Arg Thr Asp Asp Lys Leu Arg Met Glu Thr Cys Phe Gln Gln Ala Cys
            355                 360                 365

Lys Gly Lys Ile Gln Ala Leu Cys Glu Asn Pro Glu Trp Ala Pro Leu
            370                 375                 380

Lys Asp Asn Arg Ile Pro Ser Tyr Gly Val Leu Ser Val Asp Leu Ser
385                 390                 395                 400

Leu Thr Val Glu Leu Lys Ile Lys Ile Ala Ser Gly Phe Gly Pro Leu
                405                 410                 415

Ile Thr His Gly Ser Gly Met Asp Leu Tyr Lys Ser Asn His Asn Asn
                420                 425                 430

Val Tyr Trp Leu Thr Ile Pro Pro Met Lys Asn Leu Ala Leu Gly Val

```
            435                 440                 445
Ile Asn Thr Leu Glu Trp Ile Pro Arg Phe Lys Val Ser Pro Asn Leu
450                 455                 460

Phe Thr Val Pro Ile Lys Glu Ala Gly Glu Asp Cys His Ala Pro Thr
465                 470                 475                 480

Tyr Leu Pro Ala Glu Val Asp Gly Asp Val Lys Leu Ser Ser Asn Leu
                485                 490                 495

Val Ile Leu Pro Gly Gln Asp Leu Gln Tyr Val Leu Ala Thr Tyr Asp
            500                 505                 510

Thr Ser Arg Val Glu His Ala Val Val Tyr Tyr Val Tyr Ser Pro Gly
            515                 520                 525

Arg Ser Phe Ser Tyr Phe Tyr Pro Phe Arg Leu Pro Ile Lys Gly Val
530                 535                 540

Pro Ile Glu Leu Gln Val Glu Cys Phe Thr Trp Asp Gln Lys Leu Trp
545                 550                 555                 560

Cys Arg His Phe Cys Val Leu Ala Asp Ser Glu Ser Gly Gly His Ile
                565                 570                 575

Thr His Ser Gly Met Val Gly Met Gly Val Ser Cys Thr Val Thr Arg
            580                 585                 590

Glu Asp Gly Thr Asn Arg Arg
            595

<210> SEQ ID NO 107
<211> LENGTH: 529
<212> TYPE: PRT
<213> ORGANISM: Artificial sequence
<220> FEATURE:
<223> OTHER INFORMATION: synthetic DAFss-IL7-DAF fusion

<400> SEQUENCE: 107

Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Ala Asp
                20                  25                  30

Cys Asp Ile Glu Gly Lys Asp Gly Lys Gln Tyr Glu Ser Val Leu Met
            35                  40                  45

Val Ser Ile Asp Gln Leu Leu Asp Ser Met Lys Glu Ile Gly Ser Asn
50                  55                  60

Cys Leu Asn Asn Glu Phe Asn Phe Phe Lys Arg His Ile Cys Asp Ala
65                  70                  75                  80

Asn Lys Glu Gly Met Phe Leu Phe Arg Ala Ala Arg Lys Leu Arg Gln
                85                  90                  95

Phe Leu Lys Met Asn Ser Thr Gly Asp Phe Asp Leu His Leu Leu Lys
            100                 105                 110

Val Ser Glu Gly Thr Thr Ile Leu Leu Asn Cys Thr Gly Gln Val Lys
            115                 120                 125

Gly Arg Lys Pro Ala Ala Leu Gly Glu Ala Gln Pro Thr Lys Ser Leu
130                 135                 140

Glu Glu Asn Lys Ser Leu Lys Glu Gln Lys Lys Leu Asn Asp Leu Cys
145                 150                 155                 160

Phe Leu Lys Arg Leu Leu Gln Glu Ile Lys Thr Cys Trp Asn Lys Ile
                165                 170                 175

Leu Met Gly Thr Lys Glu His Cys Gly Leu Pro Pro Asp Val Pro Asn
            180                 185                 190

Ala Gln Pro Ala Leu Glu Gly Arg Thr Ser Phe Pro Glu Asp Thr Val
```

```
              195                 200                 205
Ile Thr Tyr Lys Cys Glu Glu Ser Phe Val Lys Ile Pro Gly Glu Lys
    210                 215                 220

Asp Ser Val Ile Cys Leu Lys Gly Ser Gln Trp Ser Asp Ile Glu Glu
225                 230                 235                 240

Phe Cys Asn Arg Ser Cys Glu Val Pro Thr Arg Leu Asn Ser Ala Ser
                245                 250                 255

Leu Lys Gln Pro Tyr Ile Thr Gln Asn Tyr Phe Pro Val Gly Thr Val
            260                 265                 270

Val Glu Tyr Glu Cys Arg Pro Gly Tyr Arg Arg Glu Pro Ser Leu Ser
        275                 280                 285

Pro Lys Leu Thr Cys Leu Gln Asn Leu Lys Trp Ser Thr Ala Val Glu
    290                 295                 300

Phe Cys Lys Lys Lys Ser Cys Pro Asn Pro Gly Glu Ile Arg Asn Gly
305                 310                 315                 320

Gln Ile Asp Val Pro Gly Gly Ile Leu Phe Gly Ala Thr Ile Ser Phe
                325                 330                 335

Ser Cys Asn Thr Gly Tyr Lys Leu Phe Gly Ser Thr Ser Ser Phe Cys
            340                 345                 350

Leu Ile Ser Gly Ser Ser Val Gln Trp Ser Asp Pro Leu Pro Glu Cys
        355                 360                 365

Arg Glu Ile Tyr Cys Pro Ala Pro Pro Gln Ile Asp Asn Gly Ile Ile
    370                 375                 380

Gln Gly Glu Arg Asp His Tyr Gly Tyr Arg Gln Ser Val Thr Tyr Ala
385                 390                 395                 400

Cys Asn Lys Gly Phe Thr Met Ile Gly Glu His Ser Ile Tyr Cys Thr
                405                 410                 415

Val Asn Asn Asp Glu Gly Glu Trp Ser Gly Pro Pro Pro Glu Cys Arg
            420                 425                 430

Gly Lys Ser Leu Thr Ser Lys Val Pro Pro Thr Val Gln Lys Pro Thr
        435                 440                 445

Thr Val Asn Val Pro Thr Thr Glu Val Ser Pro Thr Ser Gln Lys Thr
    450                 455                 460

Thr Thr Lys Thr Thr Thr Pro Asn Ala Gln Ala Thr Arg Ser Thr Pro
465                 470                 475                 480

Val Ser Arg Thr Thr Lys His Phe His Glu Thr Thr Pro Asn Lys Gly
                485                 490                 495

Ser Gly Thr Thr Ser Gly Thr Thr Arg Leu Leu Ser Gly His Thr Cys
            500                 505                 510

Phe Thr Leu Thr Gly Leu Leu Gly Thr Leu Val Thr Met Gly Leu Leu
        515                 520                 525

Thr

<210> SEQ ID NO 108
<211> LENGTH: 49
<212> TYPE: DNA
<213> ORGANISM: Artificial sequence
<220> FEATURE:
<223> OTHER INFORMATION: synthetic 582-1

<400> SEQUENCE: 108
acagcttagc gtaatggcta ctgacgccgt ccaaacctat ttacagact              49

<210> SEQ ID NO 109
<211> LENGTH: 49
```

```
<212> TYPE: DNA
<213> ORGANISM: Artificial sequence
<220> FEATURE:
<223> OTHER INFORMATION: synthetic 582-2

<400> SEQUENCE: 109
acagcttagg ataatggcta ctgacgccgt ccaaacctat ttacagact          49

<210> SEQ ID NO 110
<211> LENGTH: 49
<212> TYPE: DNA
<213> ORGANISM: Artificial sequence
<220> FEATURE:
<223> OTHER INFORMATION: synthetic 582-3

<400> SEQUENCE: 110
acagcttagc ataatggcta ctgacgccgt ccaaacctat tcacagact          49

<210> SEQ ID NO 111
<211> LENGTH: 49
<212> TYPE: DNA
<213> ORGANISM: Artificial sequence
<220> FEATURE:
<223> OTHER INFORMATION: synthetic 582-4

<400> SEQUENCE: 111
acagcttagc ataatggcta ctgacgccgt ccaaacctat tgacagact          49

<210> SEQ ID NO 112
<211> LENGTH: 49
<212> TYPE: DNA
<213> ORGANISM: Artificial sequence
<220> FEATURE:
<223> OTHER INFORMATION: synthetic 582-5

<400> SEQUENCE: 112
acagcatagc ataatggcta ctgacgccgt ccaaacctat ttacagact          49

<210> SEQ ID NO 113
<211> LENGTH: 49
<212> TYPE: DNA
<213> ORGANISM: Artificial sequence
<220> FEATURE:
<223> OTHER INFORMATION: synthetic 582-6

<400> SEQUENCE: 113
acagcttagc ataatggcta ctgacgccgt ccaaacctat gtacagact          49

<210> SEQ ID NO 114
<211> LENGTH: 48
<212> TYPE: DNA
<213> ORGANISM: Artificial sequence
<220> FEATURE:
<223> OTHER INFORMATION: synthetic 582-7

<400> SEQUENCE: 114
acagctagcg taatggctac tgacgccgtc caaacctatt tacagact           48

<210> SEQ ID NO 115
<211> LENGTH: 49
<212> TYPE: DNA
<213> ORGANISM: Artificial sequence
<220> FEATURE:
<223> OTHER INFORMATION: synthetic 582-8

<400> SEQUENCE: 115
```
acagcttagc attatggcta ctgacgccgt ccaaacctat ttacagact            49

<210> SEQ ID NO 116
<211> LENGTH: 48
<212> TYPE: DNA
<213> ORGANISM: Artificial sequence
<220> FEATURE:
<223> OTHER INFORMATION: synthetic 582-9

<400> SEQUENCE: 116
acagttagca taatggctac tgacgccgtc caaacctatt tacagact             48

<210> SEQ ID NO 117
<211> LENGTH: 49
<212> TYPE: DNA
<213> ORGANISM: Artificial sequence
<220> FEATURE:
<223> OTHER INFORMATION: synthetic 582-10

<400> SEQUENCE: 117
acagcttagc ataatggcta ctgacgcggt ccaaacctat ttacagact            49

<210> SEQ ID NO 118
<211> LENGTH: 49
<212> TYPE: DNA
<213> ORGANISM: Artificial sequence
<220> FEATURE:
<223> OTHER INFORMATION: synthetic 582-11

<400> SEQUENCE: 118
acagcttagc ttaatggcta ctgacgccgt ccaaacctat ttacagact            49

<210> SEQ ID NO 119
<211> LENGTH: 49
<212> TYPE: DNA
<213> ORGANISM: Artificial sequence
<220> FEATURE:
<223> OTHER INFORMATION: synthetic 582-12

<400> SEQUENCE: 119
acagcttagc ataatggcta ctgacgccgt ccaaacccat ttacagact            49

<210> SEQ ID NO 120
<211> LENGTH: 49
<212> TYPE: DNA
<213> ORGANISM: Artificial sequence
<220> FEATURE:
<223> OTHER INFORMATION: synthetic 582-13

<400> SEQUENCE: 120
acagcttagc ataatggcta ctgacgccgt ccaaaccaat ttacagact            49

<210> SEQ ID NO 121
<211> LENGTH: 49
<212> TYPE: DNA
<213> ORGANISM: Artificial sequence
<220> FEATURE:
<223> OTHER INFORMATION: synthetic 582-14

<400> SEQUENCE: 121
acagcttagc ataatggata ctgacgccgt ccaaacctat ttacagact            49

<210> SEQ ID NO 122
<211> LENGTH: 49
<212> TYPE: DNA
<213> ORGANISM: Artificial sequence

```
<220> FEATURE:
<223> OTHER INFORMATION: synthetic 582-15

<400> SEQUENCE: 122
acagcttagc attgtggcta ctgacgccgt ccaaacctat ttacagact        49

<210> SEQ ID NO 123
<211> LENGTH: 49
<212> TYPE: DNA
<213> ORGANISM: Artificial sequence
<220> FEATURE:
<223> OTHER INFORMATION: synthetic 582-16

<400> SEQUENCE: 123
acaggttagc ataatggcta ccgacgccgt ccaaacctat ttacagact        49

<210> SEQ ID NO 124
<211> LENGTH: 49
<212> TYPE: DNA
<213> ORGANISM: Artificial sequence
<220> FEATURE:
<223> OTHER INFORMATION: synthetic 582-17

<400> SEQUENCE: 124
acagcttagc gtaatggcta ctgacgccgc ccaaacctat ttacagact        49

<210> SEQ ID NO 125
<211> LENGTH: 49
<212> TYPE: DNA
<213> ORGANISM: Artificial sequence
<220> FEATURE:
<223> OTHER INFORMATION: synthetic 582-18

<400> SEQUENCE: 125
acagcttagc ataatggcta ctgacgccgt ccaaaactat ttccagact        49

<210> SEQ ID NO 126
<211> LENGTH: 49
<212> TYPE: DNA
<213> ORGANISM: Artificial sequence
<220> FEATURE:
<223> OTHER INFORMATION: synthetic 582-19

<400> SEQUENCE: 126
acagcctagc ataagggcta ctgacgccgt ccaaacctat ttacagact        49

<210> SEQ ID NO 127
<211> LENGTH: 49
<212> TYPE: DNA
<213> ORGANISM: Artificial sequence
<220> FEATURE:
<223> OTHER INFORMATION: synthetic 582-20

<400> SEQUENCE: 127
acagcttagc ataatggcta ctgaggccgt ccaaacctat ttacagact        49

<210> SEQ ID NO 128
<211> LENGTH: 49
<212> TYPE: DNA
<213> ORGANISM: Artificial sequence
<220> FEATURE:
<223> OTHER INFORMATION: synthetic 582-21

<400> SEQUENCE: 128
acagcttacc ttaatggcta ctgacgccgt ccaaacctat ttacagact        49
```

<210> SEQ ID NO 129
<211> LENGTH: 49
<212> TYPE: DNA
<213> ORGANISM: Artificial sequence
<220> FEATURE:
<223> OTHER INFORMATION: synthetic 582-22

<400> SEQUENCE: 129
acagcttagc ataatggcta ccgacgctgt ccaaacctat ttacagact                49

<210> SEQ ID NO 130
<211> LENGTH: 49
<212> TYPE: DNA
<213> ORGANISM: Artificial sequence
<220> FEATURE:
<223> OTHER INFORMATION: synthetic 582-23

<400> SEQUENCE: 130
acagcttagc gtaatggcta ctggcgccgt ccaaacctat ttacagact                49

<210> SEQ ID NO 131
<211> LENGTH: 49
<212> TYPE: DNA
<213> ORGANISM: Artificial sequence
<220> FEATURE:
<223> OTHER INFORMATION: synthetic 582-24

<400> SEQUENCE: 131
acagcttagc atactggcta ctgacgccgc ccaaacctat ttacagact                49

<210> SEQ ID NO 132
<211> LENGTH: 49
<212> TYPE: DNA
<213> ORGANISM: Artificial sequence
<220> FEATURE:
<223> OTHER INFORMATION: synthetic 582-25

<400> SEQUENCE: 132
acagcttagc ataatggcta ctgacgccgt cctaacctat ttacagact                49

<210> SEQ ID NO 133
<211> LENGTH: 49
<212> TYPE: DNA
<213> ORGANISM: Artificial sequence
<220> FEATURE:
<223> OTHER INFORMATION: synthetic 582-26

<400> SEQUENCE: 133
acaggttagc ataatgccta ctgacgccgt ccaaacctat ttacagact                49

<210> SEQ ID NO 134
<211> LENGTH: 49
<212> TYPE: DNA
<213> ORGANISM: Artificial sequence
<220> FEATURE:
<223> OTHER INFORMATION: synthetic 582-27

<400> SEQUENCE: 134
acagcttagc ataattgcta ctgacgccgt tcaaacctat ttacagact                49

<210> SEQ ID NO 135
<211> LENGTH: 49
<212> TYPE: DNA
<213> ORGANISM: Artificial sequence
<220> FEATURE:
<223> OTHER INFORMATION: synthetic 582-28

<400> SEQUENCE: 135
acagcttagc ataaaggcta ctgacgccgt ccaaacctat ttacagact                49

<210> SEQ ID NO 136
<211> LENGTH: 49
<212> TYPE: DNA
<213> ORGANISM: Artificial sequence
<220> FEATURE:
<223> OTHER INFORMATION: synthetic 582-29

<400> SEQUENCE: 136
acagcttagc gtaatggcta ctgacgccgt ctaaacctat ttccagact                49

<210> SEQ ID NO 137
<211> LENGTH: 49
<212> TYPE: DNA
<213> ORGANISM: Artificial sequence
<220> FEATURE:
<223> OTHER INFORMATION: synthetic 582-30

<400> SEQUENCE: 137
acaggttagc ataatggcta ctgacgccgt ccaaacctat ttagagact                49

<210> SEQ ID NO 138
<211> LENGTH: 49
<212> TYPE: DNA
<213> ORGANISM: Artificial sequence
<220> FEATURE:
<223> OTHER INFORMATION: synthetic 582-31

<400> SEQUENCE: 138
acagggtagc gtaatggcta ctgacgccgt ccaaacctat ttacagact                49

<210> SEQ ID NO 139
<211> LENGTH: 49
<212> TYPE: DNA
<213> ORGANISM: Artificial sequence
<220> FEATURE:
<223> OTHER INFORMATION: synthetic 582-32

<400> SEQUENCE: 139
acagcgtagc ataatggcta ctgacgccgt tcaaacctat ttacagact                49

<210> SEQ ID NO 140
<211> LENGTH: 49
<212> TYPE: DNA
<213> ORGANISM: Artificial sequence
<220> FEATURE:
<223> OTHER INFORMATION: synthetic 582-33

<400> SEQUENCE: 140
acagcttagc ataatggcta ctgacgccgt ccaaactcat ttacagact                49

<210> SEQ ID NO 141
<211> LENGTH: 49
<212> TYPE: DNA
<213> ORGANISM: Artificial sequence
<220> FEATURE:
<223> OTHER INFORMATION: synthetic 582-34

<400> SEQUENCE: 141
acagcgtagc atagtggcta ctgacgccgt ccaaacctat ttacagact                49

<210> SEQ ID NO 142

```
<211> LENGTH: 49
<212> TYPE: DNA
<213> ORGANISM: Artificial sequence
<220> FEATURE:
<223> OTHER INFORMATION: synthetic 582-35

<400> SEQUENCE: 142
acagcttagt gtaatggcta ctgacgctgt ccaaacctat ttacagact          49

<210> SEQ ID NO 143
<211> LENGTH: 49
<212> TYPE: DNA
<213> ORGANISM: Artificial sequence
<220> FEATURE:
<223> OTHER INFORMATION: synthetic 582-36

<400> SEQUENCE: 143
acagcttagc ataatggcta ctgacggcgt tcaaacctat ttacagact          49

<210> SEQ ID NO 144
<211> LENGTH: 49
<212> TYPE: DNA
<213> ORGANISM: Artificial sequence
<220> FEATURE:
<223> OTHER INFORMATION: synthetic 582-37

<400> SEQUENCE: 144
acaggttagc ataatggcta ctgacgccgt ccaaacctat ttatagact          49

<210> SEQ ID NO 145
<211> LENGTH: 48
<212> TYPE: DNA
<213> ORGANISM: Artificial sequence
<220> FEATURE:
<223> OTHER INFORMATION: synthetic 582-38

<400> SEQUENCE: 145
acagcttagc ataatggcta ctgacgccgt ccaaacctat tgtcgact           48

<210> SEQ ID NO 146
<211> LENGTH: 48
<212> TYPE: DNA
<213> ORGANISM: Artificial sequence
<220> FEATURE:
<223> OTHER INFORMATION: synthetic 582-39

<400> SEQUENCE: 146
acagcttagc ataatggcta ctgacgccgt ccaaacctat ttacgact           48

<210> SEQ ID NO 147
<211> LENGTH: 48
<212> TYPE: DNA
<213> ORGANISM: Artificial sequence
<220> FEATURE:
<223> OTHER INFORMATION: synthetic 769-1

<400> SEQUENCE: 147
acaggtcagc ataatgtgct agtgcgcctt caaacctatt tagagact           48

<210> SEQ ID NO 148
<211> LENGTH: 48
<212> TYPE: DNA
<213> ORGANISM: Artificial sequence
<220> FEATURE:
<223> OTHER INFORMATION: synthetic 769-2

<400> SEQUENCE: 148
```

```
acaggtcagc ataatgtgct agtgcgccct caaacctatt tagagact        48
```

<210> SEQ ID NO 149
<211> LENGTH: 48
<212> TYPE: DNA
<213> ORGANISM: Artificial sequence
<220> FEATURE:
<223> OTHER INFORMATION: synthetic 769-3

<400> SEQUENCE: 149

```
acaggttagc ataatgtgct attgcgcctt caaacctatt tagagact        48
```

<210> SEQ ID NO 150
<211> LENGTH: 48
<212> TYPE: DNA
<213> ORGANISM: Artificial sequence
<220> FEATURE:
<223> OTHER INFORMATION: synthetic 769-4

<400> SEQUENCE: 150

```
acaggtcagc ataatgtgct agtgcgcatt caaacctatt tagagact        48
```

<210> SEQ ID NO 151
<211> LENGTH: 48
<212> TYPE: DNA
<213> ORGANISM: Artificial sequence
<220> FEATURE:
<223> OTHER INFORMATION: synthetic 769-5

<400> SEQUENCE: 151

```
acaggttagc ataatgtgct agtgcgcctt caaacctatt ttgagact        48
```

<210> SEQ ID NO 152
<211> LENGTH: 48
<212> TYPE: DNA
<213> ORGANISM: Artificial sequence
<220> FEATURE:
<223> OTHER INFORMATION: synthetic 769-6

<400> SEQUENCE: 152

```
acaggttatc ataatgtgct agtgcgcctt caaacctatt tagagact        48
```

<210> SEQ ID NO 153
<211> LENGTH: 48
<212> TYPE: DNA
<213> ORGANISM: Artificial sequence
<220> FEATURE:
<223> OTHER INFORMATION: synthetic 769-7

<400> SEQUENCE: 153

```
acaggttagc atgatgtgct agtgcgcctt caaacctatt tagagact        48
```

<210> SEQ ID NO 154
<211> LENGTH: 48
<212> TYPE: DNA
<213> ORGANISM: Artificial sequence
<220> FEATURE:
<223> OTHER INFORMATION: synthetic 769-8

<400> SEQUENCE: 154

```
acaggttagc ataatgggct agtgcgcctt caaacctatt tagagact        48
```

<210> SEQ ID NO 155
<211> LENGTH: 48
<212> TYPE: DNA

-continued

<213> ORGANISM: Artificial sequence
<220> FEATURE:
<223> OTHER INFORMATION: synthetic 769-9

<400> SEQUENCE: 155
acaggtcagc aaaatgtgca agtgcgcctt caaacctatt tagagact           48

<210> SEQ ID NO 156
<211> LENGTH: 48
<212> TYPE: DNA
<213> ORGANISM: Artificial sequence
<220> FEATURE:
<223> OTHER INFORMATION: synthetic 769-10

<400> SEQUENCE: 156
acaggtcagc ataatgtgct agtgcgcctt caaacctatc tggagact           48

<210> SEQ ID NO 157
<211> LENGTH: 48
<212> TYPE: DNA
<213> ORGANISM: Artificial sequence
<220> FEATURE:
<223> OTHER INFORMATION: synthetic 769-11

<400> SEQUENCE: 157
acagcttagc ataatgtgct agtgcgcctt caaacctatt tagagact           48

<210> SEQ ID NO 158
<211> LENGTH: 48
<212> TYPE: DNA
<213> ORGANISM: Artificial sequence
<220> FEATURE:
<223> OTHER INFORMATION: synthetic 769-12

<400> SEQUENCE: 158
acaggtcagc ataatgtgct agtgcgcctt caaacctatt tacagact           48

<210> SEQ ID NO 159
<211> LENGTH: 48
<212> TYPE: DNA
<213> ORGANISM: Artificial sequence
<220> FEATURE:
<223> OTHER INFORMATION: synthetic 769-13

<400> SEQUENCE: 159
acaggtcagc ataatgtgct agtgcgcctt caaacatatt tagagact           48

<210> SEQ ID NO 160
<211> LENGTH: 48
<212> TYPE: DNA
<213> ORGANISM: Artificial sequence
<220> FEATURE:
<223> OTHER INFORMATION: synthetic 769-14

<400> SEQUENCE: 160
acagggtagc ataatgtgct agtgcgcctt caaacctatt tagagact           48

<210> SEQ ID NO 161
<211> LENGTH: 48
<212> TYPE: DNA
<213> ORGANISM: Artificial sequence
<220> FEATURE:
<223> OTHER INFORMATION: synthetic 769-15

<400> SEQUENCE: 161
acaggttagc ataatgtgct agtgcgccct caaacctatt tagagact           48

<210> SEQ ID NO 162
<211> LENGTH: 48
<212> TYPE: DNA
<213> ORGANISM: Artificial sequence
<220> FEATURE:
<223> OTHER INFORMATION: synthetic 769-16

<400> SEQUENCE: 162
acaggttagc ataatgtgcc agtgcgcctt caaacctatt tagagact        48

<210> SEQ ID NO 163
<211> LENGTH: 48
<212> TYPE: DNA
<213> ORGANISM: Artificial sequence
<220> FEATURE:
<223> OTHER INFORMATION: synthetic 769-17

<400> SEQUENCE: 163
acaggtcagc ataatgggct agtgcgcctt caaacctatt tagagact        48

<210> SEQ ID NO 164
<211> LENGTH: 49
<212> TYPE: DNA
<213> ORGANISM: Artificial sequence
<220> FEATURE:
<223> OTHER INFORMATION: synthetic 795-1

<400> SEQUENCE: 164
acagcgaagc ataatggcta ctgacgccct caaaccctat ttgcagact        49

<210> SEQ ID NO 165
<211> LENGTH: 49
<212> TYPE: DNA
<213> ORGANISM: Artificial sequence
<220> FEATURE:
<223> OTHER INFORMATION: synthetic 795-2

<400> SEQUENCE: 165
acagcgaagc ataatggcta ctgacgccct caaaccctat ttacagact        49

<210> SEQ ID NO 166
<211> LENGTH: 49
<212> TYPE: DNA
<213> ORGANISM: Artificial sequence
<220> FEATURE:
<223> OTHER INFORMATION: synthetic 795-3

<400> SEQUENCE: 166
acagcgaagc ataatggctt ctgacgccct caaaccctat ttgcagact        49

<210> SEQ ID NO 167
<211> LENGTH: 49
<212> TYPE: DNA
<213> ORGANISM: Artificial sequence
<220> FEATURE:
<223> OTHER INFORMATION: synthetic 795-4

<400> SEQUENCE: 167
acagccaagc atactggcta ctgacgccct caaaccctat ttgcagact        49

<210> SEQ ID NO 168
<211> LENGTH: 49
<212> TYPE: DNA
<213> ORGANISM: Artificial sequence
<220> FEATURE:

<223> OTHER INFORMATION: synthetic 795-5

<400> SEQUENCE: 168
acagcgaagc ataatggcta ctgacgcccg caaaccctat ttgcagact                49

<210> SEQ ID NO 169
<211> LENGTH: 49
<212> TYPE: DNA
<213> ORGANISM: Artificial sequence
<220> FEATURE:
<223> OTHER INFORMATION: synthetic 795-6

<400> SEQUENCE: 169
acagcgaagc ataatggcta ctgacggcct caaaccctat ttgcagact                49

<210> SEQ ID NO 170
<211> LENGTH: 49
<212> TYPE: DNA
<213> ORGANISM: Artificial sequence
<220> FEATURE:
<223> OTHER INFORMATION: synthetic 795-7

<400> SEQUENCE: 170
acagcgaggc ataatggcta ctgacgccct caaaccctat ttgcagact                49

<210> SEQ ID NO 171
<211> LENGTH: 49
<212> TYPE: DNA
<213> ORGANISM: Artificial sequence
<220> FEATURE:
<223> OTHER INFORMATION: synthetic 795-8

<400> SEQUENCE: 171
acagcgaagc ataatggcta ctgacgcctt caaaccctat ttgcagact                49

<210> SEQ ID NO 172
<211> LENGTH: 49
<212> TYPE: DNA
<213> ORGANISM: Artificial sequence
<220> FEATURE:
<223> OTHER INFORMATION: synthetic 795-9

<400> SEQUENCE: 172
acagcgaagc ataatggcta cagacgccct caaaacctat ttgcagact                49

<210> SEQ ID NO 173
<211> LENGTH: 48
<212> TYPE: DNA
<213> ORGANISM: Artificial sequence
<220> FEATURE:
<223> OTHER INFORMATION: synthetic 795-10

<400> SEQUENCE: 173
acagcgaagc ataatggcta ctgacgccct caaaccctat ttgagact                 48

<210> SEQ ID NO 174
<211> LENGTH: 48
<212> TYPE: DNA
<213> ORGANISM: Artificial sequence
<220> FEATURE:
<223> OTHER INFORMATION: synthetic 795-11

<400> SEQUENCE: 174
acagcgaagc ataatggcta ctgacgccct caaaccctat tgtcgact                 48

<210> SEQ ID NO 175
<211> LENGTH: 49
<212> TYPE: DNA
<213> ORGANISM: Artificial sequence
<220> FEATURE:
<223> OTHER INFORMATION: synthetic 795-12

<400> SEQUENCE: 175
acagccaagc ataatggcta ctgacgccct caaaccctat ttgcagact                49

<210> SEQ ID NO 176
<211> LENGTH: 49
<212> TYPE: DNA
<213> ORGANISM: Artificial sequence
<220> FEATURE:
<223> OTHER INFORMATION: synthetic 795-13

<400> SEQUENCE: 176
acagcgaagc ataatggcta ctgacgccct caaaccctat ttggcgact                49

<210> SEQ ID NO 177
<211> LENGTH: 49
<212> TYPE: DNA
<213> ORGANISM: Artificial sequence
<220> FEATURE:
<223> OTHER INFORMATION: synthetic 795-14

<400> SEQUENCE: 177
acagcgaagc ataatgtcta ctgacgccct caaaccctat ttgcagact                49

<210> SEQ ID NO 178
<211> LENGTH: 49
<212> TYPE: DNA
<213> ORGANISM: Artificial sequence
<220> FEATURE:
<223> OTHER INFORMATION: synthetic 795-15

<400> SEQUENCE: 178
acagcgaagc ataatggcta ctgacgccgt caaaccctat ttgtagact                49

<210> SEQ ID NO 179
<211> LENGTH: 49
<212> TYPE: DNA
<213> ORGANISM: Artificial sequence
<220> FEATURE:
<223> OTHER INFORMATION: synthetic 795-16

<400> SEQUENCE: 179
acagcgaagc ataatggcta ctgacgccct caaaccttat ttgcagact                49

<210> SEQ ID NO 180
<211> LENGTH: 48
<212> TYPE: DNA
<213> ORGANISM: Artificial sequence
<220> FEATURE:
<223> OTHER INFORMATION: synthetic 795-17

<400> SEQUENCE: 180
acaggtagca taatggctac tgacgccctc aaaccctatt tgcagact                 48

<210> SEQ ID NO 181
<211> LENGTH: 49
<212> TYPE: DNA
<213> ORGANISM: Artificial sequence
<220> FEATURE:
<223> OTHER INFORMATION: synthetic 795-18

```
<400> SEQUENCE: 181
acagcgaagc ataatggcta ctgacgccct caaaccctat ttctagact                49

<210> SEQ ID NO 182
<211> LENGTH: 49
<212> TYPE: DNA
<213> ORGANISM: Artificial sequence
<220> FEATURE:
<223> OTHER INFORMATION: synthetic 795-19

<400> SEQUENCE: 182
acagcgaagc ataatggcta ctgacgccct caaaccctat ttgtagact                49

<210> SEQ ID NO 183
<211> LENGTH: 48
<212> TYPE: DNA
<213> ORGANISM: Artificial sequence
<220> FEATURE:
<223> OTHER INFORMATION: synthetic 935-1

<400> SEQUENCE: 183
acagggtagc ataatgggct acttgacgcc ttcacctatt tgtagact                 48

<210> SEQ ID NO 184
<211> LENGTH: 47
<212> TYPE: DNA
<213> ORGANISM: Artificial sequence
<220> FEATURE:
<223> OTHER INFORMATION: synthetic 935-2

<400> SEQUENCE: 184
acagggtagc ataatgggct acttgacgcc ttcacctatt tgagact                  47

<210> SEQ ID NO 185
<211> LENGTH: 48
<212> TYPE: DNA
<213> ORGANISM: Artificial sequence
<220> FEATURE:
<223> OTHER INFORMATION: synthetic 935-3

<400> SEQUENCE: 185
acagggtagc ataatgggct actttacgcc ttcacctatt tgtagact                 48

<210> SEQ ID NO 186
<211> LENGTH: 48
<212> TYPE: DNA
<213> ORGANISM: Artificial sequence
<220> FEATURE:
<223> OTHER INFORMATION: synthetic 935-4

<400> SEQUENCE: 186
acagggtagc ataatgggct acttgacgcc ttcacctatt tctagact                 48

<210> SEQ ID NO 187
<211> LENGTH: 48
<212> TYPE: DNA
<213> ORGANISM: Artificial sequence
<220> FEATURE:
<223> OTHER INFORMATION: synthetic 935-5

<400> SEQUENCE: 187
acagggtagc ataatgggct acttgacgcc ttcacctatt tggagact                 48

<210> SEQ ID NO 188
<211> LENGTH: 48
```

```
<212> TYPE: DNA
<213> ORGANISM: Artificial sequence
<220> FEATURE:
<223> OTHER INFORMATION: synthetic 935-6

<400> SEQUENCE: 188
acagggtagc atagtgggct acttgacgcc ttcacctatt tgtagact       48

<210> SEQ ID NO 189
<211> LENGTH: 48
<212> TYPE: DNA
<213> ORGANISM: Artificial sequence
<220> FEATURE:
<223> OTHER INFORMATION: synthetic 935-7

<400> SEQUENCE: 189
acagggtagc atgatgggct acttgacgcc ttcacctatt tgtagact       48

<210> SEQ ID NO 190
<211> LENGTH: 48
<212> TYPE: DNA
<213> ORGANISM: Artificial sequence
<220> FEATURE:
<223> OTHER INFORMATION: synthetic 935-8

<400> SEQUENCE: 190
acagggtagc ataatgggct acttgacgcc ttcacctatt agtagact       48

<210> SEQ ID NO 191
<211> LENGTH: 48
<212> TYPE: DNA
<213> ORGANISM: Artificial sequence
<220> FEATURE:
<223> OTHER INFORMATION: synthetic 935-9

<400> SEQUENCE: 191
acagggtagc ataatgggct atttgacgcc ttcacctatt tgtagact       48

<210> SEQ ID NO 192
<211> LENGTH: 48
<212> TYPE: DNA
<213> ORGANISM: Artificial sequence
<220> FEATURE:
<223> OTHER INFORMATION: synthetic 935-10

<400> SEQUENCE: 192
acagggtagc ataatgggct acttgccgcc ttcacctatt tgtagact       48

<210> SEQ ID NO 193
<211> LENGTH: 48
<212> TYPE: DNA
<213> ORGANISM: Artificial sequence
<220> FEATURE:
<223> OTHER INFORMATION: synthetic 935-11

<400> SEQUENCE: 193
acagtgtagc ataattggct acttgacgcc ttcacctatt tgtagact       48

<210> SEQ ID NO 194
<211> LENGTH: 48
<212> TYPE: DNA
<213> ORGANISM: Artificial sequence
<220> FEATURE:
<223> OTHER INFORMATION: synthetic 935-12

<400> SEQUENCE: 194
```
acagggtagc ataatgggct acttgacgct tcaccttttt tgtagact    48

<210> SEQ ID NO 195
<211> LENGTH: 48
<212> TYPE: DNA
<213> ORGANISM: Artificial sequence
<220> FEATURE:
<223> OTHER INFORMATION: synthetic 935-13

<400> SEQUENCE: 195
acagggtagc ataaggggct acttgacgcc ttcacctatt tgtagact    48

<210> SEQ ID NO 196
<211> LENGTH: 48
<212> TYPE: DNA
<213> ORGANISM: Artificial sequence
<220> FEATURE:
<223> OTHER INFORMATION: synthetic 935-14

<400> SEQUENCE: 196
acagggtagc ataatggact acttgacgcc tccacctatt tgtagact    48

<210> SEQ ID NO 197
<211> LENGTH: 48
<212> TYPE: DNA
<213> ORGANISM: Artificial sequence
<220> FEATURE:
<223> OTHER INFORMATION: synthetic 935-15

<400> SEQUENCE: 197
acagggtagc ataatgggct acttgtcgcc ttcacctatt tgtagact    48

<210> SEQ ID NO 198
<211> LENGTH: 49
<212> TYPE: DNA
<213> ORGANISM: Artificial sequence
<220> FEATURE:
<223> OTHER INFORMATION: synthetic 946-1

<400> SEQUENCE: 198
acagcgtagc ataatgggct gcagacgccg tcaaacctat ttgcagact    49

<210> SEQ ID NO 199
<211> LENGTH: 49
<212> TYPE: DNA
<213> ORGANISM: Artificial sequence
<220> FEATURE:
<223> OTHER INFORMATION: synthetic 946-2

<400> SEQUENCE: 199
acagcgtagc ataatgggct gcagacgcag tcaaacctat ttgcagact    49

<210> SEQ ID NO 200
<211> LENGTH: 48
<212> TYPE: DNA
<213> ORGANISM: Artificial sequence
<220> FEATURE:
<223> OTHER INFORMATION: synthetic 946-3

<400> SEQUENCE: 200
acatgtagca taatgggcta ctgacgccgt caaacctatt tgcagact    48

<210> SEQ ID NO 201
<211> LENGTH: 49
<212> TYPE: DNA
<213> ORGANISM: Artificial sequence

```
<220> FEATURE:
<223> OTHER INFORMATION: synthetic 946-4

<400> SEQUENCE: 201
acagcgtagc atagtgggct gcagacgccg tcaaacctat ttgcagact        49

<210> SEQ ID NO 202
<211> LENGTH: 49
<212> TYPE: DNA
<213> ORGANISM: Artificial sequence
<220> FEATURE:
<223> OTHER INFORMATION: synthetic 946-5

<400> SEQUENCE: 202
acagtgtagc ataatgggct gcagacgcct tcaaacctat ttggagact        49

<210> SEQ ID NO 203
<211> LENGTH: 49
<212> TYPE: DNA
<213> ORGANISM: Artificial sequence
<220> FEATURE:
<223> OTHER INFORMATION: synthetic 946-6

<400> SEQUENCE: 203
acagtgtagc ataatgggct gctgacgccg tcaaacctat ttgaagact        49

<210> SEQ ID NO 204
<211> LENGTH: 49
<212> TYPE: DNA
<213> ORGANISM: Artificial sequence
<220> FEATURE:
<223> OTHER INFORMATION: synthetic 946-7

<400> SEQUENCE: 204
acagcgtagc ataatgggct acaggcgccg tcaaacctat ttgcagact        49

<210> SEQ ID NO 205
<211> LENGTH: 49
<212> TYPE: DNA
<213> ORGANISM: Artificial sequence
<220> FEATURE:
<223> OTHER INFORMATION: synthetic 946-8

<400> SEQUENCE: 205
acagcgtagc ataatgggct actggcgccg tcaaacctat ttgcagact        49

<210> SEQ ID NO 206
<211> LENGTH: 48
<212> TYPE: DNA
<213> ORGANISM: Artificial sequence
<220> FEATURE:
<223> OTHER INFORMATION: synthetic 946-9

<400> SEQUENCE: 206
acagcgtagc ataatgggct gcagacgccg tcaaacctat ttgagact         48

<210> SEQ ID NO 207
<211> LENGTH: 48
<212> TYPE: DNA
<213> ORGANISM: Artificial sequence
<220> FEATURE:
<223> OTHER INFORMATION: synthetic 946-10

<400> SEQUENCE: 207
acaggtagca taatgggctg cagacgccgt caaacctatt tgcagact         48
```

```
<210> SEQ ID NO 208
<211> LENGTH: 48
<212> TYPE: DNA
<213> ORGANISM: Artificial sequence
<220> FEATURE:
<223> OTHER INFORMATION: synthetic 946-11

<400> SEQUENCE: 208
acaggtagca taatgggctg ctgacgccgt caaacctatt tacagact          48

<210> SEQ ID NO 209
<211> LENGTH: 49
<212> TYPE: DNA
<213> ORGANISM: Artificial sequence
<220> FEATURE:
<223> OTHER INFORMATION: synthetic 946-12

<400> SEQUENCE: 209
acagcgtagc atattgggct gcagacgccg tcaaacctat ttgcagact          49

<210> SEQ ID NO 210
<211> LENGTH: 49
<212> TYPE: DNA
<213> ORGANISM: Artificial sequence
<220> FEATURE:
<223> OTHER INFORMATION: synthetic 946-13

<400> SEQUENCE: 210
acagcgtagc ataatgggct gcagacgcct tcaaacctat ttggagact          49

<210> SEQ ID NO 211
<211> LENGTH: 48
<212> TYPE: DNA
<213> ORGANISM: Artificial sequence
<220> FEATURE:
<223> OTHER INFORMATION: synthetic 946-14

<400> SEQUENCE: 211
acagtgtagc ataatgggct gcagacgccg tcaaacctat ttgagact          48

<210> SEQ ID NO 212
<211> LENGTH: 49
<212> TYPE: DNA
<213> ORGANISM: Artificial sequence
<220> FEATURE:
<223> OTHER INFORMATION: synthetic 946-15

<400> SEQUENCE: 212
acagcgtagc ataatgggct gctgacgccg tcaaacctat ttggagact          49

<210> SEQ ID NO 213
<211> LENGTH: 49
<212> TYPE: DNA
<213> ORGANISM: Artificial sequence
<220> FEATURE:
<223> OTHER INFORMATION: synthetic 946-16

<400> SEQUENCE: 213
acagcgtagc ataatgggct gcagacgccg tcaaacctat ttacagact          49

<210> SEQ ID NO 214
<211> LENGTH: 49
<212> TYPE: DNA
<213> ORGANISM: Artificial sequence
<220> FEATURE:
<223> OTHER INFORMATION: synthetic 946-17
```

<400> SEQUENCE: 214
acagcgtagc ataatgggct gctgacgccg tcaaacctat ttgcagact        49

<210> SEQ ID NO 215
<211> LENGTH: 49
<212> TYPE: DNA
<213> ORGANISM: Artificial sequence
<220> FEATURE:
<223> OTHER INFORMATION: synthetic 946-18

<400> SEQUENCE: 215
acagggtagc ataatgggct gcagacgccg tcaaacctat ttggagact        49

<210> SEQ ID NO 216
<211> LENGTH: 49
<212> TYPE: DNA
<213> ORGANISM: Artificial sequence
<220> FEATURE:
<223> OTHER INFORMATION: synthetic 946-19

<400> SEQUENCE: 216
acagcgtagc ataatgggct acagacgccg tcaaacctat ttgcagact        49

<210> SEQ ID NO 217
<211> LENGTH: 49
<212> TYPE: DNA
<213> ORGANISM: Artificial sequence
<220> FEATURE:
<223> OTHER INFORMATION: synthetic 946-20

<400> SEQUENCE: 217
acagcgtcgc ataatgggct gcagacgccg tcaaatctat ttgcagact        49

<210> SEQ ID NO 218
<211> LENGTH: 49
<212> TYPE: DNA
<213> ORGANISM: Artificial sequence
<220> FEATURE:
<223> OTHER INFORMATION: synthetic 946-21

<400> SEQUENCE: 218
acagcgtagc ataatgggct tcagacgccg tcaaacctat ttgcagact        49

<210> SEQ ID NO 219
<211> LENGTH: 48
<212> TYPE: DNA
<213> ORGANISM: Artificial sequence
<220> FEATURE:
<223> OTHER INFORMATION: synthetic 946-22

<400> SEQUENCE: 219
acatgtagca taatgggctg cagacgccgt caaacctatt tggagact         48

<210> SEQ ID NO 220
<211> LENGTH: 47
<212> TYPE: DNA
<213> ORGANISM: Artificial sequence
<220> FEATURE:
<223> OTHER INFORMATION: synthetic 961-1

<400> SEQUENCE: 220
acaccgtagc ataatgggct actgccgccg tcgaccttt ggagact           47

<210> SEQ ID NO 221

```
<211> LENGTH: 46
<212> TYPE: DNA
<213> ORGANISM: Artificial sequence
<220> FEATURE:
<223> OTHER INFORMATION: synthetic 996-1

<400> SEQUENCE: 221
acagggtagc ataatggctt aggacgcctt caaacctatc aagact        46

<210> SEQ ID NO 222
<211> LENGTH: 49
<212> TYPE: DNA
<213> ORGANISM: Artificial sequence
<220> FEATURE:
<223> OTHER INFORMATION: synthetic Family 582 Consensus
<220> FEATURE:
<221> NAME/KEY: misc_feature
<222> LOCATION: (5)..(5)
<223> OTHER INFORMATION: n at position 5 can be C, G, or no nucleotide
<220> FEATURE:
<221> NAME/KEY: misc_feature
<222> LOCATION: (6)..(6)
<223> OTHER INFORMATION: n at position 6 can be A, C, G, T, or no
      nucleotide
<220> FEATURE:
<221> NAME/KEY: misc_feature
<222> LOCATION: (45)..(45)
<223> OTHER INFORMATION: n at position 45 can be A or no nucleotide

<400> SEQUENCE: 222
acagnntasb dtwvdksmta cygrsgsbgy yywaamyhat kbhbngact     49

<210> SEQ ID NO 223
<211> LENGTH: 48
<212> TYPE: DNA
<213> ORGANISM: Artificial sequence
<220> FEATURE:
<223> OTHER INFORMATION: synthetic Family 769 Consensus

<400> SEQUENCE: 223
acagskyakc awratgkgch aktgcgcmyt caaacmtaty tdsagact     48

<210> SEQ ID NO 224
<211> LENGTH: 49
<212> TYPE: DNA
<213> ORGANISM: Artificial sequence
<220> FEATURE:
<223> OTHER INFORMATION: synthetic Family 795 Consensus
<220> FEATURE:
<221> NAME/KEY: misc_feature
<222> LOCATION: (5)..(5)
<223> OTHER INFORMATION: n at position 5 can be C or no nucleotide
<220> FEATURE:
<221> NAME/KEY: misc_feature
<222> LOCATION: (40)..(40)
<223> OTHER INFORMATION: n at position 40 can be T or no nucleotide
<220> FEATURE:
<221> NAME/KEY: misc_feature
<222> LOCATION: (44)..(44)
<223> OTHER INFORMATION: n at position 44 can be C, G, T, or no
      nucleotide

<400> SEQUENCE: 224
acagnswrgc atamtgkctw cwgacgscbk caaamcytan ttvnmgact    49

<210> SEQ ID NO 225
<211> LENGTH: 48
<212> TYPE: DNA
<213> ORGANISM: Artificial sequence
<220> FEATURE:
<223> OTHER INFORMATION: synthetic Family 935 Consensus
```

```
<220> FEATURE:
<221> NAME/KEY: misc_feature
<222> LOCATION: (43)..(43)
<223> OTHER INFORMATION: n at position 43 can be G, T, or no nucleotide

<400> SEQUENCE: 225
acagkgtcgc atrrkkgrct ayttkhcgcy tycacctwtt wsnagact                        48

<210> SEQ ID NO 226
<211> LENGTH: 49
<212> TYPE: DNA
<213> ORGANISM: Artificial sequence
<220> FEATURE:
<223> OTHER INFORMATION: synthetic Family 946 Consensus
<220> FEATURE:
<221> NAME/KEY: misc_feature
<222> LOCATION: (4)..(4)
<223> OTHER INFORMATION: n at position 4 can be G or no nucleotide
<220> FEATURE:
<221> NAME/KEY: misc_feature
<222> LOCATION: (5)..(5)
<223> OTHER INFORMATION: n at position 5 can be C, G, T, or no
      nucleotide
<220> FEATURE:
<221> NAME/KEY: misc_feature
<222> LOCATION: (44)..(44)
<223> OTHER INFORMATION: n at position 44 can be A, C, G, or no
      nucleotide

<400> SEQUENCE: 226
acanngtmgc atadtgggct dcwgrcgcmk tcaaayctat ttrnagact                      49

<210> SEQ ID NO 227
<211> LENGTH: 11
<212> TYPE: PRT
<213> ORGANISM: Artificial sequence
<220> FEATURE:
<223> OTHER INFORMATION: synthetic Membrane-targeting domain of
      Src-Flag-Vpx

<400> SEQUENCE: 227

Met Gly Ser Ser Lys Ser Lys Pro Lys Asp Pro
1               5                   10

<210> SEQ ID NO 228
<211> LENGTH: 8
<212> TYPE: PRT
<213> ORGANISM: Artificial sequence
<220> FEATURE:
<223> OTHER INFORMATION: synthetic Viral protease cleavage domain

<400> SEQUENCE: 228

Lys Ala Arg Val Leu Ala Glu Ala
1               5

<210> SEQ ID NO 229
<211> LENGTH: 458
<212> TYPE: PRT
<213> ORGANISM: Homo sapiens

<400> SEQUENCE: 229

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
            35                  40                  45
```

-continued

```
Asn Gly Ser Gln His Ser Leu Thr Cys Ala Phe Glu Asp Pro Asp Val
 50                  55                  60
Asn Ile Thr Asn Leu Glu Phe Glu Ile Cys Gly Ala Leu Val Glu Val
 65                  70                  75                  80
Lys Cys Leu Asn Phe Arg Lys Leu Gln Glu Ile Tyr Phe Ile Glu Thr
                 85                  90                  95
Lys Lys Phe Leu Leu Ile Gly Lys Ser Asn Ile Cys Val Lys Val Gly
                100                 105                 110
Glu Lys Ser Leu Thr Cys Lys Lys Ile Asp Leu Thr Thr Ile Val Lys
                115                 120                 125
Pro Glu Ala Pro Phe Asp Leu Ser Val Val Tyr Arg Glu Gly Ala Asn
130                 135                 140
Asp Phe Val Val Thr Phe Asn Thr Ser His Leu Gln Lys Lys Tyr Val
145                 150                 155                 160
Lys Val Leu Met His Asp Val Ala Tyr Arg Gln Glu Lys Asp Glu Asn
                165                 170                 175
Lys Trp Thr His Val Asn Leu Ser Ser Thr Lys Leu Thr Leu Leu Gln
                180                 185                 190
Arg Lys Leu Gln Pro Ala Ala Met Tyr Glu Ile Lys Val Arg Ser Ile
                195                 200                 205
Pro Asp His Tyr Phe Lys Gly Phe Trp Ser Glu Trp Ser Pro Ser Tyr
210                 215                 220
Tyr Phe Arg Thr Pro Glu Ile Asn Asn Ser Ser Gly Glu Met Asp Pro
225                 230                 235                 240
Ile Leu Leu Thr Ile Ser Ile Leu Ser Phe Phe Ser Val Ala Leu Leu
                245                 250                 255
Val Ile Leu Ala Cys Val Leu Trp Lys Lys Arg Ile Lys Pro Ile Val
                260                 265                 270
Trp Pro Ser Leu Pro Asp His Lys Lys Thr Leu Glu His Leu Cys Lys
                275                 280                 285
Lys Pro Arg Lys Asn Leu Asn Val Ser Phe Asn Pro Glu Ser Phe Leu
                290                 295                 300
Asp Cys Gln Ile His Arg Val Asp Asp Ile Gln Ala Arg Asp Glu Val
305                 310                 315                 320
Glu Gly Phe Leu Gln Asp Thr Phe Pro Gln Gln Leu Glu Glu Ser Glu
                325                 330                 335
Lys Gln Arg Leu Gly Gly Asp Val Gln Ser Pro Asn Cys Pro Ser Glu
                340                 345                 350
Asp Val Val Ile Thr Pro Glu Ser Phe Gly Arg Asp Ser Ser Leu Thr
                355                 360                 365
Cys Leu Ala Gly Asn Val Ser Ala Cys Asp Ala Pro Ile Leu Ser Ser
370                 375                 380
Ser Arg Ser Leu Asp Cys Arg Glu Ser Gly Lys Asn Gly Pro His Val
385                 390                 395                 400
Tyr Gln Asp Leu Leu Leu Ser Leu Gly Thr Thr Asn Ser Thr Leu Pro
                405                 410                 415
Pro Pro Phe Ser Leu Gln Ser Gly Ile Leu Thr Leu Asn Pro Val Ala
                420                 425                 430
Gln Gly Gln Pro Ile Leu Thr Ser Leu Gly Ser Asn Gln Glu Glu Ala
                435                 440                 445
Tyr Val Thr Met Ser Ser Phe Tyr Gln Asn
450                 455
```

```
<210> SEQ ID NO 230
<211> LENGTH: 723
<212> TYPE: PRT
<213> ORGANISM: Artificial sequence
<220> FEATURE:
<223> OTHER INFORMATION: synthetic GFP - linker - P2A -IL7Ra IncPPCL
      codon(exceptP2A) and splice optimized

<400> SEQUENCE: 230

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
    210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Thr Ile Leu Gly Thr Thr Phe Gly Met Val Phe
            260                 265                 270

Ser Leu Leu Gln Val Val Ser Gly Glu Ser Gly Tyr Ala Gln Asn Gly
        275                 280                 285

Asp Leu Glu Asp Ala Glu Leu Asp Asp Tyr Ser Phe Ser Cys Tyr Ser
    290                 295                 300

Gln Leu Glu Val Asn Gly Ser Gln His Ser Leu Thr Cys Ala Phe Glu
305                 310                 315                 320

Asp Pro Asp Val Asn Ile Thr Asn Leu Glu Phe Glu Ile Cys Gly Ala
                325                 330                 335

Leu Val Glu Val Lys Cys Leu Asn Phe Arg Lys Leu Gln Glu Ile Tyr
            340                 345                 350

Phe Ile Glu Thr Lys Lys Phe Leu Leu Ile Gly Lys Ser Asn Ile Cys
        355                 360                 365
```

```
Val Lys Val Gly Glu Lys Ser Leu Thr Cys Lys Lys Ile Asp Leu Thr
370                 375                 380

Thr Ile Val Lys Pro Glu Ala Pro Phe Asp Leu Ser Val Val Tyr Arg
385                 390                 395                 400

Glu Gly Ala Asn Asp Phe Val Val Thr Phe Asn Thr Ser His Leu Gln
                405                 410                 415

Lys Lys Tyr Val Lys Val Leu Met His Asp Val Ala Tyr Arg Gln Glu
                420                 425                 430

Lys Asp Glu Asn Lys Trp Thr His Val Asn Leu Ser Ser Thr Lys Leu
            435                 440                 445

Thr Leu Leu Gln Arg Lys Leu Gln Pro Ala Ala Met Tyr Glu Ile Lys
450                 455                 460

Val Arg Ser Ile Pro Asp His Tyr Phe Lys Gly Phe Trp Ser Glu Trp
465                 470                 475                 480

Ser Pro Ser Tyr Tyr Phe Arg Thr Pro Glu Ile Asn Asn Ser Ser Gly
                485                 490                 495

Glu Met Asp Pro Ile Leu Leu Pro Pro Cys Leu Thr Ile Ser Ile Leu
                500                 505                 510

Ser Phe Phe Ser Val Ala Leu Leu Val Ile Leu Ala Cys Val Leu Trp
            515                 520                 525

Lys Lys Arg Ile Lys Pro Ile Val Trp Pro Ser Leu Pro Asp His Lys
530                 535                 540

Lys Thr Leu Glu His Leu Cys Lys Lys Pro Arg Lys Asn Leu Asn Val
545                 550                 555                 560

Ser Phe Asn Pro Glu Ser Phe Leu Asp Cys Gln Ile His Arg Val Asp
                565                 570                 575

Asp Ile Gln Ala Arg Asp Glu Val Glu Gly Phe Leu Gln Asp Thr Phe
            580                 585                 590

Pro Gln Gln Leu Glu Glu Ser Glu Lys Gln Arg Leu Gly Gly Asp Val
                595                 600                 605

Gln Ser Pro Asn Cys Pro Ser Glu Asp Val Val Ile Thr Pro Glu Ser
610                 615                 620

Phe Gly Arg Asp Ser Ser Leu Thr Cys Leu Ala Gly Asn Val Ser Ala
625                 630                 635                 640

Cys Asp Ala Pro Ile Leu Ser Ser Ser Arg Ser Leu Asp Cys Arg Glu
                645                 650                 655

Ser Gly Lys Asn Gly Pro His Val Tyr Gln Asp Leu Leu Leu Ser Leu
                660                 665                 670

Gly Thr Thr Asn Ser Thr Leu Pro Pro Pro Phe Ser Leu Gln Ser Gly
            675                 680                 685

Ile Leu Thr Leu Asn Pro Val Ala Gln Gly Gln Pro Ile Leu Thr Ser
690                 695                 700

Leu Gly Ser Asn Gln Glu Glu Ala Tyr Val Thr Met Ser Ser Phe Tyr
705                 710                 715                 720

Gln Asn Gln
```

<210> SEQ ID NO 231
<211> LENGTH: 733
<212> TYPE: PRT
<213> ORGANISM: Artificial sequence
<220> FEATURE:
<223> OTHER INFORMATION: synthetic GFP - linker - P2A - Myc Tag - IL7Ra
      IncPPCL codon(exceptP2A) and splice optimized

<400> SEQUENCE: 231

```
Met Ser Gly Gly Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
            35                  40                  45

Thr Thr Gly Lys Leu Pro Val Pro Trp Pro Thr Leu Val Thr Thr Leu
        50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
                100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
        130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
                180                 185                 190

Val Leu Ile Pro Ile Asn His Tyr Leu Ser Thr Gln Thr Lys Ile Ser
            195                 200                 205

Lys Asp Arg Asn Glu Ala Arg Asp His Met Val Leu Leu Glu Ser Phe
210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Thr Ile Leu Gly Thr Thr Phe Gly Met Val Phe
                260                 265                 270

Ser Leu Leu Gln Val Val Ser Gly Glu Gln Lys Leu Ile Ser Glu Glu
        275                 280                 285

Asp Leu Glu Ser Gly Tyr Ala Gln Asn Gly Asp Leu Glu Asp Ala Glu
        290                 295                 300

Leu Asp Asp Tyr Ser Phe Ser Cys Tyr Ser Gln Leu Glu Val Asn Gly
305                 310                 315                 320

Ser Gln His Ser Leu Thr Cys Ala Phe Glu Asp Pro Asp Val Asn Ile
                325                 330                 335

Thr Asn Leu Glu Phe Glu Ile Cys Gly Ala Leu Val Glu Val Lys Cys
                340                 345                 350

Leu Asn Phe Arg Lys Leu Gln Glu Ile Tyr Phe Ile Glu Thr Lys Lys
                355                 360                 365

Phe Leu Leu Ile Gly Lys Ser Asn Ile Cys Val Lys Val Gly Glu Lys
        370                 375                 380

Ser Leu Thr Cys Lys Lys Ile Asp Leu Thr Thr Ile Val Lys Pro Glu
385                 390                 395                 400

Ala Pro Phe Asp Leu Ser Val Val Tyr Arg Glu Gly Ala Asn Asp Phe
                405                 410                 415

Val Val Thr Phe Asn Thr Ser His Leu Gln Lys Lys Tyr Val Lys Val
```

```
                420             425             430
Leu Met His Asp Val Ala Tyr Arg Gln Glu Lys Asp Glu Asn Lys Trp
            435                 440                 445

Thr His Val Asn Leu Ser Ser Thr Lys Leu Thr Leu Leu Gln Arg Lys
    450                 455                 460

Leu Gln Pro Ala Ala Met Tyr Glu Ile Lys Val Arg Ser Ile Pro Asp
465                 470                 475                 480

His Tyr Phe Lys Gly Phe Trp Ser Glu Trp Ser Pro Ser Tyr Tyr Phe
                485                 490                 495

Arg Thr Pro Glu Ile Asn Asn Ser Ser Gly Glu Met Asp Pro Ile Leu
            500                 505                 510

Leu Pro Pro Cys Leu Thr Ile Ser Ile Leu Ser Phe Phe Ser Val Ala
                515                 520                 525

Leu Leu Val Ile Leu Ala Cys Val Leu Trp Lys Lys Arg Ile Lys Pro
            530                 535                 540

Ile Val Trp Pro Ser Leu Pro Asp His Lys Lys Thr Leu Glu His Leu
545                 550                 555                 560

Cys Lys Lys Pro Arg Lys Asn Leu Asn Val Ser Phe Asn Pro Glu Ser
                565                 570                 575

Phe Leu Asp Cys Gln Ile His Arg Val Asp Asp Ile Gln Ala Arg Asp
                580                 585                 590

Glu Val Glu Gly Phe Leu Gln Asp Thr Phe Pro Gln Gln Leu Glu Glu
            595                 600                 605

Ser Glu Lys Gln Arg Leu Gly Gly Asp Val Gln Ser Pro Asn Cys Pro
            610                 615                 620

Ser Glu Asp Val Val Ile Thr Pro Glu Ser Phe Gly Arg Asp Ser Ser
625                 630                 635                 640

Leu Thr Cys Leu Ala Gly Asn Val Ser Ala Cys Asp Ala Pro Ile Leu
                645                 650                 655

Ser Ser Ser Arg Ser Leu Asp Cys Arg Glu Ser Gly Lys Asn Gly Pro
                660                 665                 670

His Val Tyr Gln Asp Leu Leu Leu Ser Leu Gly Thr Thr Asn Ser Thr
                675                 680                 685

Leu Pro Pro Pro Phe Ser Leu Gln Ser Gly Ile Leu Thr Leu Asn Pro
            690                 695                 700

Val Ala Gln Gly Gln Pro Ile Leu Thr Ser Leu Gly Ser Asn Gln Glu
705                 710                 715                 720

Glu Ala Tyr Val Thr Met Ser Ser Phe Tyr Gln Asn Gln
                725                 730

<210> SEQ ID NO 232
<211> LENGTH: 572
<212> TYPE: PRT
<213> ORGANISM: Artificial sequence
<220> FEATURE:
<223> OTHER INFORMATION: synthetic GFP - linker - P2A - IL7RaSP - Myc
      Tag - IL7RaIncPPCL C-terminal truncation codon(exceptP2A) and
      splice

<400> SEQUENCE: 232

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45
```

```
Thr Thr Gly Lys Leu Pro Val Pro Trp Pro Thr Leu Val Thr Thr Leu
     50                  55                  60

Cys Tyr Gly Ile Gln Cys Phe Ala Arg Tyr Pro Glu His Met Lys Met
 65                  70                  75                  80

Asn Asp Phe Phe Lys Ser Ala Met Pro Glu Gly Tyr Ile Gln Glu Arg
                 85                  90                  95

Thr Ile Gln Phe Gln Asp Asp Gly Lys Tyr Lys Thr Arg Gly Glu Val
                100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
        130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
                180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Thr Ile Leu Gly Thr Thr Phe Gly Met Val Phe
                260                 265                 270

Ser Leu Leu Gln Val Val Ser Gly Glu Gln Lys Leu Ile Ser Glu Glu
        275                 280                 285

Asp Leu Glu Ser Gly Tyr Ala Gln Asn Gly Asp Leu Glu Asp Ala Glu
        290                 295                 300

Leu Asp Asp Tyr Ser Phe Ser Cys Tyr Ser Gln Leu Glu Val Asn Gly
305                 310                 315                 320

Ser Gln His Ser Leu Thr Cys Ala Phe Glu Asp Pro Asp Val Asn Ile
                325                 330                 335

Thr Asn Leu Glu Phe Glu Ile Cys Gly Ala Leu Val Glu Val Lys Cys
                340                 345                 350

Leu Asn Phe Arg Lys Leu Gln Glu Ile Tyr Phe Ile Glu Thr Lys Lys
                355                 360                 365

Phe Leu Leu Ile Gly Lys Ser Asn Ile Cys Val Lys Val Gly Glu Lys
        370                 375                 380

Ser Leu Thr Cys Lys Lys Ile Asp Leu Thr Thr Ile Val Lys Pro Glu
385                 390                 395                 400

Ala Pro Phe Asp Leu Ser Val Val Tyr Arg Glu Gly Ala Asn Asp Phe
                405                 410                 415

Val Val Thr Phe Asn Thr Ser His Leu Gln Lys Lys Tyr Val Lys Val
                420                 425                 430

Leu Met His Asp Val Ala Tyr Arg Gln Glu Lys Asp Glu Asn Lys Trp
        435                 440                 445

Thr His Val Asn Leu Ser Ser Thr Lys Leu Thr Leu Leu Gln Arg Lys
        450                 455                 460
```

```
Leu Gln Pro Ala Ala Met Tyr Glu Ile Lys Val Arg Ser Ile Pro Asp
465                 470                 475                 480

His Tyr Phe Lys Gly Phe Trp Ser Glu Trp Ser Pro Ser Tyr Tyr Phe
                485                 490                 495

Arg Thr Pro Glu Ile Asn Asn Ser Ser Gly Glu Met Asp Pro Ile Leu
            500                 505                 510

Leu Pro Pro Cys Leu Thr Ile Ser Ile Leu Ser Phe Phe Ser Val Ala
            515                 520                 525

Leu Leu Val Ile Leu Ala Cys Val Leu Trp Lys Lys Arg Ile Lys Pro
            530                 535                 540

Ile Val Trp Pro Ser Leu Pro Asp His Lys Lys Thr Leu Glu His Leu
545                 550                 555                 560

Cys Lys Lys Pro Arg Lys Val Ser Val Phe Gly Ala
                565                 570
```

```
<210> SEQ ID NO 233
<211> LENGTH: 562
<212> TYPE: PRT
<213> ORGANISM: Artificial sequence
<220> FEATURE:
<223> OTHER INFORMATION: synthetic GFP - linker - P2A - IL7RaSP -
      IL7RaIncPPCL C-terminal truncation codon(exceptP2A) and splice
      optimized

<400> SEQUENCE: 233

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

Gly Glu Gly Asp Ala Asp Tyr Gly Lys Leu Glu Ile Lys Phe Ile Cys
        35                  40                  45

Thr Thr Gly Lys Leu Pro Val Pro Trp Pro Thr Leu Val Thr Thr Leu
    50                  55                  60

Cys Tyr Gly Ile Gln Cys Phe Ala Arg Tyr Pro Glu His Met Lys Met
65                  70                  75                  80

Asn Asp Phe Phe Lys Ser Ala Met Pro Glu Gly Tyr Ile Gln Glu Arg
                85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
        115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
    210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
```

245                 250                 255
Asn Pro Gly Pro Met Thr Ile Leu Gly Thr Thr Phe Gly Met Val Phe
            260                 265                 270

Ser Leu Leu Gln Val Val Ser Gly Glu Ser Gly Tyr Ala Gln Asn Gly
        275                 280                 285

Asp Leu Glu Asp Ala Glu Leu Asp Asp Tyr Ser Phe Ser Cys Tyr Ser
    290                 295                 300

Gln Leu Glu Val Asn Gly Ser Gln His Ser Leu Thr Cys Ala Phe Glu
305                 310                 315                 320

Asp Pro Asp Val Asn Ile Thr Asn Leu Glu Phe Glu Ile Cys Gly Ala
                325                 330                 335

Leu Val Glu Val Lys Cys Leu Asn Phe Arg Lys Leu Gln Glu Ile Tyr
            340                 345                 350

Phe Ile Glu Thr Lys Lys Phe Leu Leu Ile Gly Lys Ser Asn Ile Cys
        355                 360                 365

Val Lys Val Gly Glu Lys Ser Leu Thr Cys Lys Ile Asp Leu Thr
    370                 375                 380

Thr Ile Val Lys Pro Glu Ala Pro Phe Asp Leu Ser Val Val Tyr Arg
385                 390                 395                 400

Glu Gly Ala Asn Asp Phe Val Val Thr Phe Asn Thr Ser His Leu Gln
                405                 410                 415

Lys Lys Tyr Val Lys Val Leu Met His Asp Val Ala Tyr Arg Gln Glu
            420                 425                 430

Lys Asp Glu Asn Lys Trp Thr His Val Asn Leu Ser Ser Thr Lys Leu
        435                 440                 445

Thr Leu Leu Gln Arg Lys Leu Gln Pro Ala Ala Met Tyr Glu Ile Lys
    450                 455                 460

Val Arg Ser Ile Pro Asp His Tyr Phe Lys Gly Phe Trp Ser Glu Trp
465                 470                 475                 480

Ser Pro Ser Tyr Tyr Phe Arg Thr Pro Glu Ile Asn Asn Ser Ser Gly
                485                 490                 495

Glu Met Asp Pro Ile Leu Leu Pro Pro Cys Leu Thr Ile Ser Ile Leu
            500                 505                 510

Ser Phe Phe Ser Val Ala Leu Leu Val Ile Leu Ala Cys Val Leu Trp
        515                 520                 525

Lys Lys Arg Ile Lys Pro Ile Val Trp Pro Ser Leu Pro Asp His Lys
    530                 535                 540

Lys Thr Leu Glu His Leu Cys Lys Lys Pro Arg Lys Val Ser Val Phe
545                 550                 555                 560

Gly Ala

<210> SEQ ID NO 234
<211> LENGTH: 824
<212> TYPE: PRT
<213> ORGANISM: Artificial sequence
<220> FEATURE:
<223> OTHER INFORMATION: synthetic GFP - linker - P2A - eTag -
      IL7RaIncPPCL N-terminal deletion codon(exceptP2A) and splice
      optimized

<400> SEQUENCE: 234

Met Ser Gly Gly Glu Glu Leu Phe Ala Gly Ile Val Pro Val Leu Ile
1               5                   10                  15

Glu Leu Asp Gly Asp Val His Gly His Lys Phe Ser Val Arg Gly Glu
            20                  25                  30

-continued

Gly Glu Gly Asp Ala Asp Tyr Gly Lys Leu Glu Ile Lys Phe Ile Cys
         35                  40                  45

Thr Thr Gly Lys Leu Pro Val Pro Trp Pro Thr Leu Val Thr Thr Leu
 50                  55                  60

Cys Tyr Gly Ile Gln Cys Phe Ala Arg Tyr Pro Glu His Met Lys Met
 65                  70                  75                  80

Asn Asp Phe Phe Lys Ser Ala Met Pro Glu Gly Tyr Ile Gln Glu Arg
                 85                  90                  95

Thr Ile Gln Phe Gln Asp Asp Gly Lys Tyr Lys Thr Arg Gly Glu Val
            100                 105                 110

Lys Phe Glu Gly Asp Thr Leu Val Asn Arg Ile Glu Leu Lys Gly Lys
            115                 120                 125

Asp Phe Lys Glu Asp Gly Asn Ile Leu Gly His Lys Leu Glu Tyr Ser
    130                 135                 140

Phe Asn Ser His Asn Val Tyr Ile Arg Pro Asp Lys Ala Asn Asn Gly
145                 150                 155                 160

Leu Glu Ala Asn Phe Lys Thr Arg His Asn Ile Glu Gly Gly Gly Val
                165                 170                 175

Gln Leu Ala Asp His Tyr Gln Thr Asn Val Pro Leu Gly Asp Gly Pro
            180                 185                 190

Val Leu Ile Pro Ile Asn His Tyr Leu Ser Thr Gln Thr Lys Ile Ser
        195                 200                 205

Lys Asp Arg Asn Glu Ala Arg Asp His Met Val Leu Leu Glu Ser Phe
    210                 215                 220

Ser Ala Cys Cys His Thr His Gly Met Asp Glu Leu Tyr Arg Gly Ser
225                 230                 235                 240

Gly Ala Thr Asn Phe Ser Leu Leu Lys Gln Ala Gly Asp Val Glu Glu
                245                 250                 255

Asn Pro Gly Pro Met Leu Leu Val Thr Ser Leu Leu Cys Glu
            260                 265                 270

Leu Pro His Pro Ala Phe Leu Leu Ile Pro Arg Lys Val Cys Asn Gly
            275                 280                 285

Ile Gly Ile Gly Glu Phe Lys Asp Ser Leu Ser Ile Asn Ala Thr Asn
    290                 295                 300

Ile Lys His Phe Lys Asn Cys Thr Ser Ile Ser Gly Asp Leu His Ile
305                 310                 315                 320

Leu Pro Val Ala Phe Arg Gly Asp Ser Phe Thr His Thr Pro Pro Leu
                325                 330                 335

Asp Pro Gln Glu Leu Asp Ile Leu Lys Thr Val Lys Glu Ile Thr Gly
            340                 345                 350

Phe Leu Leu Ile Gln Ala Trp Pro Glu Asn Arg Thr Asp Leu His Ala
        355                 360                 365

Phe Glu Asn Leu Glu Ile Ile Arg Gly Arg Thr Lys Gln His Gly Gln
    370                 375                 380

Phe Ser Leu Ala Val Val Ser Leu Asn Ile Thr Ser Leu Gly Leu Arg
385                 390                 395                 400

Ser Leu Lys Glu Ile Ser Asp Gly Asp Val Ile Ile Ser Gly Asn Lys
                405                 410                 415

Asn Leu Cys Tyr Ala Asn Thr Ile Asn Trp Lys Lys Leu Phe Gly Thr
            420                 425                 430

Ser Gly Gln Lys Thr Lys Ile Ile Ser Asn Arg Gly Glu Asn Ser Cys
        435                 440                 445

Lys Ala Thr Gly Gln Val Cys His Ala Leu Cys Ser Pro Glu Gly Cys

```
                        450                 455                 460
Trp Gly Pro Glu Pro Arg Asp Cys Val Ser Cys Arg Asn Val Ser Arg
465                 470                 475                 480

Gly Arg Glu Cys Val Asp Lys Cys Asn Leu Leu Glu Gly Glu Pro Arg
                    485                 490                 495

Glu Phe Val Glu Asn Ser Glu Cys Ile Gln Cys His Pro Glu Cys Leu
                500                 505                 510

Pro Gln Ala Met Asn Ile Thr Cys Thr Gly Arg Gly Pro Asp Asn Cys
            515                 520                 525

Ile Gln Cys Ala His Tyr Ile Asp Gly Pro His Cys Val Lys Thr Cys
        530                 535                 540

Pro Ala Gly Val Met Gly Glu Asn Asn Thr Leu Val Trp Lys Tyr Ala
545                 550                 555                 560

Asp Ala Gly His Val Cys His Leu Cys His Pro Asn Cys Thr Tyr Gly
                565                 570                 575

Cys Thr Gly Pro Gly Leu Glu Gly Cys Pro Thr Asn Gly Pro Glu Ile
                580                 585                 590

Asn Asn Ser Ser Gly Glu Met Asp Pro Ile Leu Leu Pro Pro Cys Leu
                595                 600                 605

Thr Ile Ser Ile Leu Ser Phe Phe Ser Val Ala Leu Leu Val Ile Leu
            610                 615                 620

Ala Cys Val Leu Trp Lys Lys Arg Ile Lys Pro Ile Val Trp Pro Ser
625                 630                 635                 640

Leu Pro Asp His Lys Lys Thr Leu Glu His Leu Cys Lys Lys Pro Arg
                645                 650                 655

Lys Asn Leu Asn Val Ser Phe Asn Pro Glu Ser Phe Leu Asp Cys Gln
                660                 665                 670

Ile His Arg Val Asp Asp Ile Gln Ala Arg Asp Glu Val Glu Gly Phe
            675                 680                 685

Leu Gln Asp Thr Phe Pro Gln Gln Leu Glu Glu Ser Glu Lys Gln Arg
        690                 695                 700

Leu Gly Gly Asp Val Gln Ser Pro Asn Cys Pro Ser Glu Asp Val Val
705                 710                 715                 720

Ile Thr Pro Glu Ser Phe Gly Arg Asp Ser Ser Leu Thr Cys Leu Ala
                725                 730                 735

Gly Asn Val Ser Ala Cys Asp Ala Pro Ile Leu Ser Ser Arg Ser
                740                 745                 750

Leu Asp Cys Arg Glu Ser Gly Lys Asn Gly Pro His Val Tyr Gln Asp
            755                 760                 765

Leu Leu Leu Ser Leu Gly Thr Thr Asn Ser Thr Leu Pro Pro Pro Phe
        770                 775                 780

Ser Leu Gln Ser Gly Ile Leu Thr Leu Asn Pro Val Ala Gln Gly Gln
785                 790                 795                 800

Pro Ile Leu Thr Ser Leu Gly Ser Asn Gln Glu Glu Ala Tyr Val Thr
                805                 810                 815

Met Ser Ser Phe Tyr Gln Asn Gln
            820

<210> SEQ ID NO 235
<211> LENGTH: 593
<212> TYPE: PRT
<213> ORGANISM: Artificial sequence
<220> FEATURE:
<223> OTHER INFORMATION: synthetic MV(ed)-HD24
```

-continued

```
<400> SEQUENCE: 235

Met Asn Arg Glu His Leu Met Ile Asp Arg Pro Tyr Val Leu Leu Ala
1               5                   10                  15

Val Leu Phe Val Met Ser Leu Ser Leu Ile Gly Leu Leu Ala Ile Ala
            20                  25                  30

Gly Ile Arg Leu His Arg Ala Ala Ile Tyr Thr Ala Glu Ile His Lys
        35                  40                  45

Ser Leu Ser Thr Asn Leu Asp Val Thr Asn Ser Ile Glu His Gln Val
    50                  55                  60

Lys Asp Val Leu Thr Pro Leu Phe Lys Ile Ile Gly Asp Glu Val Gly
65                  70                  75                  80

Leu Arg Thr Pro Gln Arg Phe Thr Asp Leu Val Lys Phe Ile Ser Asp
                85                  90                  95

Lys Ile Lys Phe Leu Asn Pro Asp Arg Glu Tyr Asp Phe Arg Asp Leu
            100                 105                 110

Thr Trp Cys Ile Asn Pro Pro Glu Arg Ile Lys Leu Asp Tyr Asp Gln
        115                 120                 125

Tyr Cys Ala Asp Val Ala Ala Glu Glu Leu Met Asn Ala Leu Val Asn
    130                 135                 140

Ser Thr Leu Leu Glu Thr Arg Thr Thr Asn Gln Phe Leu Ala Val Ser
145                 150                 155                 160

Lys Gly Asn Cys Ser Gly Pro Thr Thr Ile Arg Gly Gln Phe Ser Asn
                165                 170                 175

Met Ser Leu Ser Leu Leu Asp Leu Tyr Leu Ser Arg Gly Tyr Asn Val
            180                 185                 190

Ser Ser Ile Val Thr Met Thr Ser Gln Gly Met Tyr Gly Gly Thr Tyr
        195                 200                 205

Leu Val Glu Lys Pro Asn Leu Ser Ser Lys Arg Ser Glu Leu Ser Gln
    210                 215                 220

Leu Ser Met Tyr Arg Val Phe Glu Val Gly Val Ile Arg Asn Pro Gly
225                 230                 235                 240

Leu Gly Ala Pro Val Phe His Met Thr Asn Tyr Leu Glu Gln Pro Val
                245                 250                 255

Ser Asn Asp Leu Ser Asn Cys Met Val Ala Leu Gly Glu Leu Lys Leu
            260                 265                 270

Ala Ala Leu Cys His Gly Glu Asp Ser Ile Thr Ile Pro Tyr Gln Gly
        275                 280                 285

Ser Gly Lys Gly Val Ser Phe Gln Leu Val Lys Leu Gly Val Trp Lys
    290                 295                 300

Ser Pro Thr Asp Met Gln Ser Trp Val Pro Leu Ser Thr Asp Asp Pro
305                 310                 315                 320

Val Ile Asp Arg Leu Tyr Leu Ser Ser His Arg Gly Val Ile Ala Asp
                325                 330                 335

Asn Gln Ala Lys Trp Ala Val Pro Thr Thr Arg Thr Asp Asp Lys Leu
            340                 345                 350

Arg Met Glu Thr Cys Phe Gln Gln Ala Cys Lys Gly Lys Ile Gln Ala
        355                 360                 365

Leu Cys Glu Asn Pro Glu Trp Ala Pro Leu Lys Asp Asn Arg Ile Pro
    370                 375                 380

Ser Tyr Gly Val Leu Ser Val Asp Leu Ser Leu Thr Val Glu Leu Lys
385                 390                 395                 400

Ile Lys Ile Ala Ser Gly Phe Gly Pro Leu Ile Thr His Gly Ser Gly
                405                 410                 415
```

Met Asp Leu Tyr Lys Ser Asn His Asn Asn Val Tyr Trp Leu Thr Ile
                420                 425                 430

Pro Pro Met Lys Asn Leu Ala Leu Gly Val Ile Asn Thr Leu Glu Trp
            435                 440                 445

Ile Pro Arg Phe Lys Val Ser Pro Asn Leu Phe Thr Val Pro Ile Lys
        450                 455                 460

Glu Ala Gly Glu Asp Cys His Ala Pro Thr Tyr Leu Pro Ala Glu Val
465                 470                 475                 480

Asp Gly Asp Val Lys Leu Ser Ser Asn Leu Val Ile Leu Pro Gly Gln
                485                 490                 495

Asp Leu Gln Tyr Val Leu Ala Thr Tyr Asp Thr Ser Arg Val Glu His
            500                 505                 510

Ala Val Val Tyr Tyr Val Tyr Ser Pro Gly Arg Ser Phe Ser Tyr Phe
        515                 520                 525

Tyr Pro Phe Arg Leu Pro Ile Lys Gly Val Pro Ile Glu Leu Gln Val
            530                 535                 540

Glu Cys Phe Thr Trp Asp Gln Lys Leu Trp Cys Arg His Phe Cys Val
545                 550                 555                 560

Leu Ala Asp Ser Glu Ser Gly Gly His Ile Thr His Ser Gly Met Val
                565                 570                 575

Gly Met Gly Val Ser Cys Thr Val Thr Arg Glu Asp Gly Thr Asn Arg
            580                 585                 590

Arg

<210> SEQ ID NO 236
<211> LENGTH: 1275
<212> TYPE: DNA
<213> ORGANISM: Mesoplasma florum

<400> SEQUENCE: 236
aaaaaaaata aaatcaatag caaatattaa gatttttaag aaataaaaaa ttaatattaa      60
tttacaactg aatataaaag aaacttatac agggtagcat aatgggctac tgaccccgcc     120
ttcaaaccta tttggagact ataagtgaaa aaccactctt taattattaa agtttctttt     180
tatgtccaaa agacaagaag aaactttttt atttagttga atttataata agagaaaaag     240
aaaggatatt atatggcaaa aataaaaaac caatattaca acgagtctgt ttcgccaatt     300
gaatatgcgc aacaaggatt taaggaaaa atgcgttcag taaactgaaa cgtagtaaat      360
gatgaaaaag atttagaggt atgaaataga attcacaaaa acttctgatt gcctgaaaaa     420
attccagttt caaatgattt aacttcatga agaactttga caccagaatg acaagaatta     480
attacaagaa cttttacagg attaacattg ttagatacaa ttcaagctac tgttggtgat     540
gtggctcaag ttcctaactc attaactgac catgaacaag taatttacac aaactttgca     600
tttatggttg cagttcacgc tagatcatat ggttcaatct tttcaacttt atgttcaagt     660
gaacaaattg aagaggctca tgaatgagtt atcaatacag aaacattaca agaaagagct     720
aaagcattaa ttccttatta tgtgaatgat gaccctttaa agtcaaaagt tgcagctgct     780
ttaatgccag gcttcttatt atatggaggc ttctatttac catttaccct atcagctaga     840
ggtaaattac caaacacttc agatattatt agattaatat taagagataa agttatacat     900
aactactata gtggttataa atatcaaaag aaagttgcta aactttctcc agaaaaacaa     960
gctgaaatga aagaatttgt ttttaaatta ttatatgaat taatagattt agaaaaagct    1020
tatttgaaag aattgtatga ggattttgga ttagctgatg atgctattag atttagtgtt    1080

```
tacaacgcag gtaaattttt acaaaattta ggttatgatt caccgtttac agaagaagaa    1140
acaagaattg agccagaaat attcacacaa ttatcagcta gagctgatga aaaccatgat    1200
ttcttttcag ggaatggctc atcatatatt atgggagttt cagaagaaac tgaagatgac    1260
gattgggagt tttaa                                                    1275

<210> SEQ ID NO 237
<211> LENGTH: 64
<212> TYPE: RNA
<213> ORGANISM: Mesoplasma florum

<400> SEQUENCE: 237
acuuauacag gguagcauaa ugggcuacug accccgccuu caaaccuauu uggagacuau    60
aagu                                                                64

<210> SEQ ID NO 238
<211> LENGTH: 69
<212> TYPE: RNA
<213> ORGANISM: Artificial sequence
<220> FEATURE:
<223> OTHER INFORMATION: synthetic Deoxyguanosine riboswitch aptamer
      mutations
<220> FEATURE:
<221> NAME/KEY: misc_feature
<222> LOCATION: (10)..(13)
<223> OTHER INFORMATION: n at positions 10-13 can be A, C, G, or T
<220> FEATURE:
<221> NAME/KEY: misc_feature
<222> LOCATION: (27)..(29)
<223> OTHER INFORMATION: n at positions 27-29 can be A, C, G, or T
<220> FEATURE:
<221> NAME/KEY: misc_feature
<222> LOCATION: (31)..(32)
<223> OTHER INFORMATION: n at positions 31-32 can be A, C, G, or T
<220> FEATURE:
<221> NAME/KEY: misc_feature
<222> LOCATION: (33)..(40)
<223> OTHER INFORMATION: n at positions 33-40 can be A, C, G, T, or no
      nucleotide
<220> FEATURE:
<221> NAME/KEY: misc_feature
<222> LOCATION: (44)..(46)
<223> OTHER INFORMATION: n at positions 44-46 can be A, C, G, or T
<220> FEATURE:
<221> NAME/KEY: misc_feature
<222> LOCATION: (57)..(59)
<223> OTHER INFORMATION: n at positions 57-59 can be A, C, G, or T

<400> SEQUENCE: 238
acuuauacan nnnagcauaa ugggcunnng nnnnnnnnnn gccnnnaaac cuauuunnng    60
acuauaagu                                                           69

<210> SEQ ID NO 239
<211> LENGTH: 84
<212> TYPE: DNA
<213> ORGANISM: Artificial sequence
<220> FEATURE:
<223> OTHER INFORMATION: synthetic Oligo library for screen
<220> FEATURE:
<221> NAME/KEY: misc_feature
<222> LOCATION: (19)..(21)
<223> OTHER INFORMATION: n at positions 19-21 can be A, C, G, or T
<220> FEATURE:
<221> NAME/KEY: misc_feature
<222> LOCATION: (32)..(34)
<223> OTHER INFORMATION: n at positions 32-34 can be A, C, G, or T
<220> FEATURE:
<221> NAME/KEY: misc_feature
<222> LOCATION: (38)..(39)
```

<223> OTHER INFORMATION: n at positions 38-39 can be A, C, G, or T
<220> FEATURE:
<221> NAME/KEY: misc_feature
<222> LOCATION: (40)..(47)
<223> OTHER INFORMATION: n at positions 40-47 can be A, C, G, T, or no
      nucleotide
<220> FEATURE:
<221> NAME/KEY: misc_feature
<222> LOCATION: (49)..(51)
<223> OTHER INFORMATION: n at positions 49-51 can be A, C, G, or T
<220> FEATURE:
<221> NAME/KEY: misc_feature
<222> LOCATION: (65)..(68)
<223> OTHER INFORMATION: n at positions 65-68 can be A, C, G, or T

<400> SEQUENCE: 239
cgcgcgacac ttatagtcnn naaataggtt tnnnggcnnn nnnnnnncnn nagcccatta      60
tgctnnnntg tataagtgcc gccc                                            84

<210> SEQ ID NO 240
<211> LENGTH: 33
<212> TYPE: DNA
<213> ORGANISM: Artificial sequence
<220> FEATURE:
<223> OTHER INFORMATION: synthetic T7 promoter amplification primer

<400> SEQUENCE: 240
taatacgact cactataggg cggcacttat aca                                  33

<210> SEQ ID NO 241
<211> LENGTH: 18
<212> TYPE: DNA
<213> ORGANISM: Artificial sequence
<220> FEATURE:
<223> OTHER INFORMATION: synthetic Reverse amplification primer

<400> SEQUENCE: 241
cgcgcgacac ttatagtc                                                   18

<210> SEQ ID NO 242
<211> LENGTH: 915
<212> TYPE: DNA
<213> ORGANISM: Bacillus subtilis

<400> SEQUENCE: 242
tcaaaagcct ggcggcgcgg tcgtcagact cttttatatc gaatcccctt gaaatacgaa     60
tgatatctaa aaaacaaaa ttaaagttcg ggaatttta ttttcagcct atgcaagaga      120
ttagaatctt gatataattt attacaatat aataggaaca ctcatataat cgcgtggata    180
tggcacgcaa gtttctaccg ggcaccgtaa atgtccgact atgggtgagc aatggaaccg    240
cacgtgtacg gttttttgtg atatcagcat tgcttgctct ttatttgagc gggcaatgct    300 tttttattc tcataacgga ggtagacagg atggaagcac tgaaacggaa aatagaggaa     360
gaaggcgtcg tattatctga tcaggtattg aaagtggatt cttttttgaa tcaccaaatt    420
gatccgctgc ttatgcagag aattggtgat gaatttgcgt ctaggtttgc aaaagacggt    480
attaccaaaa ttgtgacaat cgaatcatca ggtatcgctc ccgctgtaat gacgggcttg    540
aagctgggtg tgccagttgt cttcgcgaga agcataaat cgttaacact caccgacaac     600
ttgctgacag cgtctgttta ttcctttacg aagcaaacag aaagccaaat cgcagtgtct    660
gggacccacc tgtcggatca ggatcatgtg ctgattatcg atgatttttt ggcaaatgga    720
caggcagcgc acgggcttgt gtcgattgtg aagcaagcgg agcttctat tgcgggaatc     780

```
ggcattgtta ttgaaaagtc atttcagccg ggaagagatg aacttgtaaa actgggctac    840
cgagtggaat ctttggcaag aattcagtct ttagaagaag gaaaagtgtc cttcgtacag    900
gaggttcatt catga                                                     915
```

<210> SEQ ID NO 243
<211> LENGTH: 69
<212> TYPE: RNA
<213> ORGANISM: Bacillus subtilis

<400> SEQUENCE: 243

```
cacucauaua aucgcgugga uauggcacgc aaguuucuac cgggcaccgu aaauguccga    60
cuaugggug                                                            69
```

<210> SEQ ID NO 244
<211> LENGTH: 74
<212> TYPE: RNA
<213> ORGANISM: Artificial sequence
<220> FEATURE:
<223> OTHER INFORMATION: synthetic Guanosine xpt riboswitch aptamer
      mutations
<220> FEATURE:
<221> NAME/KEY: misc_feature
<222> LOCATION: (11)..(14)
<223> OTHER INFORMATION: n at positions 11-14 can be A, C, G, or T
<220> FEATURE:
<221> NAME/KEY: misc_feature
<222> LOCATION: (30)..(35)
<223> OTHER INFORMATION: n at positions 30-35 can be A, C, G, or T
<220> FEATURE:
<221> NAME/KEY: misc_feature
<222> LOCATION: (36)..(43)
<223> OTHER INFORMATION: n at positions 36-43 can be A, C, G, T, or no
      nucleotide
<220> FEATURE:
<221> NAME/KEY: misc_feature
<222> LOCATION: (47)..(49)
<223> OTHER INFORMATION: n at positions 47-49 can be A, C, G, or T
<220> FEATURE:
<221> NAME/KEY: misc_feature
<222> LOCATION: (61)..(63)
<223> OTHER INFORMATION: n at positions 61-63 can be A, C, G, or T

<400> SEQUENCE: 244

```
cacucauaua nnnncgugga uauggcacgn nngnnnnnnn nnnaccnnnu accguaaaug    60
nnngacuaug ggug                                                      74
```

<210> SEQ ID NO 245
<211> LENGTH: 89
<212> TYPE: DNA
<213> ORGANISM: Artificial sequence
<220> FEATURE:
<223> OTHER INFORMATION: synthetic Oligo library for screen
<220> FEATURE:
<221> NAME/KEY: misc_feature
<222> LOCATION: (20)..(22)
<223> OTHER INFORMATION: n at positions 20-22 can be A, C, G, or T
<220> FEATURE:
<221> NAME/KEY: misc_feature
<222> LOCATION: (34)..(36)
<223> OTHER INFORMATION: n at positions 34-36 can be A, C, G, or T
<220> FEATURE:
<221> NAME/KEY: misc_feature
<222> LOCATION: (40)..(41)
<223> OTHER INFORMATION: n at positions 40-41 can be A, C, G, or T
<220> FEATURE:
<221> NAME/KEY: misc_feature
<222> LOCATION: (42)..(49)
<223> OTHER INFORMATION: n at positions 42-49 can be A, C, G, T, or no
      nucleotide
<220> FEATURE:

```
<221> NAME/KEY: misc_feature
<222> LOCATION: (51)..(53)
<223> OTHER INFORMATION: n at positions 51-53 can be A, C, G, or T
<220> FEATURE:
<221> NAME/KEY: misc_feature
<222> LOCATION: (69)..(72)
<223> OTHER INFORMATION: n at positions 69-72 can be A, C, G, or T

<400> SEQUENCE: 245
cgcgcgacca cccatagtcn nncatttacg gtgnnnggtn nnnnnnnnnc nnncgtgcca    60
tatccacgnn nntatatgag tggccgccc                                    89

<210> SEQ ID NO 246
<211> LENGTH: 34
<212> TYPE: DNA
<213> ORGANISM: Artificial sequence
<220> FEATURE:
<223> OTHER INFORMATION: synthetic T7 promoter amplification primer

<400> SEQUENCE: 246
taatacgact cactataggg cggccactca tata                              34

<210> SEQ ID NO 247
<211> LENGTH: 19
<212> TYPE: DNA
<213> ORGANISM: Artificial sequence
<220> FEATURE:
<223> OTHER INFORMATION: synthetic Reverse amplification primer

<400> SEQUENCE: 247
cgcgcgacca cccatagtc                                               19

<210> SEQ ID NO 248
<211> LENGTH: 76
<212> TYPE: RNA
<213> ORGANISM: Artificial sequence
<220> FEATURE:
<223> OTHER INFORMATION: synthetic Oligo 1 Transcribed RNA

<400> SEQUENCE: 248
gggcggcacu uauacagggu agcauaaugg gcuacugacg ccuucaaacc uauuuggaga    60
cuauaagugu cgcgcg                                                  76

<210> SEQ ID NO 249
<211> LENGTH: 76
<212> TYPE: DNA
<213> ORGANISM: Artificial sequence
<220> FEATURE:
<223> OTHER INFORMATION: synthetic Oligo 1 Synthesized template

<400> SEQUENCE: 249
cgcgcgacac ttatagtctc caaataggtt tgaaggcgtc agtagcccat tatgctaccc    60
tgtataagtg ccgccc                                                  76

<210> SEQ ID NO 250
<211> LENGTH: 79
<212> TYPE: RNA
<213> ORGANISM: Artificial sequence
<220> FEATURE:
<223> OTHER INFORMATION: synthetic Oligo 2 Transcribed RNA

<400> SEQUENCE: 250
gggcggcacu uauacagggu agcauaaugg gcuacugacc ccgccuucaa accuauuugg    60
agacuauaag ugucgcgcg                                               79
```

<210> SEQ ID NO 251
<211> LENGTH: 79
<212> TYPE: DNA
<213> ORGANISM: Artificial sequence
<220> FEATURE:
<223> OTHER INFORMATION: synthetic Oligo 2 Synthesized template

<400> SEQUENCE: 251
cgcgcgacac ttatagtctc caaataggtt tgaaggcggg gtcagtagcc cattatgcta    60
ccctgtataa gtgccgccc    79

<210> SEQ ID NO 252
<211> LENGTH: 560
<212> TYPE: PRT
<213> ORGANISM: Artificial sequence
<220> FEATURE:
<223> OTHER INFORMATION: synthetic DAFss-aCD3scFv(UCHT1)IgG1 Fc-CD14GPI

<400> SEQUENCE: 252

```
Met Thr Val Ala Arg Pro Ser Val Pro Ala Ala Leu Pro Leu Leu Gly
1               5                   10                  15

Glu Leu Pro Arg Leu Leu Leu Leu Val Leu Leu Cys Leu Pro Asp Ile
            20                  25                  30

Gln Met Thr Gln Ser Pro Ser Ser Leu Ser Ala Ser Val Gly Asp Arg
        35                  40                  45

Val Thr Ile Thr Cys Arg Ala Ser Gln Asp Ile Arg Asn Tyr Leu Asn
    50                  55                  60

Trp Tyr Gln Gln Lys Pro Gly Lys Ala Pro Lys Leu Leu Ile Tyr Tyr
65                  70                  75                  80

Thr Ser Arg Leu Glu Ser Gly Val Pro Ser Arg Phe Ser Gly Ser Gly
                85                  90                  95

Ser Gly Thr Asp Tyr Thr Leu Thr Ile Ser Ser Leu Gln Pro Glu Asp
            100                 105                 110

Phe Ala Thr Tyr Tyr Cys Gln Gln Gly Asn Thr Leu Pro Trp Thr Phe
        115                 120                 125

Gly Gln Gly Thr Lys Val Glu Ile Lys Gly Gly Gly Ser Gly Gly
    130                 135                 140

Gly Gly Ser Gly Gly Gly Ser Glu Val Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Tyr Ser Phe Thr Gly Tyr Thr Met Asn Trp Val Arg Gln Ala
            180                 185                 190

Pro Gly Lys Gly Leu Glu Trp Val Ala Leu Ile Asn Pro Tyr Lys Gly
        195                 200                 205

Val Ser Thr Tyr Asn Gln Lys Phe Lys Asp Arg Phe Thr Ile Ser Val
    210                 215                 220

Asp Lys Ser Lys Asn Thr Ala Tyr Leu Gln Met Asn Ser Leu Arg Ala
225                 230                 235                 240

Glu Asp Thr Ala Val Tyr Tyr Cys Ala Arg Ser Gly Tyr Tyr Gly Asp
                245                 250                 255

Ser Asp Trp Tyr Phe Asp Val Trp Gly Gln Gly Thr Leu Val Thr Val
            260                 265                 270

Ser Ser Glu Pro Lys Ser Cys Asp Lys Thr His Thr Cys Pro Pro Cys
        275                 280                 285
```

```
Pro Ala Pro Glu Leu Leu Gly Gly Pro Ser Val Phe Leu Phe Pro Pro
            290                 295                 300
Lys Pro Lys Asp Thr Leu Met Ile Ser Arg Thr Pro Glu Val Thr Cys
305                 310                 315                 320
Val Val Val Asp Val Ser His Glu Asp Pro Glu Val Lys Phe Asn Trp
                325                 330                 335
Tyr Val Asp Gly Val Glu Val His Asn Ala Lys Thr Lys Pro Arg Glu
            340                 345                 350
Glu Gln Tyr Asn Ser Thr Tyr Arg Val Val Ser Val Leu Thr Val Leu
        355                 360                 365
His Gln Asp Trp Leu Asn Gly Lys Glu Tyr Lys Cys Lys Val Ser Asn
    370                 375                 380
Lys Ala Leu Pro Ala Pro Ile Glu Lys Thr Ile Ser Lys Ala Lys Gly
385                 390                 395                 400
Gln Pro Arg Glu Pro Gln Val Tyr Thr Leu Pro Pro Ser Arg Glu Glu
                405                 410                 415
Met Thr Lys Asn Gln Val Ser Leu Thr Cys Leu Val Lys Gly Phe Tyr
            420                 425                 430
Pro Ser Asp Ile Ala Val Glu Trp Glu Ser Asn Gly Gln Pro Glu Asn
        435                 440                 445
Asn Tyr Lys Thr Thr Pro Pro Val Leu Asp Ser Asp Gly Ser Phe Phe
    450                 455                 460
Leu Tyr Ser Lys Leu Thr Val Asp Lys Ser Arg Trp Gln Gln Gly Asn
465                 470                 475                 480
Val Phe Ser Cys Ser Val Met His Glu Ala Leu His Asn His Tyr Thr
                485                 490                 495
Gln Lys Ser Leu Ser Leu Ser Pro Gly Val Asp Asn Leu Thr Leu Asp
            500                 505                 510
Gly Asn Pro Phe Leu Val Pro Gly Thr Ala Leu Pro His Glu Gly Ser
        515                 520                 525
Met Asn Ser Gly Val Val Pro Ala Cys Ala Arg Ser Thr Leu Ser Val
    530                 535                 540
Gly Val Ser Gly Thr Leu Val Leu Leu Gln Gly Ala Arg Gly Phe Ala
545                 550                 555                 560

<210> SEQ ID NO 253
<211> LENGTH: 276
<212> TYPE: PRT
<213> ORGANISM: Artificial sequence
<220> FEATURE:
<223> OTHER INFORMATION: synthetic DAFss-CD80ECD-CD16GPI

<400> SEQUENCE: 253

Met Thr Val Ala Arg Pro Ser Val Pro Ala Ala Leu Pro Leu Leu Gly
1               5                   10                  15
Glu Leu Pro Arg Leu Leu Leu Leu Val Leu Leu Cys Leu Pro Val Ile
            20                  25                  30
His Val Thr Lys Glu Val Lys Glu Val Ala Thr Leu Ser Cys Gly His
        35                  40                  45
Asn Val Ser Val Glu Glu Leu Ala Gln Thr Arg Ile Tyr Trp Gln Lys
    50                  55                  60
Glu Lys Lys Met Val Leu Thr Met Met Ser Gly Asp Met Asn Ile Trp
65                  70                  75                  80
Pro Glu Tyr Lys Asn Arg Thr Ile Phe Asp Ile Thr Asn Asn Leu Ser
                85                  90                  95
```

```
Ile Val Ile Leu Ala Leu Arg Pro Ser Asp Glu Gly Thr Tyr Glu Cys
            100                 105                 110

Val Val Leu Lys Tyr Glu Lys Asp Ala Phe Lys Arg Glu His Leu Ala
            115                 120                 125

Glu Val Thr Leu Ser Val Lys Ala Asp Phe Pro Thr Pro Ser Ile Ser
        130                 135                 140

Asp Phe Glu Ile Pro Thr Ser Asn Ile Arg Arg Ile Ile Cys Ser Thr
145                 150                 155                 160

Ser Gly Gly Phe Pro Glu Pro His Leu Ser Trp Leu Glu Asn Gly Glu
                165                 170                 175

Glu Leu Asn Ala Ile Asn Thr Thr Val Ser Gln Asp Pro Glu Thr Glu
            180                 185                 190

Leu Tyr Ala Val Ser Ser Lys Leu Asp Phe Asn Met Thr Thr Asn His
        195                 200                 205

Ser Phe Met Cys Leu Ile Lys Tyr Gly His Leu Arg Val Asn Gln Thr
    210                 215                 220

Phe Asn Trp Asn Thr Thr Lys Gln Glu His Phe Pro Asp Asn Val Ser
225                 230                 235                 240

Thr Ile Ser Ser Phe Ser Pro Pro Gly Tyr Gln Val Ser Phe Cys Leu
                245                 250                 255

Val Met Val Leu Leu Phe Ala Val Asp Thr Gly Leu Tyr Phe Ser Val
            260                 265                 270

Lys Thr Asn Ile
            275

<210> SEQ ID NO 254
<211> LENGTH: 533
<212> TYPE: PRT
<213> ORGANISM: Artificial sequence
<220> FEATURE:
<223> OTHER INFORMATION: synthetic DAFss-IL7-DAF

<400> SEQUENCE: 254

Met Ala Thr Thr Met Thr Val Ala Arg Pro Ser Val Pro Ala Ala Leu
1               5                   10                  15

Pro Leu Leu Gly Glu Leu Pro Arg Leu Leu Leu Val Leu Leu Leu Cys
            20                  25                  30

Leu Pro Ala Asp Cys Asp Ile Glu Gly Lys Asp Gly Lys Gln Tyr Glu
        35                  40                  45

Ser Val Leu Met Val Ser Ile Asp Gln Leu Leu Asp Ser Met Lys Glu
    50                  55                  60

Ile Gly Ser Asn Cys Leu Asn Asn Glu Phe Asn Phe Phe Lys Arg His
65                  70                  75                  80

Ile Cys Asp Ala Asn Lys Glu Gly Met Phe Leu Phe Arg Ala Ala Arg
                85                  90                  95

Lys Leu Arg Gln Phe Leu Lys Met Asn Ser Thr Gly Asp Phe Asp Leu
            100                 105                 110

His Leu Leu Lys Val Ser Glu Gly Thr Thr Ile Leu Leu Asn Cys Thr
        115                 120                 125

Gly Gln Val Lys Gly Arg Lys Pro Ala Ala Leu Gly Glu Ala Gln Pro
    130                 135                 140

Thr Lys Ser Leu Glu Glu Asn Lys Ser Leu Lys Glu Gln Lys Lys Leu
145                 150                 155                 160

Asn Asp Leu Cys Phe Leu Lys Arg Leu Leu Gln Glu Ile Lys Thr Cys
                165                 170                 175
```

```
Trp Asn Lys Ile Leu Met Gly Thr Lys Glu His Cys Gly Leu Pro Pro
            180                 185                 190
Asp Val Pro Asn Ala Gln Pro Ala Leu Glu Gly Arg Thr Ser Phe Pro
        195                 200                 205
Glu Asp Thr Val Ile Thr Tyr Lys Cys Glu Glu Ser Phe Val Lys Ile
    210                 215                 220
Pro Gly Glu Lys Asp Ser Val Ile Cys Leu Lys Gly Ser Gln Trp Ser
225                 230                 235                 240
Asp Ile Glu Glu Phe Cys Asn Arg Ser Cys Glu Val Pro Thr Arg Leu
                245                 250                 255
Asn Ser Ala Ser Leu Lys Gln Pro Tyr Ile Thr Gln Asn Tyr Phe Pro
            260                 265                 270
Val Gly Thr Val Val Glu Tyr Glu Cys Arg Pro Gly Tyr Arg Arg Glu
        275                 280                 285
Pro Ser Leu Ser Pro Lys Leu Thr Cys Leu Gln Asn Leu Lys Trp Ser
    290                 295                 300
Thr Ala Val Glu Phe Cys Lys Lys Ser Cys Pro Asn Pro Gly Glu
305                 310                 315                 320
Ile Arg Asn Gly Gln Ile Asp Val Pro Gly Gly Ile Leu Phe Gly Ala
                325                 330                 335
Thr Ile Ser Phe Ser Cys Asn Thr Gly Tyr Lys Leu Phe Gly Ser Thr
            340                 345                 350
Ser Ser Phe Cys Leu Ile Ser Gly Ser Ser Val Gln Trp Ser Asp Pro
        355                 360                 365
Leu Pro Glu Cys Arg Glu Ile Tyr Cys Pro Ala Pro Pro Gln Ile Asp
    370                 375                 380
Asn Gly Ile Ile Gln Gly Glu Arg Asp His Tyr Gly Tyr Arg Gln Ser
385                 390                 395                 400
Val Thr Tyr Ala Cys Asn Lys Gly Phe Thr Met Ile Gly Glu His Ser
                405                 410                 415
Ile Tyr Cys Thr Val Asn Asn Asp Glu Gly Glu Trp Ser Gly Pro Pro
            420                 425                 430
Pro Glu Cys Arg Gly Lys Ser Leu Thr Ser Lys Val Pro Pro Thr Val
        435                 440                 445
Gln Lys Pro Thr Thr Val Asn Val Pro Thr Thr Glu Val Ser Pro Thr
    450                 455                 460
Ser Gln Lys Thr Thr Thr Lys Thr Thr Thr Pro Asn Ala Gln Ala Thr
465                 470                 475                 480
Arg Ser Thr Pro Val Ser Arg Thr Thr Lys His Phe His Glu Thr Thr
                485                 490                 495
Pro Asn Lys Gly Ser Gly Thr Thr Ser Gly Thr Thr Arg Leu Leu Ser
            500                 505                 510
Gly His Thr Cys Phe Thr Leu Thr Gly Leu Leu Gly Thr Leu Val Thr
        515                 520                 525
Met Gly Leu Leu Thr
    530

<210> SEQ ID NO 255
<211> LENGTH: 1823
<212> TYPE: DNA
<213> ORGANISM: Artificial sequence
<220> FEATURE:
<223> OTHER INFORMATION: synthetic EF-1a promoter with miRs

<400> SEQUENCE: 255
```

```
ggctccggtg cccgtcagtg ggcagagcgc acatcgccca cagtccccga gaagttgggg      60
ggaggggtcg gcaattgaac cggtgcctag agaaggtggc gcggggtaaa ctgggaaagt     120
gatgtcgtgt actggctccg ccttttccc gagggtgggg gagaaccgta tataagtgca     180
gtagtcgccg tgaacgttct ttttcgcaac gggtttgccg ccagaacaca ggtaagtgcc     240
gtgtgtggtt cccgcgggcc tggcctcttt acgggttatg gcccttgcgt gccttgaatt     300
acttccacct ggctgcagta cgtgattctt gatcccgagc ttcgggttgg aagtgggtgg     360
gagagttcga ggccttgcgc ttaaggagcc ccttcgcctc gtgcttgagt tgaggcctgg     420
cctgggcgct ggggccgccg cgtgcgaatc tggtggcacc ttcgcgcctg tctcgctgct     480
ttcgataagt ctctagccat ttaaaatttt tgatgacctg ctgcgacgct ttttttctgg     540
caagatagtc ttgtaaatgc gggccaagat ctgcacactg gtatttcggt ttttggggcc     600
gcgggcggcg acggggcccg tgcgtcccag cgcacatgtt cggcgaggcg gggcctgcga     660
gcgcggccac cgagaatcgg acggggtag tctcaagctg gccggcctgc tctggtgcct     720
ggcctcgcgc cgccgtgtat cgccccgcc tgggcggcaa ggctggcccg gtcggcacca     780
gttgcgtgag cggaaagatg gccgcttccc ggccctgctg cagggagctc aaaatggagg     840
acgcggcgct cgggagagcg ggcgggtgag tcacccacac aaaggaaaag ggcctttccg     900
tcctcagccg tcgcttcatg tgactccact gagtaccggg cgccgtccag gcacctcgat     960
tagttcctgg aggcttgctg aaggctgtat gctgacatgg tacagttcaa tggtggtttt    1020
ggccactgac tgaccaccat tgctgtacca tgtcaggaca caaggcctgt tactagcact    1080
cacatggaac aaatggccca cattggtgcc ggatgaagct cttatgttgc acggtcatct    1140
ggaggcttgc tgaaggctgt atgctgtcag tctgttcatc ttctggcgtt ttggccactg    1200
actgacgcca gaaggaacag actgacagga cacaaggcct gttactagca ctcacatgga    1260
acaaatggcc gttgccggag tcttggcagc gagagatcac tatcaactaa ctggaggctt    1320
gctgaaggct gtatgctgaa gcgtgaagtg aatcaacggg ttttggccac tgactgaccc    1380
gttgatactt cacgcttcag gacacaaggc ctgttactag cactcacatg gaacaaatgg    1440
ccgtgttaat tgtccatgta gcgaggcatc cttatggcgt ggctggaggc ttgctgaagg    1500
ctgtatgctg gcagtatcct agtacattga cgttttggcc actgactgac gtcaatgtta    1560
ggatactgcc aggacacaag gcctgttact agcactcaca tggaacaaat ggccgctttt    1620
ggagtacgtc gtctttaggt tggggggagg ggttttatgc gatggagttt ccccacactg    1680
agtgggtgga gactgaagtt aggccagctt ggcacttgat gtaattctcc ttggaatttg    1740
cccttttga gtttggatct tggttcattc tcaagcctca gacagtggtt caaagttttt    1800
ttcttccatt tcaggtgtcg tga                                             1823
```